US012692518B2

(12) United States Patent
Rawlings et al.

(10) Patent No.: US 12,692,518 B2
(45) Date of Patent: *Jul. 28, 2026

(54) THERAPEUTIC GENOME EDITING IN WISKOTT-ALDRICH SYNDROME AND X-LINKED THROMBOCYTOPENIA

(71) Applicant: Seattle Children's Hospital, Seattle, WA (US)

(72) Inventors: David J. Rawlings, Seattle, WA (US); Iram Khan, Issaquah, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,235

(22) Filed: Apr. 5, 2023

(65) Prior Publication Data

US 2024/0141389 A1 May 2, 2024

Related U.S. Application Data

(63) Continuation of application No. 16/605,748, filed as application No. PCT/US2018/028442 on Apr. 19, 2018, now Pat. No. 11,643,671.

(60) Provisional application No. 62/488,249, filed on Apr. 21, 2017.

(51) Int. Cl.
*C12N 15/90* (2006.01)
*C12N 9/22* (2006.01)

(52) U.S. Cl.
CPC ............. *C12N 15/907* (2013.01); *C12N 9/22* (2013.01)

(58) Field of Classification Search
None
See application file for complete search history.

(56) References Cited

U.S. PATENT DOCUMENTS

| | | | |
|---|---|---|---|
| 10,968,253 B2 | 4/2021 | Ohlmann et al. | |
| 11,643,671 B2 | 5/2023 | Rawlings et al. | |
| 2006/0134673 A1 | 6/2006 | Zhang | |
| 2020/0006322 A1 | 1/2020 | Then et al. | |

FOREIGN PATENT DOCUMENTS

| | | | | |
|---|---|---|---|---|
| WO | WO-2006065758 A2 * | 6/2006 | ........... | C12Q 1/6883 |
| WO | WO 15/048577 | 4/2015 | | |
| WO | WO 15/057980 | 4/2015 | | |
| WO | WO 16/057961 | 4/2016 | | |
| WO | WO 18/058064 | 3/2018 | | |
| WO | WO-2018058064 A1 * | 3/2018 | ............. | A61K 48/00 |
| WO | WO-2018195360 A1 * | 10/2018 | ............. | A61K 48/00 |
| WO | WO 19/209912 | 10/2019 | | |
| WO | WO 19/210216 | 10/2019 | | |

OTHER PUBLICATIONS

Buchbinder et al (Wiskott-Aldrich syndrome: diagnosis, current management, and emerging treatments. Appl Clin Genet. 2014;7:55-66. Published Apr. 3, 2014) (Year: 2014).*
Lin et al (CRISPR/Cas9 systems have off-target activity with insertions or deletions between target DNA and guide RNA sequences. Nucleic Acids Res. Jun. 2014;42(11):7473-85) (Year: 2014).*
Singh et al., Mar. 2017, Safe and effective gene therapy for murine Wiskott-Aldrich syndrome using an insulated lentiviral vector, Molecular Therapy—Methods & Clinical Development, 4:1-16.
Abina et al., Apr. 21, 2015, Outcomes following gene therapy in patients with severe Wiskott-Aldrich Syndrome, JAMA, 313(15):1550-1563.
Aiuti et al., Aug. 23, 2013, Lentiviral hematopoietic stem cell gene therapy in patients with Wiskott-Aldrich Syndrome, Science, 341:6148.
Boztug et al., 2010, Stem-cell gene therapy for the Wiskott-drich Syndrome, N Engl J Med, 363(20):1918-1927.
Braun et al., Mar. 12, 2014, Gene therapy for Wiskott-Aldrich Syndrome—long-term efficacy and genotoxicity, Sci Transl Med, 6(227):ra33.
Khan et al., May 10-13, 2017, Targeted homologous recombination within the WAS locus in human hematopoietic stem cells, 20th Annual Meeting of the American Society of Gene and Cell Therapy, 25(5S1):80.
Khan et al., May 2016, Precision editing of the WAS locus via homologous recombination in primary human hematopoietic cells mediated by either TALEN or CRISPR/Cas nucleases, Molecular Therapy, 24(Supp 1):S227.
Laskowski, 2016, Gene correction of iPSCs from a Wiskott-Aldrich Syndrome patient normalizes the lymphoid developmental and functional defects, Stem Cell Reports, vol. 7.
Mandal et al., May 2016, 568. Transient manipulation of DNA damage repair pathway choice improves homology-directed repair during CRISPR/Cas9-mediated genome editing, Molecular Therapy, 24(Suppl. 1):S227.
Pattabhi et al., Sep. 1, 2019, In vivo outcome of homology-directed repair at the HBB gene in HSC using alternative donor template delivery method, Molecular Therapy: Nucleic Acids, 17:277-288.
Rai et al., Aug. 12, 2020, Targeted gene correction of human hematopoietic stem cells for the treatment of Wiskott-Adlrich syndrome, Nature Communications, 11(1), 15 pp.
Sambrook et al., Molecular Cloning, A Laboratory Manual, Cold Springs Harbor Press (Cold Springs Harbor, NY 1989.

(Continued)

*Primary Examiner* — Zachariah Lucas
*Assistant Examiner* — Sarah A Alsomairy
(74) *Attorney, Agent, or Firm* — KNOBBE, MARTENS, OLSON & BEAR, LLP

(57) ABSTRACT

Described herein are systems and methods for treating, inhibiting, or ameliorating X-linked disorders including Wiskott-Aldrich Syndrome (WAS) and X-linked thrombocytopenia (XLT) in subjects that have been identified or selected as being ones that would benefit from a therapy to treat, inhibit, or ameliorate WAS or XLT. The systems include nuclease and vector donor constructs configured for co-delivery to modify endogenous WAS locus.

19 Claims, 49 Drawing Sheets

Specification includes a Sequence Listing.

(56) References Cited

OTHER PUBLICATIONS

Singh et al., Mar. 2015, BTK-promoter LV vectors utilizing conserved intron element mediate functional rescue in murine XLA, Molecular Therapy, 23(Suppl. 1):S93 (abstract).

Singleton et al., Dictionary of Microbiology and Molecular Biology 2nd ed., J. Wiley & Sons (New York, NY 1994).

Wang, Yebo et al., "Integration-defective lentiviral vector mediates efficient gene editing through homology-directed repair in human embryonic stem cells" Nucleic Acids Research, 2017, pp. 1-12, vol. 45, No. 5, e29.

Zhu et al., Oct. 1, 1997, Wiskott-Aldrich syndrome/X-linked thrombocytopenia: WASP gene mutations, protein expression, and phenotype, Blood, 90(7):2680-2689.

International Search Report for PCT/US2018/028442 dated Aug. 1, 2018.

* cited by examiner

Mock

AAV

AAV+RNP

SEQUENCE LISTING

```
Sequence total quantity: 41
SEQ ID NO: 1            moltype = DNA   length = 2934
FEATURE                 Location/Qualifiers
misc_feature            1..2934
                        note = Sequence of Full chemically modified guide #1
source                  1..2934
                        mol_type = other DNA
                        organism = synthetic construct
SEQUENCE: 1
atggcgccgc ggcctcctaa gaagaagcgg aaagtcgaat tcgtggatct gcgaacactg   60
ggctatagcc agcagcagca ggagaagatc aaacccaagg tgaggtccac agtcgcacag  120
caccatgaag ccctggtggg ccacgggttc actcacgctc atattgtcgc actgtctcag  180
catccagccg ctctgggaac cgtggcagtc acataccagc acatcattac tgccctgccc  240
gaggctaccc atgaagacat cgtgggagtc ggcaaacagt ggagcggcgc acgggccctg  300
gaggctctgc tgaccgacgc aggggaactg agaggacccc ctctgcagct ggatacaggg  360
cagctggtga agattgctaa gagggaggg gtgacagcaa tggaagccgt ccacgcaagc  420
aggaacgcac tgacaggggc ccccctgaac ctgaccccgg accaagtggt ggctatcgcc  480
agccacgatg gcggcaagca agcgctcgaa acggtgcagc ggctgttgcc ggtgctgtgc  540
caggaccatg gcctgacccc ggaccaagtg gtggctatcg ccagcaacgg tggcggcaag  600
caagcgctcg aaacggtgca gcggctgttg ccggtgctgt gccaggacca tggcctgacc  660
ccggaccaag tggtggctat cgccagccac gatggcggca agcaagcgct cgaaacggtg  720
cagcggctgt tgccggtgct gtgccaggac catggcctga ccccggacca agtggtggct  780
atcgccagcc acgatggcgg caagcaagcg ctcgaaacgg tgcagcggct gttgccggtg  840
ctgtgccagg accatggcct gactccggac caagtggtgg ctatcgccag caacggtggc  900
ggcaagcaag cgctcgaaac ggtgcagcgg ctgttgccgg tgctgtgcca ggaccatggc  960
ctgaccccgg accaagtggt ggctatcgcc agcaacattg gcggcaagca agcgctcgaa 1020
acggtgcagc ggctgttgcc ggtgctgtgc caggaccatg gcctgactcc ggaccaagtg 1080
gtggctatcg ccagcaacaa tggcggcaag caagcgctcg aaacggtgca gcggctgttg 1140
ccggtgctgt gccaggacca tggcctgacc ccggaccaag tggtggctat cgccagcaac 1200
attggcggca agcaagcgct cgaaacggtg cagcggctgt tgccggtgct gtgccaggac 1260
catggcctga ccccggacca agtggtggct atcgccagca acattggcgg caagcaagcg 1320
ctcgaaacgg tgcagcggct gttgccggtg ctgtgccagg accatggcct gactccggac 1380
caagtggtgg ctatcgccag caacggtggc ggcaagcaag cgctcgaaac ggtgcagcaac 1440
ctgttgccgg tgctgtgcca ggaccatggc ctgaccccgg accaagtggt ggctatcgcc 1500
agcaacggtg gcggcaagca agcgctcgaa acggtgcagc ggctgttgcc ggtgctgtgc 1560
caggaccatg gcctgacccc ggaccaagtg gtggctatcg ccagcaacgg tggcggcaag 1620
caagcgctcg aaacggtgca gcggctgttg ccggtgctgt gccaggacca tggcctgacc 1680
```

```
ccggaccaag tggtggctat cgccagccac gatggcggca agcaagcgct cgaaacggtg  1740
cagcggctgt tgccggtgct gtgccaggac catggcctga ccccggacca agtggtggct  1800
atcgccagcc acgatggcgg caagcaagcg ctcgaaacgg tgcagcggct gttgccggtg  1860
ctgtgccagg accatggcct gaccccggac caagtggtgg ctatcgccag ccacgatggc  1920
ggcaagcaag cgctcgaaac ggtgcagcgg ctgttgccgg tgctgtgcca ggaccatggc  1980
ctgactccgg accaagtggt ggctatcgcc agcaacaatg gcggcaagca agcgctcgaa  2040
acggtgcagc ggctgttgcc ggtgctgtgc caggaccatg gcctgacccc ggaccaagtg  2100
gtggctatcg ccagcaacgg tggcggcaag caagcgctcg aaagcattgt ggcccagctg  2160
agccggcctg atccggcgtt ggccgcgttg accaacgacc acctggtcgc tctggcttgc  2220
ctgggaggac gccctgctat ggacgctgtg aagaaaggac tgccccacgc acccgaactg  2280
attagacggg tgaaccggag aatcggcgag agaacatccc atagggtggc aatctctaga  2340
actcagctgg tcaagagtga actggaggaa aagaaatcag agctgcgcca caagctgaaa  2400
tacgtgcctc atgagtatat cgaactgatc gagattgctc gcaattcaac ccaggaccgg  2460
atcctggaaa tgaaagtgat ggagttcttt atgaaagtct acggatatcg ggggaaacac  2520
ctgggaggga gcagaaagcc agatggggcc atctacacag tgggatcccc catcgactat  2580
ggcgtgattg tcgatactaa agcctacagc ggaggctata acctgcctat cggccaggct  2640
gacgagatgc agagatacgt ggaggaaaac cagacccgca ataagcatat taaccccaat  2700
gaatggtgga aagtgtatcc tagctccgtc acagagttca agtttctgtt cgtgagcgga  2760
cactttaagg gcaactacaa agcacagctg actaggctga atcatatcac caactgcaat  2820
ggagccgtgc tgtctgtcga ggaactgctg atcggggag agatgattaa ggctggcaca  2880
ctgactctgg aggaagtgag gcgcaagttc aacaatgggg aaatcaactt ctaa       2934
```

```
SEQ ID NO: 2            moltype = DNA   length = 3036
FEATURE                 Location/Qualifiers
misc_feature            1..3036
                        note = Sequence of Full chemically modified guide #1
source                  1..3036
                        mol_type = other DNA
                        organism = synthetic construct
SEQUENCE: 2
atggcgccgc ggcctcctaa gaagaagcgg aaagtcgaat tcgtggatct gcgaacactg  60
ggctatagcc agcagcagca ggagaagatc aaacccaagg tgaggtccac agtcgcacag  120
caccatgaag ccctggtggg ccacgggttc actcacgctc atattgtcgc actgtctcag  180
catccagccg ctctgggaac cgtggcagtc acataccagc acatcattac tgccctgccc  240
gaggctaccc atgaagacat cgtgggagtc ggcaaacagt ggagcggcgc acgggccctg  300
gaggctctgc tgaccgacgc aggggaactg agaggacccc ctctgcagct ggatacaggg  360
cagctggtga agattgctaa gaggggaggg gtgacagcaa tggaagccgt ccacgcaagc  420
aggaacgcac tgacaggggc ccccctgaac ctgaccccgg accaagtggt ggctatcgtc  480
agcaacattg gcggcaagca agcgctcgaa acggtgcagc ggctgttgcc ggtgctgtgc  540
caggaccatg gcctgacccc ggaccaagtg gtggctatcg ccagcaacaa tggcggcaag  600
caagcgctcg aaacggtgca gcggctgttg ccggtgctgt gccaggacca tggcctgacc  660
ccggaccaag tggtggctat cgccagcaac attggcggca agcaagcgct cgaaacggtg  720
cagcggctgt tgccggtgct gtgccaggac catggcctga ccccggacca agtggtggct  780
atcgccagcc acgatggcgg caagcaagcg ctcgaaacgg tgcagcggct gttgccggtg  840
ctgtgccagg accatggcct gactccggac caagtggtgg ctatcgccag caacattggc  900
ggcaagcaag cgctcgaaac ggtgcagcgg ctgttgccgg tgctgtgcca ggaccatggc  960
ctgaccccgg accaagtggt ggctatcgcc agcaacggcg cggcaagca agcgctcgaa  1020
acggtgcagc ggctgttgcc ggtgctgtgc caggaccatg gcctgactcc ggaccaagtg  1080
gtggctatcg ccagcaacgg tggcggcaag caagcgctcg aaacggtgca gcggctgttg  1140
ccggtgctgt gccaggacca tggcctgacc ccggaccaag tggtggctat cgccagcaac  1200
aatggcggca agcaagcgct cgaaacggtg cagcggctgt tgccggtgct gtgccaggac  1260
catggcctga ccccggacca agtggtggct atcgccagca acattggcgg caagcaagcg  1320
ctcgaaacgg tgcagcggct gttgccggtg ctgtgccagg accatggcct gactccggac  1380
caagtggtgg ctatcgccag caacaatggc ggcaagcaag cgctcgaaac ggtgcagcgg  1440
ctgttgccgg tgctgtgcca ggaccatggc ctgaccccgg accaagtggt ggctatcgcc  1500
agcaacattg gcggcaagca agcgctcgaa acggtgcagc ggctgttgcc ggtgctgtgc  1560
caggaccatg gcctgacccc ggaccaagtg gtggctatcg ccagcaacgg tggcggcaag  1620
caagcgctcg aaacggtgca gcggctgttg ccggtgctgt gccaggacca tggcctgacc  1680
ccggaccaag tggtggctat cgccagccac gatggcggca agcaagcgct cgaaacggtg  1740
cagcggctgt tgccggtgct gtgccaggac catggcctga ccccggacca agtggtggct  1800
atcgccagca acggtggcgg caagcaagcg ctcgaaacgg tgcagcggct gttgccggtg  1860
ctgtgccagg accatggcct gaccccggac caagtggtgg ctatcgccag caacggtggc  1920
ggcaagcaag cgctcgaaac ggtgcagcgg ctgttgccgg tgctgtgcca ggaccatggc  1980
ctgactccgg accaagtggt ggctatcgcc agcaacgaagca agtggtggct  2040
acggtgcagc ggctgttgcc ggtgctgtgc caggaccatg gcctgacccc ggaccaagtg  2100
gtggctatcg ccagccacga tggcggcaag caagcgctcg aaacggtgca gcggctgttg  2160
ccggtgctgt gccaggacca tggcctgacc ccggaccaag tggtggctat cgccagcaac  2220
ggtggcggca agcaagcgct cgaaagcatt gtggcccagc tgacgcggcc tgatccggcg  2280
ttggccgcgt tgaccaacga ccacctggtc gctctggctt gcctgggagg acgccctg   2340
atggacgctg tgaagaaagg actgccccac gcacccgaac tgattagacg ggtgaaccgg  2400
agaatcggcg agagaacatc ccatagggtg gcaatctcta gaactcagct ggtcaagagt  2460
gaactggagg aaaagaaatc agagctgcgc acaagctga atacgtgcc tcatgagtat  2520
atcgaactga tcgagattgc tcgcaattca acccaggacc ggatcctgga aatgaaagtg  2580
atggagttct ttatgaaagt ctacggatat cgggggaaac acctgggagg gagcagaaag  2640
ccagatgggg ccatctacac agtgggatcc cccatcgact atggcgtgat tgtcgatact  2700
aaagcctaca gcggaggcta taacctgcct atcggccagg ctgacgagat gcagagatac  2760
gtggaggaaa accagacccg caataagcat attaacccca tgaatggtg gaaagtgtat  2820
cctagctccg tcacagagtt caagtttctg ttcgtgagcg gacactttaa gggcaactac  2880
aaagcacagc tgactaggct gaatcatatc accaactgca atggagccgt gctgtctgtc  2940
```

```
gaggaactgc tgatcggggg agagatgatt aaggctggca cactgactct ggaggaagtg  3000
aggcgcaagt tcaacaatgg ggaaatcaac ttctaa                            3036

SEQ ID NO: 3              moltype = DNA   length = 20
FEATURE                   Location/Qualifiers
misc_feature              1..20
                          note = Sequence of Full chemically modified guide #1
source                    1..20
                          mol_type = other DNA
                          organism = synthetic construct
SEQUENCE: 3
ggtatgttct gctgaaccgc                                              20

SEQ ID NO: 4              moltype = DNA   length = 9634
FEATURE                   Location/Qualifiers
misc_feature              1..9634
                          note = Sequence of Full chemically modified guide #1
source                    1..9634
                          mol_type = other DNA
                          organism = synthetic construct
SEQUENCE: 4
agcagaaggg gttctgaacc taggttcagg agagaggctt tgaacctgca cgtgtgggaa  60
gccatggaag tttccaggaa ggactgcagg tcccaactgg agatgtgccg ttcctccttc  120
aggtacctgg gaatgtcagt cacaccccag acctgctcag ctcccccaaa ctgctgttcc  180
tgtatctgag agcttcaagt ctccaaatgg cctacctcat acatggggaa actgaggcct  240
ggggaggccg gggactgagc tagcattcac ttgtggaaat agtctggcat catctggaga  300
agttagagac atgcaaaccc tacagccctc agattcccgt ctgagagtct gcatgcctat  360
gtggaccagg agatgtgtgc gggagtgaac actgcagtgt tgctcccaac agcaagaacc  420
agaagcagcc caaagggctg ttacaggaga atatggacac ccaggctgca catgcacacc  480
atggaatgct gtatggcagt ggaaataaat gaacagctac cactataggc aaacaggaat  540
cacagcaaca gccaagagtg aaggcgtgga gggacgagac catgcactca cacctggcct  600
gcctggctcg cactccgggc aaaggggtca gaacagtgac tggcacacac gttaagtgct  660
atgtgagtgt taagataaaa ctaggatgtc cagtggggag aaagcaagcc tttgaagatt  720
atgtgctttt acaaacttca agtgcaatga aaactaaaca agatgttgtt caggcattca  780
tatatgatat aaagttcctt tctttaaaaa agggatgggc tgggcacggt ggctcacgcc  840
tgtaattcta atactttggg aggccgaggc aggtggatca cgaggtcgag aaatcgagac  900
catcctggcc aacatggtga aaccctgtct ctactaaaaa tacaaaaaaa ttagctgggc  960
gtggtggcgt gtgcctgtag tcccagctac ttgggaggct gaggcaggag agtcacttga  1020
acccgggagg caaaggttgc agtgagccga gatcgtcca ccgcactcca gcctggcgac  1080
agagtgagac tccatctcaa aaaaaaaaag aaaaaaaaaa gtatgacaag cagaaagtaa  1140
tttgggagct gcggggaggc aagggtaagg gatggggaag tggaccagag gcatatgcgt  1200
cattggcagt gtctaagcac tcacgatagg cgtggatcac aggggctcgc tctgtaatta  1260
aaaggaaaag ggttttttgtt gtgttgttgt tgttgctgtt tttgagacaa gggtcttgct  1320
ctgtcatcat ccaggctgga gtgcagtggt gcagtctcag ctcactgcaa cctccgcctc  1380
ctgggttcaa gcgattctcc tgcctcagcc tcctgagcag ctaggactac aggtgtgtgc  1440
caccatgcct ggctaatttt tgtatttttt agtggaaatg gggtttttgcc atgttgccca  1500
ggctcgtctt gaactcctga cctcaagtga tccactcgtc tcggcctccc aaagtgctgg  1560
gattacaggt gtgagctatt gtccccagcc aaaaggaaaa gttttactgt agtaaccctt  1620
ccggactagg gacctcgggc ctcagcctca ggctacctag gtgctttaga aaggaggcca  1680
cccaggccca tgactactcc ttgccacagg gagccctgca cacagatgtg ctaagctctc  1740
gctgccagcc agaggggagga gggtctgagc cagtcagaag gagatgggcc ccagagacta  1800
agaaaggggg aggaggaccc aagctgatcc aaaaggtggg tctaagcagt caagtggagg  1860
agggttccaa tctgatggcg gagggcccaa gctcagccta acgaggaggc caggcccacc  1920
aagggggcccc tggaggactt gtttcccttg tccttgtgg ttttttgcat ttcctgttcc  1980
cttgctgctc attgcggaag ttcctcttct taccctgcca ccagacctc gccagagaag  2040
acaagggcag aaagcaccat gagtggggge ccaatgggag gaaggcccgg gggccgagga  2100
gcaccagcgg ttcagcagaa cataccctcc accctcctcc aggaccacga gaaccagcga  2160
ctctttgaga tgcttggacg aaaatgcttg gtgagctggg gatctcctgc ccccgcccccg  2220
tccccaccgt ttcttcctct tcctctcctc cttctctctc ttcccctcct cccgctcctc  2280
ctttccctct ccatcatctc ctctcctaga atttcccgtc ataatccacc cttcccagga  2340
agatctcaat gtctacttgc cttccctctg gctgcagctc ttccttttggg cccatgactg  2400
tcatgaggca ggaaggacca ggtctggctc caagaccttg tggctacccc tgaccagact  2460
ccactgaccc ctgctttcct ctcccagacg ctggccactg cagttgttca gctgtacctg  2520
gcgctgcccc ctggagctga gcactggacc aaggagcatt gtgggggctgt gtgcttgtgga  2580
aaggataacc cccagaagtc ctacttcatc cgcctttacg gccttcaggt gacccccca  2640
cccccgactg gacttgcaag ccagttctca acccgcaaac ccagatctgt gtccatatgt  2700
gtccatagct tcaagacctc agacctgatc agtgaatccc tgagcccag aaccaaagac  2760
tcatccagat ggcaaactct gacttgcctt tctaagtctg caatgactgg ccccagtctc  2820
cgtatcaaga tctctaaagc ccccagtatt agtctgctgc ctaagcctaa tctttttccac  2880
aaattccaat aaatgagcac tgtatttgta cctgaacctc aaatctattc taaactcaac  2940
attttcgatc ccaggaatct ctcatcaaaa ctcctgaacc ccagatgttt gccaagctcc  3000
taagtcataa atctcgttcaa caaacccaa agttgaatat tccattgatc cttgaactcc  3060
aaatctgtcc ttctaaatcc acagcacaga ccccagagtt cccatattaa aattcctgaa  3120
cactcaaata ccgaggtagt tcttaagcaa aaagtcttt ccaccaatcc ctgacctgaa  3180
ctttctaggt ttaagcccca aattcatcct tttaaaccca taaagatgga cccagcataa  3240
cttccagatc ccaaggctat caaatatcca ccaaactcct aaaccataac tctctccaca  3300
aacccccaaat tgcacttact ttagctggac tccccgcgaa actcccaagt ctatgtgtct  3360
gaacttcaaa tctcaactcc aacccccaaa tactagaatc ctacctgtca tgaattgggg  3420
ctggggtggt ggggaggggc atggattgaa tctgtgaatg agcctcaact tcctaagact  3480
```

```
agagtcctaa attatgaaat tcaagccccc aagtcccaga tctagggccc caaaccccaa  3540
atccaaacct ctcacaaaag tgtatggctc ccagactata ccccacaatc cacaccctta  3600
gacaccaact ctctggtgct gagctgaaaa tctccaaacc agactatgag gctcccaaat  3660
ccagacaccc tgctccctgc ccagctaaca aaagcctgcc accccggcg tgcctcagtg  3720
ccactgtgcc tcccacccta cacctctcca ggctggtcgg ctgctctggg aacaggagct  3780
gtactcacag cttgtctact ccacccccac ccccttcttc cacaccttcg ctggagatgt  3840
aagtgatcaa ccagccctcg ggcctcactt ggggtgtgga gaggagatgg gaaagttgcg  3900
ggggacctgg gaggcggctg accccaaggt atgtgcagga ctgccaagcg gggctgaact  3960
ttgcagacga ggacgaggcc caggccttcc gggccctcgt gcaggagaag atacaaaaaa  4020
ggaatcagag gcaaagtgga ggtgaggagg ccacagggga ggaaaggaag ttgggcagag  4080
gtgagtgcaa gcctggggaa ctagaaaagt cccctctcat ggtcctggct cccaatccat  4140
ctatccacag acagacgcca gctacccca ccaccaacac cagccaatga aggtgagtcc  4200
tctagtgcaa gtaggggtaa taaggggcta gcccaggaac ctgtggcagg gctgtgataa  4260
ctctctacac attccatctt cccagagaga agaggagggc tcccacccct gcccctgcat  4320
ccaggtggag accaaggagg tgcgtgctga ttcttccctg tgtctctgga tggatgggta  4380
agagtggatg gaggaatgag gagttggatg ggtgcgtaag tgggtgaatg gataggtaga  4440
ttgataggta tgtggatgga cgagcaggtg catggatgtg tggactgatg gatgggtgga  4500
tggattggcg gtagatggct gagtagaggg atgaattgat ggaggatgga agtctaagt  4560
agatagatgc ataggtgaat gggtatgtgg ataaatgaat gaaaaggtag atggatgact  4620
gagtaaatta atcaatgagt gaatgaatga acagtgaata aatgactaaa tgacaagttt  4680
cagtcagtga agaaagcatg attgaatgaa taaatgagta aatgaatatt ttaacaaatt  4740
cattagtcaa tgagccagtg aatgataaag catgagggaa tgaaaacatg aatgaatcag  4800
tgaatgtatg aatggtttgt gggatccacc cacttctcca tagaccctac ttgaaccctt  4860
cacccactac ctccatgacc atccaacaca cacacagatt tccctcaagg cttccgtttc  4920
ttgcccctgt gctttggttg gttggtaagt gggtcaatga gccaaccacc ctattttccc  4980
cacaggccct ccagtgggtc cgctctccct ggggctggcg acagtggaca tccagaaccc  5040
tgacatcacg agttcacgat accgtgggct cccagcacct ggacctagcc cagctgataa  5100
gaaacgctca gggaagaaga agatcagcaa agctgatatt ggtgcaccca gtggattcaa  5160
gtgagagcca ctccccagtg gacccacaga ttcctggggg cagaggggca catgaacaag  5220
tggacagctg agtgaatgga aggatgggca gatgggcaga tggctgggtg gctgagtggg  5280
taaatgggtg gttggatagg taggtgcagg gctgggtcta gggagaggta aataaggcac  5340
caagggtaca aaatttaagg aggcactcac tctcagaggc atgcaactgt aattcctgac  5400
tctcagagtg agtgactcac ttaaattttg caccctaggc accttacttg cctcaccctg  5460
ggcccactct gggtgggctg ttaggagagc aggtgggtgg gcaggtgaac aaatggatag  5520
atagatgagg tagatgatgg atgagaaggg ctggtgggta ggtgggtgag tggatgggtg  5580
gatggatgga taaatgaatg gatgaatgaa tgggttgaag aatgaatgga taagtggttg  5640
gatggacaag tttatgggtg gatgggttga tgggaggtgc gtggatagat agatgggtga  5700
gtggataggt gtgtggacag attgatatgc aggctgattg gctcacagac aaggtggatg  5760
gggatggaca ggtggacaga tacgtggatg aatggacagt tcaatggata agtgaacaga  5820
agtgtgtggt tgcatgggta gaaaaatgag tggatggata gatggaaagg tgggcacatg  5880
ggtaggtgga tgggtggatg gacaagtgtg tgtgaggaca gactggtgga caaatgggtg  5940
aacagacata tgtgggcaga tagttgcaga gacagatgta tggacagatc agtagtccaa  6000
cagatgaatg tgaatgaata ggtggacaaa tgcatgggat agatggggaa agagggatgg  6060
gtggatggat cagcaccaca aactatggag cccttctaat tccataactc ctgcctatac  6120
tcattcactc attcagtctc attcattaat tctggcccct cagagtctct ttgggcagga  6180
gagggcaaga gggtttcact atgaaggag ggaaggaagg gcagtgagga ttcactggag  6240
tctcttcacc tctcccaggc atgtcagcca cgtggggtgg gacccccaga atggatttga  6300
cgtgagtaac ttcagagtct cttggactcc actaaacttc cacccaccct tccaaagacc  6360
actgctgaga ccccacccc agatcgtgcc cttcccacac ccctctcaga tcccttgctg  6420
ggatggaccc aacgacaatc catgtcgctt gtctcctcgc cttattcctc tactcctgcc  6480
cctggccttt ttcctcctgg gcaggtgaac aacctcgacc cagatctgcg gagtctgttc  6540
tccagggcag gaatcagcga ggcccagctc accgacgccg agacctctaa acttatctac  6600
gacttcattg aggaccaggg tgggctggag gctgtgcggc aggagatgag gcgccagggt  6660
gagaccctgc ttccatacgc tcccttctct agcccaagca gctcatagct aagatacgca  6720
ctaagtcact cagtccttat gggagcacct atactgcttc agtcaggagt tggtcagtgg  6780
gggtacccat tttacaaatg agcaaaactg aggctcagaa gaaatcaatg agagttacag  6840
ctatgtgtta tacccctcc acagagccac ttccgccgcc cccaccgcca tctcgaggag  6900
ggaaccagct cccccggccc cctattgtgg ggggtaacaa gggtcgttct ggtccactgc  6960
ccctgtacc tttggggatt gccccaccc caccaacacc ccgggacc ccaccccag  7020
gccgaggggg ccctccacca ccaccccctc cagctactgg acgttctgga ccactgcccc  7080
ctccaccccc tggagctggt gggccaccca tgccaccacc accgccacca ccgccaccgc  7140
cgcccagctc cgggaatgga ccagcccctc cccactccc tcctgctctg tgcctgccg  7200
ggggcctggc ccctggtggg ggtcggggag cgcttttgga tcaaatccgg cagggaattc  7260
agctgaacaa ggtgaggaca ggcaggatgg aggattgggg gtctaggact ctggggtgtc  7320
ccgtctaagt caggatactg ggggggctgag gccaggactg aggagagtgc caggccttag  7380
ggattcagta atagggttga aaggttggtg ggaagccttg aaggggactg gagtgtgtgg  7440
gagagaaaat attgatggag gggcggggag aaatgctcct ttcccaggcc ctaagccctc  7500
tgtgctgatc cctgcctgct gcagaccct ggggcccag agagctcagc gctgcagcca  7560
ccacctcaga gctcagaggg actggtgggg gcctgatgc acgtgatgca gaagagaagc  7620
agagccatcc actcctccgg tgagctgatc ctgccggggc ctcaaacctg gctcccaggg  7680
ctagcactgg cctcaaaaca atcccagcag tcaccaccaa tagtgacatc agccccatct  7740
gtttgacagc attaacatga atcttgtgtc agcctcgttt ttgacaatgt taacattaag  7800
tcattatgtg acaataatat aattaactcc aactttgaca gtaatattaa cattaatgcc  7860
agggtgtgtc cacaatatta atgtcattcc cacatgttca gtactactaa catcagctgg  7920
ccgggcgcg tggctcatgc ctgtaatcca ggaactttgg gaggctaagg caggaggatc  7980
acttgagccc aggagttcga gaccagcctg ggcaatatag tgagacctcg tttccataaa  8040
aactaaattc aaaaaaagta gtcaagcata gtggtgtgtg cctgtggtcc cagctacttg  8100
ggaggctgag gtgggaggat tgcttgaccc tgggaggtca aggcagcagt gatccatgat  8160
tgtgccactg cactccagcc tgggtgacag agatcctatc tcaaaaaaaa aaaaaattaa  8220
```

-continued

```
cccattatgt gatgacaata ttatgaagaa cactattgtt gacaatatta attttaattc   8280
catgtattaa cagatttaca ttaattcatt atgacgtaac ctaatctaat cttttaaaaa   8340
attttttttga aacagggtct cgctctgtgt cccaggctgg agtacagtgg tgcaatcatg   8400
gctcagtgca gcctcaacct cccaggctca agcgatcctc ccgcctcagc tcccaaagta   8460
gctgggacta caggcgtgtg ccaccatacc tggctaattt ttggtgtttt tttggtagtg   8520
atgagctctc actaccaagc tctcactact ctcatgttgc ccaggctgct ctgcaactcc   8580
agggctcaag cgatctgccc cgcctcagcc tcccagagtg ctgggattac aggcatgagc   8640
caccaggcct ggctgttaac ctaatctttt tataataatg ttactattac tctcttaatc   8700
tgtcagcaat actgtcacta atccattata tgatgcaaat attagtatca acctactata   8760
ggaacttcat ctttcgacaa tgatttttttt ttttcttttttg agacggagtc ttgctctgtc   8820
acccaggctg gagtgcagtg gcgcgatctt ggctaactgc agactctgcc tcctgggttc   8880
aagcgattct cctgcctcag ccttccgagt agctgggact acaggcacgc cactacgccc   8940
agctaatttt gatgttattg tcattaaccc cattatgtgt caaaaatatt agcgttaacc   9000
agacaggaag caataatata ttatcacacc tttgctaata ttatttaaat tcaccctatt   9060
atgtgataaa taggttaaca ttaacccttt gtttgacaat atctcgacta accacatttt   9120
tgacagcata aacttcaact ccaactagaa ctcagacccc aactataatc cctttcttgt   9180
cccaaatgga aactctaact tgccctcctc tagcatgaga cctcagaacc ccagggtcca   9240
gtcctcacct cccaggccct atgaagcccc ccaccaacct ccagggcat cttatctttc   9300
tctttccctc cagacgaagg ggaggaccag gctggcgatg aagatgaaga tgatgaatgg   9360
gatgactgag tggctgagtt acttgctgcc ctgtgctcct ccccgcagga catggctccc   9420
cctccacctg ctctgtgccc accctccact ctcctcttcc aggcccccaa cccccatctt   9480
cttccccacc aaccctcca atgctgttat ccctgcctgg tcctcacact cacccaacaa   9540
tcccaaggcc cttttttatac aaaaattctc agttctcttc actcaaggat ttttaaagaa   9600
aaataaaaga attgtctttc tgtctctcta taaa                               9634
```

```
SEQ ID NO: 5            moltype = DNA    length = 7264
FEATURE                 Location/Qualifiers
misc_feature            1..7264
                        note = Sequence of Full chemically modified guide #1
source                  1..7264
                        mol_type = other DNA
                        organism = synthetic construct
SEQUENCE: 5
cagctgcgcg ctcgctcgct cactgaggcc gccgggcaa agcccgggcg tcgggcgacc    60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggcctctg cataaataaa aaaaattagt cagccatgag cttggacgcg    240
tgtatgacaa gcagaaagta atttgggagc tgcggggagg caagggtaag ggatggggaa    300
gtggaccaga ggcatatgcg tcattggcag tgtctaagca ctcacgatag gcgtggatca    360
caggggctcg ctctgtaatt aaaaggaaaa gggtttttgt tgtgttgttg ttgttgctgt    420
ttttgagaca agggtcttgc tctgtcatca tccaggctgg agtgcagtgg tgcagtctca    480
gctcactgca acctccgcct cctgggttca agcgattctc ctgcctcagc ctcctgagca    540
gctaggacta caggtgtgtg ccaccatgcc tggctaattt ttgtattttt tagtggaaat    600
ggggttttgc catgttgccc aggctcgtct tgaactcctg acctcaagtg atccactcgt    660
ctcggcctcc caaagtgctg ggattacagg tgtgagctat tgtccccagc caaaaggaaa    720
agttttactg tagtaaccct tccggactag ggacctcggg cctcagcctc aggctaccta    780
ggtgctttag aaaggaggcc acccaggccc atgactactc cttgccacag ggagccctgc    840
acacagatgt gctaagctct cgctgccagc cagaggggagg agggtctgag ccagtcagaa    900
ggagatgggc cccagagagt aagaaagggg gaggaggacc caagctgatc caaaaggtgg    960
gtctaagcag tcaagtggag gagggttcca atctgatggc ggagggccca agctcagcct    1020
aacgaggagg ccaggcccac caaggggccc ctggaggact tgtttccctt gtcccttgca    1080
gtttttttgca tttcctgttc ccttgctgct cattgcggaa gttcctcttc ttaccctgca    1140
cccagagcct cgccagagaa gacaagggca gaaagcacca tgagtggggg cccaatggga    1200
ggaaggcccg ggggccgagg agcacgaaca gagaaacagg agaatatggg ccaaacagga    1260
tatctgtggt aagcagttcc tgccccggct cagggccaag aacagttgga acagcagaat    1320
atgggccaaa caggatatct gtggtaagca gttcctgccc cggctcaggg ccaagaacag    1380
atggtccccca gatgcggtcc cgccctcagc agtttctaga gaaccatcag atgtttccag    1440
ggtgccccaa ggacctgaaa tgaccctgtg ccttatttga actaaccaat cagttcgctt    1500
ctcgcttctg ttcgcgcgct tctgctcccc gagctctata taagcagagc tcgtttagtg    1560
aaccgtcaga tcgcctggag acgccatcca cgctgttttg acttccatag aaggatctgc    1620
aggccaccat ggtgagcaag ggcgaggagc tgttcaccgg ggtggtgccc atcctggtcg    1680
agctggacgg cgacgtaaac ggccacaagt tcagcgtgtc cggcgagggc gagggcgatg    1740
ccacctacgg caagctgacc ctgaagttca tctgcaccac cggcaagctg cccgtgccct    1800
ggcccaccct cgtgaccacc ctgacctacg gcgtgcagtg cttcagccgc taccccgacc    1860
acatgaagca gcacgacttc ttcaagtccg ccatgcccga aggctacgtc caggagcgca    1920
ccatcttctt caaggacgac ggcaactaca agacccgcgc cgaggtgaag ttcgagggcg    1980
acaccctggt gaaccgcatc gagctgaagg gcatcgactt caaggaggac ggcaacatcc    2040
tggggcacaa gctggagtac aactacaaca gccacaacgt ctatatcatg gccgacaagc    2100
agaagaacgg catcaaggtg aacttcaaga tccgccacaa catcgaggac ggcagcgtgc    2160
agctcgccga ccactaccag cagaacaccc ccatccgcga cggccccgtg ctgctgcccg    2220
acaaccacta cctgagcacc cagtccgccc tgagcaaaga ccccaacgag aagcgcgatc    2280
acatggtcct gctggagttc gtgaccgccg ccgggatcac tctcggcatg gacgagctgt    2340
acaagtaaac tagtgtcgac tgctttattt gtgaaatttg tgatgctatt gctttatttg    2400
taaccattat aagctgcaat aaacaagtta acaacaacaa ttgcattcat tttatgtttc    2460
aggttcaggg ggaggtgtgg gaggtttttt aaaacagcggt tcagcagaac ataccctcca    2520
ccctcctcca ggaccacgag aaccagcgac tctttgagat gcttggacga aaatgcttgg    2580
tgagctgggg atcctctgcc cccgcccgt cccaccgtt tcttcctctt cctcctcc       2640
ttctctctct tcccctcctc ccgctcctcc tttccctctc catcatctcc tctcctagaa    2700
tttcccgtca taatccaccc ttcccaggaa gatctcaatg tctacttgcc ttccctctgg    2760
```

-continued

```
ctgcagctct tcctttgggc ccatgactgt catgaggcag gaaggaccag gtctggctcc    2820
aagaccttgt ggctacccct gaccagactc cactgacccc tgctttcctc tcccagacgc    2880
tggccactgc agttgttcag ctgtacctgg cgctgccccc tggagctgag cactggacca    2940
aggagcattg tggggctgtg tgcttcgtga aggataaccc ccagaagtcc tacttcatcc    3000
gcctttacgg ccttcaggtg accccccac ccccgactgg acttgcaagc cagttctcaa    3060
cccgcaaacc cagatctgtg tccatatgtg tccatagctt caagacctca gacctgatca    3120
gtgaatccct gagccccaga accaaagact catccagatg gcaaactctg acttgccttt    3180
ctaagtctgc aatgactggc cccagtctcc gtatcaagat ctctaaagcc cccagtatta    3240
gtctgctgcc taagcctaat cttttccaca aattccaata aatgagcact gtatttgtac    3300
ctgaacctca aatctattct aaactcaaca ttttgcatcc caggaatctc tcatcaaaac    3360
tcctgaaccc cagatgtttg ccaagctcct aagtcataaa tctgttcaac aaaccccaaa    3420
gttgaatatt ccattgatcc ttgaactcca aatctgtcct tctaaatcca cagcacagac    3480
cccagagttc ccatctagag catggctacg tagataagta gcatggcggg ttaatcatta    3540
actacaagga acccctagtg atggagttgg ccactccctc tctgcgcgct cgctcgctca    3600
ctgaggccgg gcgaccaaag gtcgcccgac gcccgggctt tgcccgggcg gcctcagtga    3660
gcgagcgagc gcgccagctg gcgtaatagc gaagaggccc gcaccgatcg cccttcccaa    3720
cagttgcgca gcctgaatgg cgaatggcga ttccgttgca atggctggcg gtaatattgt    3780
tctggatatt accagcaagg ccgatagttt gagttcttct actcaggcaa gtgatgttat    3840
tactaatcaa agaagtattg cgacaacggt taatttgcgt gatggacaga ctcttttact    3900
cggtggcctc actgattata aaaacacttc tcaggattct ggcgtaccgt tcctgtctaa    3960
aatcccttta atcggcctcc tgtttagctc ccgctctgat tctaacgagg aaagcacgtt    4020
atacgtgctc gtcaaagcaa ccatagtacg cgccctgtag cggcgcatta agcgcggcgg    4080
gtgtggtggt tacgcgcagc gtgaccgcta cacttgccag cgccctagcg cccgctcctt    4140
tcgctttctt cccttccttt ctcgccacgt tcgccggctt tccccgtcaa gctctaaatc    4200
gggggctccc tttagggttc cgatttagtg ctttacggca cctcgacccc aaaaaacttg    4260
attagggtga tggttcacgt agtgggccat cgccctgata gacggttttt cgccctttga    4320
cgttggagtc cacgttcttt aatagtggac tcttgttcca aactggaaca acactcaacc    4380
ctatctcggt ctattctttt gatttataag ggattttgcc gatttcggcc tattggttaa    4440
aaaatgagct gatttaacaa aaatttaacg cgaattttaa caaaatatta acgtttacaa    4500
tttaaatatt tgcttataca atcttcctgt ttttggggga tttctgatta tcaaccggggc    4560
tacatatgat tgacatgcta gttttacgat taccgttcat cgattctctt gtttgctcca    4620
gactctcagg caatgacctg atagcctttg tagagacctc tcaaaaatag ctaccctctc    4680
cggcatgaat ttatcagcta gaacggttga atatcatatt gatggtgatt tgactgtctc    4740
cggcctttct cacccgtttg aatctttacc tacacattac tcaggcattg catttaaaat    4800
atatgagggt tctaaaaatt tttatccttg cgttgaaata aaggcttctc ccgcaaaagt    4860
attacagggt cataatgttt ttggtacaac cgatttagct ttatgctctg aggctttatt    4920
gcttaatttt gctaattctt tgccttgcct gtatgattta ttggatgttg gaatcgcctg    4980
atgcggtatt ttctccttac gcatctgtgc ggtatttcac accgcatatg gtgcactctc    5040
agtacaatct gctctgatgc cgcatagtta agccagcccc gacacccgcc aacacccgct    5100
gacgcgccct gacgggcttg tctgctcccg gcatccgctt acagacaagc tgtgaccgtc    5160
tccgggagct gcatgtgtca gaggttttca ccgtcatcac cgaaacgcgc gagacgaaag    5220
ggcctcgtga tacgcctatt tttataggtt aatgtcatga taataatggt ttcttagacg    5280
tcaggtggca ctttttgggg aatgtgcgc ggaaccccta tttgtttatt tttctaaata    5340
cattcaaata tgtatccgct catgagacaa taaccctgat aaatgcttca ataatattga    5400
aaaaggaaga gtatgagtat tcaacatttc cgtgtcgccc ttattccctt ttttgcggca    5460
ttttgccttc ctgtttttgc tcacccagaa acgctggtga agtaaaaga tgctgaagat    5520
cagttgggtg cacgagtggg ttacatcgaa ctggatctca acagcggtaa gatccttgag    5580
agttttcgcc ccgaagaacg ttttccaatg atgagcactt ttaaagttct gctatgtggc    5640
gcggtattat cccgtattga cgccgggcaa gagcaactcg gtcgccgcat acactattct    5700
cagaatgact tggttgagta ctcaccagtc acagaaaagc atcttacgga tggcatgaca    5760
gtaagagaat tatgcagtgc tgccataacc atgagtgata acactgcggc caacttactt    5820
ctgacaacga tcggaggacc gaaggagcta accgcttttt tgcacaacat ggggggatcat    5880
gtaactcgcc ttgatcgttg ggaaccggag ctgaatgaag ccataccaaa cgacgagcgt    5940
gacaccacga tgcctgtagc aatggcaaca cgttgcgca aactattaac tggcgaacta    6000
cttactctag cttcccggca acaattaata gactggatgg aggcggataa agttgcagga    6060
ccacttctgc gctcggccct tccggctggc tggtttattg ctgataaatc tggagccggt    6120
gagcgtgggt ctcgcggtat cattgcagca ctggggccag atggtaagcc ctcccgtatc    6180
gtagttatct acacgacggg gagtcaggca actatggatg aacgaaatag acagatcgct    6240
gagataggtg cctcactgat taagcattgg taactgtcag accaagttta ctcatatata    6300
ctttagattg atttaaaact tcatttttaa tttaaaagga tctaggtgaa gatcctttt    6360
gataatctca tgaccaaaat cccttaacgt gagttttcgt tccactgagc gtcagacccc    6420
gtagaaaaga tcaaaggatc ttcttgagat cctttttttc tgcgcgtaat ctgctgcttg    6480
caaacaaaaa aaccaccgct accagcggtg gtttgtttgc cggatcaaga gctaccaact    6540
cttttccga aggtaactgg cttcagcaga gcgcagatac caaatactgt ccttctagtg    6600
tagccgtagt taggccacca cttcaagaac tctgtagcac cgcctacata cctcgctctg    6660
ctaatcctgt taccagtggc tgctgccagt ggcgataagt cgtgtcttac cgggttggac    6720
tcaagacgat agttaccgga taaggcgcag cggtcgggct gaacggggg ttcgtgcaca    6780
cagcccagct tggagcgaac gacctacacc gaactgagat acctacagcg tgagctatga    6840
gaaagcgcca cgcttcccga agggagaaag gcggacaggt atccggtaag cggcagggtc    6900
ggaacaggag agcgcacgag ggagcttcca gggggaaacg cctggtatct ttatagtcct    6960
gtcgggtttc gccacctctg acttgagcgt cgatttttgt gatgctcgtc aggggggcgg    7020
agcctatgga aaaacgccag caacgcggcc ttttttacggt tcctggcctt ttgctggcct    7080
tttgctcaca tgttctttcc tgcgttatcc cctgattctg tggataaccg tattaccgcc    7140
tttgagtgag ctgataccgc tcgccgcagc cgaacgaccg agcgcagcga gtcagtgagc    7200
gaggaagcgg aagagcgccc aatacgcaaa ccgcctctcc ccgcgcgttg ccgattcatt    7260
aatg                                                                7264
```

SEQ ID NO: 6          moltype = DNA  length = 7265
FEATURE               Location/Qualifiers

```
misc_feature        1..7265
                    note = Sequence of Full chemically modified guide #1
source              1..7265
                    mol_type = other DNA
                    organism = synthetic construct
SEQUENCE: 6
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc  120
actaggggtt ccttgtagtt aatgattaac ccgccatgct acttatctac gtagccatgc  180
tctagcggcc tcggcctctg cataaataaa aaaaattagt cagccatgag cttggacgcg  240
tgtatgacaa gcagaaagta atttgggagc tgcggggagg caagggtaag ggatggggaa  300
gtggaccaga ggcatatgcg tcattggcag tgtctaagca ctcacgatag gcgtggatca  360
caggggctcg ctctgtaatt aaaaggaaaa gggtttttgt tgtgttgttg ttgttgctgt  420
ttttgagaca agggtcttgc tctgtcatca tccaggctgg agtgcagtgg tgcagtctca  480
gctcactgca acctccgcct cctgggttca agcgattctc ctgcctcagc ctcctgagca  540
gctaggacta caggtgtgtg ccaccatgcc tggctaattt ttgtattttt tagtggaaat  600
ggggttttgc catgttgccc aggctcgtct tgaactcctg acctcaagtg atccactcgt  660
ctcggcctcc caaagtgctg ggattacagg tgtgagctat tgtccccagc caaaaggaaa  720
agttttactg tagtaaccct tccggactag ggacctcggg cctcagcctc aggctaccta  780
ggtgctttag aaaggaggcc acccaggccc atgactactc cttgccacag ggagccctgc  840
acacagatgt gctaagctct cgctgccagc cagagggagg agggtctgag ccagtcagaa  900
ggagatgggc cccagagagt aagaaagggg gaggaggacc caagctgatc caaaaggtgg  960
gtctaagcag tcaagtggag gagggttcca atctgatggc ggagggccca agctcagcct  1020
aacgaggagg ccaggcccac caaggggccc ctggaggact tgtttccctt gtcccttgtg  1080
gtttttttgca tttcctgttc ccttgctgct cattgcggaa gttcctcttc ttaccctgca  1140
cccagagcct cgccagagaa gacaaagggca gaaagcacca tgagtgggggg cccaatggga  1200
ggaaggcccg ggggccgagg agcacgaaca gagaaacagg agaatatggg ccaaacagga  1260
tatctgtggt aagcagttcc tgccccggct cagggcaag aacagttgga acagcagaat  1320
atgggccaaa caggatatct gtggtaagca gttcctgccc cggctcaggg ccaagaacag  1380
atggtcccca gatgcggtcc cgccctcagc agtttctaga gaaccatcag atgtttccag  1440
ggtgccccaa ggacctgaaa tgaccctgtg ccttatttga actaaccaat cagttcgctt  1500
ctcgcttctg ttcgcgcgct tctgctcccc gagctctata taagcagagc tcgtttagtg  1560
aaccgtcaga tcgcctggag acgccatcca cgctgttttg acttccatag aaggatctcg  1620
aggccaccat ggtgagcaag ggcgaggagc tgttcaccgg ggtggtgccc atcctggtcg  1680
agctggacgg cgacgtaaac ggccacaagt tcagcgtgtc cggcgaggc gagggcgatg  1740
ccacctacgg caagctgacc ctgaagttca tctgcaccac cggcaagctg cccgtgccct  1800
ggcccaccct cgtgaccacc ctgacctacg gcgtgcagtg cttcagccgc taccccgacc  1860
acatgaagca gcacgacttc ttcaagtccg ccatgcccga aggctacgtc caggagcgca  1920
ccatcttctt caaggacgac ggcaactaca agacccgcgc cgaggtgaag ttcgagggcg  1980
acaccctggt gaaccgcatc gagctgaagg gcatcgactt caaggaggac ggcaacatcc  2040
tggggcacaa gctggagtac aactacaaca gccacaacgt ctatatcatg gccgacaagc  2100
agaagaacgg catcaaggtg aacttcaaga tccgccacaa catcgaggac ggcagcgtgc  2160
agctcgccga ccactaccag cagaacaccc ccatcggcga cggccccgtg ctgctgcccg  2220
acaaccacta cctgagcacc cagtccgccc tgagcaaaga ccccaacgag aagcgcgatc  2280
acatggtcct gctggagttc gtgaccgccg ccgggatcac tctcggcatg gacgagctgt  2340
acaagtaaac tagtgtcgac tgctttattt gtgaaatttg tgatgctatt gctttatttg  2400
taaccattat aagctgcaat aaacaagtta caaacaacaa ttgcattcat tttatgtttc  2460
aggttcaggg ggaggtgtgg gaggtttttt aaacagcggt tcagcagaac ataccctcca  2520
ccctcctcca ggaccacgag aaccagcgac tctttgagat gcttggacga aaatgcttgg  2580
tgagctgggg atctcctgcc cccgcccgt ccccaccgtt tcttcctctt cctctcctcc  2640
ttctctctct tcccctcctc ccgctcctcc tttccctcc catcatctcc actcctagaa  2700
tttcccgtca taatccaccc ttcccaggaa gatctcaatg tcttcttgcc ttccctctgg  2760
ctgcagctct tcctttgggc ccatgactgt catgaggcag gaaggaccag gtctggctcc  2820
aagaccttgt ggctacccct gaccagactc cactgacccc tgctttcctc tcccagacgc  2880
tggccactgc agttgttcag ctgtacctgg cgctgccccc tggagctgag cactggacca  2940
aggagcattg tggggctgtg tgcttcgtga aggataaccc ccagaagtcc tacttcatcc  3000
gcctttacgg ccttcaggtg acccccccac ccccgactgg acttgcaagc cagttctcaa  3060
cccgcaaacc cagatctgtg tccatatgtg tccatagctt caagacctca gacctgatca  3120
gtgaatccct gagccccaga accaaagact catccagatg gcaaactctg acttgccttt  3180
ctaagtctgc aatgactggc cccagtctcc gtatcaagat ctctaaagcc cccagtatta  3240
gtctgctgcc taagcctaat cttttccaca aattccaata aatgagcact gtatttgtac  3300
ctgaacctca aatctattct aaactcaaca ttttgcatcc caggaatctc tcatcaaaac  3360
tcctgaaccc cagatgtttg ccaagctcct aagtcataaa tctgttcaac aaaccccaaa  3420
gttgaatatt ccattgatcc ttgaactcca aatctgtcct tctaaatcca cagcacagac  3480
cccagagttc ccatctagag catggctacg tagataagta gcatggcggg ttaatcatta  3540
actacaagga acccctagtg atggagttgg ccactccctc tctgcgcgct cgctcgctca  3600
ctgaggccgg gcgaccaaag gtcgcccgac gcccgggctt tgcccgggcg gcctcagtga  3660
gcgagcgagc gcgccagctg gcgtaatagc gaagaggccc gcaccgatcg cccttcccaa  3720
cagttgcgca gcctgaatgg cgaatgggcga ttccgttgca atggctggcg gtaatattgt  3780
tctggatatt accagcaagg ccgatagttt gagttcttct actcaggcaa gtgatgttat  3840
tactaatcaa agaagtattg cgacaacggt taatttgcgt gatggacaga ctcttttact  3900
cggtggcctc actgattata aaaacacttc tcaggattct ggcgtaccgt tcctgtctaa  3960
aatcccttta atcggcctcc tgtttagctc ccgctctgat tctaacgagg aaagcacgtt  4020
atacgtgctc gtcaaagcaa ccatagtacg cgccctgtag cggcgcatta agcgcggcgg  4080
gtgtggtggt tacgcgcagc gtgaccgcta cacttgccag cgccctagcg cccgctcctt  4140
tcgctttctt cccttccttt ctcgccacgt tcgccggctt tccccgtcaa gctctaaatc  4200
gggggctccc tttagggttc cgatttagtg ctttacggca cctcgacccc aaaaaacttg  4260
attagggtga tggttcacgt agtgggccat cgccctgata gacggttttt cgccctttga  4320
cgttggagtc cacgttcttt aatagtggac tcttgttcca aactggaaca acactcaacc  4380
```

-continued

```
ctatctcggt ctattctttt gatttataag ggattttgcc gatttcggcc tattggttaa  4440
aaaatgagct gatttaacaa aaatttaacg cgaattttaa caaaatatta acgtttacaa  4500
tttaaatatt tgcttataca atcttcctgt ttttggggct tttctgatta tcaaccgggg  4560
tacatatgat tgacatgcta gttttacgat taccgttcat cgattctctt gtttgctcca  4620
gactctcagg caatgacctg atagcctttg tagagacctc tcaaaaatag ctaccctctg  4680
cggcatgaat ttatcagcta gaacggttga atatcatatt gatggtgatt tgactgtctc  4740
cggcctttct cacccgtttg aatctttacc tacacattac tcaggcattg catttaaaat  4800
atatgagggt tctaaaaatt tttatccttg cgttgaaata aaggcttctc ccgcaaaagt  4860
attacagggt cataatgttt ttggtacaac cgatttagct ttatgctctg aggctttatt  4920
gcttaatttt gctaattctt tgccttgcct gtatgattta ttggatgttg gaatcgcctg  4980
atgcggtatt ttctccttac gcatctgtgc ggtatttcac accgcatatg gtgcactctc  5040
agtacaatct gctctgatgc cgcatagtta agccagcccc gacacccgcc aacacccgct  5100
gacgcgccct gacgggcttg tctgctcccg gcatccgctt acagacaagc tgtgaccgtc  5160
tccgggagct gcatgtgtca gaggttttca ccgtcatcac cgaaacgcgc gagacgaaag  5220
ggcctcgtga tacgcctatt tttataggtt aatgtcatga taataatggt ttcttagacg  5280
tcaggtggca cttttcgggg aaatgtgcgc ggaaccccta tttgtttatt tttctaaata  5340
cattcaaata tgtatccgct catgagacaa taaccctgat aaatgcttca ataatattga  5400
aaaaggaaga gtatgagtat tcaacatttc cgtgtcgccc ttattccctt ttttgcggca  5460
ttttgccttc ctgtttttgc tcacccagaa acgctggtga aagtaaaaga tgctgaagat  5520
cagttgggtg cacgagtggg ttacatcgaa ctggatctca acagcggtaa gatccttgag  5580
agttttcgcc ccgaagaacg ttttccaatg atgagcactt ttaaagttct gctatgtggc  5640
gcggtattat cccgtattga cgccgggcaa gagcaactcg gtcgccgcat acactattct  5700
cagaatgact tggttgagta ctcaccagtc acagaaaagc atcttacgga tggcatgaca  5760
gtaagagaat tatgcagtgc tgccataacc atgagtgata acactgcggc caacttactt  5820
ctgacaacga tcggaggacc gaaggagcta accgcttttt tgcacaacat gggggatcat  5880
gtaactcgcc ttgatcgttg ggaaccggag ctgaatgaag ccataccaaa cgacgagcgt  5940
gacaccacga tgcctgtagc aatggcaaca acgttgcgca aactattaac tggcgaacta  6000
cttactctag cttcccggca acaattaata gactggatgg aggcggataa agttgcagga  6060
ccacttctgc gctcggccct tccggctggc tggtttattg ctgataaatc tggagccggt  6120
gagcgtgggt ctcgcggtat cattgcagca ctggggccag atggtaagcc ctcccgtatc  6180
gtagttatct acacgacggg gagtcaggca actatggatg aacgaaatag acagatcgct  6240
gagataggtg cctcactgat taagcattgg taactgtcag accaagttta ctcatatata  6300
ctttagattg atttaaaact tcatttttaa tttaaaagga tctaggtgaa gatcctttttt  6360
gataatctca tgaccaaaat cccttaacgt gagttttcgt tccactgagc gtcagacccc  6420
gtagaaaaga tcaaaggatc ttcttgagat cctttttttc tgcgcgtaat ctgctgcttg  6480
caaacaaaaa aaccaccgct accagcggtg gtttgtttgc cggatcaaga gctaccaact  6540
cttttttccga aggtaactgg cttcagcaga gcgcagatac caaatactgt ccttctagtg  6600
tagccgtagt taggccacca cttcaagaac tctgtagcac cgcctacata cctcgctctg  6660
ctaatcctgt taccagtggc tgctgccagt ggcgataagt cgtgtcttac cgggttggac  6720
tcaagacgat agttaccgga taaggcgcag cggtcgggct gaacggggggg ttcgtgcaca  6780
cagcccagct tggagcgaac gacctacacc gaactgagat acctacagcg tgagctatga  6840
gaaagcgcca cgcttcccga agggagaaag gcggacaggt atccgtaag cggcagggtc  6900
ggaacaggag agcgcacgag ggagcttcca gggggaaacg cctggtatct ttatagtcct  6960
gtcgggtttc gccacctctg acttgagcgt cgatttttgt gatgctcgtc aggggggcgg  7020
agcctatgga aaaacgccag caacgcggcc ttttttacggt tcctggcctt ttgctggcct  7080
tttgctcaca tgttctttcc tgcgttatcc cctgattctg tggataaccg tattaccgcc  7140
tttgagtgag ctgataccgc tcgccgcagc cgaacgaccg agcgcagcga gtcagtgagc  7200
gaggaagcgg aagagcgccc aatacgcaaa ccgcctctcc ccgcgcgttg gccgattcat  7260
taatg                                                               7265
```

```
SEQ ID NO: 7           moltype = DNA  length = 7047
FEATURE                Location/Qualifiers
misc_feature           1..7047
                       note = Sequence of Full chemically modified guide #1
source                 1..7047
                       mol_type = other DNA
                       organism = synthetic construct
SEQUENCE: 7
cagctgcgcg ctcgctcgct cactgaggcc gcccgggcaa agcccgggcg tcgggcgacc  60
tttggtcgcc cggcctcagt gagcgagcga gcgcgcagag agggagtggc caactccatc  120
actaggggtt ccttgtagtt aatgattaac ccgccatgct acttatctac gtagccatgc  180
tctagcggcc tcggcctctg cataaataaa aaaaattagt cagccatgag cttggacgcg  240
tgtatgacaa gcagaaagta atttgggagc tgcggggagg caagggtaag ggatggggaa  300
gtggaccaga ggcatatgcg tcattggcag tgtctaagca ctcacgatag gcgtggatca  360
caggggctcg ctctgtaatt aaaaggaaaa gggtttttgt tgtgttgttg ttgttgctgt  420
ttttgagaca agggtcttgc tctgtcatca tccaggctgg agtgcagtgg tgcagtctca  480
gctcactgca acctccgcct cctgggttca agcgattctc ctgcctcagc ctcctgagca  540
gctaggacta caggtgtgtg ccaccatgcc tggctaattt ttgtattttt tagtggaaat  600
ggggttttgc catgttgccc aggctcgtct tgaactcctg acctcaagtg atccactcgt  660
ctcggcctcc caaagtgctg ggattacagg tgtgagctat tgtccccagc caaaaggaaa  720
agttttactg tagtaaccct tccggactag ggacctcggg cctcagcctc aggctaccta  780
ggtgctttag aaaggaggcc acccaggccc atgactactc cttgccacag ggagccctgc  840
acacagatgt gctaagctct cgctgccagc cagagggagg agggtctgag ccagtcagaa  900
ggagatgggc cccagagagt aagaaagggg gaggaggaac caagctgatc caaaaggtgg  960
gtctaagcag tcaagtggag gagggttcca atctgatgcc ggaggggcca agctcagcct  1020
aacgaggagg ccaggcccac caaggggccc ctggaggact tgtttccctt gtccttgtg  1080
gtttttttgca tttcctgttc ccttgctgct cattgcggaa gttcctcttc ttaccctgca  1140
cccagagcct cgcagagaa gacaaaggca gaaagcacca tgagtggggg cccaatggga  1200
ggaaggcccg gggccgagg agcacgaaca gagaaacagg agaatatggg ccaaacagga  1260
```

-continued

```
tatctgtggt aagcagttcc tgccccggct cagggccaag aacagttgga acagcagaat  1320
atgggccaaa caggatatct gtggtaagca gttcctgccc cggctcaggg ccaagaacag  1380
atggtcccca gatgcggtcc cgccctcagc agtttctaga gaaccatcag atgtttccag  1440
ggtgccccaa ggacctgaaa tgaccctgtg ccttatttga actaaccaat cagttcgctt  1500
ctcgcttctg ttcgcgcgct tctgctcccc gagctctata taagcagagc tcgtttagtg  1560
aaccgtcaga tcgcctggag acgccatcca cgctgttttg acttccatag aaggatctcg  1620
aggccaccat ggtgaggcaag ggcgaggagc tgttcaccgg ggtggtgccc atcctggtcg  1680
agctggacgg cgacgtaaac ggccacaagt tcagcgtgtc cggcgagggc gagggcgatg  1740
ccacctacgg caagctgacc ctgaagttca tctgcaccac cggcaagctg cccgtgccct  1800
ggcccaccct cgtgaccacc ctgacctacg gcgtgcagtg cttcagccgc tacccccgacc  1860
acatgaagca gcacgacttc ttcaagtccg ccatgcccga aggctacgtc caggagcgca  1920
ccatcttctt caaggacgac ggcaactaca agacccgcgc cgaggtgaag ttcgagggcg  1980
acaccctggt gaaccgcatc gagctgaagg gcatcgactt caaggaggac ggcaacatcc  2040
tggggcacaa gctggagtac aactacaaca gccacaacgt ctatatcatg gccgacaagc  2100
agaagaacgg catcaaggtg aacttcaaga tccgccacaa catcgaggac ggcagcgtgc  2160
agctcgccga ccactaccag cagaacaccc ccatcggcga cggccccgtg ctgctgcccg  2220
acaaccacta cctgagcacc cagtccgccc tgagcaaaga ccccaacgag aagcgcgatc  2280
acatggtcct gctggagttc gtgaccgccg ccgggatcac tctcggcatg gacgagctgt  2340
acaagtaaac tagtgtcgac tgctttattt gtgaaatttg tgatgctatt gctttatttg  2400
taaccattat aagctgcaat aaacaagtta caacaacaa ttgcattcat tttatgtttc  2460
aggttcaggg ggaggtgtgg gaggtttttt aaaaatccac ccttcccagg aagatctcaa  2520
tgtctacttg ccttccctct ggctgcagct cttcctttgg cccatgact gtcatgaggc  2580
aggaaggacc aggtctggct ccaagacctt gtggctaccc ctgaccagac tccactgacc  2640
cctgctttcc tctcccagac gctgccact gcagttgttc agctgtacct ggcgctgccc  2700
cctggagctg agcactggac caaggagcat tgtgggctg tgtgcttcgt gaaggataac  2760
ccccagaagt cctacttcat ccgcctttac ggccttcagg tacccccccc accccgacc  2820
ggacttgcaa gccagttctc aacccgcaaa cccagatctg tgtccatatg tgtccatagc  2880
ttcaagacct cagacctgat cagtgaatcc ctgagcccca gaaccaaaga ctcatccaga  2940
tggcaaactc tgacttgcct ttctaagtct gcaatgactg gccccagtct ccgtatcaag  3000
atctctaaag cccccagtat tagtctgctg cctaagccta atcttttcca caaattccaa  3060
taaatgagca ctgtatttgt acctgaacct caaatctatt ctaaactcaa cattttgcat  3120
cccaggaatc tctcatcaaa actcctgaac cccagatgtt tgccaagctc ctaagtcata  3180
aatctgttca acaaaccca aagttgaata ttccattgat ccttgaactc caaatctgtc  3240
cttctaaatc cacagcacag accccagagt tcccatctag agcatggcta cgtagataag  3300
tagcatggcg ggttaatcat taactacaag gaaccctag tgatggagtt ggccactccc  3360
tctctgcgcg ctcgctcgct cactgaggcc gggcgaccaa aggtcgcccg acgcccgggc  3420
tttgcccggg cggcctcagt gagcgagcga gcgcgccagc tggcgtaata gcgaagaggc  3480
ccgcaccgat cgcccttccc aacagttgcg cagcctgaat ggcgaatggc gattccgttg  3540
caatggctgg cggtaatatt gttctggata ttaccagcaa ggccgatagt ttgagttctt  3600
ctactcaggc aagtgatgtt attactaatc aaagaagtat tgcgacaacg gttaatttgc  3660
gtgatggaca gactctttta ctcggtggcc tcactgatta taaaaacact tctcaggatt  3720
ctggcgtacc gttcctgtct aaaatccctt taatcggcct cctgtttagc tcccgctctg  3780
attctaacga ggaaagcacg ttatacgtgc tcgtcaaagc aaccatagta cgcgccctgt  3840
agcggcgcat taagcgcggc gggtgtggtg gttacgcgca gcgtgaccgc tacacttgcc  3900
agcgccctag cgcccgctcc tttcgctttc ttcccttcct ttctcgccac gttcgccggc  3960
tttccccgtc aagctctaaa tcggggggctc cctttagggt tccgatttag tgctttacgg  4020
cacctcgacc ccaaaaaact tgattagggt gatggttcac gtagtgggcc atcgccctga  4080
tagacggttt ttcgcccttt gacgttggag tccacgttct ttaatagtgg actcttgttc  4140
caaactggaa caacactcaa ccctatctcg gtctattctt ttgatttata agggattttg  4200
ccgatttcgg cctattggtt aaaaaatgag ctgatttaac aaaaatttaa cgcgaatttt  4260
aacaaaatat taacgtttac aatttaaata tttgcttata caatcttcct gtttttgggg  4320
cttttctgat tatcaaccgg ggtacatatg attgacatgc tagttttacg attaccgttc  4380
atcgattctc ttgtttgctc cagactctca ggcaatgacc tgatagcctt tgtagagacc  4440
tctcaaaaat agctaccctc tccggcatga atttatcagc tagaacggtt gaatatcata  4500
ttgatggtga tttgactgtc tccggccttt ctcacccgtt tgaatcttta cctacacatt  4560
actcaggcat tgcatttaaa atatatgagg gttctaaaaa tttttatcct tgcgttgaaa  4620
taaaggcttc tcccgcaaaa gtattacagg gtcataatgt ttttggtaca accgatttag  4680
ctttatgctc tgaggctta ttgcttaatt ttgctaattc tttgccttgc ctgtatgatt  4740
tattggatgt tggaatcgcc tgatgcggta ttttctcctt acgcatctgt gcggtatttc  4800
acaccgcata tggtgcactc tcagtacaat ctgctctgat gccgcatagt taagccagcc  4860
ccgacacccg ccaacacccg ctgacgcgcc ctgacgggct tgtctgctcc cggcatccgc  4920
ttacagacaa gctgtgaccg tctccgggag ctgcatgtgt cagaggtttt caccgtcatc  4980
accgaaacgc gcgagacgaa agggcctcgt gatacgccta ttttttatagg ttaatgtcat  5040
gataataatg gtttcttaga cgtcaggtgg cacttttcgg ggaaatgtgc gcggaacccc  5100
tatttgttta tttttctaaa tacattcaaa tatgtatccg ctcatgagac aataaccctg  5160
ataaatgctt caataatatt gaaaaaggaa gagtatgagt attcaacatt tccgtgtcgc  5220
ccttattccc ttttttgcgg cattttgcct tcctgttttt gctcacccag aaacgctggt  5280
gaaagtaaaa gatgctgaag atcagttggg tgcacgagtg ggttacatcg aactggatct  5340
caacagcggt aagatccttg agagttttcg ccccgaagaa cgttttccaa tgatgagcac  5400
ttttaaagtt ctgctatgtg gcgcggtatt atcccgtatt gacgccgggc aagagcaact  5460
cggtcgccgc atacactatt ctcagaatga cttggttgag tactcaccag tcacagaaaa  5520
gcatcttacg gatggcatga cagtaagaga attatgcagt gctgccataa ccatgagtga  5580
taacactgcg gccaacttac ttctgacaac gatcggagga ccgaaggagc taaccgcttt  5640
tttgcacaac atggggatc atgtaactcg ccttgatcgt tgggaaccgg agctgaatga  5700
agccatacca aacgacgagc gtgacaccac gatgcctgta gcaatggcaa caacgttgcg  5760
caaactatta actggcgaac tacttactct agcttcccgg caacaattaa tagactggat  5820
ggaggcggat aaagttgcag gaccacttct gcgctcggcc cttccggctg ctggttat  5880
tgctgataaa tctggagccg gtgagcgtgg gtctcgcggt atcattgcag cactgggccc  5940
agatggtaag ccctcccgta tcgtagttat ctacacgacg gggagtcagg caactatgga  6000
```

```
tgaacgaaat agacagatcg ctgagatagg tgcctcactg attaagcatt ggtaactgtc  6060
agaccaagtt tactcatata tactttagat tgatttaaaa cttcatttt aatttaaaag   6120
gatctaggtg aagatccttt ttgataatct catgaccaaa atcccttaac gtgagttttc   6180
gttccactga gcgtcagacc ccgtagaaaa gatcaaagga tcttcttgag atccttttt    6240
tctgcgcgta atctgctgct tgcaaacaaa aaaaccaccg ctaccagcgg tggtttgttt   6300
gccggatcaa gagctaccaa ctctttttcc gaaggtaact ggcttcagca gagcgcagat   6360
accaaatact gtccttctag tgtagccgta gttaggccac cacttcaaga actctgtagc   6420
accgcctaca tacctcgctc tgctaatcct gttaccagtg gctgctgcca gtggcgataa   6480
gtcgtgtctt accgggttgg actcaagacg atagttaccg gataaggcgc agcggtcggg   6540
ctgaacgggg ggttcgtgca cacagcccag cttggagcga acgacctaca ccgaactgag   6600
atacctacag cgtgagctat gagaaagcgc cacgcttccc gaaggagaa  aggcggacag    6660
gtatccggta agcggcaggg tcggaacagg agagcgcacg agggagcttc caggggaaa    6720
cgcctggtat ctttatagtc ctgtcgggtt tcgccacctc tgacttgagc gtcgatttt    6780
gtgatgctcg tcaggggggc ggagcctatg gaaaaacgcc agcaacgcgg ccttttacg     6840
gttcctggcc ttttgctggc cttttgctca catgttcttt cctgcgttat ccctgattc     6900
tgtggataac cgtattaccg cctttgagtg agctgatacc gctcgccgca gccgaacgac    6960
cgagcgcagc gagtcagtga gcgaggaagc ggaagagcgc ccaatacgca aaccgcctct   7020
ccccgcgcgt tggccgattc attaatg                                        7047
```

```
SEQ ID NO: 8                moltype = DNA   length = 3451
FEATURE                     Location/Qualifiers
misc_feature                1..3451
                            note = Sequence of Full chemically modified guide #1
source                      1..3451
                            mol_type = other DNA
                            organism = synthetic construct
SEQUENCE: 8
aagcttcccg gggggatctg ggccactccc tctctgcgcg ctcgctcgct cactgaggcc  60
gggcgaccaa aggtcgcccg acgcccgggc tttgcccggg cggcctcagt gagcgagcga   120
gcgcgcagag agggagtggc caactccatc actaggggtt cctggagggg tggagtcgtg   180
acctaggcga tttaaattca tgtacaaaaa agcaggcttt aaaggaacca attcagtcga   240
ctggatccgg taccaaggtc gggcaggaag agggcctatt tcccatgatt ccttcatatt   300
tgcatatacg atacaaggct gttagagaga taattagaat taatttgact gtaaacacaa   360
agatattagt acaaaatacg tgacgtagaa agtaataatt tcttgggtag tttgcagttt   420
taaaattatg ttttaaaatg gactatcata tgcttaccgt aacttgaaag tatttcgatt   480
tcttggcttt atatatcttg tggaaaggac gaaacaccgg tatgttctgc tgaaccgcgt   540
tttagagcta gaaatagcaa gttaaaataa ggctagtccg ttatcaactt gaaaaagtgg   600
caccgagtcg gtgcttttt  tctagaccca gctttcttgt acaaagttgg cattaactag    660
tccactccct ctctgcgcgc tcgctcgctc actgaggccg ggcgaccaaa ggtcgcccga   720
cgcccgggct ttgcccgggc ggcctcagtg agcgagcgag cgcgcagaga gggacagatc   780
cgggcccgca tgcgtcgaca attcactggc cgtcgtttta caacgtcgtg actgggaaaa   840
ccctggcgtt acccaactta atcgccttgc agcacatccc cctttcgcca gctggcgtaa   900
tagcgaagag gcccgcaccg atcgcccttc ccaacagttg cgcagcctga atggcgaatg   960
gcgcctgatg cggtattttc tccttacgca tctgtgcggt atttcacacc gcatatggtg  1020
cactctcagt acaatctgct ctgatgccgc atagttaagc cagccccgac acccgccaac   1080
acccgctgac gcgccctgac gggcttgtct gctcccggca tccgcttaca gacaagctgt   1140
gaccgtctcc gggagctgca tgtgtcagag gttttcaccg tcatcaccga aacgcgcgag   1200
acgaaagggc ctcgtgatac gcctattttt ataggttaat gtcatgataa taatggtttc   1260
ttagacgtca ggtggcactt ttcggggaaa tgtgcgcgga accccatttt gtttattttt   1320
ctaaatacat tcaaatatgt atccgctcat gagacaataa ccctgataaa tgcttcaata   1380
atattgaaaa aggaagagta tgagtattca acatttccgt gtcgccctta ttccctttt    1440
tgcggcattt tgccttcctg tttttgctca cccagaaacg ctggtgaaag taaaagatgc   1500
tgaagatcag ttgggtgcac gagtgggtta catcgaactg gatctcaaca gcggtaagat   1560
ccttgagagt tttcgccccg aagaacgttt tccaatgatg agcacttta  aagttctgct    1620
atgtggcgcg gtattatccc gtattgacgc cgggcaagag caactcggtc gccgcataca   1680
ctattctcag aatgacttgg ttgagtactc accagtcaca gaaaagcatc ttacggatgg   1740
catgacagta agagaattat gcagtgctgc cataaccatg agtgataaca ctgcggccaa   1800
cttacttctg acaacgatcg gaggaccgaa ggagctaacc gcttttttgc acaacatggg   1860
ggatcatgta actcgccttg atcgttggga accggagctg aatgaagcca taccaaacga   1920
cgagcgtgac accacgatgc ctgtagcaat ggcaacaacg ttgcgcaaac tattaactgg   1980
cgaactactt actctagctt cccggcaaca attaatagac tggatggagg cggataaagt   2040
tgcaggacca cttctgcgct cggcccttcc ggctggctgg tttattgctg ataaatctgg   2100
agccggtgag cgtgggtctc gcggtatcat tgcagcactg gggccagatg gtaagccctc   2160
ccgtatcgta gttatctaca cgacggggag tcaggcaact atggatgaac gaaatagaca   2220
gatcgctgag ataggtgcct cactgattaa gcattggtaa ctgtcagacc aagtttactc   2280
atatatactt tagattgatt taaaacttca ttttaatttt aaaaggatct aggtgaagat   2340
cctttttgat aatctcatga ccaaaatccc ttaacgtgag ttttcgttcc actgagcgtc   2400
agaccccgta gaaaagatca aaggatcttc ttgagatcct tttttctgc  gcgtaatctg    2460
ctgcttgcaa acaaaaaaac caccgctacc agcggtggtt tgtttgccgg atcaagagct   2520
accaactctt tttccgaagg taactggctt cagcagagcg cagataccaa atactgttct   2580
tctagtgtag ccgtagttag gccaccactt caagaactct gtagcaccgc ctacatacct   2640
cgctctgcta atcctgttac cagtggctgc tgccagtggc gataagtcgt gtcttaccgg   2700
gttggactca agacgatagt taccggataa ggcgcagcgg tcgggctgaa cggggggttc   2760
gtgcacacag cccagcttgg agcgaacgac ctacaccgaa ctgagatacc tacaccgtga   2820
gctatgagaa agcgccacgc ttcccgaagg agaaaggcg  gacaggtatc cggtaagcgg    2880
cagggtcgga acaggagagc gcacgaggga gcttccaggg ggaaacgcct ggtatcttta   2940
tagtcctgtc gggtttcgcc acctctgact tgagcgtcga tttttgtgat gctcgtcagg   3000
ggggcggagc ctatggaaaa acgccagcaa cgcggccttt ttacggttcc tggcctttg    3060
ctggcctttt gctcacatgt tctttcctgc gttatcccct gattctgtgg ataaccgtat   3120
```

```
taccgccttt gagtgagctg ataccgctcg ccgcagccga acgaccgagc gcagcgagtc   3180
agtgagcgag gaagcggaag agcgcccaat acgcaaaccg cctctccccg cgcgttggcc   3240
gattcattaa tgcagctggc acgacaggtt tcccgactgg aaagcgggca gtgagcgcaa   3300
cgcaattaat gtgagttagc tcactcatta ggcaccccag gctttacact ttatgcttcc   3360
ggctcgtatg ttgtgtggaa ttgtgagcgg ataacaattt cacacaggaa acagctatga   3420
ccatgattac gccaagctct cgagatctag a                                  3451

SEQ ID NO: 9              moltype = DNA   length = 7691
FEATURE                   Location/Qualifiers
misc_feature             1..7691
                          note = Sequence of Full chemically modified guide #1
source                   1..7691
                          mol_type = other DNA
                          organism = synthetic construct
SEQUENCE: 9
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt ccttgtagtt aatgattaac ccgccatgct acttatctac gtagccatgc   180
tctagcggcc tcggcctctg cataaataaa aaaaattagt cagccatgag cttggacgcg   240
ttgtacaaaa aagcaggctt aaaggaacc aattcagtcg actggatccg gtaccaaggt     300
cgggcaggaa gagggcctat ttcccatgat tccttcatat ttgcatatac gatacaaggc   360
tgttagagag ataattagaa ttaatttgac tgtaaacaca aagatattag tacaaaatac   420
gtgacgtaga aagtaataat ttcttgggta gtttgcagtt ttaaaattat gttttaaaat   480
ggactatcat atgcttaccg taacttgaaa gtatttcgat ttcttggctt tatatatctt   540
gtggaaagga cgaaacaccg gtatgttctg ctgaaccgcg ttttagagct agaaatagca   600
agttaaaata aggctagtcc gttatcaact tgaaaaagtg gcaccgagtc ggtgctttt    660
tacgcgtgta tgacaagcag aaagtaattt gggagctggg gggaggcaag ggtaagggat   720
ggggaagtgg accagaggca tatgcgtcat tggcagtgtc taagcactca cgataggcgt   780
ggatcacagg ggctcgctct gtaattaaaa ggaaaagggt ttttgttgtg ttgttgttgt   840
tgctgttttt gagacaaggg tcttgctctg tcatcatcca ggctggagtg cagtggtgca   900
gtctcagctc actgcaacct ccgcctcctg ggttcaagcg attctcctgc ctcagcctcc   960
tgagcagcta ggactacagg tgtgtgccac catgcctggc taattttttgt attttttagt   1020
ggaaatgggg ttttgccatg ttgcccaggc tcgtcttgaa ctcctgacct caagtgatcc   1080
actcgtctcg gcctcccaaa gtgctgggat tacaggtgtg agctattgtc ccagccaaa    1140
aggaaaagtt ttactgtagt aacccttccg gactagggac ctcgggcctc agcctcaggc   1200
tacctaggtg ctttagaaag gaggccaccc aggcccatga ctactccttg ccacagggag   1260
ccctgcacac agatgtgcta agctctcgct gccagccaga gggaggaggg tctgagccag   1320
tcagaaggag atgggcccca gagagtaaga aaggggggag aggaccaag ctgatccaaa     1380
aggtggtct aagcagtcaa gtggaggagg gttccaatct gatggcggag ggcccaagct     1440
cagcctaacg aggaggccag gcccaccaag gggcccctgg aggacttgtt tcccttgtcc   1500
cttgtggttt tttgcatttc ctgttccctt gctgctcatt gcggaagttc ctcttcttac   1560
cctgcaccca gagcctcgcc agagaagaca agggcagaaa gcaccatgag tggggcccca   1620
atgggaggaa ggcccggggg ccgaggagca cgaacagaga aacaggagaa tatgggccaa   1680
acaggatatc tgtggtaagc agttcctgcc ccggctcagg gccaagaaca gttggaacag   1740
cagaatatgg gccaaacagg atatctgtgg taagcagttc ctgcccccggc tcagggccaa   1800
gaacagatgg tccccagatg cggtcccgcc ctcagcagtt tctagagaac catcagatgt   1860
ttccagggtg ccccaaggac ctgaaatgac cctgtgcctt atttgaacta accaatcagt   1920
tcgcttctcg cttctgttcg cgcgcttctg ctccccgagc tctatataag cagagctcgt   1980
ttagtgaacc gtcagatcgc ctggagacgc catccacgct gttttgactt ccatagaagg   2040
atctcgaggc caccatggtg agcaagggcg aggagctgtt caccgggggtg gtgcccatcc   2100
tggtcgagct ggacggcgac gtaaacggcc acaagttcag cgtgtccggc gagggcgagg   2160
gcgatgccac ctacggcaag ctgaccctga agttcatctg caccaccggc aagctgcccg   2220
tgccctggcc caccctcgtg accaccctga cctacggcgt gcagtgcttc agccgctacc   2280
ccgaccacat gaagcagcac gacttcttca gtccgccat gcccgaaggc tacgtccagg     2340
agcgcaccat cttcttcaag gacgacggca actacaagac ccgcgccgag gtgaagttcg   2400
agggcgacac cctggtgaac cgcatcgagc tgaagggcat cgacttcaag gaggacggca   2460
acatcctggg gcacaagctg gagtacaact acaacagcca caacgtctat atcatggccg   2520
acaagcagaa gaacggcatc aaggtgaact tcaagatccg ccacaacatc gaggacggca   2580
gcgtgcagct cgccgaccac taccagcaga acacccccat cggcgacggc ccgtgctgc     2640
tgcccgacaa ccactacctg agcacccagt ccgccctgag caaagacccc aacgagaagc   2700
gcgatcacat ggtcctgctg gagttcgtga ccgccgccgg gatcactctc ggcatggacg   2760
agctgtacaa gtaaactagt gtcgactgct ttatttgtga aatttgtgat gctattgctt   2820
tatttgtaac cattataagc tgcaataaac aagttaacaa caacaattgc attcatttta   2880
tgtttcaggt tcagggggag gtgtgggagg ttttttaaac agcggttcag cagaacatac   2940
cctccaccct cctccaggac cacgagaacc agcgactctt tgagatgctt ggacgaaaat   3000
gcttggtgag ctgggggatct cctgcccccg cccgtcccc accgtttctt cctcttcctc     3060
tcctccttcc ctctcttccc ctcctcccgc tcctcctttc cctctccatc atctcctctc   3120
ctagaatttc ccgtcataat ccaccttcc caggaagatc tcaatgtcta cttgccttcc     3180
ctctggctgc agctcttcct ttgggcccat gactgtcatg aggcaggaag gaccaggtct   3240
ggctccaaga ccttgtggct accctgacc agactccact gaccctgct ttcctctccc     3300
agacgctggc cactgtcagt gttcagctgt acctggcgct gccccctgga gctgagcact   3360
ggaccaagga gcattgtggg gctgtgtgct tcgtgaagga taaccccag aagtcctact     3420
tcatccgcct ttacggcctt caggtgaccc ccaccccc gactggactt gcaagccagt      3480
tctcaaccg caaacccaga tctgtgtcca tatgtgtcca tagcttcaag acctcagacc   3540
tgatcagtga atccctgagc cccagaacca aagactcatc cagatggcaa actctgactt   3600
gcctttctaa gtctgcaatg actggcccca gtctccgtat caagatctct aaagccccca   3660
gtattagtct gctgcctaag cctaatcttt tccacaaatt ccaataaatg agcactgtat   3720
ttgtacctga acctcaaatc tattctaaac tcaacatttt gcatcccagg aatctctcat   3780
caaaactcct gaaccccaga tgtttgccaa gctcctaagt cataaatctg ttcaacaaac   3840
```

```
cccaaagttg aatattccat tgatccttga actccaaatc tgtccttcta aatccacagc   3900
acagacccca gagttcccat ctagagcatg gctacgtaga taagtagcat ggcgggttaa   3960
tcattaacta caaggaaccc ctagtgatgg agttggccac tccctctctg cgcgctcgct   4020
cgctcactga ggccgggcga ccaaaggtcg cccgacgccc gggctttgcc cgggcggcct   4080
cagtgagcga gcgagcgcgc cagctggcgt aatagcgaag aggcccgcac cgatcgccct   4140
tcccaacagt tgcgcagcct gaatggcgaa tggcgattcc gttgcaatgg ctggcggtaa   4200
tattgttctg gatattacca gcaaggccga tagtttgagt tcttctactc aggcaagtga   4260
tgttattact aatcaaagaa gtattgcgac aacggttaat ttgcgtgatg gacagactct   4320
tttactcggt ggcctcactg attataaaaa cacttctcag gattctggcg taccgttcct   4380
gtctaaaatc cctttaatcg gcctcctgtt tagctcccgc tctgattcta acgaggaaag   4440
cacgttatac gtgctcgtca aagcaaccat agtacgcgcc ctgtagcggc gcattaagcg   4500
cggcgggtgt ggtggttacg cgcagcgtga ccgctacact tgccagcgcc ctagcgcccg   4560
ctcctttcgc tttcttccct tcctttctcg ccacgttcgc cggctttccc cgtcaagctc   4620
taaatcgggg gctccctta gggttccgat ttagtgcttt acggcacctc gaccccaaaa   4680
aacttgatta gggtgatggt tcacgtagtg ggccatcgcc ctgatagacg gtttttcgcc   4740
ctttgacgtt ggagtccacg ttctttaata gtggactctt gttccaaact ggaacaacac   4800
tcaaccctat ctcggtctat tcttttgatt tataagggat tttgccgatt tcggcctatt   4860
ggttaaaaaa tgagctgatt taacaaaaat ttaacgcgaa ttttaacaaa atattaacgt   4920
ttacaattta aatatttgct tatacaatct tcctgttttt ggggcttttc tgattatcaa   4980
ccggggtaca tatgattgac atgctagttt tacgattacc gttcatcgat tctcttgttt   5040
gctccagact ctcaggcaat gacctgatag cctttgtaga gacctctcaa aaatagctac   5100
cctctccggc atgaatttat cagctagaac ggttgaatat catattgatg gtgatttgac   5160
tgtctccggc ctttctcacc cgtttgaatc tttacctaca cattactcag gcattgcatt   5220
taaaatatat gagggttcta aaaatttta tccttgcgtt gaaataaagg cttctcccgc   5280
aaaagtatta caggtcata atgttttgg tacaaccgat ttagctttat gctctgaggc   5340
tttattgctt aattttgcta attctttgcc ttgcctgtat gatttattgg atgttggaat   5400
cgcctgatgc ggtatttct ccttacgcat ctgtgcggta tttcacaccg catatggtgc   5460
actctcagta caatctgctc tgatgccgca tagttaagcc agccccgaca cccgccaaca   5520
cccgctgacg cgccctgacg ggcttgtctg ctcccggcat ccgcttacag acaagctgtg   5580
accgtctccg ggagctgcat gtgtcagagg ttttcaccgt catcaccgaa acgcgcgaga   5640
cgaaagggcc tcgtgatacg cctattttta taggttaatg tcatgataat aatggtttct   5700
tagacgtcag gtggcacttt tcggggaaat gtgcgcggaa cccctatttg tttatttttc   5760
taaatacatt caaatatgta tccgctcatg agacaataac cctgataaat gcttcaataa   5820
tattgaaaaa ggaagagtat gagtattcaa catttccgtg tcgcccttat tcccttttt   5880
gcggcatttt gccttcctgt ttttgctcac ccagaaacgc tggtgaaagt aaaagatgct   5940
gaagatcagt tgggtgcacg agtgggttac atcgaactgg atctcaacag cggtaagatc   6000
cttgagagtt ttcgccccga agaacgtttt ccaatgatga gcactttaa agttctgcta   6060
tgtggcgcg tattatcccg tattgacgcc gggcaagagc aactcggtcg ccgcatacac   6120
tattctcaga atgacttggt tgagtactca ccagtcacag aaaagcatct tacggatggc   6180
atgacagtaa gagaattatg cagtgctgcc ataaccatga gtgataacac tgcggccaac   6240
ttacttctga caacgatcgg aggaccgaag gagctaaccg cttttttgca caacatgggg   6300
gatcatgtaa ctcgccttga tcgttgggaa ccggagctga atgaagccat accaaacgac   6360
gagcgtgaca ccacgatgcc tgtagcaatg gcaacaacgt tgcgcaaact attaactggc   6420
gaactactta ctctagcttc ccggcaacaa ttaatagact ggatggaggc ggataaagtt   6480
gcaggaccac ttctgcgctc ggcccttccg gctggctggt ttattgctga taaatctgga   6540
gccggtgagc gtgggtctcg cggtatcatt gcagcactgg ggccagatgg taagccctcc   6600
cgtatcgtag ttatctacac gacggggagt caggcaacta tggatgaacg aaatagacag   6660
atcgctgaga taggtgcctc actgattaag cattggtaac tgtcagacca agtttactca   6720
tatatacttt agattgattt aaaacttcat ttttaattta aaaggatcta ggtgaagatc   6780
ctttttgata atctcatgac caaaatccct taacgtgagt tttcgttcca ctgagcgtca   6840
gaccccgtag aaaagatcaa aggatcttct tgagatcctt tttttctgcg cgtaatctgc   6900
tgcttgcaaa caaaaaaacc accgctacca gcggtggttt gtttgccgga tcaagagcta   6960
ccaactcttt ttccgaaggt aactggcttc agcagagcgc agataccaaa tactgtcctt   7020
ctagtgtagc cgtagttagg ccaccacttc aagaactctg tagcaccgcc tacatacctc   7080
gctctgctaa tcctgttacc agtggctgct gccagtggcg ataagtcgtg tcttaccggg   7140
ttggactcaa gacgatagtt accggataag gcgcagcggt cgggctgaac ggggggttcg   7200
tgcacacagc ccagcttgga gcgaacgacc tacaccgaac tgagatacct acagcgtgag   7260
ctatgagaaa gcgccacgct tcccgaaggg agaaaggcgg acaggtatcc ggtaagcggc   7320
agggtcggaa caggagagcg cacgagggag cttccaggg gaaacgcctg gtatctttat   7380
agtcctgtcg ggtttcgcca cctctgactt gagcgtcgat ttttgtgatg ctcgtcaggg   7440
gggcggagcc tatggaaaaa cgccagcaac gcggcctttt tacggttcct ggccttttgc   7500
tggccttttg ctcacatgtt ctttcctgcg ttatccctg attctgtgga taaccgtatt   7560
accgcctttg agtgagctga taccgctcgc cgcagccgaa cgaccgagcg cagcgagtca   7620
gtgagcgagg aagcggaaga cgcccaata cgcaaaccgc ctctcccgc gcgttggccg   7680
attcattaat g                                                       7691
```

```
SEQ ID NO: 10              moltype = RNA  length = 100
FEATURE                    Location/Qualifiers
misc_feature               1..100
                           note = Sequence of Full chemically modified guide #1
source                     1..100
                           mol_type = other RNA
                           organism = synthetic construct
SEQUENCE: 10
ggtatgttct gctgaaccgc gttttagagc tagaaatagc aagttaaaat aaggctagtc   60
cgttatcaac ttgaaaaagt ggcaccgagt cggtgctttt                         100

SEQ ID NO: 11              moltype = DNA  length = 984
FEATURE                    Location/Qualifiers
```

```
misc_feature            1..984
                        note = Upstream homology arm (common in #1201, #1262
                         and#1244)
source                  1..984
                        mol_type = other DNA
                        organism = synthetic construct
SEQUENCE: 11
gtatgacaag cagaaagtaa tttgggagct gcggggaggc aagggtaagg gatggggaag    60
tggaccagag gcatatgcgt cattggcagt gtctaagcac tcacgatagg cgtggatcac   120
aggggctcgc tctgtaatta aaaggaaaag ggtttttgtt gtgttgttgt tgttgctgtt   180
tttgagacaa gggtcttgct ctgtcatcat ccaggctgga gtgcagtggt gcagtctcag   240
ctcactgcaa cctccgcctc ctgggttcaa gcgattctcc tgcctcagcc tcctgagcag   300
ctaggactac aggtgtgtgc caccatgcct ggctaatttt tgtatttttt agtggaaatg   360
gggtttgcc atgttgccca ggctcgtctt gaactcctga cctcaagtga tccactcgtc   420
tcggcctccc aaagtgctgg gattacaggt gtgagctatt gtcccagcc aaaaggaaaa    480
gttttactgt agtaacccttt ccggactagg gacctcgggc ctcagcctca ggctacctag   540
gtgctttaga aaggaggcca cccaggccca tgactactcc ttgccacagg gagccctgca   600
cacagatgtg ctaagctctc gctgccagcc agagggagga gggtctgagc cagtcagaag   660
gagatgggcc ccagagagta agaaaggggg aggaggaccc aagctgatcc aaaaggtggg   720
tctaagcagt caagtggagg agggttccaa tctgatggcg gagggcccaa gctcagccta   780
acgaggaggc caggcccacc aagggcccc tggaggactt gtttcccttg tcccttgtgg    840
tttttttgcat ttcctgttcc cttgctgctc attgcggaag ttcctcttct taccctgcac  900
ccagagcctc gccagagaag acaagggcag aaagcaccat gagtgggggc ccaatgggag   960
gaaggcccgg gggccgagga gcac                                         984

SEQ ID NO: 12             moltype = DNA  length = 1000
FEATURE                   Location/Qualifiers
misc_feature              1..1000
                          note = Downstream homology arm for #1201
source                    1..1000
                          mol_type = other DNA
                          organism = synthetic construct
SEQUENCE: 12
cagcggttca gcagaacata ccctccaccc tcctccagga ccacgagaac cagcgactct    60
ttgagatgct tggacgaaaa tgcttggtga gctggggatc tcctgccccc gccccgtccc   120
caccgtttct tcctcttcct ctcctccttc tctctcttcc cctcctcccg ctcctccttt   180
ccctctccat catctcctct cctagaattt cccgtcataa tccacccttc ccaggaagat   240
ctcaatgtct acttgccttc cctctggctg cagctcttcc tttgggccca tgactgtcat   300
gaggcaggaa ggaccaggtc tggctccaag accttgtggc taccctgac cagactccac    360
tgaccctgc tttcctctcc cagacgctgg ccactgcagt tgttcagctg tacctggcgc    420
tgcccctgg agctgagcac tggaccaagg agcattgtgg ggctgtgtgc ttcgtgaagg    480
ataaccccca gaagtcctac ttcatccgcc tttacggcct tcaggtgacc cccccacccc   540
cgactggact tgcaagccag ttctcaaccc gcaaacccag atctgtgtcc atatgtgtcc   600
atagcttcaa gacctcagac ctgatcagtg aatccctgag ccccagaacc aaagactcat   660
ccagatggca aactctgact tgcctttcta agtctgcaat gactggcccc agtctccgta   720
tcaagatctc taaagccccc agtattagtc tgctgcctaa gcctaatctt ttccacaaat   780
tccaataaat gagcactgta tttgtacctg aacctcaaat ctattctaaa ctcaacattt   840
tgcatcccag gaatctctca tcaaaactcc tgaaccccag atgtttgcca agctcctaag   900
tcataaatct gttcaacaaa ccccaaagtt gaatattcca ttgatccttg aactccaaat   960
ctgtccttct aaatccacag cacagacccc agagttccca                        1000

SEQ ID NO: 13             moltype = DNA  length = 1000
FEATURE                   Location/Qualifiers
misc_feature              1..1000
                          note = Downstream homology arm #1244
source                    1..1000
                          mol_type = other DNA
                          organism = synthetic construct
SEQUENCE: 13
cagcggttca gcagaacata ccctccaccc tcctccagga ccacgagaac cagcgactct    60
ttgagatgct tggacgaaaa tgcttggtga gctggggatc tcctgccccc gccccgtccc   120
caccgtttct tcctcttcct ctcctccttc tctctcttcc cctcctcccg ctcctccttt   180
ccctctccat catctccact cctagaattt cccgtcataa tccacccttc ccaggaagat   240
ctcaatgtct tcttgccttc cctctggctg cagctcttcc tttgggccca tgactgtcat   300
gaggcaggaa ggaccaggtc tggctccaag accttgtggc taccctgac cagactccac    360
tgaccctgc tttcctctcc cagacgctgg ccactgcagt tgttcagctg tacctggcgc    420
tgcccctgg agctgagcac tggaccaagg agcattgtgg ggctgtgtgc ttcgtgaagg    480
ataaccccca gaagtcctac ttcatccgcc tttacggcct tcaggtgacc cccccacccc   540
cgactggact tgcaagccag ttctcaaccc gcaaacccag atctgtgtcc atatgtgtcc   600
atagcttcaa gacctcagac ctgatcagtg aatccctgag ccccagaacc aaagactcat   660
ccagatggca aactctgact tgcctttcta agtctgcaat gactggcccc agtctccgta   720
tcaagatctc taaagccccc agtattagtc tgctgcctaa gcctaatctt ttccacaaat   780
tccaataaat gagcactgta tttgtacctg aacctcaaat ctattctaaa ctcaacattt   840
tgcatcccag gaatctctca tcaaaactcc tgaaccccag atgtttgcca agctcctaag   900
tcataaatct gttcaacaaa ccccaaagtt gaatattcca ttgatccttg aactccaaat   960
ctgtccttct aaatccacag cacagacccc agagttccca                        1000

SEQ ID NO: 14             moltype = DNA  length = 782
FEATURE                   Location/Qualifiers
```

-continued

```
misc_feature            1..782
                        note = Downstream homology arm #1262
source                  1..782
                        mol_type = other DNA
                        organism = synthetic construct
SEQUENCE: 14
aatccaccct tcccaggaag atctcaatgt ctacttgcct tccctctggc tgcagctctt     60
cctttgggcc catgactgtc atgaggcagg aaggaccagg tctggctcca agaccttgtg    120
gctaccccty accagactcc actgacccct gctttcctct cccagacgct ggccactgca    180
gttgttcagc tgtacctggc gctgcccct ggagctgagc actgaccaa ggagcattgt      240
ggggctgtgt gcttcgtgaa ggataacccc cagaagtcct acttcatccg cctttacggc    300
cttcaggtga cccccccacc cccgactgga cttgcaagcc agttctcaac ccgcaaaccc    360
agatctgtgt ccatatgtgt ccatagcttc aagacctcag acctgatcag tgaatccctg    420
agccccagaa ccaaagactc atccagatgg caaactctga cttgcctttc taagtctgca    480
atgactggcc ccagtctccg tatcaagatc tctaaagccc ccagtattag tctgctgcct    540
aagcctaatc ttttccacaa attccaataa atgagcactg tatttgtacc tgaacctcaa    600
atctattcta aactcaacat tttgcatccc aggaatctct catcaaaact cctgaacccc    660
agatgtttgc caagctccta agtcataaat ctgttcaaca aaccccaaag ttgaatattc    720
cattgatcct tgaactccaa atctgtcctt ctaaatccac agcacagacc ccagagttcc    780
ca                                                                    782

SEQ ID NO: 15              moltype = DNA  length = 17
FEATURE                    Location/Qualifiers
misc_feature               1..17
                           note = WAS TALEN binding site on the genome(forward-TALEN)
source                     1..17
                           mol_type = other DNA
                           organism = synthetic construct
SEQUENCE: 15
ctcctagaat ttcccgt                                                     17

SEQ ID NO: 16              moltype = DNA  length = 18
FEATURE                    Location/Qualifiers
misc_feature               1..18
                           note = WAS TALEN binding site on the genome(reverse-TALEN)
source                     1..18
                           mol_type = other DNA
                           organism = synthetic construct
SEQUENCE: 16
aggaagatct caatgtct                                                    18

SEQ ID NO: 17              moltype = DNA  length = 17
FEATURE                    Location/Qualifiers
misc_feature               1..17
                           note = TALEN cleavage site (spacer sequence)
source                     1..17
                           mol_type = other DNA
                           organism = synthetic construct
SEQUENCE: 17
cataatccac ccttccc                                                     17

SEQ ID NO: 18              moltype = DNA  length = 141
FEATURE                    Location/Qualifiers
misc_feature               1..141
                           note = WAS exon 2
source                     1..141
                           mol_type = other DNA
                           organism = synthetic construct
SEQUENCE: 18
acgctggcca ctgcagttgt tcagctgtac ctggcgctgc ccctggagc tgagcactgg       60
accaaggagc attgtggggc tgtgtgcttc gtgaaggata accccagaa gtcctacttc      120
atccgccttt acggccttca g                                               141

SEQ ID NO: 19              moltype = DNA  length = 189
FEATURE                    Location/Qualifiers
misc_feature               1..189
                           note = WAS exon 1 sequence
source                     1..189
                           mol_type = other DNA
                           organism = synthetic construct
SEQUENCE: 19
tcctcttctt accctgcacc cagagcctcg ccagagaaga caagggcaga aagcaccatg       60
agtggggggcc caatgggagg aaggcccggg ggccgaggag caccagcggt tcagcagaac      120
ataccctcca ccctcctcca ggaccacgag aaccagcgac tctttgagat gcttggacga      180
aaatgcttg                                                             189

SEQ ID NO: 20              moltype = DNA  length = 7468
FEATURE                    Location/Qualifiers
misc_feature               1..7468
```

-continued

```
                         note = pWNY.2xNLS.Cas9.mCherry
source                   1..7468
                         mol_type = other DNA
                         organism = synthetic construct
SEQUENCE: 20
tcgcgcgttt cggtgatgac ggtgaaaacc tctgacacat gcagctcccg gagacggtca   60
cagcttgtct gtaagcggat gccgggagca gacaagcccg tcaggcgcg tcagcgggtg    120
ttggcgggtg tcgggctgg cttaactatg cggcatcaga gcagattgta ctgagagtgc    180
accatacact tagtgtaata cgactcacta tagggagagc ggccgctttt tcagcaagat   240
taagccgcca ccatggcgcc gcggcctcct aagaagaagc ggaaagtcga attctacgta   300
atggacaaga agtactccat tgggctcgat atcggcacaa acagcgtcgg ctgggccgtc    360
attacggacg agtacaaggt gccgagcaaa aaattcaaag ttctgggcaa taccgatcgc   420
cacagcataa agaagaacct cattggcgcc ctcctgttcg actccgggga gacggccgaa   480
gccacgcggc tcaaaagaac agcacggcgc agatataccc gcagaaagaa tcggatcgc     540
tacctgcagg agatctttag taatgagatg gctaaggtgg atgactcttt cttccatagg    600
ctggaggagt cctttttggt ggaggaggat aaaaagcacg agcgccaccc aatctttggc    660
aatatcgtgg acgaggtggc gtaccatgaa aagtacccaa ccatatatca tctgaggaag    720
aagcttgtag acagtactga taaggctgac ttgcggttga tctatctcgc gctggcgcat    780
atgatcaaat ttcggggaca cttcctcatc gagggggacc tgaacccaga caacagcgat    840
gtcgacaaac tctttatcca actggttcag acttacaatc agcttttcga agagaacccg    900
atcaacgcat ccgagttga cgccaaagca atcctgagcg ctaggctgtc caaatcccgg     960
cggctcgaaa acctcatcgc acagtccct ggggagaaga agaacggcct gtttggtaat    1020
cttatcgccc tgtcactcgg gctgaccccc aactttaaat ctaacttcga cctggccgaa   1080
gatgccaagc ttcaactgag caaagacacc tacgatgatg atctcgacaa tctgctggcc   1140
cagatcggcg accagtacgc agaccttttt ttggcggcaa agaacctgtc agacgccatt   1200
ctgctgagtg atattctgcg agtgaacacg gagatcacca agctccgct gagcgctagt    1260
atgatcaagc gctatgatga gcaccaccaa gacttgactt tgctgaaggc ccttgtcaga   1320
cagcaactgc ctgagaagta caaggaaatt ttcttcgatc agtctaaaaa tggctacgcc    1380
ggatacattg acggcggagc aagccaggag gaattttaca aatttattaa gcccatcttg    1440
gaaaaaatgg acggcaccga ggagctgctg gtaaagctta acagagaaga tctgttgcgc    1500
aaacagcgca ctttcgacaa tggaagcatc ccccaccaga ttcacctggg cgaactgcac    1560
gctatcctca ggcggcaaga ggatttctac ccctttttga aagataacag ggaaaagatt    1620
gagaaaatcc tcacatttcg gatacctac tatgtaggcc ccctcgcccg gggaaattcc     1680
agattcgcgt ggatgactcg caaatcagaa gagacaatca ctccctggaa cttcgaggaa    1740
gtcgtggata aggggggcctc tgcccagtcc ttcatcgaaa ggatgactaa cttttgataaa  1800
aatctgccta cgaaaaggt gcttcctaaa cactctctgc tgtacgagta cttcacagtt    1860
tataacgagc tcaccaaggt caaatacgtc acagaaggga tgagaaagcc agcattcctg    1920
tctggagagc agaagaaagc tatcgtggac ctcctcttca agacgaaccg gaaagttacc   1980
gtgaaacagc tcaaagaaga ctatttcaaa aagattgaat gtttcgactc tgttgaaatc   2040
agcggagtgg aggatcgctt caacgcatcc ctgggaacgt atcacgatct cctgaaaatc   2100
attaaagaca aggacttcct ggacaatgag gagaacgagg acattcttga ggacattgtc   2160
ctcacccctta cgttgtttga agatagggag atgattgaag aacgcttgaa aacttacgct    2220
catctcttcg acgacaaagt catgaaacag ctcaagaggc gccgatatac aggatggggg    2280
cggctgtcaa gaaaactgat caatgggatc cgagacaagc agagtggaaa gacaatcctg    2340
gatttcttaa gtccgatgg atttgccaac cggaacttca tgcagttgat ccatgatgac    2400
tctctcacct ttaaggagga catccagaaa gcacaagttt ctggccaggg ggacagtctt    2460
cacgagcaca tcgctaatct tgcaggtagc ccagctatca aaaagggaat actgcagacc   2520
gttaaggtcg tggatgaact cgtcaaagta atgggaaggc ataagcccga gaatatcgtt    2580
atcgagatgg cccgagagaa ccaaactacc cagaagggac agaagaacag tagggaaagg   2640
atgaagagga ttgaagaggg tataaaagaa ctggggtccc aaatccttaa ggaacaccca   2700
gttgaaaaca cccagcttca gaatgagaag ctctacctgt actacctgca gaacggcagg   2760
gacatgtacg tggatcagga actggacatc aatcggctct ccgactacga cgtggatcat   2820
atcgtgcccc agtcttttct caaagatgat tctattgata taaaagtgtt gacaagatcc   2880
gataaaaata gagggaagag tgataacgtc ccctcagaag aagttgtcaa gaaaatgaaa   2940
aattattggc ggcagctgct gaacgccaaa ctgatcacac aacggaagtt cgataatctg    3000
actaaggctg aacgaggtgg cctgtctgag ttggataaag ccggcttcat caaaaggcag    3060
cttgttgaga cacgccagat caccaagcac gtggcccaaa ttctcgattc acgcatgaac   3120
accaagtacg atgaaaatga caaactgatt cgagaggtga agttattac tctgaagtct    3180
aagctggtgt ccgatttcag aaaggacttt cagttttata aggtgagaga gatcaacaat    3240
taccaccatg cgcatgatgc ctacctgaat gcagtggtag tgcactgcact tatcaaaaaa   3300
tatcccaagc ttgaatctga atttgtttac ggagactata aagtgtacga tgttaggaaa   3360
atgatcgcaa agtctgagca ggaaataggc aaggccaccg ctaagtactt cttttacagc   3420
aatattatga atttttttcaa gaccgagatt acactggcca atggagagat tcggaagcga   3480
ccacttatcg aaacaaacgg agaaacagga gaaatcgttt gggataaag tagggatttc    3540
gcgacagtcc ggaaggtcct gtccatgccg caggtgaaca tcgttaaaaa gaccgaagta    3600
cagaccggag gcttctccaa ggaaagtatc ctcccgaaaa ggaacagcga caagctgatc   3660
gcacgcaaaa aagattggga ccccaagaaa tacggcggat tcgattctcc tacagtcgct   3720
tacagtgtac tggttgtggc caaagtggag aaagggaagt ctaaaaaact caaaagcgtc   3780
aaggaactgc tgggcatcac aatcatggag cgatcaagtc tcgaaaaaaa ccccatcgac   3840
tttctcgagg cgaaaggata taaagaggtc aaaaaagacc tcatcattaa gcttcccaag    3900
tactctctct ttgagcttga aaacggccgg aaacgaatgc tcgctagtgc gggcgagctg   3960
cagaaaggta cgagctggc actgccctct aaatacgtta attcttgta tctggccagc      4020
cactatgaaa agctcaaagg ctctcccgaa gataatgagc agaagcagct gttcgtggaa   4080
caacacaaac actaccttga tgagtcaata gcgaattctc caaaagagtg             4140
atcctcgccg acgctaacct cgataaggtg ctttctgctt acaataagca cagggataag    4200
cccatcaggg agcaggcaga aaacattatc cacttgttta tctctaccaa cttgggcgcg   4260
cctgcagcct tcaagtactt cgacaccacc atagacagaa agcggtacac ctctacaaag    4320
gaggtcctgg acgccacact gattcatcag tcaattacgg ggctctatga aacaagaatc    4380
gacctctctc agctcggtgg agacagcagg gctgacccca agaagaagag gaaggtggct   4440
```

```
agcggaagcg gaggtgaggg cagaggaagt cttctaacat gcggtgacgt ggaggagaat  4500
ccggccctg tgagcaaggg cgaggaggat aacatggcca tcatcaagga gttcatgcgc  4560
ttcaaggtgc acatggaggg ctccgtgaac ggccacgagt tcgagatcga gggcgagggc  4620
gagggccgc cctacgaggg cacccagacc gccaagctga aggtgaccaa gggtggcccc  4680
ctgcccttcg cctgggacat cctgtccct cagttcatgt acggctccaa ggcctacgtg  4740
aagcacccg ccgacatccc cgactacttg aagctgtcct tccccgaggg cttcaagtgg  4800
gagcgcgtga tgaacttcga ggacggcggc gtggtgaccg tgacccagga ctcctctctg  4860
caggacggc agttcatcta caaggtgaag ctgcgcggca ccaacttccc ctccgacggc  4920
cccgtaatgc agaagaagac catgggctgg gaggcctcct ccgagcggat gtaccccgag  4980
gacggcgccc tgaagggcga gatcaagcag aggctgaagc tgaaggacgg cggccactac  5040
gacgctgagg tcaagaccac ctacaaggcc aagaagcccg tgcagctgcc cggcgcctac  5100
aacgtcaaca tcaagttgga catcacctcc cacaacgagg actacaccat cgtggaacag  5160
tacgaacgcg ccgagggccg ccactccacc ggcggcatgg acgagctgta caagtgaggt  5220
acccgtacga gcttggcgta atcatggtca tagctgtttc ctgtgtgaaa ttgttatccg  5280
ctcacaattc cacacaacat acgagccgga agcataaagt gtaaagcctg gggtgcctaa  5340
tgagtgagct aactcacatt aattgcgttg cgctcactgc ccgctttcca gtcgggaaac  5400
ctgtcgtgcc agctgcatta tgaatcggc caacgcgcgg ggagaggcgg tttgcgtatt  5460
gggcgctctt ccgcttcctc gctcactgac tcgctgcgct cggtcgttcg gctgcggcga  5520
gcggtatcag ctcactcaaa ggcggtaata cggttatcca cagaatcagg ggataacgca  5580
ggaaagaaca tgtgagcaaa aggccagcaa aaggccagga accgtaaaaa ggccgcgttg  5640
ctggcgtttt tccataggct ccgcccccct gacgagcatc acaaaaatcg acgctcaagt  5700
cagaggtggc gaaacccgac aggactataa agataccagg cgtttccccc tggaagctcc  5760
ctcgtgcgct ctcctgttcc gaccctgccg cttaccggat acctgtccgc ctttctccct  5820
tcgggaagcg tggcgctttc tcatagctca cgctgtaggt atctcagttc ggtgtaggtc  5880
gttcgctcca agctgggctg tgtgcacgaa ccccccgttc agcccgaccg ctgcgcctta  5940
tccggtaact atcgtcttga gtccaacccg gtaagacacg acttatcgcc actggcagca  6000
gccactggta acaggattag cagagcgagg tatgtaggcg gtgctacaga gttcttgaag  6060
tggtggccta actacggcta cactagaaga acagtatttg gtatctgcgc tctgctgaag  6120
ccagttacct tcggaaaaag agttggtagc tcttgatccg gcaaacaaac caccgctggt  6180
agcggtggtt tttttgtttg caagcagcag attacgcgca gaaaaaaagg atctcaagaa  6240
gatcctttga tcttttctac ggggtctgac gctcagtgga acgaaaactc acgttaaggg  6300
attttggtca tgagattatc aaaaaggatc ttcacctaga tccttttaaa ttaaaaatga  6360
agttttaaat caatctaaag tatatatgag taaacttggt ctgacagtta ccaatgctta  6420
atcagtgagg cacctatctc agcgatctgt ctatttcgtt catccatagt tgcctgactc  6480
cccgtcgtgt agataactac gatacgggag ggcttaccat ctggccccag tgctgcaatg  6540
ataccgcgag acccacgctc accggctcca gatttatcag caataaacca gccagccgga  6600
agggccgagc gcagaagtgg tcctgcaact ttatccgcct ccatccagtc tattaattgt  6660
tgccgggaag ctagagtaag tagttcgcca gttaatagtt tgcgcaacgt tgttgccatt  6720
gctacaggca tcgtggtgtc acgctcgtcg tttggtatgg cttcattcag ctccggttcc  6780
caacgatcaa ggcgagttac atgatccccc atgttgtgca aaaaagcggt tagctccttc  6840
ggtcctccga tcgttgtcag aagtaagttg gccgcagtgt tatcactcat ggttatggca  6900
gcactgcata attctcttac tgtcatgcca tccgtaagat gcttttctgt gactggtgag  6960
tactcaacca agtcattctg agaatagtgt atgcggcgac cgagttgctc ttgcccggcg  7020
tcaatacggg ataataccgc gccacatagc agaactttaa aagtgctcat cattggaaaa  7080
cgttcttcgg ggcgaaaact ctcaaggatc ttaccgctgt tgagatccag ttcgatgtaa  7140
cccactcgtg cacccaactg atcttcagca tcttttactt tcaccagcgt ttctgggtga  7200
gcaaaaacag gaaggcaaaa tgccgcaaaa aagggaataa gggcgacacg gaaatgttga  7260
atactcatac tcttcctttt tcaatattat tgaagcattt atcagggtta ttgtctcatg  7320
agcggataca tatttgaatg tatttagaaa aataaacaaa taggggttcc gcgcacattt  7380
ccccgaaaag tgccacctga cgtctaagaa accattatta tcatgacatt aacctataaa  7440
aataggcgta tcacgaggcc ctttcgtc                                     7468
```

SEQ ID NO: 21                 moltype = DNA  length = 3452
FEATURE                       Location/Qualifiers
misc_feature                  1..3452
                              note = 1190 scAAV.U6.guideRNA2
source                        1..3452
                              mol_type = other DNA
                              organism = synthetic construct
SEQUENCE: 21

```
aagcttccg gggggatctg ggccactccc tctctgcgcg ctcgctcgct cactgaggcc   60
gggcgaccaa aggtcgcccg acgcccgggc tttgcccggg cggcctcagt gagcgagcga  120
gcgcgcagag agggagtggc caactccatc actaggggtt cctggagggg tggagtcgtg  180
acctaggcca tttaaattca tgtacaaaaa agcaggcttt aaaggaacca attcagtcga  240
ctggatccgg taccaaggtc gggcaggaag agggcctatt tcccatgatt ccttcatatt  300
tgcatatacg atacaaggct gttagagaga taattagaat taatttgact gtaaacacaa  360
agatattagt acaaaatacg tgacgtagaa agtaataatt tcttgggtag tttgcagttt  420
taaaattatg ttttaaaatg gactatcata tgcttaccgt aacttgaaag tatttcgatt  480
tcttggcttt atatatcttg tggaaaggac gaaacaccgc aaagagtcgc tggttctcgg  540
ttttagagct agaaatagca agttaaaata aggctagtcc gttatcaact tgaaaaagtg  600
gcaccgagtc ggtgcttttt ttctagaccc agctttcttg tacaaagttg gcattaacta  660
gtccactccc tctctgcgcg ctcgctcgct cactgaggcc gggcgaccaa aggtcgcccg  720
acgcccgggc tttgcccggg cggcctcagt gagcgagcga gcgcgcagag agggacagat  780
ccgggggcg atgcgtcgac aattcactgg ccgtcgtttt acaacgtcgt gactgggaa   840
accctggcgt tacccaactt aatcgccttg cagcacatcc ccctttcgcc agctggcgta  900
atagcgaaga ggcccgcacc gatcgccctt cccaacagtt gcgcagcctg aatggcgaat  960
ggcgcctgat gcggtatttt ctccttacgc atctgtgcgg tatttcacac cgcatatggt 1020
gcactctcag tacaatctgc tctgatgccg catagttaag ccagccccga cacccgccaa 1080
cacccgctga cgcgccctga cgggcttgtc tgctcccggc atccgcttac agacaagctg 1140
```

```
tgaccgtctc cgggagctgc atgtgtcaga ggtttcacc gtcatcaccg aaacgcgcga 1200
gacgaaaggg cctcgtgata cgcctatttt tataggttaa tgtcatgata ataatggttt 1260
cttagacgtc aggtggcact tttcggggaa atgtgcgcgg aaccctatt tgtttatttt 1320
tctaaatca ttcaaatatg tatccgctca tgagacaata accctgataa atgcttcaat 1380
aatattgaaa aaggaagagt atgagtattc aacatttccg tgtcgcctt attcccttt 1440
ttgcggcatt ttgccttcct gtttttgctc acccagaaac gctggtgaaa gtaaaagatg 1500
ctgaagatca gttgggtgca cgagtgggtt acatcgaact ggatctcaac agcggtaaga 1560
tccttgagag ttttcgcccc gaagaacgtt ttccaatgat gagcactttt aaagttctgc 1620
tatgtggcgc ggtattatcc cgtattgacg ccgggcaaga gcaactcggt cgccgcatac 1680
actattctca gaatgacttg gttgagtact caccagtcac agaaaagcat cttacggatg 1740
gcatgacagt aagagaatta tgcagtgctg ccataaccat gagtgataac actgcggcca 1800
acttacttct gacaacgatc ggaggaccga aggagctaac cgctttttg cacaacatgg 1860
gggatcatgt aactcgcctt gatcgttggg aaccggagct gaatgaagcc ataccaaacg 1920
acgagcgtga caccacgatg cctgtagcaa tggcaacaac gttgcgcaaa ctattaactg 1980
gcgaactact tactctagct tcccggcaac aattaataga ctggatggag gcggataaag 2040
ttgcaggacc acttctgcgc tcggcccttc cggctggctg gtttattgct gataaatctg 2100
gagccggtga gcgtgggtct cgcggtatca ttgcagcact ggggccagat ggtaagccct 2160
cccgtatcgt agttatctac acgacgggga gtcaggcaac tatggatgaa cgaaatagac 2220
agatcgctga gataggtgcc tcactgatta gcattggta actgtcagac caagtttact 2280
catatatact ttagattgat ttaaaacttc attttaatt taaaaggatc taggtgaaga 2340
tcctttttga taatctcatg accaaaatcc cttaacgtga gttttcgttc cactgagcgt 2400
cagaccccgt agaaaagatc aaaggatctt cttgagatcc tttttttctg gcgcgtaatct 2460
gctgcttgca aacaaaaaaa ccaccgctac cagcggtggt ttgtttgccg gatcaagagc 2520
taccaactct ttttccgaag gtaactggct tcagcagagc gcagatacca aatactgttc 2580
ttctagtgta gccgtagtta ggccaccact tcaagaactc tgtagcaccg cctacatacc 2640
tcgctctgct aatcctgtta ccagtggctg ctgccatgta cgataagtcg tgtcttaccg 2700
ggttggactc aagacgatag ttaccggata aggcgcagcg tcgggctga acggggggt 2760
cgtgcacaca gcccagcttg gagcgaacga cctacaccga actgagatac ctacagcgtg 2820
agctatgaga aagcgccacg cttcccgaag ggagaaaggc ggacaggtat ccggtaagcg 2880
gcagggtcgg aacaggagag cgcacgaggg agcttccagg gggaaacgcc tggtatcttt 2940
atagtcctgt cgggtttcgc cacctctgac ttgagcgtcg attttgtga tgctcgtcag 3000
ggggggcggag cctatggaaa aacgccagca acgcggcctt tttacggttc ctggcctttt 3060
gctggccttt tgctcacatg ttctttcctg cgttatcccc tgattctgtg gataaccgta 3120
ttaccgcctt tgagtgagct gataccgctc gccgcagccg aacgaccgag cgcagcgagt 3180
cagtgagcga ggaagcggaa gagcgcccaa tacgcaaacc gcctctcccc gcgcgttggc 3240
cgattcatta atgcagctgg cacgacaggt ttcccgactg gaaagcgggc agtgagcgca 3300
acgcaattaa tgtgagttag ctcactcatt aggcacccca ggctttacac tttatgcttc 3360
cggctcgtat gttgtgtgga attgtgagcg ataacaatt tcacacagga aacagctatg 3420
accatgatta cgccaagctc tcgagatcta ga                                3452
```

```
SEQ ID NO: 22            moltype = DNA   length = 3452
FEATURE                  Location/Qualifiers
misc_feature             1..3452
                         note = #1191 scAAV.U6.guideRNA3
source                   1..3452
                         mol_type = other DNA
                         organism = synthetic construct
SEQUENCE: 22
aagcttcccg ggggatctg ggccactccc tctctgcgcg ctcgctcgct cactgaggcc 60
gggcgaccaa aggtcgcccg acgcccgggc tttgcccggg cggcctcagt gagcgagcga 120
gcgcgcagag agggagtggc caactccatc actaggggtt cctggagggg tggagtcgtg 180
acctaggcga tttaaattca tgtacaaaaa agcaggcttt aaaggaacca attcagtcga 240
ctggatccgg taccaaggtc gggcaggaag agggcctatt tcccatgatt ccttcatatt 300
tgcatatacg atacaaggct gttagagaga taattagaat taatttgact gtaaacacaa 360
agatattagt acaaaatacg tgacgtagaa agtaataatt tcttgggtag tttgcagttt 420
taaaattatg ttttaaaatg gactatcata tgcttaccgt aacttgaaag tatttcgatt 480
tcttggcttt atatatcttg tggaaaggac gaaacaccgc aagcatctca aagagtcgcg 540
ttttagagct agaaatagca agttaaaata aggctagtcc gttatcaact tgaaaaagtg 600
gcaccgagtc ggtgcttttt ttctagaccc agctttcttg tacaaagttg gcattaacta 660
gtccactccc tctctgcgcg ctcgctcgct cactgaggcc gggcgaccaa aggtcgcccg 720
acgcccgggc tttgcccggg cggcctcagt gagcgagcga gcgcgcagag agggacagat 780
ccgggcccg atgcgtcgac aattcactgg ccgtcgtttt acaacgtcgt gactgggaaa 840
accctggcgt tacccaactt aatcgccttg cagcacatcc cctttcgcc agctggcgta 900
atagcgaaga ggcccgcacc gatcgccctt cccaacagtt gcgcagcctg aatggcgaat 960
ggcgcctgat gcggtatttt ctccttacg atctgtgcgg tatttcacac cgcatatggt 1020
gcactctcag tacaatctgc tctgatgccg catagttaag ccagccccga cacccgccaa 1080
cacccgctga cgcgccctga cgggcttgtc tgctcccggc atccgcttac agacaagctg 1140
tgaccgtctc cgggagctgc atgtgtcaga ggtttcacc gtcatcaccg aaacgcgcga 1200
gacgaaaggg cctcgtgata cgcctatttt tataggttaa tgtcatgata ataatggttt 1260
cttagacgtc aggtggcact tttcggggaa atgtgcgcgg aaccctatt tgtttatttt 1320
tctaaatca ttcaaatatg tatccgctca tgagacaata accctgataa atgcttcaat 1380
aatattgaaa aaggaagagt atgagtattc aacatttccg tgtcgcctt attcccttt 1440
ttgcggcatt ttgccttcct gtttttgctc acccagaaac gctggtgaaa gtaaaagatg 1500
ctgaagatca gttgggtgca cgagtgggtt acatcgaact ggatctcaac agcggtaaga 1560
tccttgagag ttttcgcccc gaagaacgtt ttccaatgat gagcactttt aaagttctgc 1620
tatgtggcgc ggtattatcc cgtattgacg ccgggcaaga gcaactcggt cgccgcatac 1680
actattctca gaatgacttg gttgagtact caccagtcac agaaaagcat cttacggatg 1740
gcatgacagt aagagaatta tgcagtgctg ccataaccat gagtgataac actgcggcca 1800
acttacttct gacaacgatc ggaggaccga aggagctaac cgctttttg cacaacatgg 1860
```

```
gggatcatgt aactcgcctt gatcgttggg aaccggagct gaatgaagcc ataccaaacg   1920
acgagcgtga caccacgatg cctgtagcaa tggcaacaac gttgcgcaaa ctattaactg   1980
gcgaactact tactctagct tcccggcaac aattaataga ctggatggag gcggataaag   2040
ttgcaggacc acttctgcgc tcggcccttc cggctggctg gtttattgct gataaatctg   2100
gagccggtga gcgtgggtct cgcggtatca ttgcagcact ggggccagat ggtaagccct   2160
cccgtatcgt agttatctac acgacgggga gtcaggcaac tatggatgaa cgaaatagac   2220
agatcgctga gataggtgcc tcactgatta agcattggta actgtcagac caagtttact   2280
catatatact ttagattgat ttaaaacttc atttttaatt taaaaggatc taggtgaaga   2340
tcctttttga taatctcatg accaaaatcc cttaacgtga gttttcgttc cactgagcgt   2400
cagaccccgt agaaaagatc aaaggatctt cttgagatcc ttttttttctg cgcgtaatct   2460
gctgcttgca aacaaaaaaa ccaccgctac cagcggtggt ttgtttgccg gatcaagagc   2520
taccaactct ttttccgaag gtaactggct tcagcagagc gcagatacca aatactgttc   2580
ttctagtgta gccgtagtta ggccaccact tcaagaactc tgtagcaccg cctacatacc   2640
tcgctctgct aatcctgtta ccagtggctg ctgccagtgg cgataagtcg tgtcttaccg   2700
ggttggactc aagacgatag ttaccggata aggcgcagcg gtcgggctga acggggggtt   2760
cgtgcacaca gcccagcttg gagcgaacga cctacaccga actgagatac ctacagcgtg   2820
agctatgaga aagcgccacg cttcccgaag ggagaaaggc ggacaggtat ccggtaagcg   2880
gcagggtcgg aacaggagag cgcacgaggg agcttccagg gggaaacgcc tggtatcttt   2940
atagtcctgt cgggtttcgc cacctctgac ttgagcgtcg attttgtga tgctcgtcag   3000
gggggcggag cctatggaaa aacgccagca acgcggcctt tttacggttc ctggccttt   3060
gctggccttt tgctcacatg ttctttcctg cgttatcccc tgattctgtg gataaccgta   3120
ttaccgcctt tgagtgagct gataccgctc gccgcagccg aacgaccgag cgcagcgagt   3180
cagtgagcga ggaagcggaa gagcgcccaa tacgcaaacc gcctctcccc gcgcgttggc   3240
cgattcatta atgcagctgg cacgacaggt ttcccgactg gaaagcgggc agtgagcgca   3300
acgcaattaa tgtgagttag ctcactcatt aggcaccca ggctttacac tttatgcttc   3360
cggctcgtat gttgtgtgga attgtgagcg gataacaatt tcacacagga aacagctatg   3420
accatgatta cgccaagctc tcgagatcta ga                                 3452
```

```
SEQ ID NO: 23             moltype = DNA  length = 3452
FEATURE                   Location/Qualifiers
misc_feature              1..3452
                          note = #1192 scAAV.U6.guideRNA4
source                    1..3452
                          mol_type = other DNA
                          organism = synthetic construct
SEQUENCE: 23
aagcttcccg gggggatctg ggccactccc tctctgcgcg ctcgctcgct cactgaggcc   60
gggcgaccaa aggtcgcccg acgcccgggc tttgcccggg cggcctcagt gagcgagcga   120
gcgcgcagag agggagtggc caactccatc actaggggtt cctggagggg tggagtcgtg   180
acctaggcga tttaaattca tgtacaaaaa agcaggcttt aaaggaacca attcagtcga   240
ctggatccgg taccaaggtc gggcaggaag agggcctatt tcccatgatt ccttcatatt   300
tgcatatacg atacaaggct gttagagaga taattagaat taatttgact gtaaacacaa   360
agatattagt acaaaatacg tgacgtagaa agtaataatt tcttgggtag tttgcagttt   420
taaaattatg ttttaaaatg gactatcata tgcttaccgt aacttgaaag tatttcgatt   480
tcttggcttt atatatcttg tggaaaggac gaaacaccga ccatgagtgg gggcccaatg   540
ttttagagct agaaatagca agttaaaata aggctagtcc gttatcaact tgaaaaagtg   600
gcaccgagtc ggtgcttttt ttctagaccc agcttcttg tacaaagttg gcattaacta   660
gtccactccc tctctgcgcg ctcgctcgct cactgaggcc gggcgaccaa aggtcgcccg   720
acgcccgggc tttgcccggg cggcctcagt gagcgagcga gcgcgcagag agggacagat   780
ccgggcccg atgcgtcgac aattcactgg ccgtcgtttt acaacgtcgt gactgggaaa   840
accctggcgt tacccaactt aatcgccttg cagcacatcc ccctttcgcc agctggcgta   900
atagcgaaga ggcccgcacc gatcgccctt cccaacagtt gcgcagcctg aatggcgaat   960
ggcgcctgat gcggtatttt ctccttacgc atctgtgcgg tatttcacac cgcatatggt   1020
gcactctcag tacaatctgc tctgatgccg catagttaag ccagccccga cacccgccaa   1080
cacccgctga cgcgccctga cgggcttgtc tgctcccggc atccgcttac agacaagctg   1140
tgaccgtctc cgggagctgc atgtgtcaga ggttttcacc gtcatcaccg aaacgcgcga   1200
gacgaaaggg cctcgtgata cgcctatttt tataggttaa tgtcatgata ataatggttt   1260
cttagacgtc aggtggcact tttcggggaa atgtgcgcgg aaccctatt tgtttatttt   1320
tctaaataca ttcaaatatg tatccgctca tgagacaata accctgataa atgcttcaat   1380
aatattgaaa aaggaagagt atgagtattc aacatttccg tgtcgccctt attccctttt   1440
ttgcggcatt ttgccttcct gttttgctc acccagaaac gctggtgaaa gtaaaagatg   1500
ctgaagatca gttgggtgca cgagtgggtt acatcgaact ggatctcaac agcggtaaga   1560
tccttgagag ttttcgcccc gaagaacgtt ttccaatgat gagcactttt aaagttctgc   1620
tatgtggcgc ggtattatcc cgtattgacg ccgggcaaga gcaactcggt cgccgcatac   1680
actattctca gaatgacttg gttgagtact caccagtcac agaaaagcat cttacggatg   1740
gcatgacagt aagagaatta tgcagtgctg ccataaccat gagtgataac actgcggcca   1800
acttacttct gacaacgatc ggaggaccga aggagctaac cgcttttttg cacaacatgg   1860
gggatcatgt aactcgcctt gatcgttggg aaccggagct gaatgaagcc ataccaaacg   1920
acgagcgtga caccacgatg cctgtagcaa tggcaacaac gttgcgcaaa ctattaactg   1980
gcgaactact tactctagct tcccggcaac aattaataga ctggatggag gcggataaag   2040
ttgcaggacc acttctgcgc tcggcccttc cggctggctg gtttattgct gataaatctg   2100
gagccggtga gcgtgggtct cgcggtatca ttgcagcact ggggccagat ggtaagccct   2160
cccgtatcgt agttatctac acgacgggga gtcaggcaac tatggatgaa cgaaatagac   2220
agatcgctga gataggtgcc tcactgatta agcattggta actgtcagac caagtttact   2280
catatatact ttagattgat ttaaaacttc atttttaatt taaaaggatc taggtgaaga   2340
tcctttttga taatctcatg accaaaatcc cttaacgtga gttttcgttc cactgagcgt   2400
cagaccccgt agaaaagatc aaaggatctt cttgagatcc ttttttttctg cgcgtaatct   2460
gctgcttgca aacaaaaaaa ccaccgctac cagcggtggt ttgtttgccg gatcaagagc   2520
taccaactct ttttccgaag gtaactggct tcagcagagc gcagatacca aatactgttc   2580
```

```
ttctagtgta gccgtagtta ggccaccact tcaagaactc tgtagcaccg cctacatacc  2640
tcgctctgct aatcctgtta ccagtggctg ctgccagtgg cgataagtcg tgtcttaccg  2700
ggttggactc aagacgatag ttaccggata aggcgcagcg gtcgggctga acggggggtt  2760
cgtgcacaca gcccagcttg gagcgaacga cctacaccga actgagatac ctacagcgtg  2820
agctatgaga aagcgccacg cttcccgaag ggagaaaggc gacaggtat ccggtaagcg  2880
gcagggtcgg aacaggagag cgcacgaggg agcttccagg gggaaacgcc tggtatcttt  2940
atagtcctgt cgggtttcgc cacctctgac ttgagcgtcg attttgtga tgctcgtcag  3000
gggggcggag cctatggaaa aacgccagca acgcggcctt tttacggttc ctggcctttt  3060
gctggccttt tgctcacatg ttctttcctg cgttatcccc tgattctgtg gataaccgta  3120
ttaccgcctt tgagtgagct gataccgctc gccgcagccg aacgaccgag cgcagcgagt  3180
cagtgagcga ggaagcggaa gagcgcccaa tacgcaaacc gcctctcccc gcgcgttggc  3240
cgattcatta atgcagctgg cacgacaggt ttcccgactg gaaagcgggc agtgagcgca  3300
acgcaattaa tgtgagttag ctcactcatt aggcacccca ggctttacac tttatgcttc  3360
cggctcgtat gttgtgtgga attgtgagcg gataacaatt tcacacagga aacagctatg  3420
accatgatta cgccaagctc tcgagatcta ga                                 3452
```

```
SEQ ID NO: 24             moltype = DNA  length = 3036
FEATURE                   Location/Qualifiers
misc_feature              1..3036
                          note = WAS TALEN #2 forward
source                    1..3036
                          mol_type = other DNA
                          organism = synthetic construct
SEQUENCE: 24
atggcgccgc ggcctcctaa gaagaagcgg aaagtcgaat tcgtggatct gcgaacactg  60
ggctatagcc agcagcagca ggagaagatc aaacccaagg tgaggtccac agtcgcacag  120
caccatgaag ccctggtggg ccacgggttc actcacgctc atattgtcgc actgtctcag  180
catccagccg ctctgggaac cgtggcagtc acataccagc acatcattac tgccctgccc  240
gaggctaccc atgaagacat cgtgggagtc ggcaaacagt ggagcggcgc acgggccctg  300
gaggctctgc tgaccgacgc aggggaactg agaggacccc ctctgcagct ggatacaggg  360
cagctggtga agattgctaa gagggagggg gtgacagcaa tggaagccgt ccacgcaagc  420
aggaacgcac tgcagggggc ccccctgaac ctgaccccgg accaagtggt ggctatcgcc  480
agccacgatg gcggcaagca agcgctcgaa acggtgcagc ggctgttgcc ggtgctgtgc  540
caggaccatg gcctgacccc ggaccaagtg gtggctatcg ccagcaacgg tggcggcaag  600
caagcgctcg aaacggtgca gcggctgttg ccggtgctgt gccaggacca tggcctgacc  660
ccggaccaag tggtggctat cgccagcaac aatggcggca agcaagcct cgaaacggtg  720
cagcggctgt tgccggtgct gtgccaggac catggcctga ccccggacca agtggtggct  780
atcgccagca acaatggcgg caagcaagcg ctcgaaacgg tgcagcggct gttgccggtg  840
ctgtgccagg accatggcct gactccggac caagtggtgg ctatcgccag ccacgatggc  900
ggcaagcaag cgctcgaaac ggtgcagcgg ctgttgccgg tgctgtgcca ggaccatggc  960
ctgaccccgg accaagtggt ggctatcgcc agcaacggtg cggcaagca agcgctcgaa  1020
acggtgcagc ggctgttgcc ggtgctgtgc caggaccatg gcctgactcc ggaccaagtg  1080
gtggctatcg ccagcaacaa tggcggcaag caagcgctcg aaacggtgca gcggctgttg  1140
ccggtgctgt gccaggacca tggcctgacc ccggaccaag tggtggctat cgccagccac  1200
gatggcggca gcaagcgct cgaaacggtg cagcggctgt tgccggtgct gtgccaggac  1260
catggcctga ccccggacca gtggtggct atcgccagca acattggcgg caagcaagcg  1320
ctcgaaacgg tgcagcggct gttgccggtg ctgtgccaag accatggcct gactccggac  1380
caagtggtgg ctatcgccag caacaatggc ggcaagcaag cgctcgaaac ggtgcagcgg  1440
ctgttgccgg tgctgtgcca ggaccatggc ctgaccccgg accaagtggt ggctatcgcc  1500
agccacgatg gcggcaagca agcgctcgaa acggtgcagc ggctgttgcc ggtgctgtgc  1560
caggaccatg gcctgacccc ggaccaagtg gtggctatcg ccagcaacgg tggcggcaag  1620
caagcgctcg aaacggtgca gcggctgttg ccggtgctgt gccaggacca tggcctgacc  1680
ccggaccaag tggtggctat cgccagccac gatggcggca gcaagcgct cgaaacggtg  1740
cagcggctgt tgccggtgct gtgccaggac catggcctga ccccggacca agtggtggct  1800
atcgccagca acggtggcgg caagcaagcg ctcgaaacgg tgcagcggct gttgccggtg  1860
ctgtgccagg accatggcct gaccccggac caagtggtgg ctatcgccag caacggtggc  1920
ggcaagcaag cgctcgaaac ggtgcagcgg ctgttgccgg tgctgtgcca ggaccatggc  1980
ctgactccgg accaagtggt ggctatcgcc agccacgatg gcggcaagca agcgctcgaa  2040
acggtgcagc ggctgttgcc ggtgctgtgc caggaccatg gcctgacccc ggaccaagtg  2100
gtggctatcg ccagccacga tggcggcaag caagcgctcg aaacggtgca gcggctgttg  2160
ccggtgctgt gccaggacca tggcctgacc ccggaccaag tggtggctat cgccagcaac  2220
ggtggcggca gcaagcgct cgaaagcatt gtggcccagc tgagccggcc tgatccggcg  2280
ttggccgcgt tgaccaacga ccacctggtc gctctggctt gcctgggagg acgccctgct  2340
atggacgtga tgaagaaagg actgcccac gcacccgaac tgattacgcg gcaggaaccgg  2400
agaatcggcg agagaacatc ccatagggtg gcaatctcta gaactcagct ggtcaagagt  2460
gaactggagg aaaagaaatc agagctgcgc cacaagctga aatacgtgcc tcatgagtat  2520
atcgaactga tcgagattgc tcgcaattca acccaggacc ggatcctgga aatgaaagtg  2580
atggagttct ttatgaaagt ctacggatat cgggggaaac acctgggagg gagcagaaag  2640
ccagatgggg ccatctacac agtgggatcc cccatcgact atggcgtgat tgtcgatact  2700
aaagcctaca gcggaggcta taacctgcct atcggccagg ctgacgagat gcagagatac  2760
gtggaggaaa accagacccg caataagcat attaacccca atgaatggtg gaaagtgtat  2820
cctagctccg tcacagagtt caagtttctg ttcgtgagcg gacactttaa gggcaactac  2880
aaagcacagc tgactaggct gaatcatatc accaactgca atggagccgt gctgtctgtc  2940
gaggaactgc tgatcggggg agagatgatt aaggctggca cactgactct ggaggaagtg  3000
aggcgcaagt tcaacaatgg ggaaatcaac ttctaa                             3036
```

```
SEQ ID NO: 25             moltype = DNA  length = 2934
FEATURE                   Location/Qualifiers
misc_feature              1..2934
```

```
                          note = WAS TALEN #2 Reverse
source                    1..2934
                          mol_type = other DNA
                          organism = synthetic construct
SEQUENCE: 25
atggcgccgc ggcctcctaa gaagaagcgg aaagtcgaat tcgtggatct gcgaacactg    60
ggctatagcc agcagcagca ggagaagatc aaacccaagg tgaggtccac agtcgcacag   120
caccatgaag ccctggtggg ccacgggttc actcacgctc atattgtcgc actgtctcag   180
catccagccg ctctgggaac cgtggcagtc acataccagc acatcattac tgccctgccc   240
gaggctaccc atgaagacat cgtgggagtc ggcaaacagt ggagcggcgc acgggccctg   300
gaggctctgc tgaccgacgc aggggaactg agaggacccc ctctgcagct ggatacaggg   360
cagctggtga agattgctaa gaggggaggg gtgacagcaa tggaagccgt ccacgcaagc   420
aggaacgcac tgacaggggc ccccctgaac ctgaccccgg accaagtggt ggctatcgcc   480
agcaacaatg gcggcaagca agcgctcgaa acggtgcagc ggctgttgcc ggtgctgtgc   540
caggaccatg gcctgacccc ggaccaagtg gtggctatcg ccagcaacaa tggcggcaag   600
caagcgctcg aaacggtgca gcggctgttg ccggtgctgt gccaggacca tggcctgacc   660
ccggaccaag tggtggctat cgccagcaac ggtggcggca agcaagcgct cgaaacggtg   720
cagcggctgt tgccggtgct gtgccaggac catggcctga ccccggacca agtggtggct   780
atcgccagcc acgatggcgg caagcaagcg ctcgaaacgg tgcagcggca gttgccggtg   840
ctgtgccagg accatggcct gactccggac caagtggtgg ctatcgccag ccacgatggc   900
ggcaagcaag cgctcgaaac ggtgcagcgg ctgttgccgg tgctgtgcca ggaccatggc   960
ctgaccccgg accaagtggt ggctatcgcc agcaacggtg gcggcaagca agcgctcgaa  1020
acggtgcagc ggctgttgcc ggtgctgtgc caggaccatg gcctgactcc ggaccaagtg  1080
gtggctatcg ccagcaacgg tggcggcaag caagcgctcg aaacggtgca gcggctgttg  1140
ccggtgctgt gccaggacca tggcctgacc ccggaccaag tggtggctat cgccagccac  1200
gatggcggca agcaagcgct cgaaacggtg cagcggctgt tgccggtgct gtgccaggac  1260
catggcctga ccccggacca agtggtggct atcgccagcc acgatggcgg caagcaagcg  1320
ctcgaaacgg tgcagcggct gttgccggtg ctgtgccagg accatggcct gactccggac  1380
caagtggtgg ctatcgccag caacggtggc ggcaagcaag cgctcgaaac ggtgcagcgg  1440
ctgttgccgg tgctgtgcca ggaccatggc ctgaccccgg accaagtggt ggctatcgcc  1500
agcaacaatg gcggcaagca agcgctcgaa acggtgcagc ggctgttgcc ggtgctgtgc  1560
caggaccatg gcctgacccc ggaccaagtg gtggctatcg ccagccacga tggcggcaag  1620
caagcgctcg aaacggtgca gcggctgttg ccggtgctgt gccaggacca tggcctgacc  1680
ccggaccaag tggtggctat cgccagccac gatggcggca agcaagcgct cgaaacggtg  1740
cagcggctgt tgccggtgct gtgccaggac catggcctga ccccggacca agtggtggct  1800
atcgccagca acggtggcgg caagcaagcg ctcgaaacgg tgcagcggct gttgccggtg  1860
ctgtgccagg accatggcct gaccccggac caagtggtgg ctatcgccag ccacgatggc  1920
ggcaagcaag cgctcgaaac ggtgcagcgg ctgttgccgg tgctgtgcca ggaccatggc  1980
ctgactccgg accaagttgg ggctatcgcc agcaacattg gcggcaagca agcgctcgaa  2040
acggtgcagc ggctgttgcc ggtgctgtgc caggaccatg gcctgacccc ggaccaagtg  2100
gtggctatcg ccagcaacgg tggcggcaag caagcgctcg aaagcattgt ggcccagctg  2160
agccggcctg atccggcgtt ggccgcgttg accaacgacc acctggtcgc tctggcttgc  2220
ctgggaggac gccctgctat ggacgctgtg aagaaaggac tgccccacgc acccgaactg  2280
attagacggg tgaaccggag aatcggcgag agaacatccc atagggtggc aatctctaga  2340
actcagctgg tcaagagtga actggaggaa aagaaatcag agctgcgcca caagctgaaa  2400
tacgtgcctc atgagtatat cgaactgatc gagattgctc gcaattcaac ccaggaccgg  2460
atcctggaaa tgaaagtgat ggagttcttt atgaaagtct acggatatcg ggggaaaac   2520
ctgggaggga gcagaaagcc agatggggcc atctacacag tgggatcccc catcgactat  2580
ggcgtgattg tcgatactaa agcctacagc ggaggctata acctgcctat cggccaggct  2640
gacgagatgc agagatacgt ggaggaaaac cagacccgca ataagcatat taaccccaat  2700
gaatggtgga aagtgtatcc tagctccgtc acagagttca agtttctgtt cgtgagcgga  2760
cactttaagg gcaactacaa agcacagctg actaggctga atcatatcac caactgcaat  2820
ggagccgtgc tgtctgtcga ggaactgctg atcgggggag agatgattaa ggctggcaca  2880
ctgactctgg aggaagtgag gcgcaagttc aacaatgggg aaatcaactt ctaa         2934

SEQ ID NO: 26              moltype = DNA   length = 7084
FEATURE                   Location/Qualifiers
misc_feature              1..7084
                          note = #1380 AAV.WASATGcoWAS.WPRE3.pA
source                    1..7084
                          mol_type = other DNA
                          organism = synthetic construct
SEQUENCE: 26
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc   120
actaggggtt ccttgtagtt aatgattaac ccgccatgct acttatctac gtagccatgc   180
tctagcggc tcggcctctg cataaataaa aaaaattagt cagccatgag cttggacgcg   240
taggctcgtc ttgaactcct gacctcaagt gatccactcg tctcggcctc ccaaagtgct   300
gggattacag gtgtgagcta ttgtccccag caaaaggaa aagttttact gtagtaaccc   360
ttccggacta gggacctcgg gcctcagcct caggctacct aggtgcttta gaaaggaggc   420
cacccaggcc catgactact ccttgccaca gggagccctg cacacagatg tgctaagctc   480
tcgctgccag ccagagggag gagggtctga gccagtcaga aggagatggg ccccagagag   540
taagaaaggg ggaggaggac ccaagctgat ccaaaaggtg gtctaagca gtcaagtgga   600
ggagggttcc aatctgatgg cggagggccc aagctcagcc taacgaggag gccaggccca   660
ccaagggggc cctggaggac ttgtttccct tgtcccttgt ggtttttgc atttctgtt    720
ccccttgctgc tcattgcgga agttcctctt cttaccctgc acccagagcc tcgccagaga   780
agacaagggc agaaagcacc atgggaggaa gaccccgcgg ccgaggagcg ccagcagtgc   840
aacaaaaact tccgtcaacc ctgctgcagg accacgaaaa ccagaggctg tttgaaatgt   900
tgggacggaa gtgtctcact ctcgccacag ccgtcgtcca gctttatctt gcgcttcctc   960
```

-continued

```
ccggtgctga gcattggact aaagagcatt gcggcgcggt ctgttttgtc aaggataatc 1020
cccaaaaatc atatttcatt aggttgtacg gactccaagc tggacgcctt ctgtgggaac 1080
aagaactcta tagccagctc gtatatagca caccgacccc tttcttccat actttcgcgg 1140
gagacgactg tcaggcgggc ttgaactttg cggacgagga tgaagctcag gctttccgag 1200
cattggttca agaaaaaatc cagaaaagaa atcagcgaca gtccggagat cgccggcagc 1260
tgccgccgcc acctacaccg gccaatgagg aacggagggg aggccttccg ccacttccat 1320
tgcatccagg cggcgatcag ggtgggccac cagtagggcc cttgagtttg ggtctcgcta 1380
ctgtgggatat acagaacccg gacataacat ctagccgcta ccgcggactg ccggctccag 1440
gtccgtcccc cgctgataaa aagcgctccg gcaaaaagaa gatatctaaa gcagatatcg 1500
gtgcgccctc cggtttcaag catgtctccc atgtaggatg ggacccgcaa aatggattcg 1560
acgttaataa cctcgatccg gacctgagga gtctcttctc tcgcgcgggt atcagcgagg 1620
cacagcttac tgatgccgaa acaagtaagt tgatatacga ctttatcgag gatcaaggag 1680
ggctggaagc ggtcaggcaa gaaatgcggc gacaagaacc tttgcccccg cccccgcccc 1740
cgtccagagg cgggaaccag cttccacgcc cacctatcgt tggagggaat aaaggcaggt 1800
ctgggccact ccctccggta ccgttgggga tcgctccacc gcctcctacg cctaggggac 1860
ccccgcctcc tggtcggggg ggaccgcccc ctccgccgcc tccagccact ggtcgaagtg 1920
gacccctccc gcctcctcca cccggcgccg ggggcccacc gatgccacct cctcctccgc 1980
ccccaccgcc tcccccttct tccggcaacg gtcccgcacc tccgcccctc cctccggcat 2040
tggtccccgc gggggggcctc gcgcctggtg gtggccgggg tgcacttctg gatcaaatcc 2100
gacagggcat acagttgaat aagacgcccg gcgcccctga aagctcagct ctgcaaccgc 2160
cgcctcagtc ctctgaaggg ttggtaggcg cgctcatgca tgtaatgcag aagcgcagtc 2220
gcgctatcca ctcatcagat gaaggtgaag accaggccgg tgacgaggac gaagacgatg 2280
aatgggacga ttgactgaac tgaactagtg tcgacgataa tcaacctctg gattacaaaa 2340
tttgtgaaag attgactggt attcttaact atgttgctcc ttttacgcta tgtggatacg 2400
ctgctttaat gcctttgtat catgctattg cttcccgtat ggctttcatt ttctcctcct 2460
tgtataaatc ctggtttagtt cttgccacgg cggaactcat cgccgcctgc cttgcccgct 2520
gctggacagg ggctcggctg ttgggcactg acaattccgt gggtcgactg ctttatttgt 2580
gaaatttgtg atgctattgc tttatttgta accattataa gctgcaataa acaagttaac 2640
aacaacaatt gcattcattt tatgtttcag gttcaggggg aggtgtggga ggttttttaa 2700
acagcggttc agcagaacat accctccacc ctcctccagg accacgagaa ccagcgactc 2760
tttgagatgc ttggacgaaa atgcttggtg agctggggat ctcctgcccc cgccccgtcc 2820
ccaccgtttc ttcctcttcc tctcctcctt ctctctcttc ccctcctccc gctcctcctt 2880
tccctctcca tcatctcctc tcctagaatt tcccgtcata atccacccctt cccaggaaga 2940
tctcaatgtc tacttgcctt ccctctggct gcagctcttc ctttgggccc atgactgtca 3000
tgaggcagga aggaccaggt ctggctccaa gaccttgtgg ctacccctga ccagactcca 3060
ctgacccctg ctttcctctc ccagacgctg gccactgcag ttgttcagct gtacctggcg 3120
ctgcccctg gagctgagca ctggaccaag gagcattgtg gggctgtgtg cttcgtgaag 3180
gataacccc agaagtccta cttcatccgc ctttacggcc ttcaggtgac ccccccaccc 3240
ccgactggac ttgcaagcca gttctcaacc cgcaaaccca gatctgtgtc catatgtgtc 3300
catagcttca agtctagagc atggctacgt agataagtag catggcgggt taatcattaa 3360
ctacaaggaa ccctagtga tggagttggc cactccctct ctgcgcgctc gctcgctcac 3420
tgaggccggg cgaccaaagg tcgcccgacg cccgggcttt gcccgggcgg cctcagtgag 3480
cgagcgagcg cgcagctgg cgtaatagcg aagaggcccg caccgatcgc ccttcccaac 3540
agttgcgcag cctgaatggc gaatggcgat tccgttcaa tggctggcgg taatattgtt 3600
ctggatatta ccagcaaggc cgatagtttg agttcttcta ctcaggcaag tgatgttatt 3660
actaatcaaa gaagtattgc gacaacggtt aatttgcgtg atggacagac tcttttactc 3720
ggtggctca ctgattataa aaacacttct caggattctg gcgtaccgtt cctgtctaaa 3780
atcccttttaa tcggcctcct gtttagctcc cgctctgatt ctaacgagga aagcacgtta 3840
tacgtgctcg tcaaagcaac catagtacgc gccctgtagc ggcgcattaa gcgcggcggg 3900
tgtggtggtt acgcgcagcg tgaccgctac acttgccagc gccctagcgc ccgctccttt 3960
cgctttcttc ccttccttttc tcgccacgtt cgccggcttt ccccgtcaag tctaaatcg 4020
ggggctccct ttagggttcc gatttagtgc tttacggcac ctcgacccca aaaaacttga 4080
ttagggtgat ggttcacgta gtgggccatc gccctgatag acggtttttc gccctttgac 4140
gttggagtcc acgttcttta atagtggact cttgttccaa actggaacaa cactcaaccc 4200
tatctcggtc tattctttg atttataagg gattttgccg atttcggcct attggttaaa 4260
aaatgagctg atttaacaaa aatttaacgc gaatttttaac aaaatattaa cgtttacaat 4320
ttaaatattt gcttatacaa tcttcctgtt tttggggctt ttctgattat caaccggggt 4380
acatatgatt gacatgctag ttttacgatt accgttcatc gattctcttg tttgctccag 4440
actctcaggc aatgacctga tagcctttgt agagacctct caaaaatagc taccctctcc 4500
ggcatgaatt tatcagctag aacggttgaa tatcatattg atggtgattt gactgtctcc 4560
ggcctttctc acccgtttga atctttacct acacattact caggcattgc atttaaaata 4620
tatgagggtt ctaaaaattt ttatccttgc gttgaaataa aggcttctcc cgcaaaagta 4680
ttacagggtc ataatgtttt tggtacaacc gatttagctt tatgctctga ggctttattg 4740
cttaattttg ctaattctt gccttgcctg tatgatttat tggatgttgg aatcgcctga 4800
tgcggtattt tctccttacg catctgtgcg gtatttcaca ccgcatatgg tgcactctca 4860
gtacaatctg ctctgatgcc gcatagttaa gccagccccg acacccgcca cacccgctg 4920
acgcgccctg acgggcttgt ctgctcccgg catccgctta cagacaagct gtgaccgtct 4980
ccgggagctg catgtgtcag aggttttcac cgtcatcacc gaaacgcgcg agacgaaagg 5040
gcctcgtgat acgcctattt ttataggtta atgtcatgat aataatggtt tcttagacgt 5100
caggtggcac ttttcgggga atgtgcgcg gaacccctat ttgtttattt ttctaaatac 5160
attcaaatat gtatccgctc atgagacaat aaccctgata aatgcttcaa taatattgaa 5220
aaaggaagag tatgagtatt caacatttcc gtgtcgccct attcccttt tttgcggcat 5280
tttgccttcc tgtttttgct cacccagaaa cgctggtgaa agtaaaagat gctgaagatc 5340
agttgggtgc acgagtgggt tacatcgaac tggatctcaa cagcggtaag atccttgaga 5400
gttttcgccc cgaagaacgt tttccaatga tgagcacttt taaagttctg ctatgtggcg 5460
cggtattatc ccgtattgac gccgggcaag agcaactcgg tcgccgcata cactattctc 5520
agaatgactt ggttgagtac tcaccagtca cagaaaagca tcttacggat ggcatgacag 5580
taagagaatt atgcagtgct gccataacca tgagtgataa cactgcggcc aacttacttc 5640
tgacaacgat cggaggaccg aaggagctaa ccgcttttttt gcacaacatg ggggatcatg 5700
```

-continued

```
taactcgcct tgatcgttgg gaaccggagc tgaatgaagc cataccaaac gacgagcgtg    5760
acaccacgat gcctgtagca atggcaacaa cgttgcgcaa actattaact ggcgaactac    5820
ttactctagc ttcccggcaa caattaatag actggatgga ggcggataaa gttgcaggac    5880
cacttctgcg ctcggccctt ccggctggct ggtttattgc tgataaatct ggagccggtg    5940
agcgtgggtc tcgcggtatc attgcagcac tggggccaga tggtaagccc tcccgtatcg    6000
tagttatcta cacgacgggg agtcaggcaa ctatggatga acgaaataga cagatcgctg    6060
agataggtgc ctcactgatt aagcattggt aactgtcaga ccaagtttac tcatatatac    6120
tttagattga tttaaaactt cattttttaat ttaaaaggat ctaggtgaag atcctttttg    6180
ataatctcat gaccaaaatc ccttaacgtg agttttcgtt ccactgagcg tcagaccccg    6240
tagaaaagat caaaggatct tcttgagatc ctttttttct gcgcgtaatc tgctgcttgc    6300
aaacaaaaaa accaccgcta ccagcggtgg tttgtttgcc ggatcaagag ctaccaactc    6360
ttttttccgaa ggtaactggc ttcagcagag cgcagatacc aaatactgtc cttctagtgt    6420
agccgtagtt aggccaccac ttcaagaact ctgtagcacc gcctacatac ctcgctctgc    6480
taatcctgtt accagtggct gctgccagtg gcgataagtc gtgtcttacc gggttggact    6540
caagacgata gttaccggat aaggcgcagc ggtcgggctg aacggggggt tcgtgcacac    6600
agcccagctt ggagcgaacg acctacaccg aactgagata cctacagcgt gagctatgag    6660
aaagcgccac gcttcccgaa gggagaaagg cggacaggta tccggtaagc ggcagggtcg    6720
gaacaggaga gcgcacgagg gagcttccag ggggaaacgc ctggtatctt tatagtcctg    6780
tcgggtttcg ccacctctga cttgagcgtc gatttttgtg atgctcgtca ggggggcgga    6840
gcctatggaa aaacgccagc aacgcggcct ttttacggtt cctggccttt tgctggcctt    6900
ttgctcacat gttctttcct gcgttatccc ctgattctgt ggataaccgt attaccgcct    6960
ttgagtgagc tgataccgct cgccgcagcc gaacgaccga gcgcagcgag tcagtgagcg    7020
aggaagcgga agagcgccca atacgcaaac cgcctctccc cgcgcgttgg ccgattcatt    7080
aatg                                                                 7084

SEQ ID NO: 27           moltype = DNA   length = 17
FEATURE                 Location/Qualifiers
misc_feature            1..17
                        note = WAS TALEN#1forward RVD sequence
source                  1..17
                        mol_type = other DNA
                        organism = synthetic construct
SEQUENCE: 27
ctcctagaat ttcccgt                                                    17

SEQ ID NO: 28           moltype = DNA   length = 18
FEATURE                 Location/Qualifiers
misc_feature            1..18
                        note = WAS TALEN#1 reverse RVD sequence
source                  1..18
                        mol_type = other DNA
                        organism = synthetic construct
SEQUENCE: 28
agacattgag atcttcct                                                   18

SEQ ID NO: 29           moltype = DNA   length = 18
FEATURE                 Location/Qualifiers
misc_feature            1..18
                        note = WAS TALEN#2 forward RVD sequence
source                  1..18
                        mol_type = other DNA
                        organism = synthetic construct
SEQUENCE: 29
ctggctgcag ctcttcct                                                   18

SEQ ID NO: 30           moltype = DNA   length = 17
FEATURE                 Location/Qualifiers
misc_feature            1..17
                        note = WAS TALEN#2 reverse RVD sequence
source                  1..17
                        mol_type = other DNA
                        organism = synthetic construct
SEQUENCE: 30
ggtccttcct gcctcat                                                    17

SEQ ID NO: 31           moltype = DNA   length = 20
FEATURE                 Location/Qualifiers
misc_feature            1..20
                        note = WAS GUIDE#1 sequence
source                  1..20
                        mol_type = other DNA
                        organism = synthetic construct
SEQUENCE: 31
ggtatgttct gctgaaccgc                                                 20

SEQ ID NO: 32           moltype = DNA   length = 20
FEATURE                 Location/Qualifiers
misc_feature            1..20
                        note = WAS GUIDE#2 sequence
```

```
source                    1..20
                          mol_type = other DNA
                          organism = synthetic construct
SEQUENCE: 32
caaagagtcg ctggttctcg                                              20

SEQ ID NO: 33            moltype = DNA  length = 20
FEATURE                  Location/Qualifiers
misc_feature             1..20
                         note = WAS GUIDE#3 sequence
source                   1..20
                         mol_type = other DNA
                         organism = synthetic construct
SEQUENCE: 33
caagcatctc aaagagtcgc                                              20

SEQ ID NO: 34            moltype = DNA  length = 20
FEATURE                  Location/Qualifiers
misc_feature             1..20
                         note = WAS GUIDE#4 sequence
source                   1..20
                         mol_type = other DNA
                         organism = synthetic construct
SEQUENCE: 34
accatgagtg ggggcccaat                                              20

SEQ ID NO: 35            moltype = DNA  length = 7265
FEATURE                  Location/Qualifiers
misc_feature             1..7265
                         note = pAAV.DT (#1201)
source                   1..7265
                         mol_type = other DNA
                         organism = synthetic construct
SEQUENCE: 35
cagctgcgcg ctcgctcgct cactgaggcc gcccgggcaa agcccgggcg tcgggcgacc  60
tttggtcgcc cggcctcagt gagcgagcga gcgcgcagag agggagtggc caactccatc  120
actaggtggt cctgtgtagtt aatgattaac ccgccatgct acttatctac gtagccatgc  180
tctagcggcc tcggcctctg cataaataaa aaaaattagt cagccatgag cttggacgcg  240
tgtatgacaa gcagaaagta atttgggagc tgcggggagg caaggtaag ggatggggaa  300
gtggaccaga ggcatatgcg tcattggcag tgtctaagca ctcacgatag gcgtggatca  360
cagggggctcg ctctgtaatt aaaaggaaaa gggtttttgt tgtgttgttg ttgttgctgt  420
ttttgagaca agggtcttgc tctgtcatca tccaggctgg agtgcagtgg tgcagtctca  480
gctcactgca acctccgcct cctgggttca agcgattctc ctgcctcagc ctcctgagca  540
gctaggacta caggtgtgtg ccaccatgcc tggctaattt ttgtattttt tagtggaaat  600
ggggttttgc catgttgccc aggctcgtct tgaactcctg acctcaagtg atccactcgt  660
ctcggcctcc caaagtgctg ggattacagg tgtgagctat tgtccccagc caaaaggaaa  720
agtttactg tagtaaccct tccggactag ggacctcggg cctcagcctc aggctaccta  780
ggtgctttag aaaggaggcc acccaggccc atgactactc cttgccacag ggagccctgc  840
acacagatgt gctaagctct cgctgccagc cagaggagg agggtctgag ccagtcagaa  900
ggagatgggc cccagagagt aagaaagggg gaggaggacc caagctgatc caaaaggtgg  960
gtctaagcag tcaagtggag gagggttcca atctgatggc ggagggccca agctcagcct  1020
aacgaggagg ccaggcccac caaggggccc ctggaggact tgtttccctt gtccttgtg  1080
gttttttgca tttcctgttc ccttgctgct cattgcggaa gttcctcttc ttaccctgca  1140
cccagagcct cgccagagaa gacaagggca gaaagcacca tgagtgggg cccaatggga  1200
ggaaggcgcg ggggcccgagg agcacgaaca gagaaacagg agaatatggg ccaaacagga  1260
tatctgtggt aagcagttcc tgccccggct cagggccaag aacagttgga acagcagaat  1320
atgggccaaa caggatatct gtggtaagca gttcctgccc cggctcaggg ccaagaacag  1380
atggtcccca gatgcggtcc cgccctcagc agtttctaga gaaccatcag atgtttccag  1440
ggtgccccaa ggacctgaaa tgaccctgtg ccttatttga actaaccaat cagttcgctt  1500
ctcgcttctg ttcgcgcgct tctgctcccc gagctctata taagcagagc tcgtttagtg  1560
aaccgtcaga tcgcctggag acgccatcca cgctgttttg acttccatag aaggatctcg  1620
aggccaccat ggtgagcaag ggcgaggagc tgttcaccgg ggtggtgccc atcctggtcg  1680
agctggacgg cgacgtaaac ggccacaagt tcagcgtgtc cggcgagggc gagggcgatg  1740
ccacctacgg caagctgacc ctgaagttca tctgcaccac cggcaagctg cccgtgccct  1800
ggcccaccct cgtgaccacc ctgacctacg gcgtgcagtg cttcagccgc taccccgacc  1860
acatgaagca gcacgacttc ttcaagtccg ccatgcccga aggctacgtc caggagcgca  1920
ccatcttctt caaggacgac ggcaactaca agacccgcgc cgaggtgaag ttcgaggggc  1980
acaccctggt gaaccgcatc gagctgaagg gcatcgtgtt caaggaggac ggcaacatcc  2040
tggggcacaa gctggagtac aactacaaca gccacaacgt ctatatcatg gccgacaagc  2100
agaagaacgg catcaaggtg aacttcaaga tccgccacaa catcgaggac ggcagcgtgc  2160
agctcgccga ccactaccag cagaacaccc ccatcggcga cggccccgtg ctgctgcccg  2220
acaaccacta cctgagcacc cagtccgccc tgagcaaaga ccccaacgag aagcgcgatc  2280
acatggtcct gctggagttc gtgaccgcgc cgggatcac tctcggcatg gacgagctgt  2340
acaagtaaac tagtgtcgac tgctttattt gtgaaatttg tgatgctatt gctttatttg  2400
taaccattat aagctgcaat aaacaagtta acaacaacaa ttgcattcat tttatgtttc  2460
aggttcaggg ggaggtgtgg gaggtttttt aaacagcggt tcagcagaac ataccctcca  2520
ccctcctcca ggaccacgag aaccagcgac tctttgagat gcttggacga aaatgcttgg  2580
tgagctgggg atcctgccc ccgccccgt ccccaccgt tcttcctctt cctctcctcc  2640
ttctctctct tccctcctc ccgctcctcc tttccctctc catcatctcc tctcctagaa  2700
```

-continued

```
tttcccgtca taatccaccc ttcccaggaa gatctcaatg tctacttgcc ttccctctgg   2760
ctgcagctct tcctttgggc ccatgactgt catgaggcag gaaggaccag gtctggctcc   2820
aagaccttgt ggctacccct gaccagactc cactgacccc tgctttcctc tcccagacgc   2880
tggccactgc agttgttcag ctgtacctgg cgctgccccc tggagctgag cactggacca   2940
aggagcattg tggggctgtg tgcttcgtga aggataaccc ccagaagtcc tacttcatcc   3000
gcctttacgg ccttcaggtg accccccac ccccgactgg acttgcaagc cagttctcaa   3060
cccgcaaacc cagatctgtg tccatatgtg tccatagctt caagacctca gacctgatca   3120
gtgaatccct gagccccaga accaaagact catccagatg gcaaactctg acttgccttt   3180
ctaagtctgc aatgactggc cccagtctcc gtatcaagat ctctaaagcc cccagtatta   3240
gtctgctgcc taagcctaat cttttccaca aattccaata aatgagcact gtatttgtac   3300
ctgaacctca aatctattct aaactcaaca ttttgcatcc caggaatctc tcatcaaaac   3360
tcctgaaccc cagatgtttg ccaagctcct aagtcataaa tctgttcaac aaaccccaaa   3420
gttgaatatt ccattgatcc ttgaactcca aatctgtcct tctaaatcca cagcacagac   3480
cccagagttc ccatctagag catggctacg tagataagta gcatggcggg ttaatcatta   3540
actacaagga accctagtg atggagttgg ccactccctc tctgcgcgct cgctcgctca   3600
ctgaggccgg gcgaccaaag gtcgcccgac gcccgggctt tgcccgggcg gcctcagtga   3660
gcgagcgagc gcgccagctg gcgtaatagc gaagaggccc gcaccgatcg cccttcccaa   3720
cagttgcgca gcctgaatgg cgaatggcga ttccgttgca atggctgtcg gtaatattgt   3780
tctggatatt accagcaagg ccgatagttt gagttcttct actcaggcaa gtgatgttat   3840
tactaatcaa agaagtattg cgacaacggt taatttgcgt gatggacaga ctcttttact   3900
cggtggcctc actgattata aaaacacttc tcaggattcc ggcgtaccgt tcctgtctaa   3960
aatccctta atcggcctcc tgtttagctc ccgctctgat tctaacgagg aaagcacgtt   4020
atacgtgctc gtcaaagcaa ccatagtacg cgccctgtag cggcgcatta agcgcggcgg   4080
gtgtggtggt tacgcgcagc gtgaccgcta cacttgccag cgccctagcg cccgctcctt   4140
tcgctttctt cccttccttt ctcgccacgt tcgccggctt tccccgtcaa gctctaaatc   4200
gggggctccc tttagggttc cgatttagtg ctttacggca cctcgacccc aaaaaacttg   4260
attagggtga tggttcacgt agtgggccat cgccctgata gacggttttt cgccctttga   4320
cgttggagtc cacgttcttt aatagtggac tcttgttcca aactggaaca acactcaacc   4380
ctatctcggt ctattctttt gatttataag ggattttgcc gatttcggcc tattggttaa   4440
aaaatgagct gatttaacaa aaatttaacg cgaattttaa caaaatatta acgtttacaa   4500
tttaaatatt tgcttataca atcttcctgt ttttgggggct tttctgatta tcaaccgggg   4560
tacatatgat tgacatgcta gttttacgat taccgttcat cgattctctt gtttgctcca   4620
gactctcagg caatgacctg atagcctttg tagagacctc tcaaaaatag ctaccctctc   4680
cggcatgaat ttatcagcta gaacggttga atatcatatt gatggtgatt tgactgtctc   4740
cggcctttct cacccgtttg aatctttacc tacacattac tcaggcattg catttaaaat   4800
atatgagggt tctaaaaatt tttatccttg cgttgaaata aaggcttctc ccgcaaaagt   4860
attacagggt cataatgttt ttggtacaac cgatttagct ttatgctctg aggctttatt   4920
gcttaatttt gctaattctt tgccttgcct gtatgattta ttggatgttg gaatcgcctg   4980
atgcggtatt ttctccttac gcatctgtgc ggtatttcac accgcatatg gtgcactctc   5040
agtacaatct gctctgatgc cgcatagtta agccagcccc gacacccgcc aacacccgct   5100
gacgcgccct gacgggcttg tctgctcccg gcatccgctt acagacaagc tgtgaccgtc   5160
tccgggagct gcatgtgtca gaggttttca ccgtcatcac cgaaacgcgc gagacgaaag   5220
ggcctcgtga tacgcctatt tttataggtt aatgtcatga taataatggt ttcttagacg   5280
tcaggtggca ctttttcgggg aaatgtgcgc ggaaccccta tttgtttatt tttctaaata   5340
cattcaaata tgtatccgct catgagacaa taaccctgat aaatgcttca ataatattga   5400
aaaaggaaga gtatgagtat tcaacatttc cgtgtcgccc ttattccctt ttttgcggca   5460
ttttgccttc ctgtttttgc tcacccagaa acgctggtga aagtaaaaga tgctgaagat   5520
cagttgggtg cacgagtggg ttacatcgaa ctggatctca acagcggtaa gatccttgag   5580
agttttcgcc ccgaagaacg ttttccaatg atgagcactt ttaaagttct gctatgtggc   5640
gcggtattat cccgtattga cgccgggcaa gagcaactcg gtcgccgcat acactattct   5700
cagaatgact tggttgagta ctcaccagtc acagaaaagc atcttacgga tggcatgaca   5760
gtaagagaat tatgcagtgc tgccataacc atgagtgata acactgcggc caacttactt   5820
ctgacaacga tcggaggacc gaaggagcta accgcttttt tgcacaacat gggggatcat   5880
gtaactcgcc ttgatcgttg ggaaccggag ctgaatgaag ccataccaaa cgacgagcgt   5940
gacaccacga tgcctgtagc aatggcaaca acgttgcgca aactattaac tggcgaacta   6000
cttactctag cttcccggca acaattaata gactggatgg aggcggataa agttgcagga   6060
ccacttctgc gctcggccct tccggctggc tggtttattg ctgataaatc tggagccggt   6120
gagcgtgggt ctcgcggtat cattgcagca ctggggccag atggtaagcc ctcccgtatc   6180
gtagttatct acacgacggg gagtcaggca actatggatg aacgaaatag acagatcgct   6240
gagataggtg cctcactgat taagcattgg taactgtcag accaagttta ctcatatata   6300
ctttagattg atttaaaact tcattttta tttaaaagga tctaggtgaa gatcctttt   6360
gataatctca tgaccaaaat cccttaacgt gagttttcgt tccactgagc gtcagacccc   6420
gtagaaaaga tcaaaggatc ttcttgagat cctttttttc tgcgcgtaat ctgctgcttg   6480
caaacaaaaa aaccaccgct accagcggtg gtttgtttgc cggatcaaga gctaccaact   6540
cttttccga aggtaactgg cttcagcaga gcgcagatac caaatactgt ccttctagtg   6600
tagccgtagt taggccacca cttcaagaac tctgtagcac cgcctacata cctcgctctg   6660
ctaatcctgt taccagtggc tgctgccagt ggcgataagt cgtgtcttac cgggttggac   6720
tcaagacgat agttaccgga taaggcgcag cggtcgggct gaacggggggg ttcgtgcaca   6780
cagcccagct tggagcgaac gacctacacc gaactgagat acctacagcg tgagctatga   6840
gaaagcgcca cgcttcccga agggagaaag gcggacaggt atccggtaag cggcagggtc   6900
ggaacaggag agcgcacgag ggagcttcca gggggaaacg cctggtatct ttatagtcct   6960
gtcgggtttc gccacctctg acttgagcgt cgatttttgt gatgctcgtc agggggggcgg   7020
agcctatgga aaaacgccag caacgcggcc ttttttacggt tcctggcctt ttgctggcct   7080
tttgctcaca tgttctttcc tgcgttatcc cctgattctg tggataaccg tattaccgcc   7140
tttgagtgag ctgataccgc tcgccgcagc cgaacgaccg agcgcagcga gtcagtgagc   7200
gaggaagcgg aagagcgccc aatacgcaaa ccgcctctcc ccgcgcgttg gccgattcat   7260
taatg                                                              7265
```

SEQ ID NO: 36       moltype = DNA   length = 7265

```
FEATURE             Location/Qualifiers
misc_feature        1..7265
                    note = pAAV.DT-M (#1244)
source              1..7265
                    mol_type = other DNA
                    organism = synthetic construct
SEQUENCE: 36
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt ccttgtagtt aatgattaac ccgccatgct acttatctac gtagccatgc   180
tctagcggcc tcggcctctg cataaataaa aaaaattagt cagccatgag cttgacgcg    240
tgtatgacaa gcagaaagta atttgggagc tgcggggagg caagggtaag ggatggggaa   300
gtggaccaga ggcatatgcg tcattggcag tgtctaagca ctcacgatag gcgtggatca   360
caggggctcg ctctgtaatt aaaaggaaaa gggtttttgt tgtgttgttg ttgttgctgt   420
ttttgagaca agggtcttgc tctgtcatca tccaggctgg agtgcagtgg tgcagtctca   480
gctcactgca acctccgcct cctgggttca agcgattctc ctgcctcagc ctcctgagca   540
gctaggacta caggtgtgtg ccaccatgcc tggctaattt ttgtattttt tagtggaaat   600
ggggttttgc catgttgccc aggctcgtct tgaactcctg acctcaagtg atccactcgt   660
ctcggcctcc caaagtgctg ggattacagg tgtgagctat tgtccccagc caaaaggaaa   720
agttttactg tagtaaccct tccggactag ggacctcggg cctcagcctc aggctaccta   780
ggtgctttag aaaggaggcc acccaggccc atgactactc cttgccacag ggagccctgc   840
acacagatgt gctaagctct cgctgccagc cagagggagg aaggtctgag ccagtcagaa   900
ggagatgggc cccagagagt aagaaaggg gaggaggacc caagctgatc caaaaggtgg   960
gtctaagcag tcaagtggag gagggttcca atctgatggc ggagggccca agctcagcct   1020
aacgaggagg ccaggcccac caaggggccc ctggaggact tgtttccctt gtcccttgtg   1080
gttttttgca tttcctgttc ccttgctgct cattgcggaa gttcctcttc ttaccctgca   1140
cccagagcct cgccagagaa gacaaggca gaaagcacca tgagtggggg cccaatggga   1200
ggaaggcccg ggggccgagg agcacgaaca gagaaacagg agaatatggg ccaaacagga   1260
tatctgtggt aagcagttcc tgccccggct cagggccaag aacagttgga acagcagaat   1320
atgggccaaa caggatatct gtggtaagca gttcctgccc cggctcaggg ccaagaacag   1380
atggtcccca gatgcggtcc cgccctcagc agtttctaga gaaccatcag atgtttccag   1440
ggtgccccaa ggacctgaaa tgaccctgtg ccttatttga actaaccaat cagttcgctt   1500
ctcgcttctg ttcgcgcgct tctgctcccc gagctctata taagcagagc tcgtttagtg   1560
aaccgtcaga tcgcctggag acgccatcca cgctgttttg acttccatag aaggatctca   1620
aggccaccat ggtgagcaag ggcgaggagc tgttcaccgg ggtggtgccc atcctggtcg   1680
agctggacgg cgacgtaaac ggccacaagt tcagcgtgtc cggcgagggc gagggcgatg   1740
ccacctacgg caagctgacc ctgaagttca tctgcaccac cggcaagctg cccgtgccct   1800
ggcccaccct cgtgaccacc ctgacctacg gcgtgcagtg cttcagccgc tacccccgacc   1860
acatgaagca gcacgacttc ttcaagtccg ccatgcccga aggctacgtc caggagcgca   1920
ccatcttctt caaggacgac ggcaactaca agacccgcgc cgaggtgaag ttcgagggcg   1980
acaccctggt gaaccgcatc gagctgaagg gcatcgactt caaggaggac ggcaacatcc   2040
tggggcacaa gctggagtac aactacaaca gccacaacgt ctatatcatg gccgacaagc   2100
agaagaacgg catcaaggtg aacttcaaga tccgccacaa catcgaggac ggcagcgtgc   2160
agctcgccga ccactaccag cagaacaccc ccatcggcga cggccccgtg ctgctgcccg   2220
acaaccacta cctgagcacc cagtccgccc tgagcaaaga ccccaacgag aagcgcgatc   2280
acatggtcct gctggagttc gtgaccgccg ccgggatcac tctcggcatg gacgagctgt   2340
acaagtaaac tagtgtcgac tgctttattt gtgaaatttg tgatgctatt gctttatttg   2400
taaccattat aagctgcaat aaacaagtta acaacaacaa ttgcattcat tttatgtttc   2460
aggttcaggg ggaggtgtgg gaggtttttt aaacagcggt tcagcagaac ataccctcca   2520
ccctcctcca ggaccacgag aaccagcgac tctttgagat gcttggacga aaatgcttgg   2580
tgagctgggg atctcctgcc cccgcccgt ccccaccgtt tcttcctctt cctctcctcc   2640
ttctctctct tccctcctc ccgctcctcc tttccctctc catcatctcc actcctagaa   2700
tttcccgtca taatccaccc ttcccaggaa gatctcaatg tcttcttgcc ttccctctgg   2760
ctgcagctct tcctttgggc ccatgactgt catgaggcag gaaggaccag gtctggctcc   2820
aagaccttgt ggctacccct gaccagactc cactgacccc tgctttcctc tcccagacgc   2880
tggccactgc agttgttcag ctgtacctgg cgctgccccc tggagctgag cactggacca   2940
aggagcattg tggggctgtg tgcttcgtga aggataaccc ccagaagtcc tacttcatcc   3000
gcctttacgg ccttcaggtg accccccccac ccccgactgg acttgcaagc cagttctcaa   3060
cccgcaaacc cagatctgtg tccatatgtg tccatagctt caagacctca gacctgatca   3120
gtgaatccct gagccccaga accaaagact catccagatg gcaaactctg acttgccttt   3180
ctaagtctgc aatgactggc cccagtctcc gtatcaagat ctctaaagcc cccagtatta   3240
gtctgctgcc taagcctaat cttttccaca aattccaata aatgagcact gtatttgtac   3300
ctgaacctca aatctattct aaactcaaca ttttgcatcc caggaatctc tcatcaaaac   3360
tcctgaaccc cagatgtttg ccaagctcct aagtcataaa tctgttcaac aaaccccaaa   3420
gttgaatatt ccattgatcc ttgaactcca aatctgtcct tctaaatcca cagcacagac   3480
cccagagttc ccatctagag catggctacg tagataagta gcatggcggg ttaatcatta   3540
actacaagga accctagtg atggagttgg ccactccctc tctgcgcgct cgctcgctca   3600
ctgaggccgg cgaccaaag gtcgcccgac gcccgggctt tgcccgggcg gcctcagtga   3660
gcgagcgagc gcgcagctg gcgtaatagc gaagaggccc gcaccgatcg cccttcccaa   3720
cagttgcgca gcctgaatgg cgaatgggcga ttccgttgca atggctggcg gtaatattgt   3780
tctggatatt accagcaagg ccgatagttt gagttcttct actcaggcaa gtgatgttat   3840
tactaatcaa agaagtattg cgacaacggt taatttgcgt gatggacaga ctcttttact   3900
cggtggcctc actgattata aaaacacttc tcaggattc ggcgtaccgt tcctgtcaa    3960
aatccctta atcggcctcc tgtttagctc ccgctctgat tctaacgagg aaagcacgtt   4020
atacgtgctc gtcaaagcaa ccatagtacg cgccctgtag cggcgcatta agcgcggcgg   4080
gtgtggtggt tacgcgcagc gtgaccgcta cacttgccag cgccctagcg cccgctcctt   4140
tcgctttctt cccttccttt ctcgccacgt tcgccggctt tccccgtcaa gctctaaatc   4200
gggggctccc tttagggttc cgatttagtg ctttacggca cctcgacccc aaaaaacttg   4260
attagggtga tggttcacgt agtgggccat cgccctgata gacggttttt cgccctttga   4320
```

```
cgttggagtc cacgttctttt aatagtggac tcttgttcca aactggaaca acactcaacc  4380
ctatctcggt ctattctttt gatttataag ggattttgcc gatttcggcc tattggttaa  4440
aaaatgagct gatttaacaa aaatttaacg cgaattttaa caaaatatta acgtttacaa  4500
tttaaatatt tgcttataca atcttcctgt ttttggggct tttctgatta tcaaccgggg  4560
tacatatgat tgacatgcta gttttacgat taccgttcat cgattctctt gtttgctcca  4620
gactctcagg caatgacctg atagcctttg tagagacctc tcaaaaatag ctaccctctc  4680
cggcatgaat ttatcagcta gaacggttga atatcatatt gatggtgatt tgactgtctc  4740
cggcctttct caccgtttg aatctttacc tacacattac tcaggcattg catttaaaat  4800
atatgagggt tctaaaaatt tttatccttg cgttgaaata aaggcttctc ccgcaaaagt  4860
attacagggt cataatgttt ttggtacaac cgatttagct ttatgctctg aggctttatt  4920
gcttaatttt gctaattctt tgccttgcct gtatgattta ttggatgttg gaatcgcctg  4980
atgcggtatt ttctccttac gcatctgtgc ggtatttcac accgcatatg gtgcactctc  5040
agtacaatct gctctgatgc cgcatagtta agccagcccc gacaccgcc aacacccgct  5100
gacgcgccct gacgggcttg tctgctcccg gcatccgctt acagacaagc tgtgaccgtc  5160
tccgggagct gcatgtgtca gaggttttca ccgtcatcac cgaaacgcgc gagacgaaag  5220
ggcctcgtga tacgcctatt tttataggtt aatgtcatga taataatggt ttcttagacg  5280
tcaggtggca cttttcggg aaatgtgcgc ggaacccta tttgtttatt tttctaaata  5340
cattcaaata tgtatccgct catgagacaa taaccctgat aaatgcttca ataatattga  5400
aaaaggaaga gtatgagtat tcaacatttc cgtgtcgccc ttattccctt ttttgcggca  5460
ttttgccttc ctgtttttgc tcacccagaa acgctggtga agtaaaaga tgctgaagat  5520
cagttgggtg cacgagtggg ttacatcgaa ctggatctca acagcggtaa gatccttgag  5580
agttttcgcc ccgaagaacg ttttccaatg atgagcactt ttaaagttct gctatgtggc  5640
gcggtattat cccgtattga cgccgggcaa gagcaactcg gtcgccgcat acactattct  5700
cagaatgact tggttgagta ctcaccagtc acagaaaagc atcttacgga tggcatgaca  5760
gtaagagaat tatgcagtgc tgccataacc atgagtgata acactgcggc caacttactt  5820
ctgacaacga tcggaggacc gaaggagcta accgcttttt tgcacaacat gggggatcat  5880
gtaactcgcc ttgatcgttg ggaaccggag ctgaatgaag ccataccaaa cgacgagcgt  5940
gacaccacga tgcctgtagc aatggcaaca acgttgcgca aactattaac tggcgaacta  6000
cttactctag cttcccggca acaattaata gactggatgg aggcggataa agttgcagga  6060
ccacttctgc gctcggccct tccggctggc tggtttattg ctgataaatc tggagccggt  6120
gagcgtgggt ctcgcggtat cattgcagca ctggggccag atggtaagcc ctcccgtatc  6180
gtagttatct acacgacggg gagtcaggca actatggatg aacgaaatag acagatcgct  6240
gagataggtg cctcactgat taagcattgg taactgtcag accaagttta ctcatatata  6300
ctttagattg atttaaaact tcattttaa tttaaaagga tctaggtgaa gatcctttt  6360
gataatctca tgaccaaaat cccttaacgt gagttttcgt tccactgagc gtcagacccc  6420
gtagaaaaga tcaaaggatc ttcttgagat cctttttttc tgcgcgtaat ctgctgcttg  6480
caaacaaaaa aaccaccgct accagcggtg gtttgtttgc cggatcaaga gctaccaact  6540
ctttttccga aggtaactgg cttcagcaga gcgcagatac caaatactgt ccttctagtg  6600
tagccgtagt taggccacca cttcaagaac tctgtagcac cgcctacata cctcgctctg  6660
ctaatcctgt taccagtggc tgctgccagt ggcgataagc cgtgtcttac cgggttggac  6720
tcaagacgat agttaccgga taaggcgcag cggtcgggct gaacgggggg ttcgtgcaca  6780
cagcccagct tggagcgaac gacctacacc gaactgagat acctacagcg tgagctatga  6840
gaaagcgcca cgcttcccga agggagaaag gcggacaggt atccggtaag cggcagggtc  6900
ggaacaggag agcgcacgag ggagcttcca gggggaaacg cctggtatct ttatagtcct  6960
gtcgggtttc gccacctctg acttgagcgt cgatttttgt gatgctcgtc aggggggcgg  7020
agcctatgga aaaacgccag caacgcggcc ttttttacggt tcctggcctt ttgctggcct  7080
tttgctcaca tgttctttcc tgcgttatcc cctgattctg tggataaccg tattaccgcc  7140
tttgagtgag ctgataccgc tcgccgcagc cgaacgaccg agcgcagcga gtcagtgagc  7200
gaggaagcgg aagagcgccc aatacgcaaa ccgcctctcc ccgcgcgttg gccgattcat  7260
taatg                                                               7265
```

```
SEQ ID NO: 37           moltype = DNA   length = 7047
FEATURE                 Location/Qualifiers
misc_feature            1..7047
                        note = pAAV.DT-D (#1262)
source                  1..7047
                        mol_type = other DNA
                        organism = synthetic construct
SEQUENCE: 37
cagctgcgcg ctcgctcgct cactgaggcc gcccgggcaa agcccgggcg tcggcgacc   60
tttggtcgcc cggcctcagt gagcgagcga gcgcgcagag agggagtggc caactccatc  120
actaggggtt ccttgtagtt aatgattaac ccgccatgct acttatctac gtagccatgc  180
tctagcggc tcggcctctg cataaataaa aaaaattagt cagccatgag cttggacgcg  240
tgtatgacaa gcagaaagta atttgggagc tgcggggaag caagggtaag ggatggggaa  300
gtggaccaga ggcatatgcg tcattggcag tgtctaagca ctcacgatag gcgtggatca  360
caggggctcg ctctgtaatt aaaaggaaaa gggtttttgt tgtgttgttg ttgttgctgt  420
ttttgagaca agggtcttgc tctgtcatca tccaggctgg agtgcagtgg tgcagtctca  480
gctcactgca acctccgcct cctgggttca agcgattctc ctgcctcagc ctcctgagca  540
gctaggacta caggtgtgtg ccaccatgcc tggctaattt ttgtattttt tagtggaaat  600
gggggttttgc catgttgccc aggctcgtct tgaactcctg acctcaagtg atccactcgt  660
ctcggcctcc caaagtgctg ggattacagg tgtgagctat tgtccccagc caaaaggaaa  720
agttttactg tagtaaccct tccggactag ggacctcggg cctcagcctc aggctaccta  780
ggtgctttag aaaggaggcc acccaggccc atgactactc cttgccacag ggagccctgc  840
acacagatgt gctaagctct cgctgccagc cagaggaggg agggtctgag ccagtcagaa  900
ggagatgggc cccagagagt aagaaagggg gaggaggacc caagctgatc caaaaggtgg  960
gtctaagcag tcagtggag gagggttcca atctgatggc ggaggcccca agctcagcct  1020
aacgaggagg ccaggcccac caaggggccc ctggaggact tgtttccctt gtcccttgtg  1080
gttttttgca tttcctgttc ccttgctgct cattgcggaa gttcctcttc ttaccctgca  1140
cccagagcct cgccagagaa gacaaagggca gaaagcacca tgagtggggg cccaatggga  1200
```

-continued

```
ggaaggcccg ggggccgagg agcacgaaca gagaaacagg agaatatggg ccaaacagga    1260
tatctgtggt aagcagttcc tgccccggct cagggccaag aacagttgga acagcagaat    1320
atgggccaaa caggatatct gtggtaagca gttcctgccc cggctcaggg ccaagaacag    1380
atggtcccca gatgcggtcc cgccctcagc agtttctaga gaaccatcag atgtttccag    1440
ggtgccccaa ggacctgaaa tgaccctgtg ccttatttga actaaccaat cagttcgctt    1500
ctcgcttctg ttcgcgcgct tctgctcccc gagctctata taagcagagc tcgtttagtg    1560
aaccgtcaga tcgcctggag acgccatcca cgctgttttg acttccatag aaggatctcg    1620
aggccaccat ggtgagcaag ggcgaggagc tgttcaccgg ggtggtgccc atcctggtcg    1680
agctggacgg cgacgtaaac ggccacaagt tcagcgtgtc cggcgagggc gagggcgatg    1740
ccacctacgg caagctgacc ctgaagttca tctgcaccac cggcaagctg cccgtgccct    1800
ggcccaccct cgtgaccacc ctgacctacg gcgtgcagtg cttcagccgc taccccgacc    1860
acatgaagca gcacgacttc ttcaagtccg ccatgcccga aggctacgtc caggagcgca    1920
ccatcttctt caaggacgac ggcaactaca agacccgcgc cgaggtgaag ttcgagggcg    1980
acaccctggt gaaccgcatc gagctgaagg gcatcgactt caaggaggac ggcaacatcc    2040
tggggcacaa gctggagtac aactacaaca gccacaacgt ctatatcatg gccgacaagc    2100
agaagaacgg catcaaggtg aacttcaaga tccgccacaa catcgaggac ggcagcgtgc    2160
agctcgccga ccactaccag cagaacaccc ccatcggcga cggccccgtg ctgctgcccg    2220
acaaccacta cctgagcacc cagtccgccc tgagcaaaga ccccaacgag aagcgcgatc    2280
acatggtcct gctggagttc gtgaccgccg ccgggatcac tctcggcatg gacgagctgt    2340
acaagtaaac tagtgtcgac tgctttattt gtgaaatttg tgatgctatt gctttatttg    2400
taaccattat aagctgcaat aaacaagtta acaacaacaa ttgcattcat tttatgtttc    2460
aggttcaggg ggaggtgtgg gaggtttttt aaaaatccac ccttcccagg aagatctcaa    2520
tgtctacttg ccttccctct ggctgcagct cttcctttgg gcccatgact gtcatgagcc    2580
aggaaggacc aggtctggct ccaagacctt gtggctaccc ctgaccagac tccactgacc    2640
cctgctttcc tctcccagac gctggccact gcagttgttc agctgtacct ggcgctgccc    2700
cctggagctg agcactggac caaggagcat tgtgtggggcg tgtgcttcgt gaaggataac    2760
ccccagaagt cctacttcat ccgcctttac ggccttcagg tgaccccccc acccccgact    2820
ggacttgcaa gccagttctc aacccgcaaa cccagatctg tgtccatatg tgtccatagc    2880
ttcaagacct cagacctgat cagtgaatcc ctgagcccca gaaccaaaga ctcatccaga    2940
tggcaaactc tgacttgcct ttctaagtct gcaatgactg gccccagtct ccgtatcaag    3000
atctctaaag cccccagtat tagtctgctg cctaagccta atcttttcca caaattccaa    3060
taaatgagca ctgtatttgt acctgaacct caaatctatt ctaaactcaa cattttgcat    3120
cccaggaatc tctcatcaaa actcctgaac cccagatgtt tgccaagctc ctaagtcata    3180
aatctgttca acaaacccca aagttgaata ttccattgat ccttgaactc caaatctgtc    3240
cttctaaatc cacagcacag accccagagt tcccatctag agcatggcta cgtagataag    3300
tagcatggcg ggttaatcat taactacaag gaacccctag tgatggagtt ggccactccc    3360
tctctgcgcg ctcgctcgct cactgaggcc gggcgaccaa aggtcgcccg acgcccgggc    3420
tttgcccggg cggcctcagt gagcgagcga gcgcgccagc tggcgtaata gcgaagaggc    3480
ccgcaccgat cgcccttccc aacagttgcg cagcctgaat ggcgaatggc gattccgttg    3540
caatggctgg cggtaatatt gttctggata ttaccagcaa ggccgatagt ttgagttctt    3600
ctactcaggc aagtgatgtt attactaatc aaagaagtat tgcgacaacg gttaatttgc    3660
gtgatggaca gactctttta ctcggtggcc tcactgatta taaaaacact tctcaggatt    3720
ctggcgtacc gttcctgtct aaaatccctt taatcggcct cctgtttagc tcccgctctg    3780
attctaacga ggaaagcacg ttatacgtgc tcgtcaaagc aaccatagta cgcgccctgt    3840
agcggcgcat taagcgcggc gggtgtggtg gttacgcgca gcgtgaccgc tacacttgcc    3900
agcgccctag cgcccgctcc tttcgctttc ttcccttcct ttctcgccac gttcgccggc    3960
tttccccgtc aagctctaaa tcggggggct ctttagggt ccgatttag tgctttacgg    4020
cacctcgacc ccaaaaaact tgattagggt gatggttcac gtagtgggcc atcgccctga    4080
tagacggttt ttcgcccttt gacgttggag tccacgttct ttaatagtgg actcttgttc    4140
caaactggaa caacactcaa ccctatctcg gtctattctt ttgatttata agggattttg    4200
ccgatttcgg cctattggtt aaaaaatgag ctgatttaac aaaaatttaa cgcgaattg    4260
aacaaaatat taacgtttac aatttaaata tttgcttata caatcttcct gttttttgggg    4320
cttttctgat tatcaaccgg ggtacatatg attgacatgc tagttttacg attaccgttc    4380
atcgattctc ttgtttgctc cagactctca ggcaatgacc tgatagcctt tgtagagacc    4440
tctcaaaaat agctaccctc tccggcatga atttatcagc tagaacggtt gaatatcata    4500
ttgatggtga tttgactgtc tccggccttt ctcacccgtt tgaatcttta cctacacatt    4560
actcaggcat tgcatttaaa atatatgagg gttctaaaaa tttttatcct tgcgttgaaa    4620
taaaggcttc tcccgcaaaa gtattacagg gtcataatgt ttttggtaca accgatttag    4680
ctttatgctc tgaggcttta ttgcttaatt ttgctaattc tttgccttgc ctgtatgatt    4740
tattggatgt tggaatcgcc tgatgcggta ttttctcctt acgcatctgt gcggtatttc    4800
acaccgcata tggtgcactc tcagtacaat ctgctctgat gccgcatagt taagccagcc    4860
ccgacacccg ccaacacccg ctgacgcgcc ctgacgggct tgtctgctcc cggcatccgc    4920
ttacagacaa gctgtgaccg tctccgggag ctgcatgtgt cagaggtttt caccgtcatc    4980
accgaaacgc gcgagacgaa agggcctcgt gatacgccta tttttatagg ttaatgtcat    5040
gataataatg gtttcttaga cgtcaggtgg cacttttcgg ggaaatgtgc gcggaacccc    5100
tatttgttta tttttctaaa tacattcaaa tatgtatccg ctcatgagac aataaccctg    5160
ataaatgctt caataatatt gaaaaaggaa gagtatgagt attcaacatt ccgtgtcgc    5220
cctattccc ttttttgcgg catttttgcc ttcctgtttt t gctcacccag aaacgctggt    5280
gaaagtaaaa gatgctgaag atcagttggg tgcacgagtg ggttacatcg aactggatct    5340
caacagcggt aagatccttg agagttttcg ccccgaagaa cgttttccaa tgatgagcac    5400
ttttaaagtt ctgctatgtg gcgcggtatt atcccgtatt gacgccgggc aagagcaact    5460
cggtcgccgc atacactatt ctcagaatga cttggttgag tactcaccag tcacagaaaa    5520
gcatcttacg gatggcatga cagtaagaga attatgcagt gctgccataa ccatgagtga    5580
taacactgcg gccaacttac ttctgacaac gatcggagga ccgaaggagc taaccgcttt    5640
tttgcacaac atgggggatc atgtaactcg ccttgatcgt tgggaaccgg agctgaatga    5700
agccatacca aacgacgagc gtgacaccac gatgcctgta gcaatggcaa caacgttgcg    5760
caaactatta actggcgaac tacttactct agcttcccgg caacaattaa tagactggat    5820
ggaggcggat aaagttgcag gaccacttct gcgctcggcc cttccggctg gctggtttat    5880
tgctgataaa tctggagccg gtgagcgtgg gtctcgcggt atcattgcag cactgggggcc    5940
```

```
agatggtaag ccctcccgta tcgtagttat ctacacgacg gggagtcagg caactatgga  6000
tgaacgaaat agacagatcg ctgagatagg tgcctcactg attaagcatt ggtaactgtc  6060
agaccaagtt tactcatata tactttagat tgatttaaaa cttcattttt aatttaaaag  6120
gatctaggtg aagatccttt ttgataatct catgaccaaa atcccttaac gtgagttttc  6180
gttccactga gcgtcagacc ccgtagaaaa gatcaaagga tcttcttgag atcctttttt  6240
tctgcgcgta atctgctgct tgcaaacaaa aaaaccaccg ctaccagcgg tggtttgttt  6300
gccggatcaa gagctaccaa ctcttttttcc gaaggtaact ggcttcagca gagcgcagat  6360
accaaatact gtccttctag tgtagccgta gttaggccac cacttcaaga actctgtagc  6420
accgcctaca tacctcgctc tgctaatcct gttaccagtg gctgctgcca gtggcgataa  6480
gtcgtgtctt accgggttgg actcaagacg atagttaccg gataaggcgc agcggtcggg  6540
ctgaacgggg ggttcgtgca cacagcccag cttggagcga acgacctaca ccgaactgag  6600
atacctacag cgtgagctat gagaaagcgc cacgcttccc gaagggagaa aggcggacag  6660
gtatccggta agcggcaggg tcggaacagg agagcgcacg agggagcttc caggggg aaa  6720
cgcctggtat ctttatagtc ctgtcgggtt cgccacctc tgacttgagc gtcgatttt  6780
gtgatgctcg tcaggggggc ggagcctatg gaaaaacgcc agcaacgcgg cctttttacg  6840
gttcctggcc ttttgctggc cttttgctca catgttcttt cctgcgttat cccctgattc  6900
tgtggataac cgtattaccg cctttgagtg agctgatacc gctcgccgca gccgaacgac  6960
cgagcgcagc gagtcagtga gcgaggaagc ggaagagcgc ccaatacgca aaccgcctct  7020
ccccgcgcgt tggccgattc attaatg                                      7047

SEQ ID NO: 38           moltype = DNA   length = 3451
FEATURE                 Location/Qualifiers
misc_feature            1..3451
                        note = pscAAV.G(#1189)
source                  1..3451
                        mol_type = other DNA
                        organism = synthetic construct
SEQUENCE: 38
aagcttcccg gggggatctg ggccactccc tctctgcgcg ctcgctcgct cactgaggcc  60
gggcgaccaa aggtcgcccg acgcccgggc tttgcccggg cggcctcagt gagcgagcga  120
gcgcgcagag agggagtggc caactccatc actagggggtt cctggagggg tggagtcgtg  180
acctaggcga tttaaattca tgtacaaaaa agcaggcttt aaaggaacca attcagtcga  240
ctggatccga taccaaggtc gggcaggaag agggcctatt tcccatgatt ccttcatatt  300
tgcatatacg atacaaggct gttagagaga taattagaat taatttgact gtaaacacaa  360
agatattagt acaaaatacg tgacgtagaa agtaataatt tcttgggtag tttgcagttt  420
taaaattatg ttttaaaatg gactatcata tgcttaccgt aacttgaaag tatttcgatt  480
tcttggcttt atatatcttg tggaaaggac gaaacaccgg tatgttctgc tgaaccgcgt  540
tttagagcta gaaatagcaa gttaaaataa ggctagtccg ttatcaactt gaaaaagtgg  600
caccgagtcg gtgctttttt tctagaccca gctttcttgt acaaagttgg cattaactag  660
tccactccct ctctgcgcgc tcgctcgctc actgaggccg gcgaccaaa ggtcgcccga  720
cgcccgggct tgcccgggc ggcctcagt agcgagcgag cgcgcagaga gggacagatc  780
cgggcccgca tgcgtcgaca attcactggc cgtcgtttta caacgtcgtg actgggaaaa  840
ccctggcgtt acccaactta atcgccttgc agcacatccc cctttcgcca gctggcgtaa  900
tagcgaagag gcccgcaccg atcgcccttc ccaacagttg cgcagcctga atggcgaatg  960
gcgcctgatg cggtatttttc tccttacgca tctgtgcggt atttcacacc gcatatggtg  1020
cactctcagt acaatctgct ctgatgccgc atagttaagc cagccccgac acccgccaac  1080
acccgctgac gcgccctgac gggcttgtct gctcccggca tccgcttaca gacaagctgt  1140
gaccgtctcc gggagctgca tgtgtcagag gttttcaccg tcatcaccga aacgcgcgag  1200
acgaaagggc ctcgtgatac gcctattttt ataggttaat gtcatgataa taatggtttc  1260
ttagacgtca ggtggcactt ttcggggaaa tgtgcgcgga accccta ttt gtttatttt  1320
ctaaatacat tcaaatatgt atccgctcat gagacaataa ccctgataaa tgcttcaata  1380
atattgaaaa aggaagagta tgagtattca acatttccgt gtcgccctta ttcccttttt  1440
tgcggcattt tgccttcctg tttttgctca cccagaaacg ctggtgaaag taaaagatgc  1500
tgaagatcag ttgggtgcac gagtgggtta catcgaactg gatctcaaca gcggtaagat  1560
ccttgagagt tttcgccccg aagaacgttt tccaatgatg agcacttttta aagttctgct  1620
atgtggcgcg gtattatccc gtattgacgc cgggcaagag caactcggtc gccgcataca  1680
ctattctcag aatgacttgg ttgagtactc accagtcaca gaaaagcatc ttacggatgg  1740
catgacagta agagaattat gcagtgctgc cataaccatg agtgataaca ctgcggccaa  1800
cttacttctg acaacgatcg gaggaccgaa ggagctaacc gcttttttgc acaacatggg  1860
ggatcatgta actcgccttg atcgttggga accggagctg aatgaagcca taccaaacga  1920
cgagcgtgac accacgatgc ctgtagcaat ggcaacaacg ttgcgcaaac tattaactgg  1980
cgaactactt actctagctt cccggcaaca attaatagac tggatggagg cggataaagt  2040
tgcaggacca cttctgcgct cggcccttcc ggctggctgg tttattgctg ataaatctgg  2100
agccggtgag cgtgggtctc gcggtatcat tgcagcactg gggccagatg gtaagccctc  2160
ccgtatcgta gttatctaca cgacggggag tcaggcaact atggatgaac gaaatagaca  2220
gatcgctgag ataggtgcct cactgattaa gcattggtaa ctgtcagacc aagtttactc  2280
atatatactt tagattgatt taaaacttca tttttaattt aaaaggatct aggtgaagat  2340
cctttttgat aatctcatga ccaaaatccc ttaacgtgag ttttcgttcc actgagcgtc  2400
agacccccgta gaaaagatca aaggatcttc ttgagatcct ttttttctgc gcgtaatctg  2460
ctgcttgcaa acaaaaaaac caccgctacc agcggtggtt tgtttgccgg atcaagagct  2520
accaactctt tttccgaagg taactggctt cagcagagcg cagataccaa atactgttct  2580
tctagtgtag ccgtagttag gccaccactt caagaactct gtagcaccgc ctacatacct  2640
cgctctgcta atcctgttac cagtggctgc tgccagtggc gataagtcgt gtcttaccgg  2700
gttggactca agacgatagt taccggataa ggcgcagcgg tcgggctgaa cggggggttc  2760
gtgcacacag cccagcttgg agcgaacgac ctacaccgaa ctgagatacc tacaggcgtga  2820
gctatgagaa agcgccacgc ttcccgaagg gagaaaggcg gacaggtatc cggtaagcgg  2880
cagggtcgga acaggagagc gcacgaggga gcttccaggg ggaaacgcct ggtatcttta  2940
tagtcctgtc gggtttcgcc acctctgact tgagcgtcga ttttttgtgat gctcgtcagg  3000
gggcggagc ctatggaaaa acgccagcaa cgcggccttt ttacggttcc tggccttttg  3060
```

```
ctggcctttt gctcacatgt tctttcctgc gttatcccct gattctgtgg ataaccgtat    3120
taccgccttt gagtgagctg ataccgctcg ccgcagccga acgaccgagc gcagcgagtc    3180
agtgagcgag gaagcggaag agcgcccaat acgcaaaccg cctctccccg cgcgttggcc    3240
gattcattaa tgcagctggc acgacaggtt tcccgactgg aaagcgggca gtgagcgcaa    3300
cgcaattaat gtgagttagc tcactcatta ggcacccag gctttacact ttatgcttcc    3360
ggctcgtatg ttgtgtggaa ttgtgagcgg ataacaattc cacacaggaa acagctatga    3420
ccatgattac gccaagctct cgagatctag a                                  3451
```

SEQ ID NO: 39        moltype = DNA  length = 7691
FEATURE              Location/Qualifiers
misc_feature         1..7691
                     note = pAAV.DTG(#1215)
source               1..7691
                     mol_type = other DNA
                     organism = synthetic construct

SEQUENCE: 39

```
cagctgcgcg ctcgctcgct cactgaggcc gcccgggcaa agcccgggcg tcgggcgacc    60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagcggcc tcggcctctg cataaataaa aaaaattagt cagccatgag cttggacgcg    240
ttgtacaaaa aagcaggctt taaaggaacc aattcagtcg actggatccg gtaccaaggt    300
cgggcaggaa gagggcctat ttcccatgat tccttcatat ttgcatatac gatacaaggc    360
tgttagagag ataattagaa ttaatttgac tgtaaacaca aagatattag tacaaaatac    420
gtgacgtaga aagtaataat ttcttgggta gtttgcagtt ttaaaattat gttttaaaat    480
ggactatcat atgcttaccg taacttgaaa gtatttcgat ttcttggctt tatatatctt    540
gtggaaagga cgaaacaccg gtatgttctg ctgaaccgcg ttttagagct agaaatagca    600
agttaaaata aggctagtcc gttatcaact gaaaaagtg gcaccgagtc ggtgcttttt    660
tacgcgtgta tgacaagcag aaagtaattt gggagctgcg gggaggcaag ggtaagggat    720
ggggaagtgg accagaggca tatgcgtcat tggcagtgtc taagcactca cgataggcgt    780
ggatcacagg ggctcgctct gtaattaaaa ggaaaaggat ttttgttgtg ttgttgttgt    840
tgctgttttt gagacaaggg tcttgctctg tcatcatcca ggctggagtg cagtggtgca    900
gtctcagctc actgcaacct ccgcctcctg ggttcaagcg attctcctgc ctcagcctcc    960
tgagcagcta ggactacagg tgtgtgccac catgcctggc taatttttgt atttttttagt    1020
ggaaatgggg ttttgccatg ttgcccaggc tcgtcttgaa ctcctgacct caagtgatcc    1080
actcgtctcg gcctcccaaa gtgctgggat tacaggtgtg agctattgtc cccagccaaa    1140
aggaaaagtt ttactgtagt aaccccttccg gactagggac ctcgggcctc agcctcaggc    1200
tacctaggtg ctttagaaag gaggccaccc aggcccatga ctactccttg ccacagggag    1260
ccctgcacac agatgtgcta agctctcgct gccagccaga gggaggaggg tctgagccag    1320
tcagaaggag atgggcccca gagagtaaga aaggggagg aggacccaag ctgatccaaa    1380
aggtgggtct aagcagtcaa gtggaggagg gttccaatct gatggcggag ggcccaagct    1440
cagcctaacg aggaggccag gcccaccaag gggcccctgg aggacttgtt tcccttgtcc    1500
cttgtggttt tttgcatttc ctgttccctt gctgctcatt gcggaagttc ctcttcttac    1560
cctgcaccca gagcctcgcc agagaagaca agggcagaaa gcaccatgag tggggggcca    1620
atgggaggaa ggcccggggg ccgaggagca cgaacagaga aacaggagaa tatgggccaa    1680
acaggatatc tgtggtaagc agttcctgcc ccggctcagg gccaagaaca gttggaacag    1740
cagaatatgg gccaaacagg atatctgtgg taagcagttc ctgccccggc tcaggggcaa    1800
gaacagatgg tccccagatg cggtcccgcc ctcagcagtt tctagagaac catcagatgt    1860
ttccagggtg ccccaaggac ctgaaatgac cctgtgcctt atttgaacta accaatcagt    1920
tcgcttctcg cttctgttcg cgcgcttctg ctccccgagc tctatataag cagagctcgt    1980
ttagtgaacc gtcagatcgc ctggagacgc catccacgct gttttgactt ccatagaagg    2040
atctgaggc caccatggtg agcaagggcg aggagctgtt caccgggggtg gtgcccatcc    2100
tggtcgagct ggacggcgac gtaaacggcc acaagttcag cgtgtccggc gagggcgagg    2160
gcgatgccac ctacggcaag ctgaccctga agttcatctg caccaccggc aagctgcccg    2220
tgccctggcc caccctcgtg accaccctga cctacggcgt gcagtgcttc agccgctacc    2280
ccgaccacat gaagcagcac gacttcttca agtccgccat gcccgaaggc tacgtccagg    2340
agcgcaccat cttcttcaag gacgacggca actacaagac ccgcgccgag gtgaagttcg    2400
agggcgacac cctggtgaac cgcatcgagc tgaagggcat cgacttcaag gaggacggca    2460
acatcctggg gcacaagctg gagtacaact acaacagcca caacgtctat atcatggccg    2520
acaagcagaa gaacggcatc aaggtgaact tcaagatccg ccacaacatc gaggacggca    2580
gcgtgcagct cgccgaccac taccagcaga acacccccat cggcgacggc cccgtgctgc    2640
tgcccgacaa ccactacctg agcacccagt ccgccctgag caaagacccc aacgagaagc    2700
gcgatcacat ggtcctgctg gagttcgtga ccgccgccgg gatcactctc ggcatggacg    2760
agctgtacaa gtaaactagt gtcgactgct ttatttgtga aatttgtgat gctattgctt    2820
tatttgtaac cattaacaagc tgcaataaac aagttaacaa caacaattgc attcatttta    2880
tgtttcaggt tcaggggggag gtgtgggagg ttttttaaac agcggttcag cagaacatac    2940
cctccaccct cctccaggac cacgagaacc agcgactctt tgagatgctt ggacgaaaat    3000
gcttggtgag ctggggatct cctgcccccg ccccgtcccc accgtttctt cctcttcctc    3060
tcctccttct ctctcttccc ctcctccccgc tcctcctttc cctctccatc atctcctctc    3120
ctagaatttc ccgtcataat ccaccttcc caggaagatc tcaatgtcta cttgccttcc    3180
ctctggctgc agctcttcct ttgggcccat gactgtcatg aggcaggaag gaccaggtct    3240
ggctccaaga ccttgtggct accccctgacc agactccact gaccccctgct ttcctctccc    3300
agacgctggc cactgcagtt gttcagctgt acctggcgct gccccctgga gctgagcact    3360
ggaccaagga gcattgtggg gctgtgtgct tcgtgaagga taaccccag aagtcctact    3420
tcatccgcct ttacggacct caggtgacc cccaccccc gactggactt gcaagcgagt    3480
tctcaacccg caaacccaga tctgtgtcca tatgtgtcca tagcttcaag acctcagacc    3540
tgatcagtga atccctgagc cccagaacca aagactcatc cagatggcaa actctgactt    3600
gcctttctaa gtctgcaatg actggcccca gtctccgtat caagatctct aaagcccca    3660
gtattagtct gctgcctaag cctaatcttt tccacaaatt ccaataaatg agcactgtat    3720
ttgtacctga acctcaaatc tattctaaac tcaacatttt gcatcccagg aatctctcat    3780
```

```
caaaactcct gaaccccaga tgtttgccaa gctcctaagt cataaatctg ttcaacaaac 3840
cccaaagttg aatattccat tgatccttga actccaaatc tgtccttcta aatccacagc 3900
acagacccca gagttcccat ctagagcatg gctacgtaga taagtagcat ggcgggttaa 3960
tcattaacta caaggaaccc ctagtgatgg agttggccac tccctctctg cgcgctcgct 4020
cgctcactga ggccgggcga ccaaaggtcg cccgacgccc gggctttgcc cgggcggcct 4080
cagtgagcga gcgagcgcgc cagctggcgt aatagcgaag aggcccgcac cgatcgccct 4140
tcccaacagt tgcgcagcct gaatggcgaa tggcgattcc gttgcaatgg ctggcggtaa 4200
tattgttctg gatattacca gcaaggccga tagtttgagt tcttctactc aggcaagtga 4260
tgttattact aatcaaagaa gtattgcgac aacggttaat ttgcgtgatg gacagactct 4320
tttactcggt ggcctcactg attataaaaa cacttctcag gattctggcg taccgttcct 4380
gtctaaaatc cctttaatcg gcctcctgtt tagctcccgc tctgattcta acgaggaaag 4440
cacgttatac gtgctcgtca aagcaaccat agtacgcgcc ctgtagcggc gcattaagcg 4500
cggcgggtgt ggtggttacg cgcagcgtga ccgctacact tgccagcgcc ctagcgcccg 4560
ctcctttcgc tttcttccct tcctttctcg ccacgttcgc cggctttccc cgtcaagctc 4620
taaatcgggg gctcccttta gggttccgat ttagtgcttt acggcacctc gaccccaaaa 4680
aacttgatta gggtgatggt tcacgtagtg ggccatcgcc ctgatagacg gttttttcgcc 4740
ctttgacgtt ggagtccacg ttctttaata gtggactctt gttccaaact ggaacaacac 4800
tcaaccctat ctcggtctat tcttttgatt tataaggggat tttgccgatt tcggcctatt 4860
ggttaaaaaa tgagctgatt taacaaaaat ttaacgcgaa ttttaacaaa atattaacgt 4920
ttacaattta aatatttgct tatacaatct tcctgttttt ggggcttttc tgattatcaa 4980
ccggggtaca tatgattgac atgctagttt tacgattacc gttcatcgat tctcttgttt 5040
gctccagact ctcaggcaat gacctgatag ccttgtaga gacctctcaa aaatagctac 5100
cctctccggc atgaatttat cagctagaac ggttgaatat catattgatg gtgatttgac 5160
tgtctccggc ctttctcacc cgtttgaatc tttacctaca cattactcag gcattgcatt 5220
taaaatatat gagggttcta aaaatttta tccttgcgtt gaaataaagg cttctcccgc 5280
aaaagtatta cagggtcata atgtttttgg tacaaccgat ttagctttat gctctgagac 5340
tttattgctt aattttgcta attctcttgcc ttgcctgtat gatttattgg atgttggaat 5400
cgcctgatgc ggtattttct ccttacgcat ctgtgcggta tttcacaccg catatggtgc 5460
actctcagta caatctgctc tgatgccgca tagttaagcc agccccgaca cccgccaaca 5520
cccgctgacg cgccctgacg ggcttgtctg ctcccggcat ccgcttacag acaagctgtg 5580
accgtctccg ggagctgcat gtgtcagagg ttttcaccgt catcaccgaa acgcgcgaga 5640
cgaaagggcc tcgtgatacg cctattttta taggttaatg tcatgataat aatggtttct 5700
tagacgtcag gtggcacttt tcggggaaat gtgcgcggaa cccctatttg tttattttc 5760
taaatacatt caaatatgta tccgctcatg agacaataac cctgataaat gcttcaataa 5820
tattgaaaaa ggaagagtat gagtattcaa catttccgtg tcgcccttat tccctttttt 5880
gcggcatttt gccttcctgt ttttgctcac ccagaaacgc tggtgaaagt aaaagatgct 5940
gaagatcagt tgggtgcacg agtgggttac atcgaactgg atctcaacag cggtaagatc 6000
cttgagagtt ttcgccccga agaacgtttt ccaatgatga gcactttaa agttctgcta 6060
tgtggcgcgg tattatcccg tattgacgcc gggcaagagc aactcggtcg ccgcatacac 6120
tattctcaga atgacttggt tgagtactca ccagtcacag aaaagcatct tacggatggc 6180
atgacagtaa gagaattatg cagtgctgcc ataaccatga gtgataacac tgcggccaac 6240
ttacttctga caacgatcgg aggaccgaag gagctaaccg ctttttttgca caacatgggg 6300
gatcatgtaa ctcgccttga tcgttgggaa ccggagctga atgaagccat accaaacgac 6360
gagcgtgaca ccacgatgcc tgtagcaatg gcaacaacgt tgcgcaaact attaactggc 6420
gaactactta ctctagcttc ccggcaacaa ttaatagact ggatggaggc ggataaagtt 6480
gcaggaccac ttctgcgctc ggcccttccg gctggctggt ttattgctga taaatctgga 6540
gccggtgagc gtgggtctcg cggtatcatt gcagcactgg ggccagatgg taagccctcc 6600
cgtatcgtag ttatctacac gacggggagt caggcaacta tggatgaacg aaatagacag 6660
atcgctgaga taggtgcctc actgattaag cattggtaac tgtcagacca gtttactca 6720
tatatacttt agattgattt aaaacttcat ttttaattta aaaggatcta ggtgaagatc 6780
ctttttgata atctcatgac caaaatccct taacgtgagt tttcgttcca cctgagcgta 6840
gaccccgtag aaaagatcaa aggatcttct tgagatcctt tttttctgcg cgtaatctgc 6900
tgcttgcaaa caaaaaaacc accgctacca gcggtggttt gtttgccgga tcaagagcta 6960
ccaactcttt ttccgaaggt aactggcttc agcagagcgc agataccaaa tactgtcctt 7020
ctagtgtagc cgtagttagg ccaccacttc aagaactctg tagcaccgcc tacatacctc 7080
gctctgctaa tcctgttacc agtggctgct gccagtggcg ataagtcgtg tcttaccggg 7140
ttggactcaa gacgatagtt accggataag gcgcagcggt cgggctgaac ggggggttcg 7200
tgcacacagc ccagcttgga gcgaacgacc tacaccgaac tgagatacct acagcgtgag 7260
ctatgagaaa gcgccacgct tcccgaaggg agaaaggcgg acaggtatcc ggtaagcggc 7320
agggtcggaa caggagagcg cacgagggag cttccagggg gaaacgcctg gtatctttat 7380
agtcctgtcg ggtttcgcca cctctgactt gagcgtcgat ttttgtgatg ctcgtcaggg 7440
gggcggagcc tatggaaaaa cgccagcaac gcggcctttt tacggttcct ggccttttgc 7500
tggccttttg ctcacatgtt ctttcctgcg ttatcccctg attctgtgga taaccgtatt 7560
accgcctttg agtgagctga taccgctcgc cgcagccgaa cgaccgagcg cagcgagtca 7620
gtgagcgagg aagcggaaga gcgcccaata cgcaaaccgc ctctccccgc gcgttggccg 7680
attcattaat g                                                        7691
```

SEQ ID NO: 40          moltype = DNA   length = 6289
FEATURE                Location/Qualifiers
misc_feature           1..6289
                       note = pAAV.ATG.GFP (#1374)
source                 1..6289
                       mol_type = other DNA
                       organism = synthetic construct
SEQUENCE: 40

```
cagctgcgcg ctcgctcgct cactgaggcc gcccgggcaa agcccgggcg tcgggcgacc 60
tttggtcgcc cggcctcagt gagcgagcga gcgcgcagag agggagtggc caactccatc 120
actaggggtt ccttgtagtt aatgattaac ccgccatgct acttatctac gtagccatgc 180
tctagcggcc tcggcctctg cataaataaa aaaaattagt cagccatgag cttggacgcg 240
```

```
taggctcgtc ttgaactcct gacctcaagt gatccactcg tctcggcctc ccaaagtgct   300
gggattacag gtgtgagcta ttgtccccag ccaaaaggaa aagttttact gtagtaaccc   360
ttccggacta gggacctcgg gcctcagcct caggctacct aggtgcttta gaaaggaggc   420
cacccaggcc catgactact ccttgccaca gggagccctg cacacagatg tgctaagctc   480
tcgctgccag ccagagggag gagggtctga gccagtcaga aggagatggt ccccagagag   540
taagaaaggg ggaggaggac ccaagctgat ccaaaaggtg ggtctaagca gtcaagtgga   600
ggagggttcc aatctgatgg cggagggccc aagctcagcc taacgaggag gccaggccca   660
ccaaggggcc cctggaggac ttgtttccct tgtcccttgt ggtttttttgc atttcctgtt   720
cccttgctgc tcattgcgga agttcctctt cttaccctgc acccagagcc tcgccagaga   780
agacaagggc agaaagcacc atggtgagca agggcgagga gctgttcacc ggggtggtgc   840
ccatcctggt cgagctggac ggcgacgtaa acggccacaa gttcagcgtg tccggcgagg   900
gcgagggcga tgccacctac ggcaagctga ccctgaagtt catctgcacc accggcaagc   960
tgcccgtgcc ctggcccacc ctcgtgacca ccctgaccta cggcgtgcag tgcttcagcc  1020
gctaccccga ccacatgaag cagcacgact tcttcaagtc cgccatgccc gaaggctacg  1080
tccaggagcg caccatcttc ttcaaggacg acggcaacta caagacccgc gccgaggtga  1140
agttcgaggg cgacaccctg gtgaaccgca tcgagctgaa gggcatcgac ttcaaggagg  1200
acggcaacat cctggggcac aagctggagt acaactacaa cagccacaac gtctatatca  1260
tggccgacaa gcagaagaac ggcatcaagg tgaacttcaa gatccgccac aacatcgagg  1320
acggcagcgt gcagctcgcc gaccactacc agcagaacac ccccatcggc gacggccccg  1380
tgctgctgcc cgacaaccac tacctgagca cccagtccgc cctgagcaaa gaccccaacg  1440
agaagcgcga tcacatggtc ctgctggagt tcgtgaccgc cgccgggatc actctcggca  1500
tggacgagct gtacaagtaa gataatcaac ctctggatta caaaatttgt gaaagattga  1560
ctggtattct taactatgtt gctccttta cgctatgtgg atacgctgct ttaatgcctt  1620
tgtatcatgc tattgcttcc cgtatggctt tcattttctc ctccttgtat aaatcctggt  1680
tagttcttgc cacggcggaa ctcatcgccg cctgccttgc ccgctgctgg acaggggctc  1740
ggctgttggg cactgacaat tccgtgggtc gactgcttta tttgtgaaat ttgtgatgct  1800
attgctttat ttgtaaccat tataagctgc aataaacaag ttaacaacaa caattgcatt  1860
cattttatgt ttcaggttca ggggggaggtg tgggaggttt tttaaacagc ggttcagcag  1920
aacatacccc ccaccctcct ccaggaccac gagaaccagc gactctttga gatgcttgga  1980
cgaaaatgct tggtgagctg gggatctcct gcccccgccc cgtccccacc gtttcttcct  2040
cttcctctcc tccttctctc tcttcccctc ctcccgctcc tcctttccct ctccatcatc  2100
tcctctccta gaatttcccg tcataatcca cccttcccag gaagatctca atgtctactt  2160
gccttccctc tggctgcagc tcttccttg ggcccatgac tgtcatgagg caggaaggac  2220
caggtctggc tccaagacct tgtggctacc cctgaccaga ctccactgac ccctgctttc  2280
ctctcccaga cgctggccac tgcagttgtt cagctgtacc tggcgctgcc ccctggagct  2340
gagcactgga ccaaggagca ttgtggggct gtgtgcttcg tgaaggataa cccccagaag  2400
tcctacttca tccgccttta cggccttcag gtgaccccc cacccccgac tggacttgca  2460
agccagttct caacccgcaa acccagatct gtgtccatat gtgtccatag cttcaagtct  2520
agagcatgga tacgtagata agtagcatgg cgggttaatc attaactaca aggaaccct  2580
agtgatggag ttggccactc cctctctgcg cgctcgctcg ctcactgagg ccgggcgacc  2640
aaaggtcgcc cgacgcccgg gctttgcccg ggcggcctca gtgagcgagc gagcgcgcca  2700
gctggcgtaa tagcgaagag gcccgcaccg atcgccctcc caacagttg cgcagcctga  2760
atggcgaatg gcgattccgt tgcaatggct ggcggtaata ttgttctgga tattaccagc  2820
aaggccgata gtttgagttc ttctactcag gcaagtgatg ttattactaa tcaaagaagt  2880
attgcgacaa cggttaattt gcgtgatgga cagactcttt tactcggtgg cctcactgat  2940
tataaaaaca cttctcagga ttctggcgta ccgttcctgt ctaaatccc tttaatcggc  3000
ctcctgttta gctcccgctc tgattctaac gaggaaagca cgttatacgt gctcgtcaaa  3060
gcaaccatag tacgcgccct gtagcggcgc attaagcgcg gcgggtgtgg tggttacgcg  3120
cagcgtgacc gctacacttg ccagcgccct agcgcccgct cctttcgctt tcttcccttc  3180
ctttctcgcc acgttcgccg gctttccccg tcaagctcta aatcggggc tccctttagg  3240
gttccgattt agtgctttac ggcacctcga ccccaaaaaa cttgattagg gtgatggttc  3300
acgtagtggg ccatcgccct gatagacggt ttttcgccct ttgacgttgg agtccacgtt  3360
ctttaatagt ggactcttgt tccaaactgg aacaacactc aaccctatct cggtctattc  3420
ttttgattta taagggattt tgccgatttc ggcctattgg ttaaaaaatg agctgattta  3480
acaaaaattt aacgcgaatt ttaacaaaat attaacgttt acaatttaaa tatttgctta  3540
tacaatcttc ctgttttgg ggcttttctg attatcaacc ggggtacata tgattgacat  3600
gctagtttta cgattaccgt tcatcgattc tcttgtttgc tccagactct caggcaatga  3660
cctgatagcc tttgtagaga cctctcaaaa atagctaccc tctccggcat gaatttatca  3720
gctagaacga ttgaatatca tattgatggt gatttgactg tctccggcct ttctcacccg  3780
tttgaatctt tacctacaca ttactcaggc attgcattta aaatatatga gggttcaaa  3840
aattttatc cttgcgttga aataaaggct tctcccgcaa aagtattaca gggtcataat  3900
gtttttggta caaccgattt agctttatgc tctgaggctt tattgcttaa ttttgctaat  3960
tctttgcctt gcctgtatga tttattggat gttggaatcg cctgatgcgg tattttctcc  4020
ttacgcatct gtgcggtatt tcacaccgca tatggtgcac tctcagtaca atctgctctg  4080
atgccgcata gttaagccag ccccgacacc cgccaacacc cgctgacgcg ccctgacggg  4140
cttgtctgct cccggcatcc gcttacgac aagctgtgac cgtctccggg agctgcatgt  4200
gtcagaggtt ttcaccgtca tcaccgaaac gcgcgagacg aaagggcctc gtgatacgcc  4260
tatttttata ggttaatgtc atgataataa tggtttctta gacgtcaggt ggcactttc  4320
ggggaaatgt gcgcggaacc cctatttgtt tatttttcta aatacattca aatatgtatc  4380
cgctcatgag acaataaccc tgataaatgc ttcaataata ttgaaaaagg aagagtatga  4440
gtattcaaca tttccgtgtc gcccttattc ccttttttgc ggcattttgc cttcctgttt  4500
ttgctcaccc agaaacgctg gtgaaagtaa aagatgctga agatcagttg ggtgcacgag  4560
tgggttacat cgaactggat ctcaacagcg gtaagatcct tgagagtttt cgccccgaag  4620
aacgttttcc aatgatgagc acttttaaag ttctgctatg tggcgcggta ttatcccgta  4680
ttgacgccgg gcaagagcaa ctcggtcgcc gcatacacta ttctcagaat gacttggttg  4740
agtactcacc agtcacagaa aagcatctta cggatggcat gacagtaaga gaattatgca  4800
gtgctgccat aaccatgagt gataacactg cggccaactt acttctgaca acgatcggag  4860
gaccgaagga gctaaccgct ttttttgcaca acatggggga tcatgtaact cgccttgatc  4920
gttgggaacc ggagctgaat gaagccatac caaacgacga gcgtgacacc acgatgcctg  4980
```

-continued

```
tagcaatggc aacaacgttg cgcaaactat taactggcga actacttact ctagcttccc   5040
ggcaacaatt aatagactgg atggaggcgg ataaagttgc aggaccactt ctgcgctcgg   5100
cccttccggc tggctggttt attgctgata aatctggagc cggtgagcgt gggtctcgcg   5160
gtatcattgc agcactgggg ccagatggta agccctccg tatcgtagtt atctacacga     5220
cggggagtca ggcaactatg gatgaacgaa atagacagat ggtcgagata ggtgcctcac   5280
tgattaagca ttggtaactg tcagaccaag tttactcata tatactttag attgatttaa   5340
aacttcattt ttaatttaaa aggatctagg tgaagatcct ttttgataat ctcatgacca   5400
aaatcccttaa acgtgagttt tcgttccact gagcgtcaga ccccgtagaa aagatcaaag   5460
gatcttcttg agatccttt tttctgcgcg taatctgctg cttgcaaaca aaaaaaccac     5520
cgctaccagc ggtggtttgt ttgccggatc aagagctacc aactcttttt ccgaaggtaa   5580
ctggcttcag cagagcgcag ataccaaata ctgtccttct agtgtagccg tagttaggcc   5640
accacttcaa gaactctgta gcaccgccta catacctcgc tctgctaatc ctgttaccag   5700
tggctgctgc cagtggcgat aagtcgtgtc ttaccgggtt ggactcaaga cgatagttac   5760
cggataaggc gcagcggtcg ggctgaacgg ggggttcgtg cacacagccc agcttggagc   5820
gaacgaccta caccgaactg agatacctac agcgtgagct atgagaaagc gccacgcttc   5880
ccgaagggag aaaggcggac aggtatccgg taagcggcag ggtcggaaca ggagagcgca   5940
cgagggagct tccaggggga aacgcctggt atctttatag tcctgtcggg tttcgccacc   6000
tctgacttga gcgtcgattt ttgtgatgct cgtcaggggg gcggagccta tggaaaaacg   6060
ccagcaacgc ggcctttta cggttcctgg ccttttgctg gccttttgct cacatgttct     6120
ttcctgcgtt atccctgat tctgtggata accgtattac cgcctttgag tgagctgata     6180
ccgctcgccg cagccgaacg accgagcgca gcgagtcagt gagcgaggaa gcggaagagc   6240
gcccaatacg caaaccgcct ctccccgcgc gttggccgat tcattaatg              6289
```

SEQ ID NO: 41          moltype = DNA   length = 7084
FEATURE                Location/Qualifiers
misc_feature           1..7084
                       note = pAAV.ATG.coWAS (#1380)
source                 1..7084
                       mol_type = other DNA
                       organism = synthetic construct
SEQUENCE: 41
```
cagctgcgcg ctcgctcgct cactgaggcc gcccgggcaa agcccgggcg tcgggcgacc   60
tttggtcgcc cggcctcagt gagcgagcga gcgcgcagag agggagtggc caactccatc   120
actaggggtt ccttgtagtt aatgattaac ccgccatgct acttatctac gtagccatgc   180
tctagcggcc tcggcctctg cataaataaa aaaaattagt cagccatgag cttggacgcg   240
taggctcgtc ttgaactcct gacctcaagt gatccactcg tctcggcctc ccaaagtgct   300
gggattacag gtgtgagcta ttgtccccag ccaaaaggaa aagttttact gtagtaaccc   360
ttccggacta gggacctcgg gcctcagcct caggctacct aggtgcttta gaaaggaggc   420
caeccaggcc catgactact ccttgccaca gggagccctg cacacagatg tgctaagctc   480
tcgctgccag ccagagggag gagggtctga gccagtcaga aggagatggg ccccagagag   540
taagaaaggg ggaggaggac ccaagctgat ccaaaaggtg ggtctaagca gtcaagtgga   600
ggagggttcc aatctgatgg cggagggccc aagctcagcc taacgaggag gccaggccca   660
ccaagggacc cctggaggac ttgtttccct tgtcccttgt ggtttttgc atttcctgtt     720
cccttgctgc tcattgcgga agttcctctt cttaccctgc acccagagcc tcgccagaga   780
agacaagggc agaaagcacc atgggaggaa gacccggcgg ccgaggagcg ccagcagtgc     840
aacaaaacat tccgtcaacc ctgctgcagg accacgaaaa ccagaggctg tttgaaatgt   900
tgggacggaa gtgtctcact ctcgccacag ccgtcgtcca gctttatctt gcgcttcctc   960
ccggtgctga gcattggact aaagagcatt gcggcgcggt ctgtttgtc aaggataatc     1020
cccaaaaatc atatttcatt aggttgtacg gactccaagc tggacgcctt ctgtgggaac   1080
aagaactcta tagccagctc gtatatagca caccgacccc tttcttccat actttcgcgg   1140
gagacgactg tcaggcgggc ttgaactttg cggacgaggg tgaagctcag gctttccgag   1200
cattggttca agaaaaaatc cagaaaagaa atcagcgaca gtccggagat cgccggcagc   1260
tgccgccgcc acctacaccg gccaatgagg aacggagggg aggcctcccg ccacttccat   1320
tgcatccagg cggcgatcag ggtgggccac cagtagggcc cttgagtttg ggtctcgcta   1380
ctgtggatat acagaacccg gacataacat ctagccgcta ccgcggactg ccggctccag   1440
gtccgtcccc cgctgataaa aagcgctccg gcaaaaagaa gatatctaaa gcagatatcg   1500
gtgcgccctc cggtttcaag catgtctccc atgtaggatg ggaccccgcaa aatggattcg   1560
acgttaataa cctcgatccg gacctgagga gtctcttctc tcgcgcgggt atcagcgagg   1620
cacagctta c tgatgccgaa acaagtaagt tgatatacga ctttatcgag gatcaaggag   1680
ggctggaagc ggtcaggcaa gaaatgcggc gacaagaacc tttgcccccg ccccgcccc     1740
cgtccagagg cgggaaccag cttccacgcc cacctatcgt tggagggaat aaaggcaggt   1800
ctgggccact ccctccggta ccgttgggga tcgctccacc gcctcctacg cctaggggac   1860
ccccgcctcc tggtcggggg ggaccgcccc ctccgccgcc tccagccact ggtcgaagtg   1920
gaccctccc gcctcctcca cccggcgccg ggggccacct ggccacct cctcct ccgac     1980
ccccaccgcc tccccttct tccggcaacg gtcccgcacc tccgcccctc cctccggcat     2040
tggtccccgc ggggggcctc gcgctggtg gtggccgggg tgcacttctg gatcaaatcc   2100
gacagggcat acagttgaat aagacgcccg gcgcccctga aagctcagct ctgcaaccgc   2160
cgcctcagtc ctctgaaggg ttggtaggcg cgctcatgca tgtaatgcag aagcgcagtc   2220
gcgctatcca ctcatcagat gaaggtgaag accaggccgg tgacgaggac gaagacgatg   2280
aatgggacga ttgactgaac tgaactagtg tcgacgataa tcaacctctg gattacaaaa   2340
tttgtgaaag attgactggt attcttaact atgttgctcc ttttacgcta tgtggatacg   2400
ctgctttaat gcctttgtat catgctattg cttcccgtat ggctttcatt ttctcctcct   2460
tgtataaatc ctggttagtt cttgccacgg cggaactcat cgccgcctgc cttgcccgct   2520
gctggacagg ggctcggctg ttgggcactg acaattccgt gggtcgactg ctttatttgt   2580
gaaatttgtg atgctattgc tttatttgta accattataa gctgcaataa acaagttaac   2640
aacaacaatt gcattcattt tatgtttcag gttcaggggg aggtgtggga ggttttttaa   2700
acagcggttc agcagaacat accctccacc ctcctccagg accacgagaa ccagcgactc   2760
tttgagatgc ttggacgaaa atgcttggtg agctggggat ctcctgcccc cgccccgtcc   2820
ccaccgtttc ttcctcttcc tctcctcctt ctctctcttc ccctcctccc gctcctcctt   2880
```

```
tccctctcca tcatctcctc tcctagaatt tcccgtcata atccaccctt cccaggaaga  2940
tctcaatgtc tacttgcctt ccctctggct gcagctcttc ctttgggccc atgactgtca  3000
tgaggcagga aggaccaggt ctggctccaa gaccttgtgg ctacccctga ccagactcca  3060
ctgacccctg ctttcctctc ccagacgctg gccactgcag ttgttcagct gtacctggcg  3120
ctgccccctg gagctgagca ctggaccaag gagcattgtg gggctgtgtg cttcgtgaag  3180
gataacccc agaagtccta cttcatccgc ctttacggcc ttcaggtgac cccccaccc  3240
ccgactggac ttgcaagcca gttctcaacc cgcaaaccca gatctgtgtc catatgtgtc  3300
catagcttca agtctagagc atggctacgt agataagtag catggcgggt taatcattaa  3360
ctacaaggaa cccctagtga tggagttggc cactccctct ctgcgcgctc gctcgctcac  3420
tgaggccggg cgaccaaagg tcgcccgacg cccgggcttt gcccgggcgg cctcagtgag  3480
cgagcgagcg cgccagctgg cgtaatagcg aagaggcccg caccgatcgc ccttcccaac  3540
agttgcgcag cctgaatggc gaatggcgat tccgttgcaa tggctggcgg taatattgtt  3600
ctggatatta ccagcaaggc cgatagtttg agttcttcta ctcaggcaag tgatgttatt  3660
actaatcaaa gaagtattgc gacaacggtt aatttgcgtg atggacagac tcttttactc  3720
ggtggcctca ctgattataa aaacacttct caggattctg gcgtaccgtt cctgtctaaa  3780
atcccttta tcggcctcct gtttagctcc cgctctgatt ctaacgagga aagcacgtta  3840
tacgtgctcg tcaaagcaac catagtacgc gccctgtagc ggcgcattaa gcgcggcggg  3900
tgtggtggtt acgcgcagcg tgaccgctac acttgccagc gccctagcgc ccgctccttt  3960
cgctttcttc ccttcctttc tcgccacgtt cgccggcttt ccccgtcaag ctctaaatcg  4020
ggggctccct ttagggttcc gatttagtgc tttacggcac ctcgacccca aaaaacttga  4080
ttagggtgat ggttcacgta gtgggccatc gccctgatag acgttttttc gccctttgac  4140
gttggagtcc acgttcttta atagtggact cttgttccaa actggaacaa cactcaaccc  4200
tatctcggtc tattctttg atttataagg gattttgccg atttcggcct attggttaaa  4260
aaatgagctg atttaacaaa aatttaacgc gaattttaac aaaatattaa cgtttacaat  4320
ttaaatattt gcttatacaa tcttcctgtt tttgggggctt ttctgattat caaccggggt  4380
acatatgatt gacatgctag ttttacgatt accgttcatc gattctcttg tttgctccag  4440
actctcaggc aatgacctga tagcctttgt agagacctct caaaaatagc taccctctcc  4500
ggcatgaatt tatcagctag aacggttgaa tatcatattg atggtgattt gactgtctcc  4560
ggcctttctc acccgtttga atctttacct acacattact caggcattgc atttaaaata  4620
tatgagggtt ctaaaaattt ttatccttgc gttgaaataa aggcttctcc cgcaaaagta  4680
ttacagggtc ataatgtttt tggtacaacc gatttagctt tatgctctga ggctttattg  4740
cttaattttg ctaattcttt gccttgcctg tatgatttat tggatgttgg aatcgcctga  4800
tgcggtattt tctccttacg catctgtgcg gtatttcaca ccgcatatgg tgcactctca  4860
gtacaatctg ctctgatgcc gcatagttaa gccagccccg acacccgcca cacccgtg  4920
acgcgccctg acgggcttgt ctgctcccgg catccgctta cagacaagct gtgaccgtct  4980
ccggagctg catgtgtcag aggttttcac cgtcatcacc gaaacgcgcg agacgaaagg  5040
gcctcgtgat acgcctattt ttataggtta atgtcatgat aataatggtt tcttagacgt  5100
caggtggcac ttttcgggga aatgtgcgcg gaacccctat ttgtttattt ttctaaatac  5160
attcaaatat gtatccgctc atgagacaat aaccctgata aatgcttcaa taatattgaa  5220
aaaggaagag tatgagtatt caacatttcc gtgtcgccct tattcccttt tttgcggcat  5280
tttgccttcc tgtttttgct cacccagaaa cgctggtgaa agtaaaagat gctgaagatc  5340
agttgggtgc acgagtgggt tacatcgaac tggatctcaa cagcggtaag atccttgaga  5400
gttttcgccc cgaagaacgt tttccaatga tgagcacttt taaagttctg ctatgtggcg  5460
cggtattatc ccgtattgac gccgggcaag agcaactcgg tcgccgcata cactattctc  5520
agaatgactt ggttgagtac tcaccagtca cagaaaagca tcttacggat ggcatgacag  5580
taagagaatt atgcagtgct gccataacca tgagtgataa cactgcggcc aacttacttc  5640
tgacaacgat cggaggaccg aaggagctaa ccgcttttt gcacaacatg ggggatcatg  5700
taactcgcct tgatcgttgg gaaccggagc tgaatgaagc cataccaaac gacgagcgtg  5760
acaccacgat gcctgtagca atggcaacaa cgttgcgcaa actattaact ggcgaactac  5820
ttactctagc ttcccggcaa caattaatag actggatgga ggcggataaa gttgcaggac  5880
cacttctgcg ctcggccctt ccggctggct ggtttattgc tgataaatct ggagccggtg  5940
agcgtgggtc tcgcggtatc attgcagcac tggggccaga tggtaagccc tcccgtatcg  6000
tagttatcta cacgacgggg agtcaggcaa ctatggatga acgaaataga cagatcgctg  6060
agataggtgc ctcactgatt aagcattggt aactgtcaga ccaagtttac tcatatatac  6120
tttagattga tttaaaactt catttttaat ttaaaaggat ctaggtgaag atcctttttg  6180
ataatctcat gaccaaaatc ccttaacgtg agttttcgtt ccactgagcg tcagaccccg  6240
tagaaaagat caaaggatct tcttgagatc ctttttttct gcgcgtaatc tgctgcttgc  6300
aaacaaaaaa accaccgcta ccagcggtgg tttgtttgcc ggatcaagag ctaccaactc  6360
tttttccgaa ggtaactggc ttcagcagag cgcagatacc aaatactgtc cttcagtgt  6420
agccgtagtt aggccaccac ttcaagaact ctgtagcacc gcctacatac ctcgctctgc  6480
taatcctgtt accagtggct gctgccagtg gcgataagtc gtgtcttacc gggttggact  6540
caagacgata gttaccggat aaggcgcagc ggtcgggctg aacggggggt tcgtgcacac  6600
agcccagctt ggagcgaacg acctacaccg aactgagata cctacagcgt gagctatgag  6660
aaagcgccac gcttcccgaa gggagaaagg cggacaggta tccggtaagc ggcagggtcg  6720
gaacaggaga gcgcacgagg gagcttccag ggggaaacgc ctggtatctt tatagtcctg  6780
tcgggtttcg ccacctctga cttgagcgtc gatttttgtg atgctcgtca gggggcgga  6840
gcctatgaa aacgccagc aacgcggcct ttttacggtt cctggccttt tgctggcctt  6900
ttgctcacat gttctttcct gcgttatccc ctgattctgt ggataaccgt attaccgcct  6960
ttgagtgagc tgataccgct cgccgcagcc gaacgaccga gcgcagcgag tcagtgagcg  7020
aggaagcgga agagcgccca atacgcaaac cgcctctccc gcgcgttggg ccgattcatt  7080
aatg                                                                7084
```

THERAPEUTIC GENOME EDITING IN WISKOTT-ALDRICH SYNDROME AND X-LINKED THROMBOCYTOPENIA

CROSS REFERENCE TO RELATED APPLICATIONS

This application is a continuation of U.S. application Ser. No. 16/605,748 filed Oct. 16, 2019 which is the U.S. National Phase of PCT Int. App. No. PCT/US2018/028442, filed on Apr. 19, 2018, designating the United States of America and published in the English language as WO 2018/195360, which claims priority to U.S. Prov. App. No. 62/488,249, filed on Apr. 21, 2017, which are each expressly incorporated by reference in its entirety.

REFERENCE TO SEQUENCE LISTING

The present application is being filed along with a Sequence Listing in electronic format. The Sequence Listing is provided as a file entitled SCRI149C1SEQLIST, created Apr. 5, 2023, which is approximately 182471 bytes in size. The information provided in the electronic format of the Sequence Listing is incorporated herein by reference in its entirety.

FIELD

Alternatives herein relate generally to gene editing in primary human hematopoietic stem cells. More particularly, alternatives herein relate to nucleic acids and vectors that are configured to provide efficient homology directed repair of genes, and methods of repairing genetic deficiencies, such as X-linked recessive disorders.

BACKGROUND

Wiskott-Aldrich syndrome (WAS) is an inherited primary immunodeficiency caused by mutations in the WAS gene, which encodes a protein that regulates the actin cytoskeleton leading to altered signaling function and/or development in multiple hematopoietic cell lineages. WAS is an X-linked recessive disease, affecting approximately one in 250,000 males. The disease is characterized by eczema, thrombocytopenia, and immune deficiency. WAS is caused by a mutation in the WAS gene, resulting in mutated or absent forms of the WAS protein (WASp).

X-linked thrombocytopenia (XLT) is an inherited clotting disorder related to WAS. XLT primarily affects the circulatory system by reducing the platelet counts in the blood, and also reducing the platelet size compared to normal or healthy individuals, which compromises the clotting process. XLT is caused by a mutation in the WAS gene, resulting in decreased, absent, or altered WASp.

WASp is an activator of the actin nucleator Arp2/3 complex in vitro and is expressed exclusively in hematopoietic cells. WASp is believed to serve as a key integrator between surface receptors and the cytoskeleton of leukocytes.

Currently, therapies for individuals with WAS or XLT focus on the symptoms. The only available curative therapy for WAS or XLT is allogeneic stem cell transplantation. Viral-based gene replacement is also being explored in several current clinical trials but the need for more therapies for WAS and XLT is manifest.

SUMMARY

Some alternatives relate to therapeutic approaches designed to correct or repair the endogenous WAS locus in autologous hematopoietic stem cells. Some alternatives include compositions and methods, which comprise transcription activator-like effector nucleases (TALENs) and clustered regularly interspaced short palindromic repeats (CRISPR)/Cas that are configured to edit the WAS locus in primary human hematopoietic cells. Some alternatives also relate to co-delivery of a nuclease and an AAV donor for modifying endogenous WAS locus in primary human hematopoietic cells.

Some alternatives concern a nucleic acid for homology directed repair (HDR) of the Wiskott-Aldrich Syndrome (WAS) gene. In some alternatives, the nucleic acid comprises a first sequence encoding a WAS gene, a second sequence encoding one or more guide RNA cleavage sites, and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nuclease binding sites is a clustered regularly interspaced short palindromic repeats (CRISPR) associated protein 9 (Cas9) binding site. In some alternatives, the nucleic acid further comprises one or more enhancer elements. In some alternatives, the nucleic acid further comprises homology arm sequences. In some alternatives, the nucleic acid further comprises a nucleic acid sequence encoding a promoter.

Some alternatives relate to a vector for promoting HDR of WAS protein (WASp) expression in a cell. In some alternatives, the vector comprises a first sequence encoding a WAS gene, a second sequence encoding one or more guide RNA cleavage sites, and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34$^+$ HSC.

Some alternatives relate to a system for promoting HDR of WAS protein (WASp) expression in a cell. In some alternatives, the system comprises a vector and a nucleic acid encoding a nuclease. In some alternatives, the nuclease is a TALEN nuclease. In some alternatives, the nuclease is a Cas nuclease. In some alternatives, the vector and nucleic acid are configured for co-delivery to the cell. In some alternatives, co-delivery to the cell modifies endogenous WAS locus. In some alternatives, the cell is a primary human hematopoietic cell.

Some alternatives relate to a cell for expressing a WASp. In some alternatives, the cell comprises a nucleic acid. In some alternatives, the nucleic acid comprises a first sequence encoding a WAS gene, a second sequence encoding a promoter, a third sequence encoding one or more guide RNA cleavage sites, and a fourth sequence encoding one or more nuclease binding sites. In some alternatives, the nucleic acid is in a vector. In some alternatives, the vector is an AAV. In some alternatives, the vector is a scAAV. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC.

Some alternatives relate to methods of promoting HDR of a WAS gene in a subject in need thereof (e.g., a subject identified or selected as one that would receive a benefit from HDR of a WAS gene, such as a subject having XLT). In some alternatives, the method comprises administering to a subject in need thereof a cell as described herein or a vector as described herein and administering to the subject a nuclease. In some alternatives, the nuclease is a TALEN nuclease. In some alternatives, the nuclease is a Cas nuclease. In some alternatives, the nuclease is co-administered to the subject with the cell or with the vector. In some alternatives, the cell is from the subject. In some alternatives, the cell is genetically modified by introducing a nucleic acid as described herein or a vector as described herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC. In some alternatives, the subject is male. In some alternatives, the subject is identified or selected as one that is suffering from Wiskott-Aldrich syndrome (WAS). In some alternatives, the subject is identified or selected as one that is suffering from X-linked thrombocytopenia (XLT).

Some alternatives provided herein relate to a method of treating, inhibiting, or ameliorating WAS and/or XLT or disease symptoms associated with WAS and/or XLT in a subject in need thereof. In some alternatives, the method comprises administering to a subject a cell as described herein or a vector as described herein, administering to the subject a nuclease, and optionally identifying or selecting the subject as one that would benefit from receiving a therapy for WAS and/or XLT or disease symptoms associated with WAS and/or XLT and/or, optionally measuring an improvement in the progression of WAS and/or XLT or an improvement in a disease symptom associated with WAS and/or XLT in said subject. In some alternatives, the nuclease is a TALEN nuclease. In some alternatives, the nuclease is a CRISPR/Cas nuclease. In some alternatives, the nuclease is co-administered to the subject with the cell or with the vector. In some alternatives, the cell is from the subject. In some alternatives, the cell is genetically modified by introducing a nucleic acid as described herein or a vector as described herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC In some alternatives, the subject is male. In some alternatives, the method improves thrombocytopenia. In some alternatives, the method increases platelet counts. In some alternatives, the subject is identified or selected as one that is suffering from Wiskott-Aldrich syndrome (WAS). In some alternatives, the subject is identified or selected as one that is suffering from X-linked thrombocytopenia (XLT).

In a first aspect, a nucleic acid for homology directed repair (HDR) of Wiskott-Aldrich Syndrome (WAS) gene is provided, the nucleic acid comprising: a first sequence encoding a WAS gene; a second sequence encoding one or more guide RNA cleavage sites; and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the nucleic acid further comprises one or more enhancer elements. In some alternatives, the nucleic acid further comprises homology arm sequences. In some alternatives, the nucleic acid further comprises a nucleic acid sequence encoding a promoter.

In a second aspect, a vector for promoting HDR of WAS protein (WASp) expression in a cell is provided, the vector comprising: a first sequence encoding a WAS gene; a second sequence encoding one or more guide RNA cleavage sites; and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34+ HSC.

In a third aspect, a system for promoting HDR of WAS protein (WASp) expression in a cell is provided, the system comprising a vector of any one of the alternatives herein and a nucleic acid encoding a nuclease. In some alternatives, the nuclease is a TALEN nuclease. In some alternatives, the nuclease is a Cas nuclease. In some alternatives, the vector and nucleic acid are configured for co-delivery to the cell. In some alternatives, co-delivery to the cell modifies endogenous WAS locus. In some alternatives, the cell is a primary human hematopoietic cell.

In a fourth aspect, a cell for expressing a WASp is provided, the cell comprising: a nucleic acid, which comprises: a first sequence encoding a WAS gene; a second sequence encoding a promoter; a third sequence encoding one or more guide RNA cleavage sites; and a fourth sequence encoding one or more nuclease binding sites. In some alternatives, the nucleic acid is in a vector. In some alternatives, the vector is an AAV. In some alternatives, the AAV is a scAAV. In some alternatives, cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC.

In a fifth aspect, a method of promoting HDR of a WAS gene in a subject in need thereof, the method comprising: administering to a subject the cell or a vector of any one of the alternatives herein; and administering to the subject a nuclease. The cell comprises: a nucleic acid, which comprises: a first sequence encoding a WAS gene; a second sequence encoding a promoter; a third sequence encoding one or more guide RNA cleavage sites; and a fourth sequence encoding one or more nuclease binding sites. The vector comprises: a first sequence encoding a WAS gene; a second sequence encoding one or more guide RNA cleavage sites; and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34+ HSC. In some alternatives, the nucleic acid is in a vector. In some alternatives, the vector is an AAV. In some alternatives, the AAV is a scAAV. In some alternatives, cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC In some alternatives, the nuclease is a TALEN nuclease. In some alternatives, the nuclease is a Cas nuclease. In some alternatives, the nuclease is co-administered to the subject with the cell or with the vector. In some alternatives, the cell is from the subject and, wherein the cell is genetically modified by introducing the nucleic acid or the vector of any one of the alternatives described herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC. In some alternatives, the subject is male. In some alternatives, the subject is suffering from Wiskott-Aldrich syndrome (WAS). In some alternatives, the subject is suffering from X-linked thrombocytopenia (XLT).

In a sixth aspect, a method of treating, inhibiting, or ameliorating WAS and/or XLT or disease symptoms associated with WAS and/or XLT in a subject in need thereof, the method comprising: administering to a subject the cell or a vector of any one of the alternatives described herein; administering to the subject a nuclease; and optionally identifying the subject as one that would benefit from receiving a therapy for WAS and/or XLT or disease symptoms associated with WAS and/or XLT and/or, optionally measuring an improvement in the progression of WAS and/or XLT or an improvement in a disease symptom associated with WAS and/or XLT in said subject. The cell comprises: a nucleic acid, which comprises: a first sequence encoding a WAS gene; a second sequence encoding a promoter; a third sequence encoding one or more guide RNA cleavage sites; and a fourth sequence encoding one or more nuclease binding sites. The vector comprises: a first sequence encoding a WAS gene; a second sequence encoding one or more guide RNA cleavage sites; and a third sequence encoding one or more nuclease binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the nuclease is a TALEN nuclease. In some alternatives, the nuclease is a CRISPR/Cas nuclease. the nuclease is co-administered to the subject with the cell or with the vector. the cell is from the subject, wherein the cell is genetically modified by introducing the nucleic acid or the vector of any one of the alternatives described herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC. In some alternatives, the subject is male. In some alternatives, the method improves thrombocytopenia. In some alternatives, the method increases platelet counts.

BRIEF DESCRIPTION OF THE DRAWINGS

FIG. 1A shows a schematic of the WAS locus with guides and TALENs annotated. Shown are the location of the WAS TALENs (TALEN #1 (T1) and TALEN #2 (T2)) and guide RNA (G1, G2, G3, and G4) cleavage sites within the human WAS gene. Scheme not drawn to scale. FIG. 1B depicts the disruption of the WAS locus with TALENs and CRISPR guides. Shown is the percentage of NHEJ events in primary human T cells detected using the T7 assay, 5 days post-transfection with TALEN mRNAs (T1, T2) or with Cas9 mRNA co-delivered with scAAV expressing gRNAs (G1-4). N=3, represents the number of independent experiments. TALEN #1 and G1 were selected for all further experiments.

FIG. 2A shows a schematic representation of the WAS locus and AAV donor templates used in targeting with WAS TALENs. Small boxes represent TALEN forward (T-for) and reverse (T-rev) binding sites. Homology arms are also depicted. X represents mutation of the T preceding the TALEN binding site designed to abolish cleavage by TALEN in #1244 vector. The #1262 vector has the entire region between the exon 1 up to the reverse TALEN binding site deleted. FIG. 2B depicts a timeline of gene editing procedure beginning with bead stimulation of primary T cells. AAVs were added at 20% of culture volume. FIGS. 2C and 2D depict time course of GFP expression indicative of HDR (FIG. 2C) and cell viability (FIG. 2D). FIG. 2E shows cells that were also transfected with TALENs and transduced with an AAV vector with an MND promoter driven blue fluorescent protein (BFP) without any homology arms. Fluorescence from this vector at day 15 is indicative of random integration of the vector. Fluorescence from this vector at Day 15 is indicative of random integration of the vector. FIG. 2F shows representative FACS plots with GFP expression at day 15 post co-delivery of TALEN mRNA and AAV donor templates. FIG. 2G provides additional representative FACS plots showing GFP expression at Day 15. N=3 and represents the number of independent experiments performed using cells from three different donors. FIG. 2H shows results from a test for nuclease specificity utilizing AAV without homology arms. Primary T cells transfected with TALENs and transduced with an AAV vector with an MND promoter driven blue fluorescent protein (BFP) without any homology arms. Fluorescence from this vector at day 15 is indicative of random integration. n=3 and represents the number of independent experiments performed using cells from 3 different donors. Data are presented as mean±SEM. FIG. 2I shows representative FACS plots with GFP expression at day 15 post co-delivery of TALEN mRNA and AAV donor templates. N=3 and represents the number of independent experiments performed using cells from three different donors.

FIG. 3A shows a schematic of editing of the WAS locus using CRISPR in primary T cells. Schematic illustration of the scAAV guide RNA vector (G), donor template DT (PAM mutated) and AAV vector containing both guide and donor sequences (DTG). PAM site was mutated in both DT and DTG templates to abolish cleavage by the guide Shown is a schematic illustration of the scAAV guide RNA vector (#1189 (G)), donor template (#1201 (PAM mutated)), and AAV vector containing both guide and donor sequences (#1215 (DTG)). Both the PAM mutated donor template and the DTG AAVs have the PAM site mutated to abolish cleavage by guide. FIGS. 3B and 3C provide graphs showing time course of % GFP+ cells (FIG. 3B) and cell viability (FIG. 3C). 10% and 20% represent the % culture volume #1215 AAV added. All other AAVs were added at 10% of culture volume. FIG. 3D provides graphs depicting BFP expression when Cas9, guide and MND.BFP vector with no homology arms were delivered. 20% represent the % of culture volume AAVs were added at. AAVs were added at 10% of culture volume unless otherwise specified. FIG. 3E provides FACS plots showing GFP expression at Day 15. N=3 and represents the number of independent experiments performed using cells from three donors. FIG. 3F Bar graphs showing time course of GFP expression. % HR is reported as % GFP at day 15. n=3 and represents the number of independent experiments performed using cells from 3 different donors. Data are presented as mean±SEM. 20% represent the % culture volume #1215 AAV added. All other AAVs were added at 10% of culture volume. % HR is reported as % GFP at day 15. n=3 and represents the number of independent experiments performed using cells from 3 different donors. Data are presented as mean±SEM. FIG. 3G shows results from a test for nuclease specificity utilizing AAV without homology arms. Bar graphs depict BFP expression when Cas9, guide and MND.BFP vector with no homology arms were delivered. n=3 and represents the number of independent experiments performed using cells from 3 different donors. Data are presented as mean±SEM. FIG. 3H provides representative FACS plots showing GFP expression at day 15.

FIG. 4A depicts a timeline of gene editing procedure for human mobilized adult CD34$^+$ cells. FIGS. 4B and 4C depicts time course of GFP expression indicative of HDR (FIG. 4B) and viability (FIG. 4C). FIG. 4D depicts representative FACS plots showing GFP expression at Day 5.

FIG. 5A shows disruption of the WAS locus in human CD34$^+$ cells using TALENs or RNP. Mobilized human CD34$^+$ cells were cultured in SCGM media supplemented with TPO, SCF, FLT3L (100 ng/mL) and IL3 (60 ng/mL) for 48 hours, followed by electroporation using Neon electroporation system with either 1 ug of each TALEN monomer mRNA or Ribonucleoprotein complex (RNP) of Cas9 protein and single guide RNA mixed in 1:1.2 ratio. The sgRNA was purchased from Trilink BioTechnologies and has chemically modified nucleotides at the three terminal positions at 5' and 3' ends. The cells were cultured for 5 days and genomic DNA was extracted. The region surrounding the cut site for WAS TALEN and guide was amplified and cloned into pJET cloning vector. Colony sequencing was performed to quantify % cleavage at the cut site by analyzing the indels. N=3 and represents the number of independent experiments performed using cells from three donors. FIG. 5B shows results from HDR editing of the WAS locus in CD34$^+$ HSCs using co-delivery of TALEN mRNA or RNP and AAV donor template. FIG. 5C shows FACS plots depicting GFP expression from Mock, AAV or AAV plus TALEN treated CD34+ cells (top row) or AAV+ RNP treated cells (bottom row) 5 days post editing. FIG. 5D shows the cell viability of the edited cells. Bar graphs represent viability of mock and edited cells 2 days post editing. N=8 for RNP, n=12 for TALEN and represents >4 independent donors. FIG. 5E shows colony forming unit (CFU) assay for TALEN edited CD34$^+$ cells and FIG. 5F shows the results from a CFU assay for RNP edited CD34$^+$ cells. Briefly, 500 cells from edited or untreated (mock) were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 experiments and 2 donors. Data are presented as mean±SEM. FIG. 5G shows results from a digital droplet PCR assay or flow cytometry staining for determining HDR.

FIG. 6A shows Graphs showing % GFP at day 5 indicative of HDR. FIG. 6B shows viability of edited cells 2 days post editing. N=7 for TALEN and N=3 for RNP and represent independent donors. FIGS. 6C and 6D show edited and mock cells that were plated one day post editing onto Methocult media for colony formation unit (CFU) assay. Briefly, 500 cells were plated in duplicate in Methocult H4034 media (Stemcell Technologies, incubated at 37° C. for 12-14 days and colonies enumerated based on their morphology and GFP expression. FIG. 6C shows data from a TALEN experiment and FIG. 6D from an RNP experiment. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid.

FIG. 7A depicts total engraftment of edited cells as defined by expression of human CD45 marker. FIG. 7B illustrates % GFP+ cells within the engrafted cells. FIG. 7C depicts FACS plots from representative mice.

DETAILED DESCRIPTION

Figure 1A:
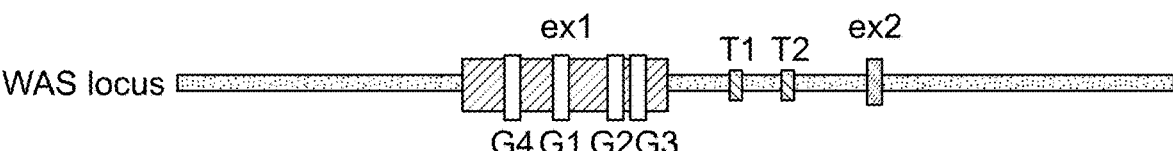
FIGS. 1A and 1B depict the assessment of cleavage efficiency of TALENs and guide RNAs in primary T cells.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Definitions

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Springs Harbor Press (Cold Springs Harbor, N Y 1989). For purposes of the present disclosure, the following terms are defined below.

The articles "a" and "an" are used herein to refer to one or to more than one (for example, to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process comprises at least the recited steps, but may include additional steps. When used in the context of a compound, composition or device, the term "comprising" means that the compound, composition or device comprises at least the recited features or components, but may also include additional features or components.

As used herein, a "subject" or a "patient" as described herein, have their plain and ordinary meaning when read in light of the specification, and may include but is not limited to, for example, an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some alternatives disclosed herein relate to selecting a subject or patient in need. In some alternatives, a patient is selected who is in need of treatment, amelioration, inhibition, progression, or improvement in disease symptoms or who is in need of curative therapy. In some alternatives, a patient is selected who has symptoms of Wiskott-Aldrich Syndrome (WAS) or X-linked thrombocytopenia (XLT), or who has been diagnosed with WAS or XLT. Such identification or selection of said subjects or patients in need can be made through clinical and/or diagnostic evaluation.

As used herein, the term "treatment" as described herein, has their plain and ordinary meaning when read in light of the specification, and may include but is not limited to, for example, an intervention made in response to a disease, disorder or physiological condition manifested by a subject, particularly a subject suffering from an X-linked disorder, such as WAS or XLT. The aim of treatment may include, but is not limited to, one or more of the alleviation or prevention of symptoms, slowing or stopping the progression or worsening of a disease, disorder, or condition, curative treatment of the disease, disorder, or condition, and the remission of the disease, disorder, or condition. In some alternatives, "treatment" refers to both treatment of the underlying disease or treatment of the disease symptoms. For example, in some alternatives, treatments reduce, alleviate, ameliorate, or eradicate the symptom(s) of the disease and/or provide curative therapy of the disease.

"Adoptive cellular therapy" or "adoptive cell transfer," as described herein, have their plain and ordinary meaning when read in light of the specification, and may include but is not limited to, for example, transfer of cells, most commonly immune-derived cells, back into the same patient or into a new recipient host with the goal of transferring the immunologic functionality and characteristics into the new host. In some alternatives, adoptive cellular therapy or adoptive cell transfer comprises administering cells for promoting homology directed repair of a WAS gene in a subject.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, the term "fusion" or "fused" as described herein, have their plain and ordinary meaning when read in light of the specification, and may include but is not limited to, for example, a first nucleic acid linked to a second nucleic acid by a phosphodiester bond, so that a coding sequence at the 3' end of the first nucleic acid is in frame with a coding sequence at the 5' end of the second nucleic acid, and by extension can further refer to a first polypeptide linked by a peptide bond to a second polypeptide at the C-terminus of the first polypeptide. As such, a "fused" (or "fusion of a") nucleic acid or peptide as used herein refers to a configuration of molecules, and does not necessarily involve performing the act of joining two molecules together. By way of example, the fusion of a first nucleic acid to a second nucleic acid can encode a single polypeptide in which a first polypeptide sequence (encoded by the first nucleic acid) is fused to a second polypeptide sequence (encoded by the second nucleic acid). In some alternatives, the molecule comprising the fused nucleic acids is referred to as a fusion nucleic acid.

As used herein, the term "vector" as described herein, have their plain and ordinary meaning when read in light of the specification, and may include but is not limited to, for example, a polynucleotide construct, typically a plasmid or a virus, used to transmit genetic material to a host cell. Vectors can be, for example, viruses, plasmids, cosmids, or phage. A vector as used herein can be composed of either DNA or RNA. In some alternatives, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein "AAV system" or "AAV expression system" as described herein, have their plain and ordinary meaning when read in light of the specification, and may include but is not limited to, for example, nucleic acids for expressing at least one transcript-encoding nucleic acid, and which are disposed on one or more AAV vectors. As used herein, "activity-dependent expression" (and variations of this root term) refers to nucleic acid expression that will be induced upon a change in a particular type of activity of a cell containing the nucleic acid, for example depolarization of the cell. In some alternatives, the cell is a neuron, and depolarization of the neuron in response to a stimulus induces "activity-dependent" nucleic acid expression. In some alternatives, an AAV vector includes a sequence as set forth in SEQ ID NOs: 5, 6, 7, 8, 9, 9, 10, 11, 12, 13, 14, 15, 21, 22, 23, or 26.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

As used herein "upstream" as described herein, have their plain and ordinary meaning when read in light of the specification, and may include but is not limited to, for example, positions 5' of a location on a polynucleotide, and positions toward the N-terminus of a location on a polypeptide. As used herein "downstream" refers to positions 3' of a location on nucleotide, and positions toward the C-terminus of a location on a polypeptide.

The term "construct," as used herein, as described herein, have their plain and ordinary meaning when read in light of the specification, and may include but is not limited to, for example, a recombinant nucleic acid that has been generated for the purpose of the expression of a specific nucleotide sequence(s), or that is to be used in the construction of other recombinant nucleotide sequences.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature. In some alternatives, the promoter described herein can be a U6 promoter or an MND promoter.

As used herein, the term "enhancer" refers to a type of regulatory element that can modulate the efficiency of transcription, regardless of the distance or orientation of the enhancer relative to the start site of transcription.

As used herein, the term "variant" as described herein, have their plain and ordinary meaning when read in light of the specification, and may include but is not limited to, for example, a polynucleotide (or polypeptide) having a sequence substantially similar to a reference polynucleotide (or polypeptide). In the case of a polynucleotide, a variant can have deletions, substitutions, or additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least 50%, 55%, 60%, 65%, 70%, 75%, 80%, 85%, 90%, 91%, 92%, 93%, 94%, 95%, 96%, 97%, 98%, 99% or more sequence identity to the reference polynucleotide as determined by sequence alignment programs known by skilled artisans, or an amount within a range defined by any two of the aforementioned values. In the case of a polypeptide, a variant can have deletions, substitutions, or additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least 60%, 65%, 70%, 75%, 80%, 85%, 90%, 91%, 92%, 93%, 94%, 95%, 96%, 97%, 98%, 99% or more sequence identity to the reference polypeptide as determined by sequence alignment programs known by skilled artisans, or an amount within a range defined by any two of the aforementioned values.

As used herein, the term "transfection" as described herein, have their plain and ordinary meaning when read in light of the specification, and may include but is not limited to, for example, introduction of a nucleic acid into a host cell, such as by contacting the cell with a recombinant AAV vector as described herein. As used herein, "transient transfection" refers to the introduction of exogenous nucleic acid(s) into a host cell by a method that does not generally result in the integration of the exogenous nucleic into the genome of the transiently transfected host cell. In some alternatives, the nucleic acid is RNA. In some alternatives, the nucleic acid is DNA. In some alternatives, when the nucleic acid is RNA, the nucleic acid does not generally integrate in the genome of the transiently transfected cell. In some alternatives, when the nucleic acid is DNA, the nucleic acid can integrate in the genome of the transiently transfected cell.

By the term "host cell" as described herein, have their plain and ordinary meaning when read in light of the specification, and may include but is not limited to, for example, a cell that is introduced with Cas9-mRNA/AAV-guide RNA according to the present alternatives, as well as, cells that are provided with the systems herein. Host cells can be prokaryotic cells or eukaryotic cells. Examples of prokaryotic host cells include, but are not limited to *E. coli*, nitrogen fixing bacteria, *Staphylococcus aureus, Staphylococcus albus, Lactobacillus acidophilus, Bacillus anthracis, Bacillus subtilis, Bacillus thuringiensis, Clostridium tetani, Clostridium botulinum, Streptococcus mutans, Streptococcus pneumoniae*, mycoplasmas, and cyanobacteria. Examples of eukaryotic host cells include, but are not limited to, protozoa, fungi, algae, plant, insect, amphibian, avian and mammalian cells. In some alternatives, a system for editing at least one target gene in a cell is provided, wherein the cell is a eukaryotic cell. In some alternatives, the cell is a mammalian cell. In some alternatives, the cell is a human cell. In some alternatives, the cell is a primary cell. In some alternatives, the cell is not a transformed cell. In some alternatives, the cell is a primary lymphocyte. In some alternatives, the cell is a primary lymphocyte, a CD34$^+$ stem cell, a hepatocyte, a cardiomyocyte, a neuron, a glial cell, a muscle cell or an intestinal cell.

"T cell precursors" as described herein, have their plain and ordinary meaning when read in light of the specification, and may include but is not limited to, for example, lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative (CD4$^-$CD8$^-$) cells. As they progress through their development, they become double-positive thymocytes (CD4$^+$CD8$^+$), and finally mature to single-positive (CD4$^+$CD8$^-$ or CD4$^-$CD8$^+$) thymocytes that are then released from the thymus to peripheral tissues.

"Hematopoietic stem cells" or "HSC" as described herein, have their plain and ordinary meaning when read in light of the specification, and may include but is not limited to, for example, precursor cells that can give rise to myeloid cells such as, for example, macrophages, monocytes, macrophages, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M). In some alternatives, the cells provided are HSC cells. In some alternatives, the cell is a primary lymphocyte or a CD34$^+$ stem cell.

As used herein, "autologous" refers to the donor and recipient of the stem cells being the same, for example, the patient or subject is the source of the cells.

"Primary human cells" as described herein, are directly cultured from their source organ tissue or blood cells. Compared to immortalized cell lines, primary human cells provide enhanced replication of in vivo. In some alternatives, the cells provided are primary human cells.

As used herein, the term "co-delivery" as described herein, have their plain and ordinary meaning when read in light of the specification, and may include but is not limited to, for example, delivery of two or more separate chemical entities, whether in vitro or in vivo. Co-delivery refers to the simultaneous delivery of separate agents; to the simultaneous delivery of a mixture of agents; as well as to the delivery of one agent followed by delivery of a second agent or additional agents. In all cases, agents that are co-delivered are intended to work in conjunction with each other. In some alternatives, for example, co-delivery comprises delivery of an mRNA of interest and an AAV vector.

The term "endonuclease" as described herein, have their plain and ordinary meaning when read in light of the specification, and may include but is not limited to, for example, enzymes that cleave the phosphodiester bond within a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An endonuclease may cut a polynucleotide symmetrically, leaving "blunt" ends, or in positions that are not directly opposing, creating overhangs, which may be referred to as "sticky ends." The methods and compositions described herein may be applied to cleavage sites generated by endonucleases. In some alternatives of the system, the system can further provide nucleic acids that encode an endonuclease, including zinc finger nucleases (ZFNs), TAL effector nucleases (TALENs), meganucleases (such as MegaTALs), and CRISPR/Cas9 or a fusion protein comprising a domain of an endonuclease, for example, Cas9, TALEN, or MegaTAL, or one or more portion thereof. These examples are not meant to be limiting and other endonucleases and alternatives of the system and methods comprising other endonucleases and variants and modifications of these exemplary alternatives are possible without undue experimentation.

The term "transcription activator-like (TAL) effector nuclease" (TALEN) as described herein, have their plain and ordinary meaning when read in light of the specification, and may include but is not limited to, for example, a nuclease comprising a TAL-effector domain fused to a nuclease domain. TAL-effector DNA binding domains may be engineered to bind to a desired target and fused to a nuclease domain, such as the FokI nuclease domain, to derive a TAL effector domain-nuclease fusion protein. The methods and systems described herein may be applied to cleavage sites generated by TAL effector nucleases. In some alternatives of the systems provided herein, the systems can further comprise a TALEN nuclease or a vector or nucleic acid encoding a TALEN nuclease. In some alternatives of the methods provided herein, the method can further comprise providing a nuclease, such as a TALEN nuclease.

CRISPRs (clustered regularly interspaced short palindromic repeats) are segments of prokaryotic DNA containing short repetitions of base sequences. Each repetition is followed by short segments of "spacer DNA" from previous exposures to a bacterial virus or plasmid.

Cas9 (CRISPR associated protein 9) is an RNA-guided DNA endonuclease enzyme associated with the CRISPR adaptive immunity system in *Streptococcus pyogenes*, among other bacteria. *S. pyogenes* utilizes Cas9 to memorize and later interrogate and cleave foreign DNA, such as invading bacteriophage DNA or plasmid DNA. Cas9 performs this interrogation by unwinding foreign DNA and checking for complementarity to the 20 base pair spacer region of the guide RNA. If the DNA substrate is complementary to the guide RNA, Cas9 cleaves the invading DNA.

The CRISPR/Cas system as described herein, is used for gene editing (adding, disrupting, or changing the sequence of specific genes) and gene regulation. By delivering the Cas9 protein, a derivative, or fragment thereof and appropriate guide RNAs into a cell, the organism's genome can be cut at any desired location. It can be possible to use CRISPR to build RNA-guided genes capable of altering the genomes of entire populations. The basic components of CRISPR/Cas9 system comprise a target gene, a guide RNA, and a Cas9 endonuclease, derivative, or fragment thereof. An important aspect of applying CRISPR/Cas9 for gene editing is the need for a system to deliver the guide RNAs efficiently to a wide variety of cell types. This could for example involve delivery of an in vitro generated guide RNA as a nucleic acid (the guide RNA generated by in vitro transcription or chemical synthesis). In some alternatives the nucleic acid encoding the guide RNA is rendered nuclease resistant by incorporation of modified bases, such as 2'O-methyl bases. In some alternatives, the CRISPR/Cas9 system described herein, whereby the polynucleotide encoding the Cas9 nuclease or a derivative or functional fragment thereof (for example, a 20 nucleic acid sequence of an mRNA vector with Cas9) is provided with a poly(T) or poly(A) tail of a desired length and prepared in accordance with the teachings described herein, for example, is provided with a guide RNA that comprises one or more modified bases, such as any one or more of the modified bases described herein.

Exemplary guide RNAs useful with the alternatives described herein, which may contain one or more of the modified bases set forth herein. In some alternatives, the modified guide RNA includes the sequences provided in SEQ ID NO: 10. Furthermore, an important system for expressing guide RNAs in this context is based on the use of adeno-associated virus (AAV) vectors because AAV vectors are able to transduce a wide range of primary cells. AAV vectors do not cause infection and are not known to integrate into the genome. Therefore, the use of AAV vectors has the benefits of being both safe and efficacious.

The term "complementary to" means that the complementary sequence is homologous to all or one or more portions of a reference polynucleotide sequence. For illustration, the nucleotide sequence "CAT" corresponds to a reference sequence "CAT" and is complementary to a reference sequence "GTA."

As used herein, "homology-directed repair" (HDR) as described herein, have their plain and ordinary meaning when read in light of the specification, and may include but is not limited to, for example, DNA repair that takes place in cells, for example, during repair of a double-stranded break (DSB) in DNA. HDR requires nucleotide sequence homology and uses a donor polynucleotide to repair the sequence where the DSB (e.g., within a target DNA sequence) occurred. The donor polynucleotide generally has the requisite sequence homology with the sequence flanking the DSB so that the donor polynucleotide can serve as a suitable template for repair. HDR results in the transfer of genetic information from, for example, the donor polynucleotide to the DNA target sequence. HDR may result in alteration of the DNA target sequence (e.g., insertion, deletion, mutation) if the donor polynucleotide sequence differs from the DNA target sequence and part or all of the donor polynucleotide is incorporated into the DNA target sequence. In some alternatives, an entire donor polynucleotide, a portion of the donor polynucleotide, or a copy of the donor polynucleotide is integrated at the site of the DNA target sequence.

As used herein, a "guide" as described herein, have their plain and ordinary meaning when read in light of the specification, and may include but is not limited to, for example, any polynucleotide that site-specifically guides a nuclease to a target nucleic acid sequence. In some alternatives, a guide comprises RNA, DNA, or combinations of RNA and DNA.

A "genomic region" is a segment of a chromosome in the genome of a host cell that is present on either side of the target nucleic acid sequence site or, alternatively, also comprises a portion of the target site. The homology arms of the donor polynucleotide have sufficient homology to undergo homologous recombination with the corresponding genomic regions. In some alternatives, the homology arms of the donor polynucleotide share significant sequence homology to the genomic region immediately flanking the target site; it is recognized that the homology arms can be designed to have sufficient homology to genomic regions farther from the target site.

As used herein, "non-homologous end joining" (NHEJ) as described herein, have their plain and ordinary meaning when read in light of the specification, and may include but is not limited to, for example, repair of a DSB in DNA by direct ligation of one end of the break to the other end of the break without a requirement for a donor polynucleotide. NHEJ is a DNA repair pathway available to cells to repair DNA without the use of a repair template. NHEJ in the absence of a donor polynucleotide often results in nucleotides being randomly inserted or deleted at the site of the DSB.

As used herein "cleavage site" refers to a sequence that mediates the separation of a first polypeptide that would otherwise be in cis to a second polypeptide. Accordingly, for simplicity, "cleavage," "cleavage site," and the like as used herein refer to the separation of any two polypeptides that are encoded by a single polynucleotide in cis. Thus, "cleavage" and "cleavage site," can, but do not necessarily refer to proteolytic sites and events, and can also refer to other mechanisms for mediating the separation of polypeptides, for example ribosomal skipping.

As used herein, the term "label" refers to a detectable molecule. A number of suitable labels comprise polypeptides. As such, as used herein, a "label nucleic acid" refers to a nucleic acid encoding a label. In some alternatives, the AAV vector systems comprise a label polynucleotide. Thus, in some alternatives, a promoter (such as an MND promoter) is operatively linked to a label polynucleotide, such that the AAV vectors described herein comprise a reporter. Example labels that are suitable in accordance with alternatives herein include, but are not limited to, green fluorescent protein (GFP), including, for example, *Aequoria victoria* GFP, *Renilla muelleri* GFP, *Renilla remformis* GFP, *Renilla ptilosarcus*, blue fluorescent protein (BFP), yellow fluorescent protein (YFP), red fluorescent protein (RFP), cyan fluorescent protein (CFP), or orange fluorescent proteins (OFP). Additional reporter genes include, but are not limited to neomycin, phosphoro-transferase, chloramphenicol acetyl transferase, thymidine kinase, luciferase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes. In some alternatives, the polypeptide of interest comprises the label itself, for example when production of label in active cells is desired. In some alternatives, an AAV construct provided herein comprises a U6 promoter driven guide RNA cassette or an MND promoter driven GFP cassette, or both, and wherein the MND promoter driven GFP cassette provides for tracking of AAV transduction efficiency.

The term "gene expression" as described herein, have their plain and ordinary meaning when read in light of the specification, and may include but is not limited to, for example, biosynthesis of a gene product. For example, in the case of a structural gene, gene expression involves transcription of the structural gene into mRNA and the translation of mRNA into one or more polypeptides.

A "polypeptide" is a polymer of amino acid residues joined by peptide bonds, whether produced naturally or synthetically. Polypeptides of less than 10 amino acid residues are commonly referred to as "peptides." A polypeptide can be considered as a protein.

A "protein" is a macromolecule comprising one or more polypeptide chains. A protein may also comprise non-peptide components, such as carbohydrate groups. Carbohydrates and other non-peptide substituents may be added to a protein by the cell in which the protein is produced, and will vary with the type of cell. Proteins are defined herein in terms of their amino acid backbone structures; substituents such as carbohydrate groups are generally not specified, but may be present nonetheless. In some alternatives, a system for editing at least one target gene in a cell is provided, wherein the method comprises a first nucleic acid sequence encoding a CRISPR guide RNA, wherein the CRISPR guide RNA is complimentary to at least one target gene in a cell and, wherein said first nucleic acid sequence is present in a vector; said system also comprising a second nucleic acid sequence encoding a Cas9 protein, a third nucleic acid sequence encoding a first adenoviral protein and a fourth nucleic acid sequence encoding a second adenoviral protein. In some alternatives, the CRISPR guide sequence is defined by SEQ ID NO: 3, 5, 6, 7 and 8. In some alternatives, the CRISPR guide sequence is defined by SEQ ID NO: 31, 32, 33, 34.

X-Linked Disorders

Some alternatives provided herein relate to treating, ameliorating, inhibiting, or improving an X-linked disorder. In some alternatives, the disorder is Wiskott-Aldrich Syndrome (WAS). WAS is a severe X-linked genetic disorder with an incidence of around 1 in 250,000 live male births. WAS is a result of mutation in the WAS gene. WAS is characterized by opportunistic viral and bacterial infections due to abnormal lymphocyte function, thrombocytopenia with small platelets, eczema, and increased risk of autoimmune disorders and malignancies. In some alternatives, the disorder is X-linked thrombocytopenia (XLT). XLT also results from mutations in the WAS gene leading primarily to thrombocytopenia and bleeding.

Hematopoietic cell transplantation (HCT) is the only widely available approach that can provide curative therapy for WAS. Overall, transplant survival has increased over the last two decades, with improvements in transplant care, donor matching, and earlier treatment. However, outcomes for patients without a human leukocyte antigen (HLA) matched donor, particularly older subjects, remain suboptimal. In addition, patients with mixed chimerism exhibit an increased risk of autoimmunity and low myeloid chimerism predicts persistent thrombocytopenia. Further, optimal conditioning regiments that limit HCT-related morbidity, as well as the late effects following conditions remain unclear.

The challenge of finding suitable donors and other significant complications associated with HCT have prompted efforts to develop alternative gene therapy (GT) strategies for WAS. Pioneering GT trials using integrating viral vectors, based on use of gamma-retroviral (RV) or self-inactivating lentiviral vectors (LV) have been carried out in Europe. Boztug et al. first reported on two patients treated by RV GT. Boztug et al. *N Engl J Med,* 2010, 363(20), 1918-1927; incorporated by reference herein in its entirety. Both patients showed a reduced frequency and severity of infections and disappearance of bleeding episodes and autoimmune manifestations. In a subsequent follow on trial using hematopoietic stem cell gene therapy, a total of 10 patients were treated. Nine patients showed successful immune reconstitution with platelet counts greater than 80,0000 cells/μL in eight of nine subjects. Braun et al. *Sci Transl Med,* 2014, 12(6), 227; incorporated by reference herein in its entirety. Strikingly, severe adverse events with insertional mutagenesis leading to leukemia occurred in seven patients.

Based on these adverse events, self-inactivating LV (SIN-LV) encoding WAS cDNA under the control of the native proximal WAS gene promoter were developed. Trials using this LV have opened in Europe and in the United States. Aiuti et al. reported on initial results in three patients treated in Italy. Aiuti et al. *Science,* 2013, 341, 6148; incorporated by reference herein in its entirety. Long-term engraftment with gene-modified cells was observed in all three patients in the range of 25-50% of the total peripheral blood cells. WASp expression was detected in a vector containing hematopoietic cells with approximate endogenous expression levels in T cells. A subset of immunological abnormalities was corrected. Thrombocytopenia improved, but unlike the results of the WAS RV trial, platelet counts were not corrected. In contrast to the RV trial, clonal analysis indicated no evidence of clonal expansion for greater than three years.

A French/UK group published the outcome of seven WAS patients who underwent GT using the identical LV. Abina et al. *JAMA,* 2015, 313, 1550-1563; incorporated by reference herein in its entirety. However, similar to data from Aiuti et al., thrombocytopenia improved but platelet counts were not corrected. In summary, to date WAS LV trials have shown sustained viral marking and WASp expression in multiple hematopoietic lineages with partial clinical improvement. However, LV therapy has failed to rescue thrombocytopenia. Further, the long-term response to immunization and infections challenge and risk for autoimmunity remain to be determined.

Thus, provided herein are systems and methods for the introduction of an intact WAS cDNA under control of the endogenous promoter and enhancer in hematopoietic stem cells (HSCs). In some alternatives, the systems and methods described herein rescue immunologic and functional defects in WAS and XLT and provide a curative therapy. As discussed above, WAS gene replacement using viral-based gene therapy has been used to partially correct this disease, current viral vector approaches have led to increased risk for malignancy (when using gamma-retroviral vectors) or have failed to correct all hematopoietic deficits, including, most notably, the failure to correct thrombocytopenia. However, the systems and methods provided herein for gene editing of the endogenous WAS gene lead to improved long-term disease correction.

Accordingly, the systems and methods described herein provide several unique opportunities for treatment of WAS and XLT. For example, some alternatives described herein relate to editing a gene product, for example, at the WAS locus. In some alternatives, the edited gene product remains under control of the endogenous promoter and enhancer elements. In some alternatives, the editing rates are performed at high efficiency in a cell, such as a hematopoietic stem cell. Accordingly, provided herein are systems and methods for achieving high efficiency editing. Also provided are systems and methods for engrafting edited cells. In some alternatives, the methods and systems provided herein include use of autologous stem cells. In comparison to prior treatments that use marrow transplantation of stem cells from an allogeneic donor, WAS gene editing as described herein uses autologous stem cells. Thus, there is no risk for graft versus host disease, a major problem and risk with transplants. In some alternatives, the methods and systems provided herein use the endogenous gene promoter/enhancer to control gene expression. In comparison to viral gene replacement therapy as used in previous treatments, the gene editing systems and methods described herein use an endogenous gene promoter/enhancer to control gene expression, which leads to endogenous levels of WASp in all relevant cell lineages. Gene editing also eliminates the risk for viral vector mutagenesis that is present in all gene replacement strategies and was observed as a serious adverse event in nearly all WAS patients treated with gamma-retroviral vectors. Gene editing also leads to more appropriate levels of WAS protein expression in comparison to current LV vector therapy. The published trials in WAS LV therapy utilized a vector containing the WAS minimal promoter, which partially rescued function in some cell types but did not rescue platelet production most likely because the minimal promoter was not sufficiently robust in platelet progenitor cells.

Furthermore, in all current therapies for WAS (transplant and LV gene therapy) conditioning regimens are being used. Conditioning is also required for successful application of gene editing in order to achieve a clinically relevant level of engraftment of edited HSC. In some alternatives, engraftment of 10%, 15%, 20%, 25%, 30%, 35%, 40%, 45%, 50%, 55%, 60%, 65% 70%, or 70% of edited cells or an amount within a range defined by any two of the aforementioned values will lead to clinical benefit. In some alternatives, treosulfan/fludarabine conditioning is used.

Some alternatives provided herein relate to unique nuclease reagents based upon either a TALEN or CRISPR/Cas9 platform in parallel with AAV based delivery of novel HDR repair templates. In some alternatives, the combination of a nuclease and an AAV vector achieves high rates of HDR at the WAS locus in human T cells and CD34$^+$ HSCs, leading to sustained gene expression in vitro and in vivo following engraftment in immunodeficient mice. In some alternatives, the methods and systems provided herein permit introduction of corrective cDNAs into the WAS locus in autologous cells from control subjects of subjects with WAS or XLT, thereby permitting lineage and developmental specific regulation of the functional gene product in vitro and in vivo. In some alternatives, the methods and systems provided herein permit long-term sustained cell lineage appropriate therapeutic WASp expression without adverse events within the host genome.

In some alternatives, the systems and methods described herein minimize the risk of mutagenesis by targeting integration of a therapeutic cassette into the WAS locus. In some alternatives, the systems described herein include an AAV donor template for integrating an expression cassette into the first exon of WAS by homology directed repair. Also provided herein are nuclease platforms targeting the WAS locus, including TALENs and CRISPR/Cas9.

Some alternatives concern methods for using adult mobilized CD34$^+$ cells and co-delivery of either TALEN mRNA or Cas9/gRNA ribonucleoprotein complexes (RNPs) and an AAV donor for targeted integration of a promoter-driven fluorescent marker. In some alternatives, the methods provided herein achieve efficient homology directed repair rates across multiple donors at an efficiency of 10%, 15%, 20%, 25%, 30%, 35%, 40%, 45%, 50%, 60%, 70%, 80%, or greater, or an efficiency within a range defined by any two of the aforementioned values for TALEN and an efficiency of 10%, 15%, 20%, 25%, 30%, 35%, 40%, 45%, 50%, 60%, 70%, 80%, or greater, or an efficiency within a range defined by any two of the aforementioned values for RNP. In some alternatives, the highest levels of cell viability is observed using RNP/AAV co-delivery. In some alternatives, edited HSC retain their potential to give rise to multiple lineages in colony forming unit assays. In some alternatives, the systems provided herein provide long-term engraftment and differentiation potential in immune-deficient mice. In some alternatives, AAV vectors carrying WAS cDNA restore expression in WAS deficient cells. In some alternatives, the systems and methods described herein provide therapeutic correction of the disease or a disease symptom in patients.

Homology Directed Repair

Homology directed repair (HDR), refers to the process of repairing DNA damage using a homologous nucleic acid (e.g., a sister chromatid or an exogenous nucleic acid). In a normal cell, HDR typically involves a series of steps such as recognition of the break, stabilization of the break, resection, stabilization of single stranded DNA, formation of a DNA crossover intermediate, resolution of the crossover intermediate, and ligation. As described herein, HDR can be used to alter a target sequence and correct (e.g., repair or edit) a mutation in the genome. While not wishing to be bound by theory, it is believed that alteration of the target sequence occurs by HDR with a donor template or template nucleic acid. For example, the donor template or the template nucleic acid provides for alteration of the target position.

Some alternatives provided herein relate to methods and systems for homology directed repair of the gene associated with a disorder. In some alternatives, the gene is a WAS gene. In some alternatives, the method comprises HDR of the WAS gene in human hematopoietic cells. In some alternatives, the disorder is an X-linked disorder. In some alternatives, the disorder is WAS. In some alternatives, the disorder is XLT. In some alternatives, the method and systems include nuclease-based HDR of the WAS gene. In some alternatives, the nuclease based HDR comprises a TALEN based nuclease. In some alternatives, the nuclease based HDR comprises a CRISPR/Cas based nuclease.

TALEN

Transcription activator-like (TAL) effector-DNA modifying enzyme (TALEN) is a restriction enzyme that can be engineered to cut specific sequences of DNA. TALENs are made by fusing a TAL-effector domain to a DNA cleavage domain.

In some alternatives, the WAS locus used in targeting with WAS TALENs is co-delivered with an AAV donor.

In some alternatives the WAS TALEN forward sequence is defined by SEQ ID NO: 27 or SEQ ID NO: 29. In some alternatives, the WAS TALEN reverse sequence is defined by SEQ ID NO: 28 or SEQ ID NO: 30. In some alternatives, the AAV donor comprises a GFP cassette under control of an MND promoter. In some alternatives, the AAV donor has a 1 kb homology arm flanking an MND promoter driven GFP cassette (SEQ ID NO: 35). In some alternatives, the AAV donor comprises one or more nucleotide mutations to abolish cleavage by TALENs. In some alternatives, the nucleotide mutation is a mutation of the T preceding the TALEN binding site (SEQ ID NO: 36). In some alternatives, the AAV donor comprises deletion of the entire region between exon 1 up to the reverse TALEN binding site (SEQ ID NO: 37).

Some alternatives provided herein relate to a TALEN nuclease for use in HDR of a gene of interest. In some alternatives, the TALEN binds to a TALEN binding site in a gene of interest. In some alternatives, the gene of interest is a WAS gene (SEQ ID NO: 4). In some alternatives, a WAS TALEN binds to native WAS sequence (SEQ ID NO: 4). The WAS locus used in targeting with WAS TALENs comprises the following components from 5' to 3': upstream homology arm (SEQ ID NO: 11); exon 1, including a guide RNA (SEQ ID NO: 19); T-for (TALEN forward binding site; SEQ ID NO: 15); cleavage site (SEQ ID NO: 17); T-rev (TALEN reverse binding site; SEQ ID NO: 16); exon 2 (SEQ ID NO: 18); and downstream homology arm (SEQ ID NOs: 12, 13, or 14).

In some alternatives, the WAS locus used in targeting with WAS TALENs is co-delivered with an AAV donor. In some alternatives the WAS TALEN forward sequence is defined by SEQ ID NO: 1 or SEQ ID NO: 24. In some alternatives, the WAS TALEN reverse sequence is defined by SEQ ID NO: 2 or SEQ ID NO: 25. In some alternatives, the AAV donor comprises a GFP cassette under control of an MND promoter. In some alternatives, the AAV donor has a 1 kb homology arm flanking an MND promoter driven GFP cassette (SEQ ID NO: 5). In some alternatives, the AAV donor comprises one or more nucleotide mutations to abolish cleavage by TALENs. In some alternatives, the nucleotide mutation is a mutation of the T preceding the TALEN binding site (SEQ ID NO: 6). In some alternatives, the AAV donor comprises deletion of the entire region between exon 1 up to the reverse TALEN binding site (SEQ ID NO: 7).

In some alternatives the WAS TALEN forward sequence is defined by SEQ ID NO: 27 or SEQ ID NO: 29. In some alternatives, the WAS TALEN reverse sequence is defined by SEQ ID NO: 28 or SEQ ID NO: 30. In some alternatives, the AAV donor comprises a GFP cassette under control of an MND promoter. In some alternatives, the AAV donor has a 1 kb homology arm flanking an MND promoter driven GFP cassette (SEQ ID NO: 35). In some alternatives, the AAV donor comprises one or more nucleotide mutations to abolish cleavage by TALENs. In some alternatives, the nucleotide mutation is a mutation of the T preceding the TALEN binding site (SEQ ID NO: 36). In some alternatives, the AAV donor comprises deletion of the entire region between exon 1 up to the reverse TALEN binding site (SEQ ID NO: 37).

CRISPR/Cas

Some alternatives provided herein relate to a Cas nuclease for use in HDR of a gene of interest. In some alternatives, the Cas nuclease is a Cas9 nuclease. Cas9 is an RNA-guided DNA endonuclease enzyme associated with the CRISPR (Clustered Regularly Interspersed Palindromic Repeats) adaptive immunity system in *Streptococcus pyogenes*, among other bacteria. *S. pyogenes* utilizes Cas9 to memorize and later interrogate and cleave foreign DNA, such as invading bacteriophage DNA or plasmid DNA. Cas9 performs this interrogation by unwinding foreign DNA and checking for if it is complementary to the 20 base pair spacer region of the guide RNA. If the DNA substrate is complementary to the guide RNA, Cas9 cleaves the invading DNA.

In some alternatives, the Cas nuclease is delivered in a complex with a single guide RNA as a ribonucleoprotein complex (RNP). In some alternatives, the CRISPR guide sequence is defined by SEQ ID NO: 3. In some alternatives, the RNP is co-delivered with an AAV donor. In some alternatives, the AAV donor is a self-complementary AAV (scAAV). In some alternatives, the AAV donor comprises a GFP cassette under control of an MND promoter wherein a protospacer adjacent motif (PAM) site is deleted (SEQ ID NO: 5). In some alternatives, the AAV donor comprises a U6 promoter driven guide RNA cassette (SEQ ID NO: 8). In some alternatives, the AAV donor comprises both the donor and guide sequences (SEQ ID NO: 9). In some alternatives, the AAV donor is an scAAV done including guide sequences, and includes a sequence defined by SEQ ID NO: 21, SEQ ID NO: 22, or SEQ ID NO: 23.

In some alternatives, the Cas nuclease is delivered in a complex with a single guide RNA as a ribonucleoprotein complex (RNP). In some alternatives, the CRISPR guide sequence is defined by SEQ ID NO: 31, 32, 33, 34. In some alternatives, the RNP is co-delivered with an AAV donor. In some alternatives, the AAV donor is a self-complementary AAV (scAAV). In some alternatives, the AAV donor comprises a GFP cassette under control of an MND promoter wherein a protospacer adjacent motif (PAM) site is deleted (SEQ ID NO: 9). In some alternatives, the AAV donor comprises a U6 promoter driven guide RNA cassette (SEQ ID NO: 38). In some alternatives, the AAV donor comprises both the donor and guide sequences (SEQ ID NO: 39).

Cells

Some alternatives provided herein relate to co-delivery of a nuclease, such as a TALEN or Cas nuclease, and an AAV donor template to modify endogenous WAS locus in a cell. In some alternatives, the cell is a mammalian cell. In some alternatives, the cell is a human cell. In some alternatives, the cell is an autologous cell. In some alternatives, the cell is a primary cell. In some alternatives, the cell is a lymphocyte. In some alternatives, the cell is not a transformed cell. In some alternatives, the cell is a primary lymphocyte. In some alternatives, the cell is a lymphocyte precursor cell. In some alternatives, the cell is a T cell. In some alternatives, the cell is a hematopoietic cell. In some alternatives, the cell is a CD34$^+$ cell. In some alternatives, the cell is a primary human hematopoietic cell.

In some alternatives, the cell is transformed by co-delivery of a nuclease, such as a TALEN nuclease or Cas nuclease, and an AAV donor template to modify endogenous WAS locus in a cell. In some alternatives, a method of editing a WAS gene in a cell is provided, wherein the method comprises introducing into a cell a first vector that comprises a first nucleic acid sequence encoding a guide RNA, such as a TALEN guide RNA or a CRISPR guide RNA, wherein the guide RNA is complimentary to at least one target gene in said cell, and introducing into said cell a second nucleic acid sequence encoding a nuclease, such as a TALEN nuclease or a Cas nuclease, a derivative, or fragment thereof. In some alternatives, a cell is provided, wherein the cell is manufactured by the said methods.

Methods of Treating, Inhibiting, or Ameliorating WAS or XLT in a Subject in Need Some alternatives provided herein related to methods of promoting HDR of a WAS gene in a subject in need thereof. In some alternatives, the method comprises selecting or identifying a subject in need thereof. A selected or identified subject in need thereof is a subject that presents with symptoms of an X-linked disorder, such as WAS or XLT, or a subject that has been diagnosed with an X-linked disorder, such WAS or XLT. Such evaluations can be made clinically or by diagnostic test.

In some alternatives, the method comprises adoptive cellular therapy or adoptive cell transfer of treated cells to a subject in need. In some alternatives, adoptive cellular therapy or adoptive cell transfer comprises administering cells for promoting homology directed repair of a WAS gene in a subject. In some alternatives, the method comprises obtaining cells from the subject in need thereof. In some alternatives, the cells from the subject in need are primary human hematopoietic cells. In some alternatives, the cells are transformed by co-delivery of a nuclease, such as a TALEN nuclease or a Cas nuclease, and an AAV donor, which modifies the endogenous WAS locus in the cell. In some alternatives, the method comprises expanding the transformed cells. In some alternatives, the method comprises selecting transformed cells that have successful modification of the WAS locus in the cell. In some alternatives, the transformed cells are administered to the patient.

In some alternatives, administration of the transformed cells to the patient comprises administration of autologous cells to the patient. In some alternatives, administration of the transformed cells to the patient treats, inhibits, or ameliorates symptoms of WAS and/or XLT. In some alternatives, administration of the transformed cells to the patient treats WAS and/or XLT. In some alternatives, the method improves thrombocytopenia. In some alternatives, the method increases platelet counts.

In some alternatives, an amount of treated cells is administered to the composition. In some alternatives, the amount of cells administered is $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, or $1 \times 10^9$ cells, or greater, or an amount within a range defined by any two of the aforementioned values.

In some alternatives, the treated cells are administered to a subject as a co-therapy with an additional therapy that is used to treat the symptoms of the disorder or used to treat the disorder. In some alternatives, the additional therapy includes immunoglobulin therapy, an antibiotic therapy, corticosteroid therapy, or transfusion therapy.

Pharmaceutical Compositions and Administration

Cells prepared by the systems or methods provided herein can be administered directly to a patient for targeted homology directed repair of a WAS locus and for therapeutic or prophylactic applications, for example, for treating, inhibiting, or ameliorating an X-linked disorder, such as WAS or XLT. In some alternatives, cells are prepared by the systems provided herein. In some alternatives, a composition is provided, wherein the composition comprises the cell. In some alternatives, the compositions described herein, can be used in methods of treating, preventing, ameliorating, or inhibiting an X-linked disorder, such as WAS or XLT or ameliorating a disease condition or symptom associated with an X-linked disorder, such as WAS or XLT.

The compositions comprising the cells are administered in any suitable manner, and in some alternatives with pharmaceutically acceptable carriers. Suitable methods of administering such compositions comprising the cells are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as, by the particular method used to administer the composition. Accordingly, there is a wide variety of suitable formulations of pharmaceutical compositions that are available (see, e.g., Remington's Pharmaceutical Sciences).

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

In some alternatives, one or more of parenteral, subcutaneous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal routes of administration are contemplated. In some alternatives, the composition to be administered can be formulated for delivery via one or more of the above noted routes.

ADDITIONAL ALTERNATIVES

Additional alternatives are disclosed in further detail in the following examples, which are not in any way intended to limit the scope of the claims. The examples provided below demonstrate genome editing tools that possess a high degree of specificity, providing the foundation for site-specific modification of the WAS locus for therapeutics.

Alternative 1

Cleavage Efficiency of TALENs in Primary T Cells

This alternative demonstrates methods for determining the cleavage efficiency of the systems described herein.

A panel of candidate guide RNAs (delivered as self-complementary AAV (scAAV) and Cas9 as mRNA) or TALEN mRNAs were prepared and tested in T cells. FIG. 1A depicts the location of the WAS TALENs (TALEN #1 and TALEN #2) and guide RNAs, termed G1, G2, G3, and G4 within the human WAS gene.

Primary human T cells were cultured in T cell growth medium supplemented with IL-2 (50 ng/mL), IL-7 (5 ng/mL), and IL-15 (5 ng/mL) and stimulated using CD3/CD28 beads (Dynabeads, Life Technologies) for 48 hours. Beads were removed and cells rested overnight followed by electroporation using Neon Transfection system with either TALEN mRNA (1 μg of each RNA monomer) or co-delivery of 1 μg of Cas9 mRNA and scAAV carrying guide RNA. Cells were cultured for 5 more days and genomic DNA was extracted. The region surrounding the cut site was amplified and purified using PCR purification kit. 200 ng of purified PCR product was incubated with T7 endonuclease (NEB), analyzed on a gel and percent disruption quantified using Licor Image Studio Lite software.

Figure 1B:
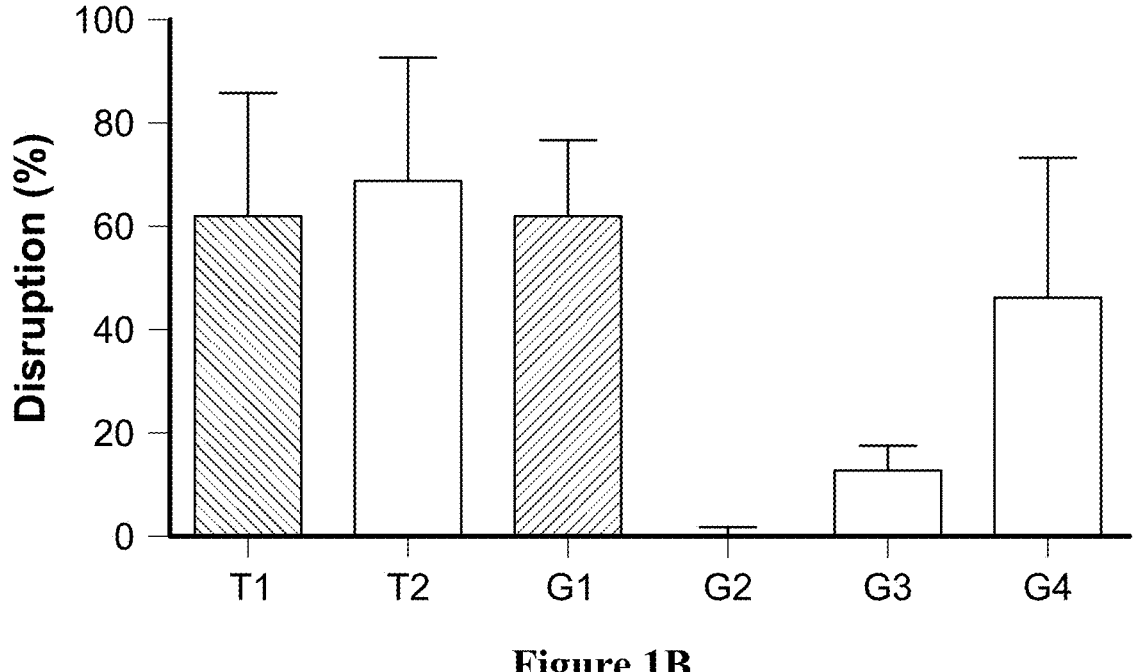

FIG. 1B depicts the percentage of non-homologous end joining (NHEJ) events in primary human T cells detected using the T7 assay, 5 days post-transfection with TALEN mRNAs (T1, T2), or with Cas9 mRNA co-delivered with scAAV expressing gRNAs (G1-4). n=2, represents the number of independent experiments. TALEN T1 and Guide G1 were used in the following examples.

Primary human T cells were cultured in T cell growth medium supplemented with IL-2 (50 ng/ml), IL-7 (5 ng/ml), and IL-15 (5 ng/ml) and stimulated using CD3/CD28 beads (Dynabeads, Life Technologies) for 48 hours. Beads were removed and cells rested overnight followed by electroporation using Neon Transfection system with either TALEN mRNA (1 μg of each RNA monomer) or co-delivery of 1 μg of Cas9 mRNA and scAAV carrying guide RNA. Cells were cultured for 5 more days and the genomic DNA was extracted. The region surrounding the cut site was amplified and purified using PCR purification kit. 200 ng of purified PCR product was incubated with T7 endonuclease (NEB), analyzed on a gel and percent disruption quantified using Licor Image Studio Lite software. TALEN T1 and Guide G1 were used in experiments in subsequent figures.

Alternative 2

Editing of Human Primary T Cells with TALEN and AAV Co-Delivery

This alternative demonstrates methods for editing primary T Cells with TALEN and AAV as described in some alternatives herein.

Figure 2A:
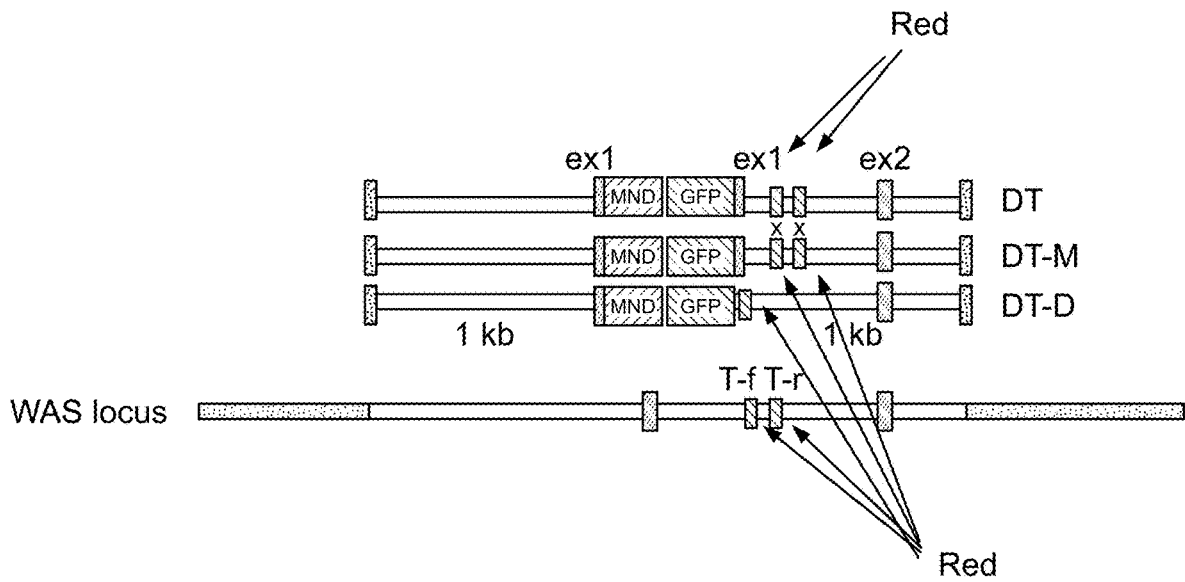
FIGS. 2A-2I depict human primary T cell editing with TALENs and rationally designed AAV donor templates.

A WAS gene was prepared using the TALEN T1 and Guide G1 as described in Example 1, and as shown in FIG. 2A. FIG. 2A depicts the WAS locus and AAV donor templates used in targeting with WAS TALENs. The WAS locus shows the TALEN binding sites, represented by T-f (TALEN forward) and T-r (TALEN reverse). Homology arms are also shown. The three AAV vectors are represented as vectors #1201, #1244, and #1262. AAV vector #1201 has 1 kb of homology arms flanking an MND promoter driven green fluorescent protein (GFP) cassette. AAV vector #1244 has couple nucleotide mutations (represented by X) to abolish cleavage by TALENs. AAV vector #1262 has the entire region between the exon 1 up to the reverse TALEN binding site deleted.

As shown in FIG. 2A small red boxes represent TALEN forward (T-for) and reverse (T-rev) binding sites. Homology arms are depicted in white. DT AAV vector has 1 kb of homology arms flanking an MND promoter driven green fluorescent protein (GFP) cassette. DT-M AAV donor has couple nucleotide mutations (represented by X) to abolish cleavage by TALENs. The #DT-D vector has the entire region between the exon 1 up to the reverse TALEN binding site deleted.

Figure 2B:
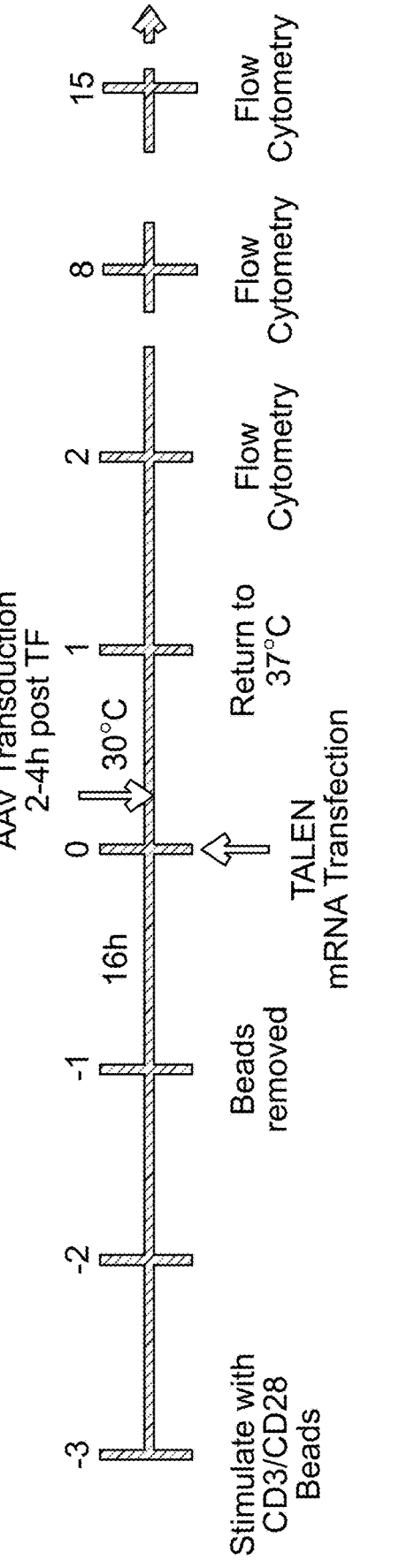
Figure 2C:
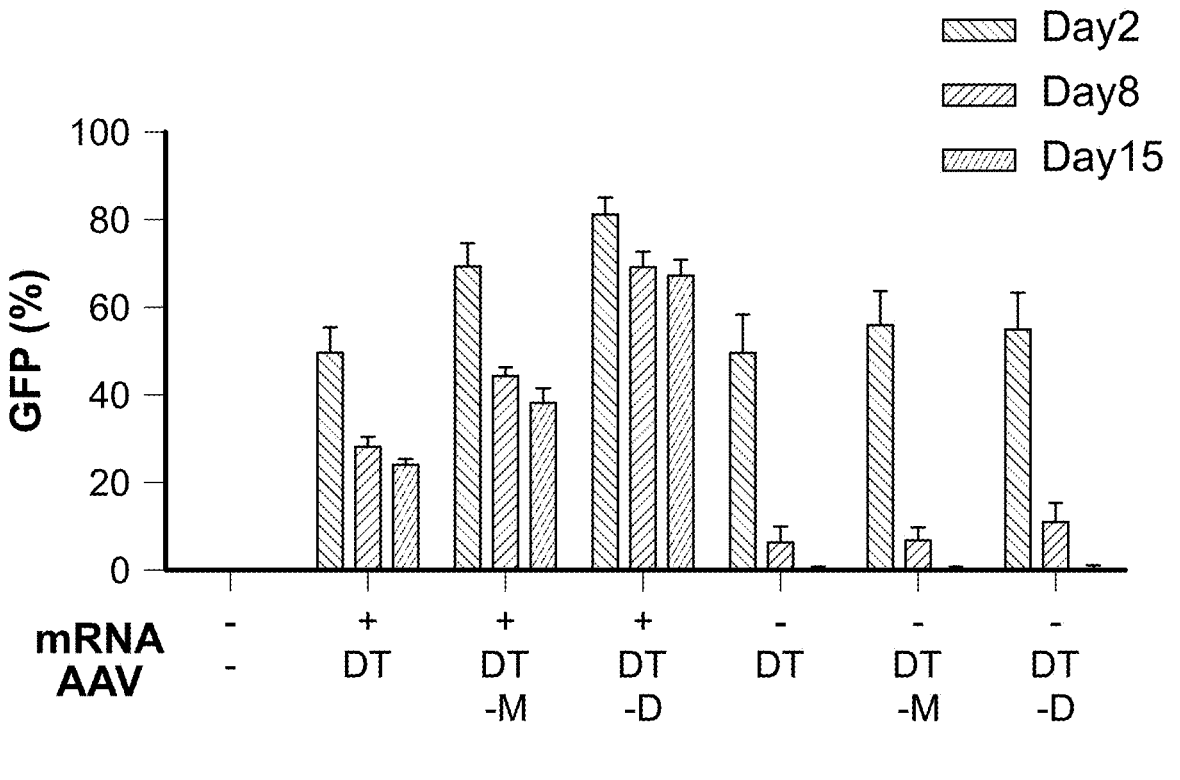
Figure 2D:
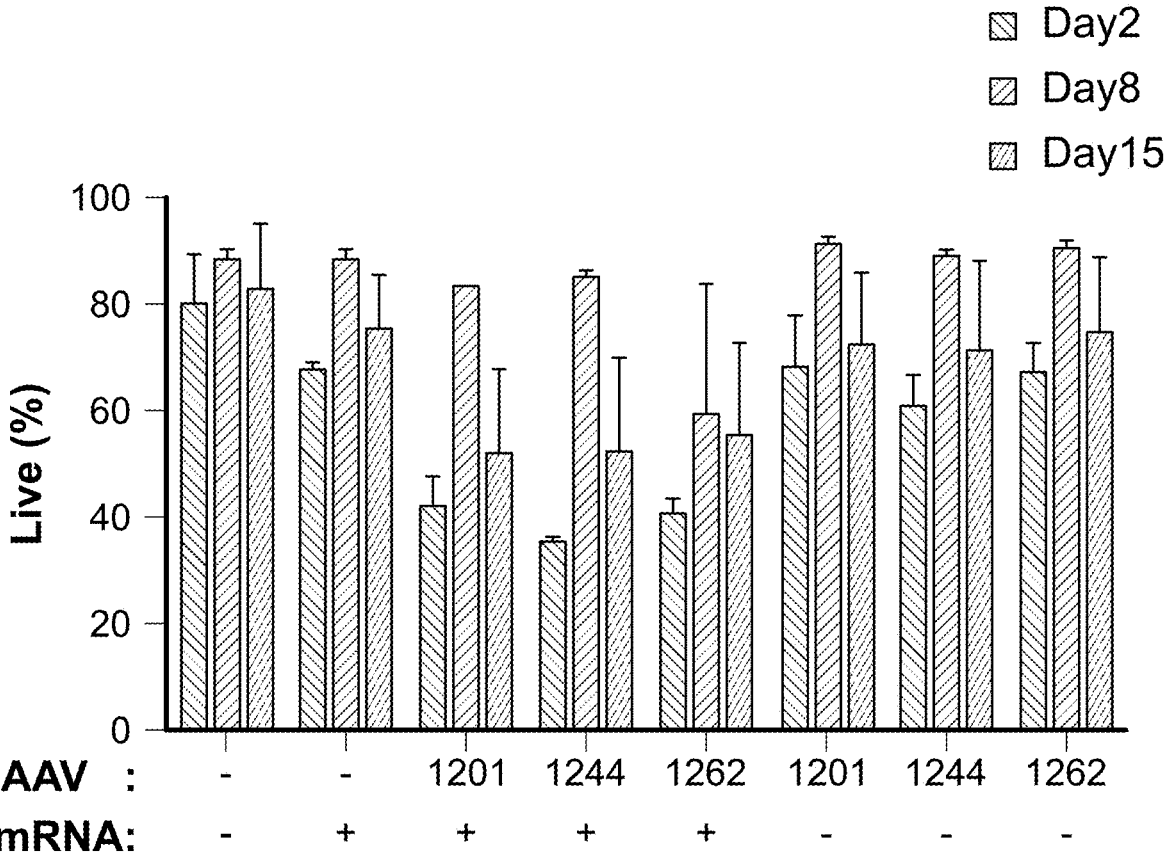
Figure 2E:
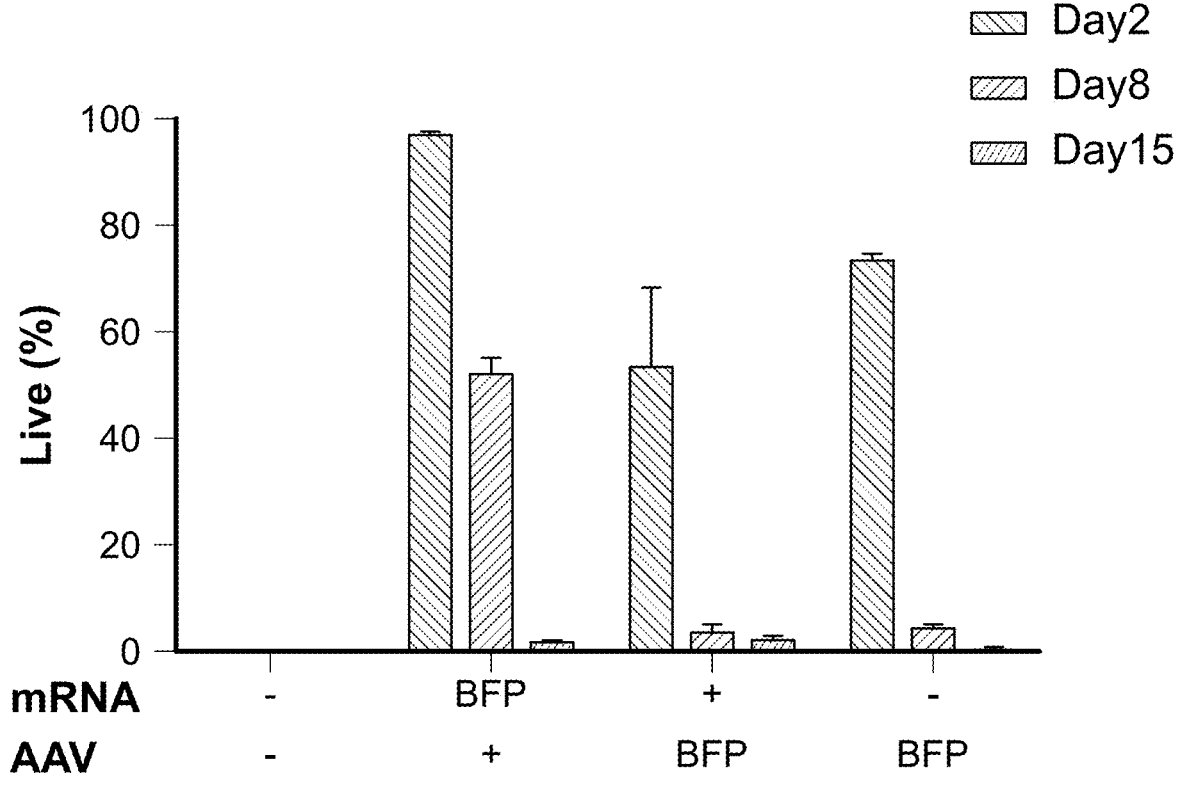
Figure 2F:
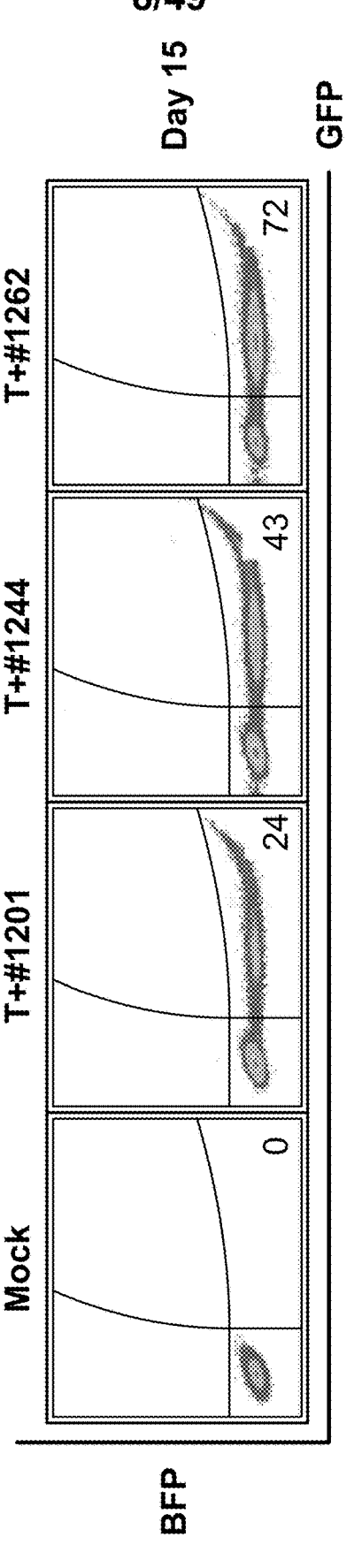
Figure 2G:
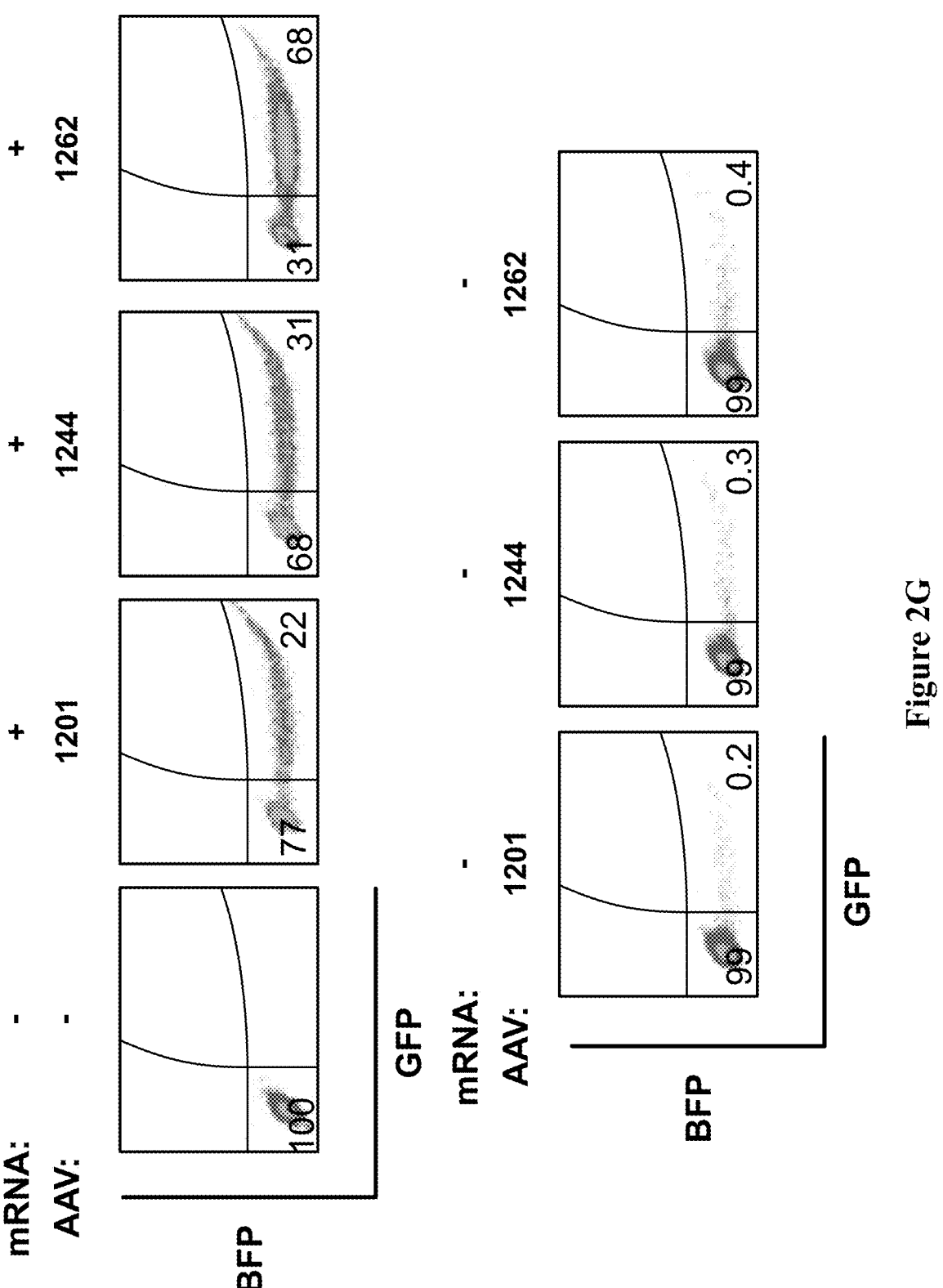
Figure 2H:
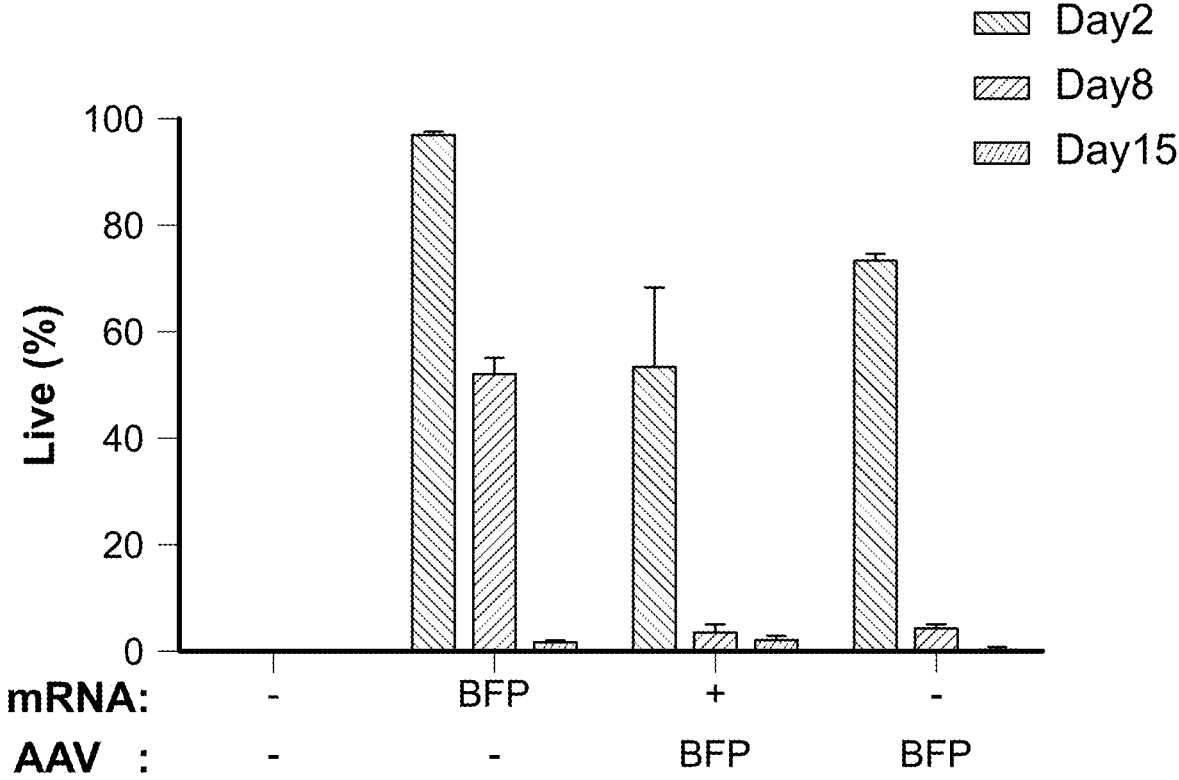
Figure 2I:
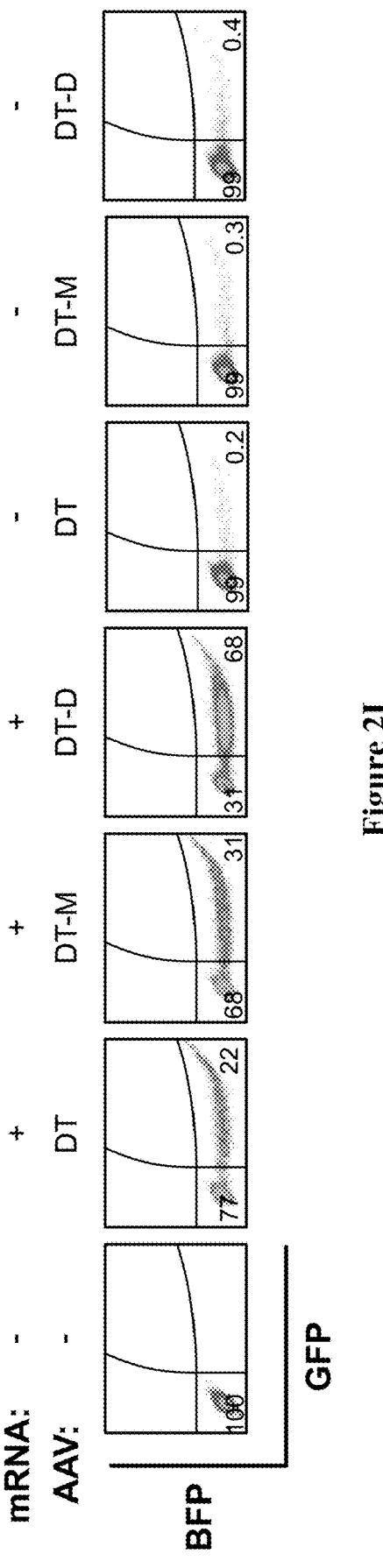

FIG. 2B depicts the timescale for the experimental method. Primary human T cells were cultured in T cell growth medium supplemented with IL-2 (50 ng/mL), IL-7 (5 ng/mL), and IL-15 (5 ng/mL) and stimulated using CD3/CD28 beads (Dynabeads, Life Technologies) for 48 hours. Primary human T cells were cultured in T cell growth medium supplemented with IL-2 (50 ng/ml), IL-7 (5 ng/ml), and IL-15 (5 ng/ml) and stimulated using CD3/CD28 beads (Dynabeads, Life Technologies) for 48 hours. Beads were removed and cells rested overnight followed by electroporation with the nuclease TALEN mRNA using Neon Transfection system. AAV donors were added 2-4 hrs. post transfection at 20% of culture volume. Cells were analyzed for GFP expression on Days 2, 8 and 15. Day 15 GFP is indicative of homology directed repair (HDR). FIG. 2C depicts the % GFP at days 2, 8, and 15 at the indicated conditions (+/−mRNA and the various AAV vectors). Primary human CD3+ T cells were cultured and bead stimulated. Cells were then transfected with TALEN mRNA and AAV donors added two hours later at 20% of culture volume. Cells were analyzed for GFP expression on Days 2, 8 and 15. GFP expression at day 15 is indicative of homology directed repair (HDR). n=3 and represents the number of independent experiments performed using cells from 3 different donors. Data are presented as mean±SEM. GFP expression at day 15 is indicative of homology directed repair (HDR). n=3 and represents the number of independent experiments performed using cells from 3 different donors. Data are presented as mean±SEM. FIG. 2D shows the cell viability under each condition. FIG. 2E are the results from a test for nuclease specificity utilizing AAV without homology arms. Primary T cells transfected with TALENs and transduced with an AAV vector with an MND promoter driven blue fluorescent protein (BFP) without any homology arms. Fluorescence from this vector at day 15 is indicative of random integration. n=3 and represents the number of independent experiments performed using cells from 3 different donors. Data are presented as mean±SEM. FIG. 2F shows representative FACS plots with GFP expression at day 15 post co-delivery of TALEN mRNA and AAV donor templates. FIG. 2G provides additional representative FACS plots showing GFP expression at Day 15. N=3 and represents the number of independent experiments performed using cells from three different donors. Shown in FIG. 2H are the results from a test for nuclease specificity utilizing AAV without homology arms. Primary T cells transfected with TALENs and transduced with an AAV vector with an MND promoter driven blue fluorescent protein (BFP) without any homology arms. Fluorescence from this vector at day 15 is indicative of random integration. n=3 and represents the number of independent experiments performed using cells from 3 different donors. Data are presented as mean±SEM. FIG. 2I shows representative FACS plots showing GFP expression at day 15. n=3 and represents the number of independent experiments performed using cells from 3 different donors.

Alternative 3

Editing of Human Primary T Cells with CRISPR and AAV Co-Delivery

This alternative demonstrates methods for editing primary T Cells with CRISPR and AAV as described in some alternatives herein.

Figure 3A:
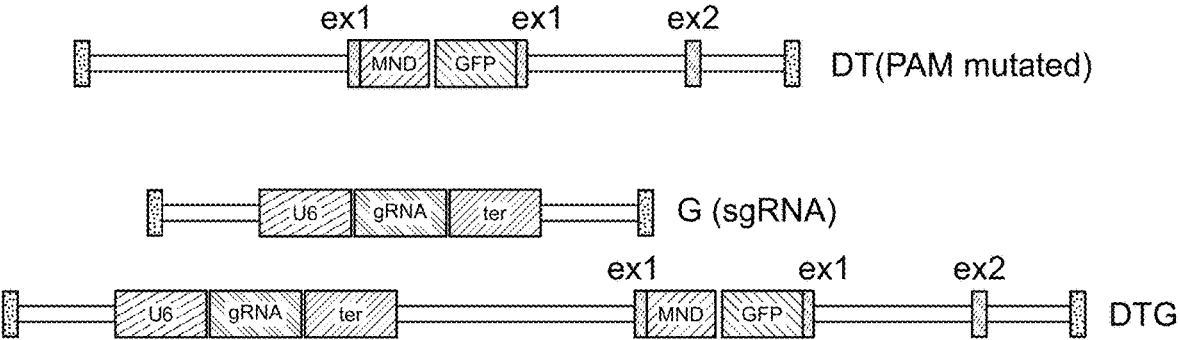
FIGS. 3A-3H depict human primary T cell editing with CRISPR and AAV donors.

FIG. 3A depicts the scAAV guide RNA vector (#1189), donor template (#1201), and AAV vector containing both guide and donor sequences (#1215). Both #1201 and #1215 AAVs have the PAM site mutated to abolish cleavage by guide.

Figure 3B:
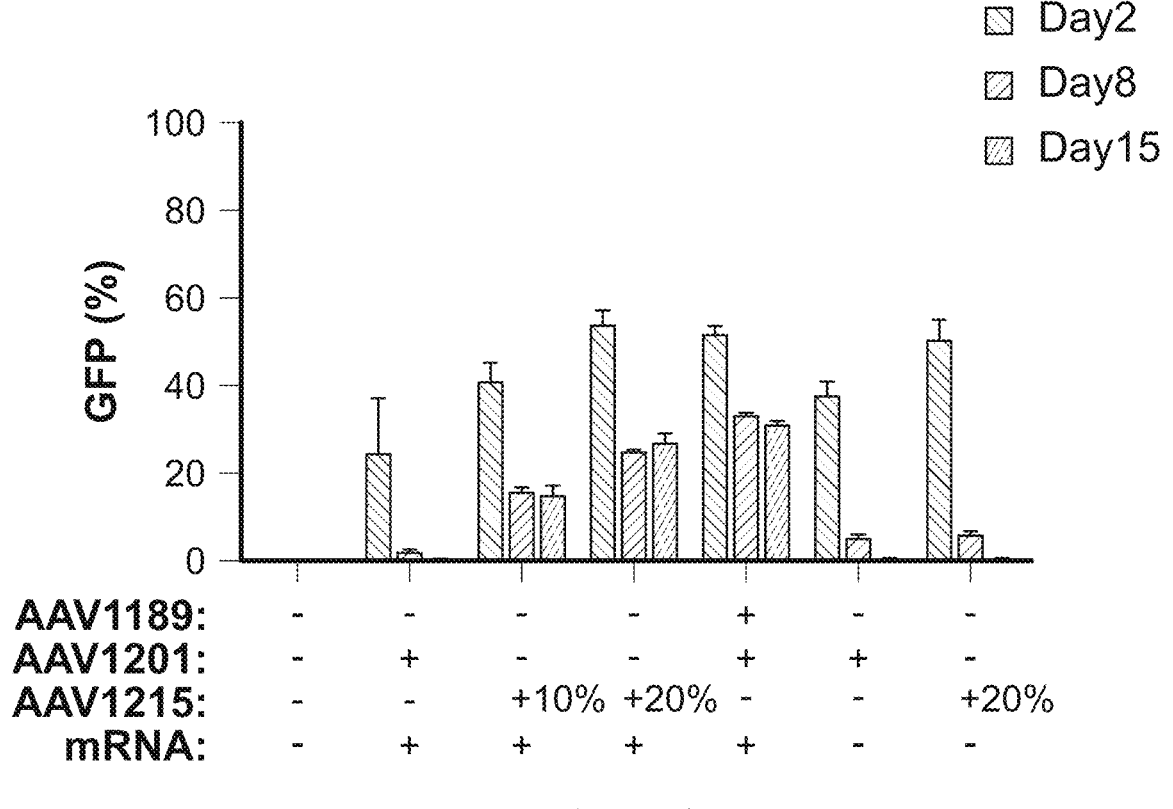
Figure 3C:
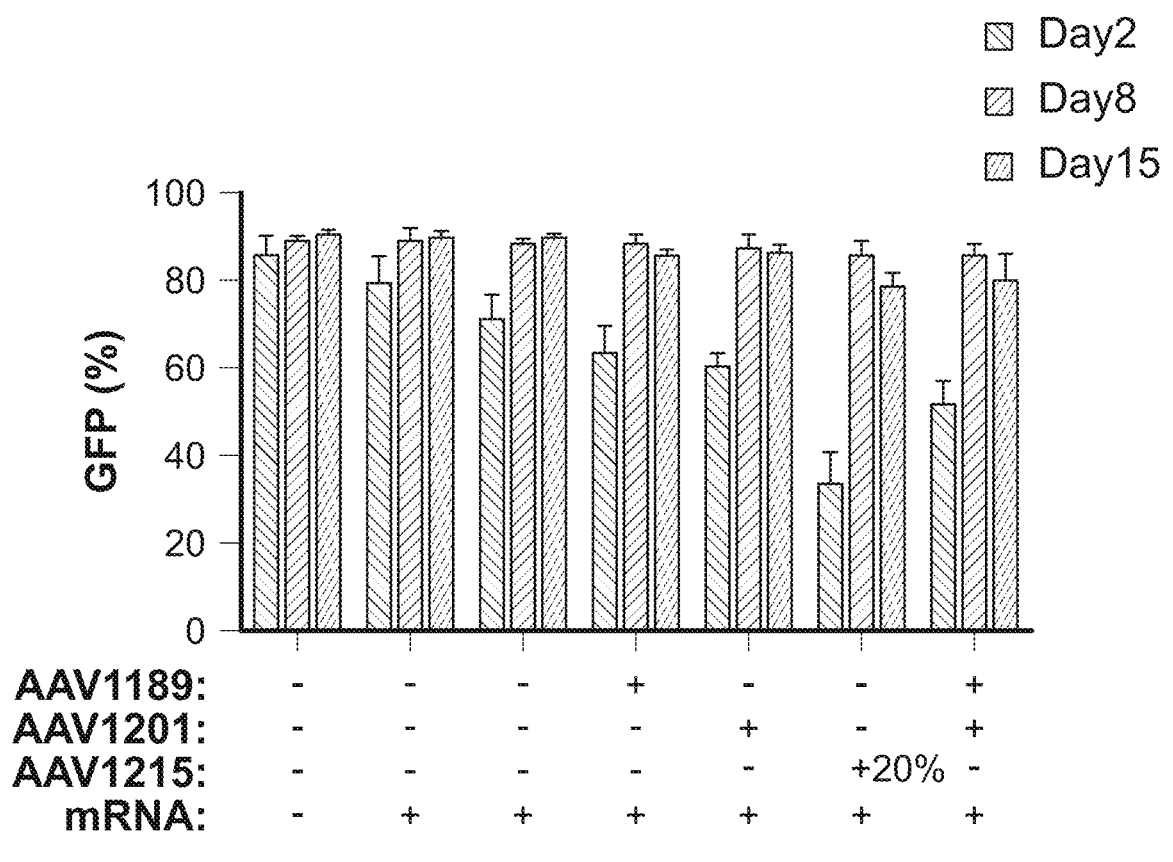
Figure 3D:
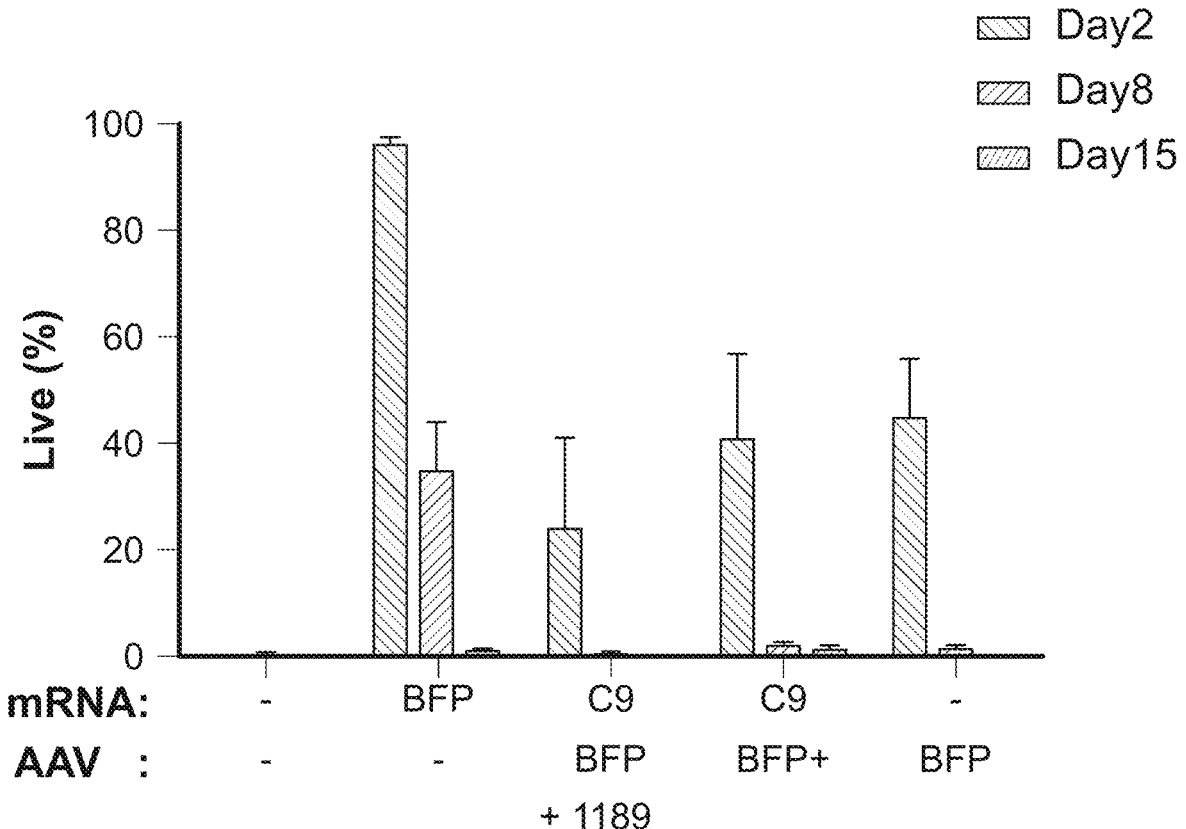
Figure 3E:
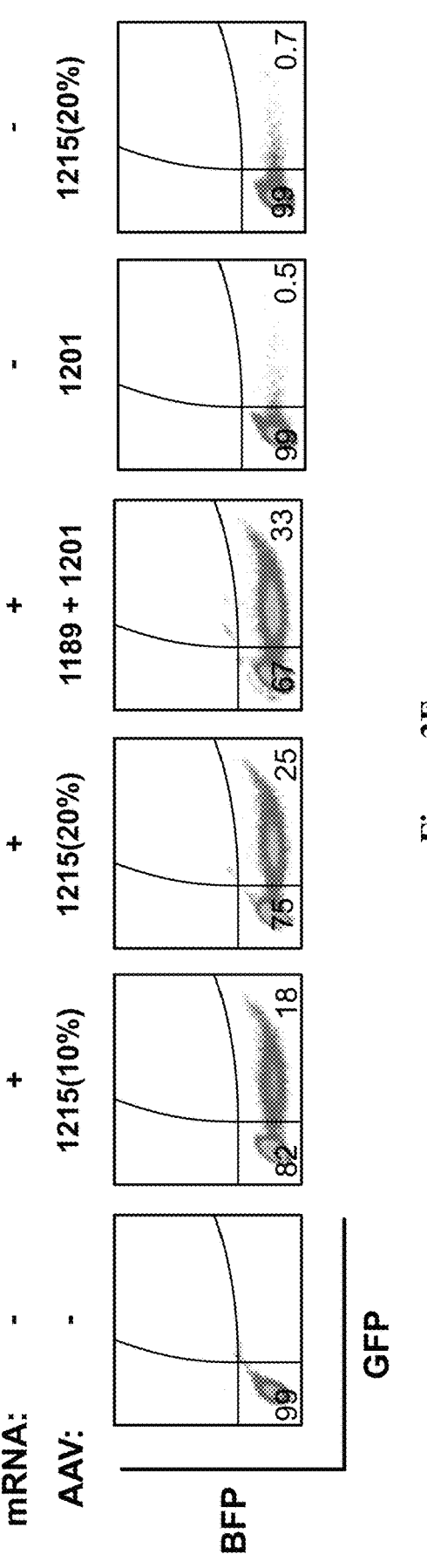
Figure 3F:
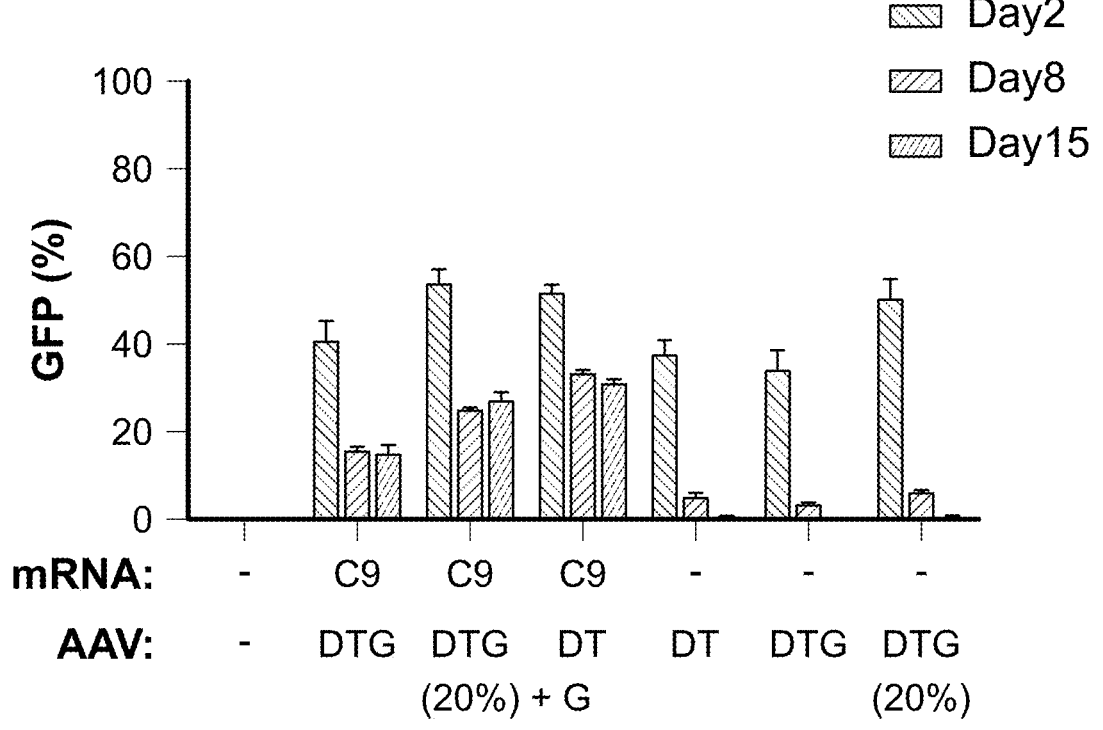
Figure 3G:
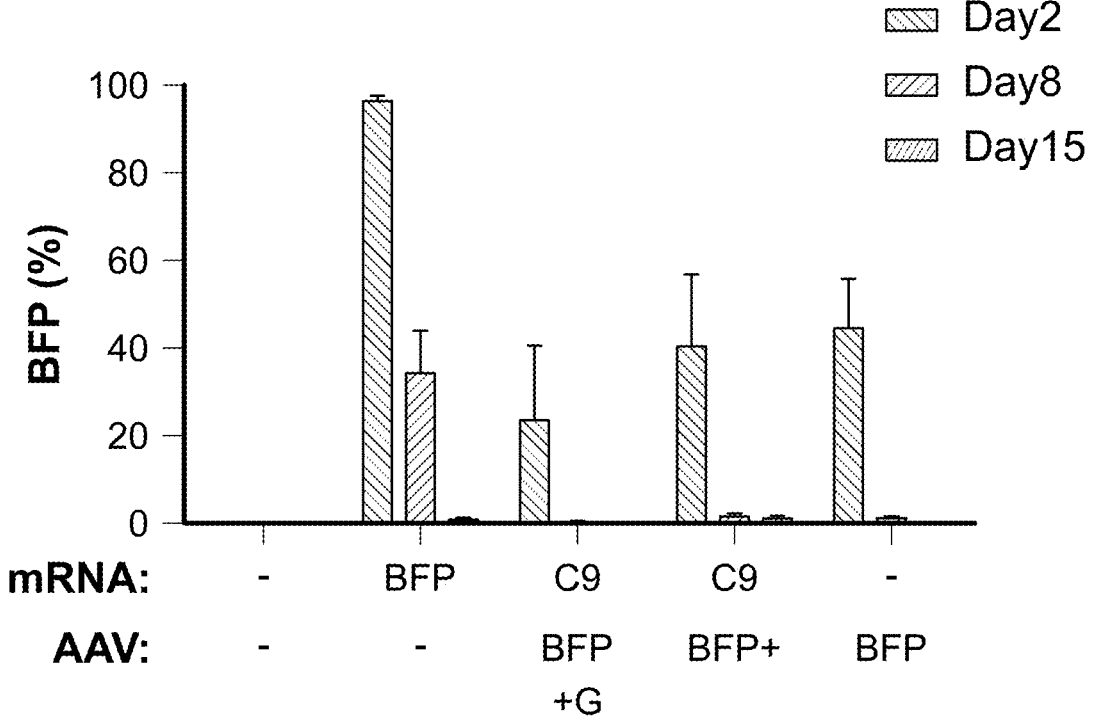
Figure 3H:
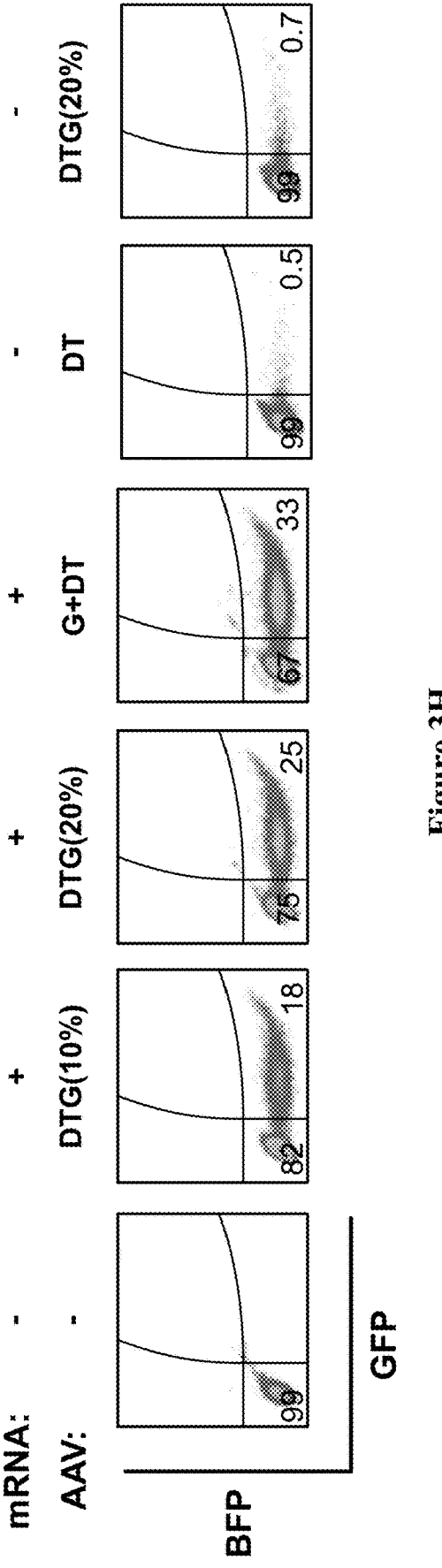

Primary human CD3 T cells were cultured as described in Example 1 and transfected with 1 μg of Cas9 mRNA followed by transduction with either vector #1189 and #1201 or #1215 AAV vectors. FIG. 3B shows the % GFP at days 2, 8, and 15, and FIG. 3C shows the cell viability at days 2, 8, and 15 under the specified conditions. 10% and 20% represent the % of culture volume #1215 AAV was added at. All other AAVs were added at 10% of culture volume. FIG. 3D depicts BFP expression when Cas9, guide and MND.BFP vector with no homology arms were delivered. FIG. 3E shows representative FACS plots showing GFP expression at Day 15. N=3 and represents the number of independent experiments performed using cells from 3 donors. FIG. 3F shows the % GFP at days 2, 8, and 15, and FIG. 3G depicts BFP expression when Cas9, guide and MND.BFP vector with no homology arms were delivered. FIG. 3H shows representative FACS plots showing GFP expression at day 15. N=3 and represents the number of independent experiments performed using cells from 3 donors.

Examples 2 and 3 show that using the T7 endonuclease assay, frequencies of 85% and 73% were achieved with TALENs and CRISPR/Cas systems, respectively. These examples also show methods that result in 70% homology directed repair (HDR) in T cells when the nucleases were co-delivered with an AAV donor template.

Alternative 4

Editing of Mobilized Adult CD34+ Cells with TALEN and AAV Co-Delivery

This alternative demonstrates methods for editing mobilized adult CD34+ cells using co-delivery of TALEN and AAV as described in some alternatives herein.

Figure 4A:
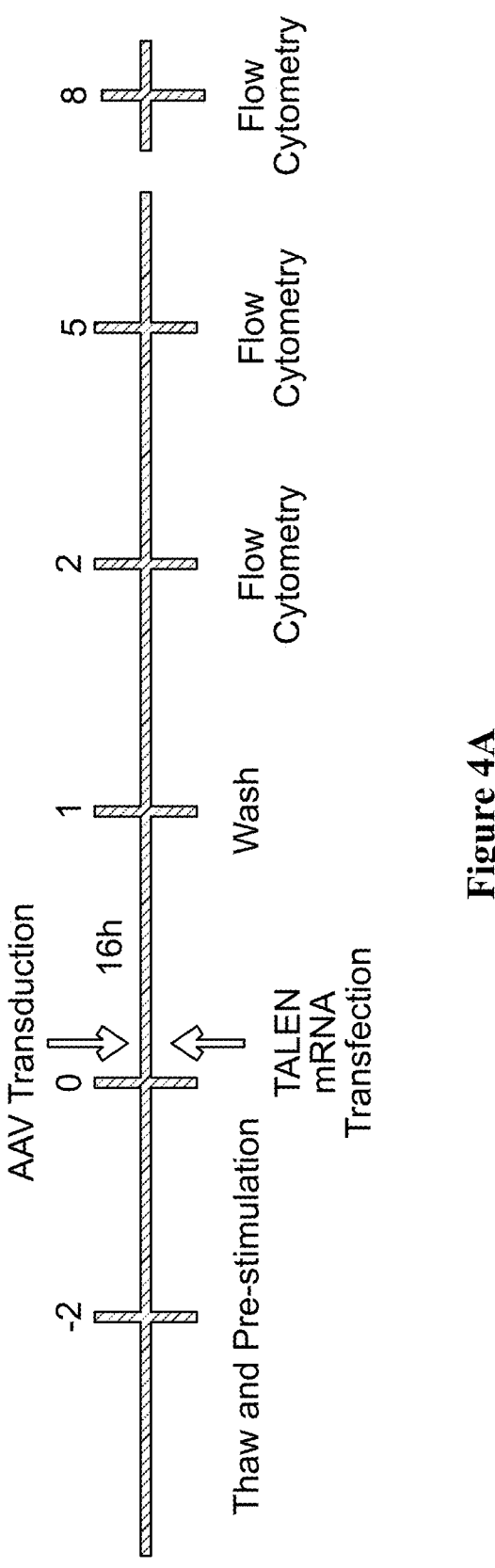
FIGS. 4A-4D depict the editing mobilized adult CD34$^+$ cells using co-delivery of TALEN and AAV.
Figure 4B:
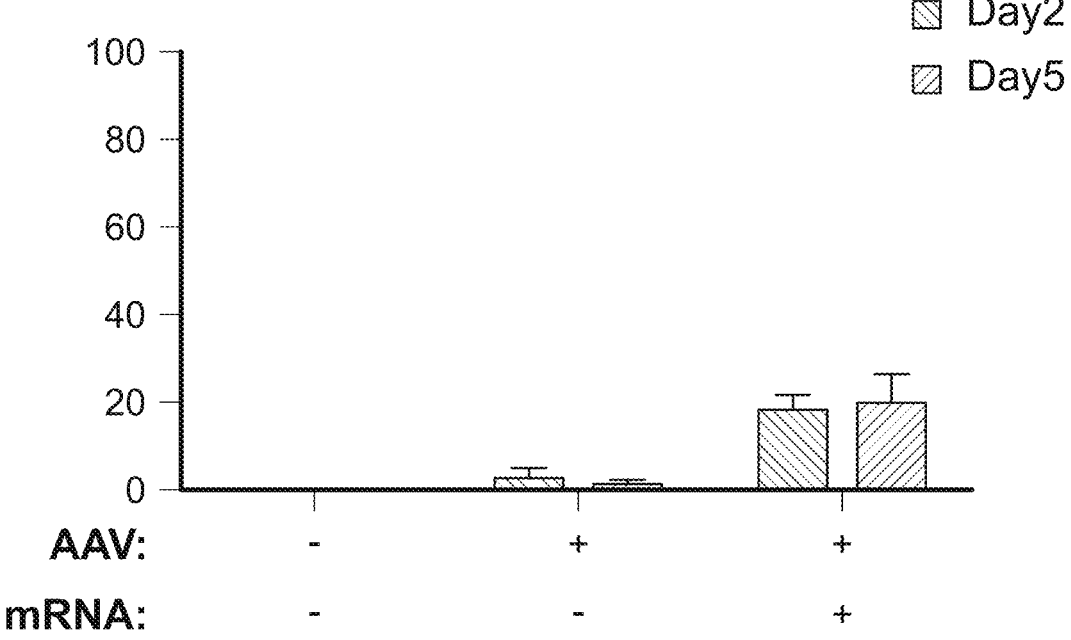
Figure 4C:
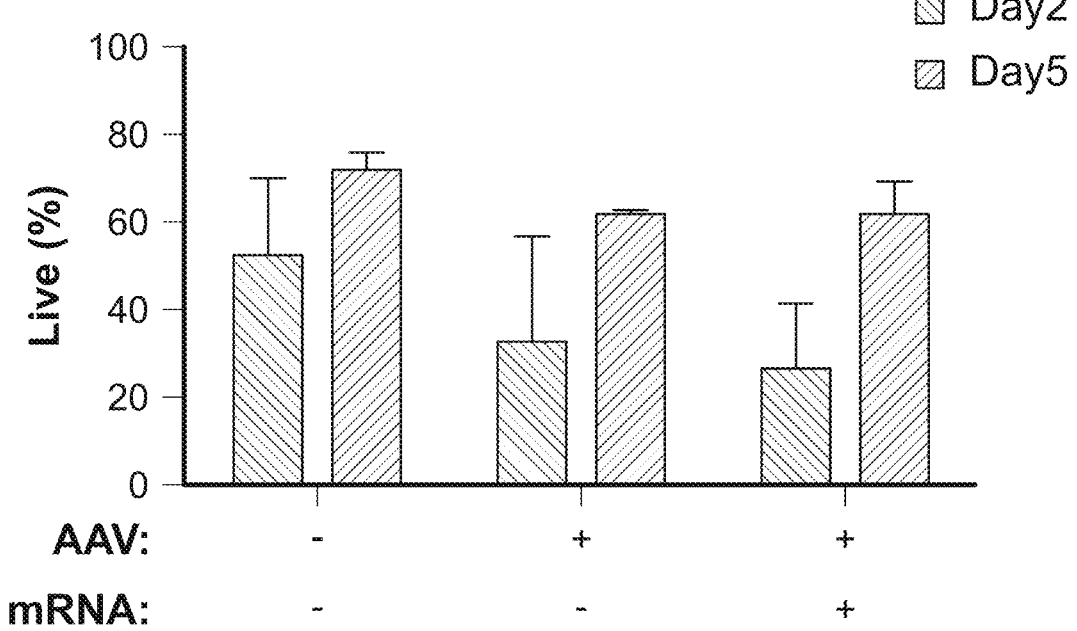
Figure 4D:
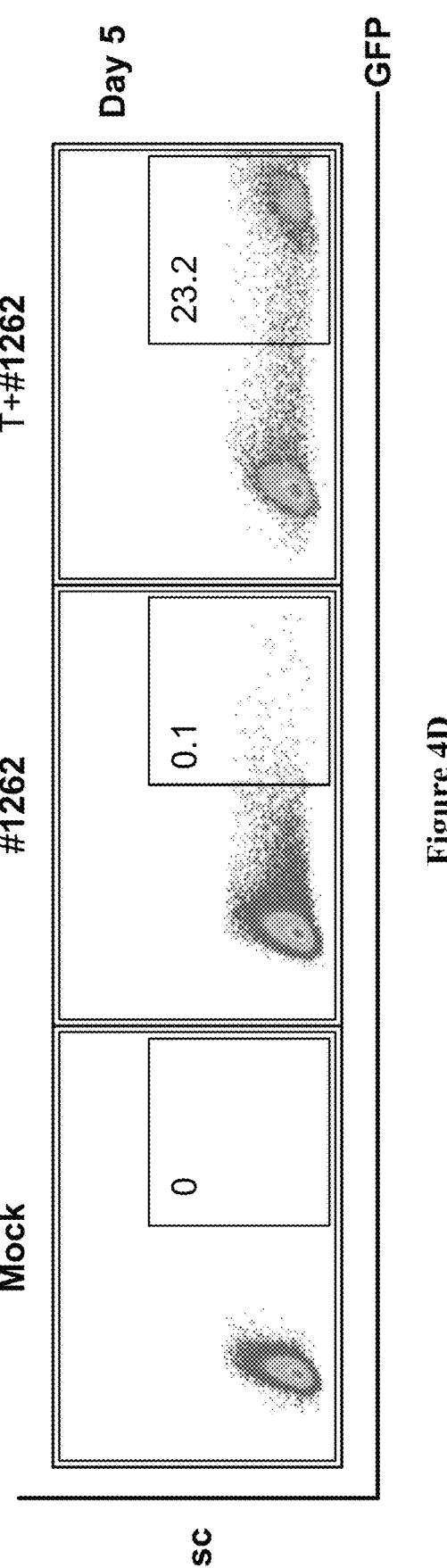

CD34+ cells were transfected as described in Example 2 with TALEN and AAV. FIG. 4A shows the timeline for the experimental conditions, where the cells were analyzed at days 2, 5, and 8 with flow cytometry. FIG. 4B shows the % GFP at days 2 and 5, and the cell viability is depicted in FIG. 4C. FIG. 4D shows representative FACS plots showing GFP expression at day 5.

This alternative demonstrates that the co-delivery of TALEN and AAV induces HDR in adult human mobilized CD34+ cells.

Alternative 5

Off-Target Cleavage with TALEN

This alternative provides potential off-target cleavage sites for TALENs.

Figure 5A:
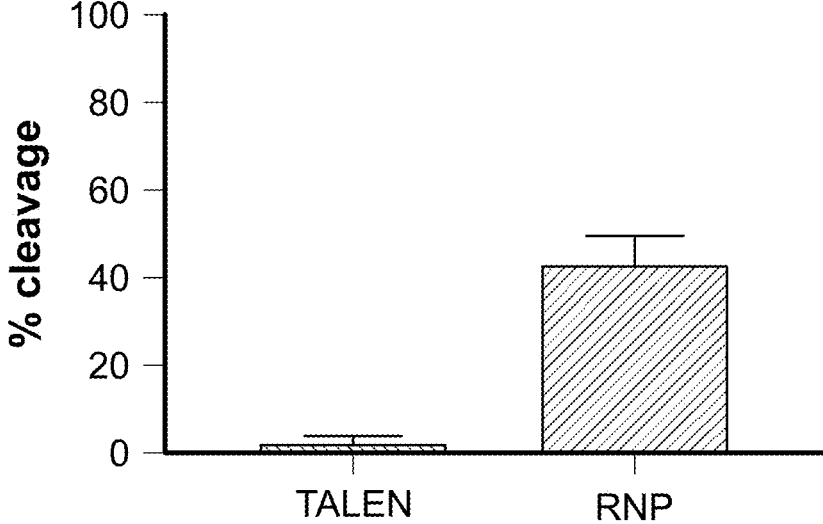
FIGS. 5A-5G depict the editing mobilized adult CD34$^+$ cells using co-delivery of TALEN mRNA or CRISPR guide delivered as RNP and AAV donor and shows disruption of the WAS locus in human CD34$^+$ cells using TALENs or RNP. Mobilized human CD34$^+$ cells were cultured in SCGM media supplemented with TPO, SCF, FLT3L (100 ng/mL) and IL3 (60 ng/mL) for 48 hours, followed by electroporation using Neon electroporation system with either 1 ug of each TALEN monomer or Ribonucleoprotein complex (RNP) of Cas9 protein and single guide RNA mixed in 1:1.2 ratio. The sgRNA was purchased from Trilink BioTechnologies and has chemically modified nucleotides at the three terminal positions at 5' and 3' ends. The cells were cultured for 5 days and genomic DNA was extracted. The region surrounding the cut site for WAS TALEN and guide was amplified and cloned into pJET cloning vector. Colony sequencing was performed to quantify % cleavage at the cut site by analyzing the indels. N=3 and represents the number of independent experiments performed using cells from three donors.

T cells were transfected with 1 μg of forward and reverse WAS TALEN. Five days post-transfection, genomic DNA was extracted, endogenous WAS locus and predicted off target loci were amplified and colony sequenced. Off-targets were predicted using Prognos software. As shown in Table 1 below, potential off-target cleavage sites for TALENs identified using the Prognos software were amplified and sequenced, with no evidence of off-target cleavage observed at any of the predicted loci.

troporation system with either 1 μg of each TALEN monomer or ribonucleoprotein complex (RNP) of Cas9 protein and single guide RNA (sgRNA) mixed in 1:1.2 ratio. The sgRNA was purchased from Trilink BioTechnologies and has chemically modified nucleotides at the three terminal positions at 5' and 3' ends. The cells were cultured for 5 days and genomic DNA was extracted. The region surrounding the cut site for WAS TALEN and guide was amplified and cloned into pJET cloning vector. Colony sequencing was performed to quantify % cleavage at the cut site by analyzing the indels. FIG. 5A depicts the % cleavage of the WAS locus in the CD34+ cells for both TALEN and RNP. N=3 and represents the number of independent experiments performed using cells from three donors.

As shown in FIG. 5A, adult human mobilized CD34+ cells were cultured in SCGM media supplemented with TPO, SCF, FLT3L (100 ng/ml) and IL-3 (60 ng/ml) for 48 hours, followed by electroporation using Neon electroporation system with either 1 μg of each TALEN monomer or Ribonucleoprotein complex (RNP) of Cas9 protein and single guide RNA mixed in 1:1.2 ratio. The sgRNA was purchased from Trilink Biotechnologies and has chemically modified nucleotides at the three terminal positions at 5' and 3' ends. The cells were cultured for 5 days and genomic DNA was extracted. The region surrounding the cut site for WAS TALEN and guide was amplified and cloned into pJET cloning vector. Colony sequencing was performed to quantify % cleavage at the cut site by analyzing the indels. N=3 and represents the number of independent experiments performed using cells from 3 donors.

Figure 5B:
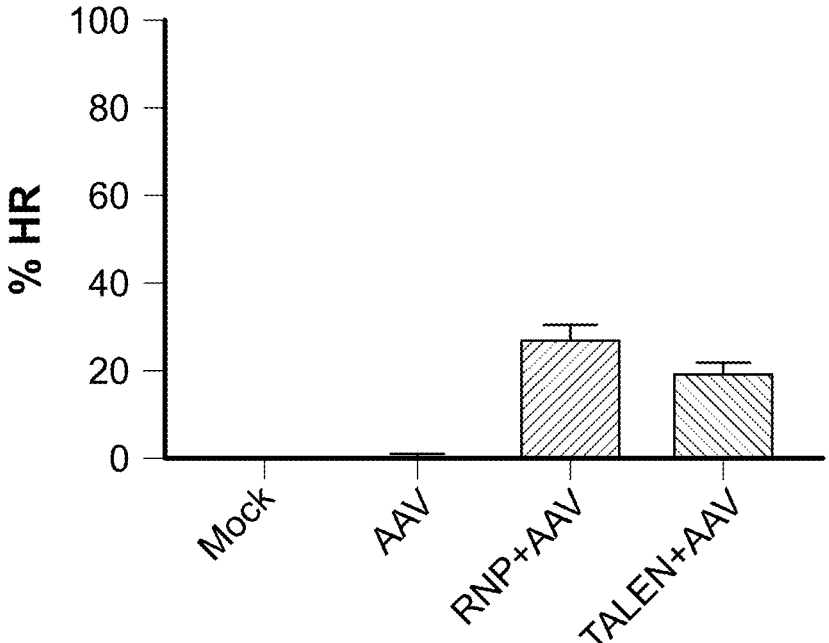

As shown in FIG. 5B, adult mobilized human CD34+ cells were cultured in SCGM media as described in FIG. 5A, followed by electroporation using Neon electroporation system with either TALEN mRNA or RNP complex (2 μg). AAV vector (MOI ranging from 62-300) carrying the donor template was added immediately after electroporation. Controls included un-manipulated cells (mock) and cells transduced with AAV only without transfection of a nuclease (AAV). Bar graphs depict % GFP at day 5, indicative of HDR. n=8 for RNP, n=15 for TALEN, and represents >4 donors.

| Ranking | TALEN Score | Orientation | Mismatches | Chr Name | Genomic Region | Closest Gene | % Cleavage |
|---|---|---|---|---|---|---|---|
| 1 | 100 | L-17-R | 0_0 | ChrX | Intron | WAS | 94% (32/34) |
| 2 | 60.25 | R-26-L | 6_2 | Chr6 | Intergenic | LRFN2 | 0% (0/30) |
| 3 | 59.44 | R-25-L | 6_3 | Chr18 | Intron | DLGAP1 | 0% (0/30) |
| 4 | 59.18 | R-30-L | 5_3 | Chr12 | Exon | MAGOHB | 0% (0/30) |
| 5 | 56.42 | R-30-R | 5_3 | Chr7 | Intergenic | INHBA | 0% (0/30) |
| 6 | 56.15 | L-13-R | 6_3 | Chr1 | Intergenic | SIKE1 | 0% (0/30) |
| 7 | 55.97 | R-16-L | 6_3 | Chr8 | Intergenic | ANGPT1 | 0% (0/30) |
| 8 | 55.74 | R-15-R | 5_3 | Chr2 | Intron | RALB | 0% (0/30) |
| 12 | 55.18 | R-11-L | 5_4 | Chr3 | Intergenic | MIR548A3 | 0% (0/30) |

Alternative 6

Disruption of WAS Locus in Human CD34+ Cells Using TALENS or RNP

This alternative demonstrates the disruption of human CD34+ cells using TALEN or a ribonucleoprotein complex (RNP).

Figure 5C:
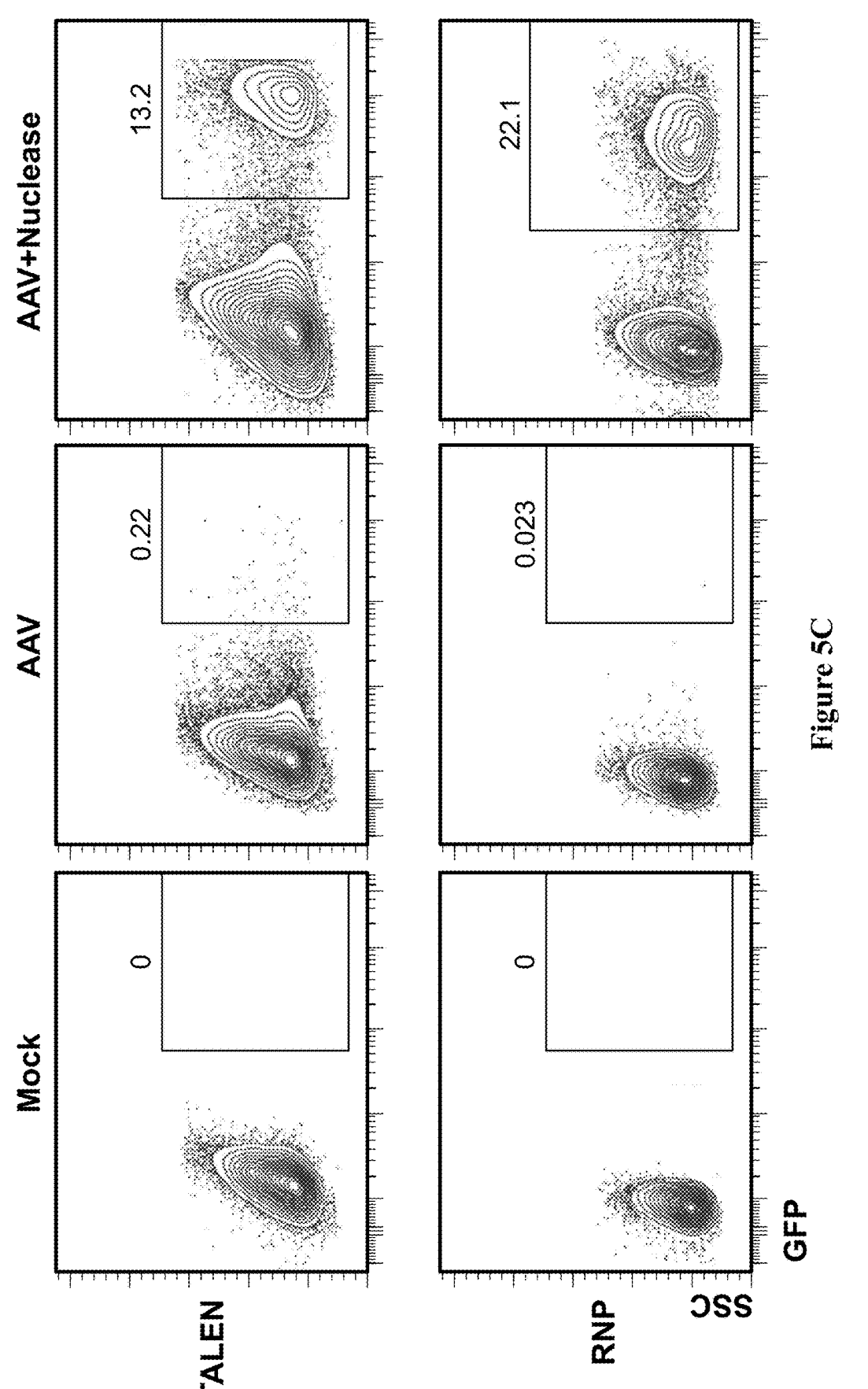

Mobilized human CD34+ cells were cultured in stem cell growth medium (SCGM) supplemented with thrombopoietin (TPO), stem cell factor (SCF), Fms-related tyrosine kinase 3 ligand (FLT-3L) (100 ng/mL) and IL-3 (60 ng/mL) for 48 hours, followed by electroporation using Neon elec- Shown in FIG. 5C, are FACS plots depicting GFP expression from Mock, AAV or AAV plus TALEN treated CD34+ cells (top row) or AAV+RNP treated cells (bottom row) 5 days post editing.

Figure 5D:
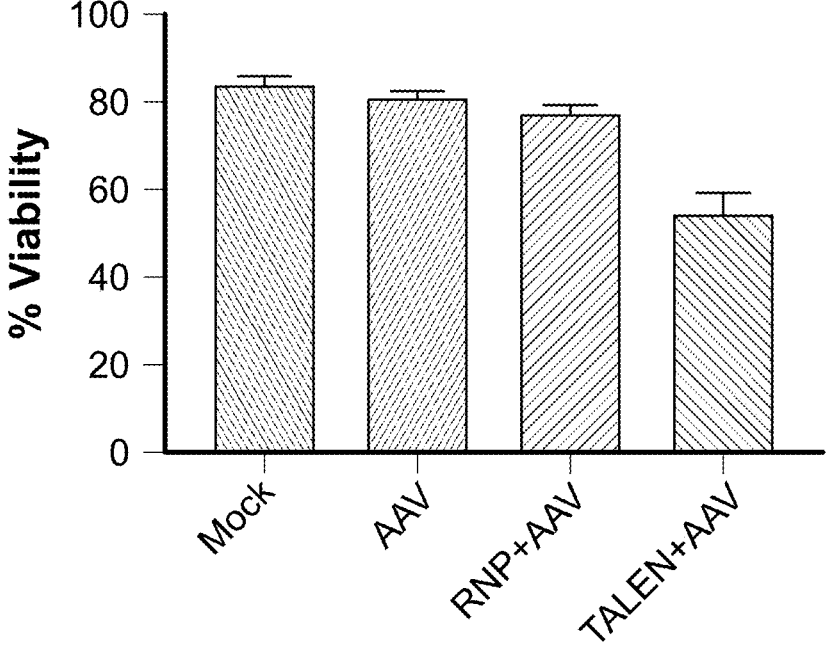

Shown in FIG. 5D, bar graphs represent viability of mock and edited cells 2 days post editing. N=8 for RNP, n=12 for TALEN and represents >4 independent donors.

Figure 5E:
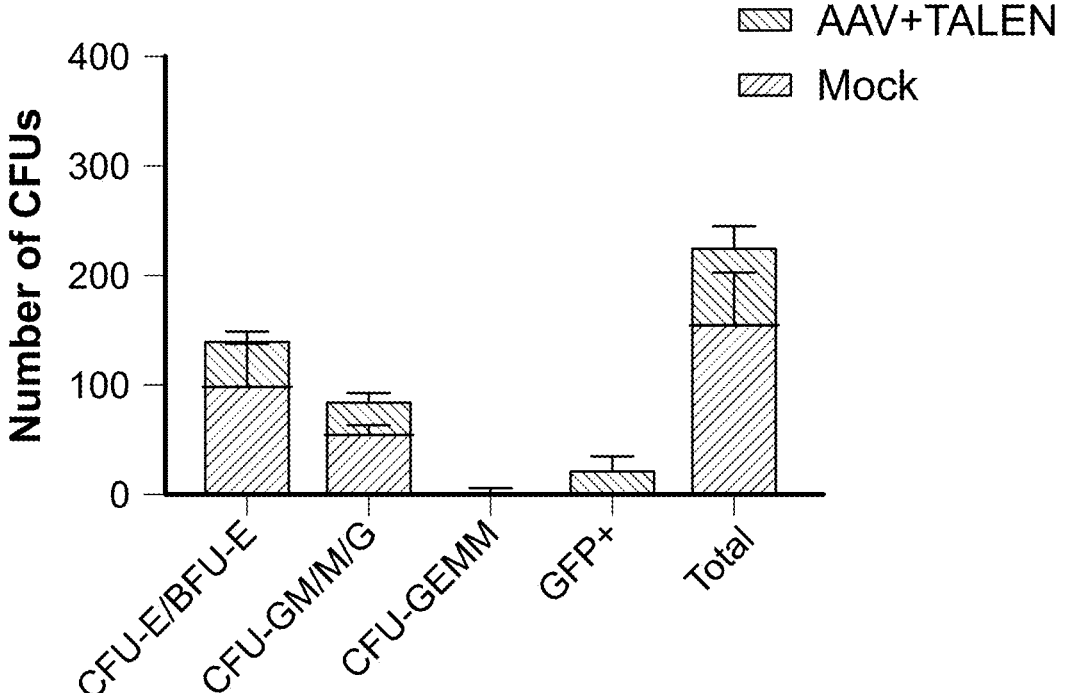

Shown in FIG. 5E, are results from a CFU assay for TALEN edited CD34+ cells. TALEN edited and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 independent donors. Data are presented as mean±SEM.

Figure 5F:
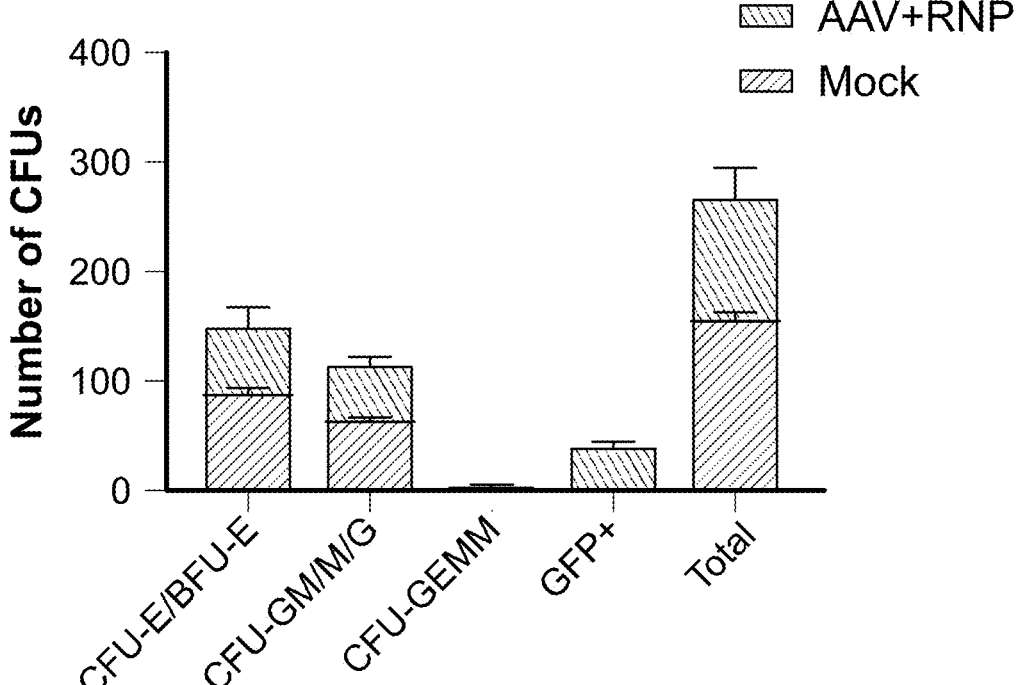

Shown in FIG. 5F, are results from a CFU assay for RNP edited CD34+ cells. RNP edited and mock cells were plated one day post editing onto Methocult media for colony formation unit (CFU) assay. Briefly, 500 cells were plated in duplicate in Methocult H4034 media (Stemcell Technologies), incubated at 37° C. for 12-14 days and colonies enumerated based on their morphology and GFP expression. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid. n=3 experiments and 2 donors. Data are presented as mean±SEM.

Figure 5G:
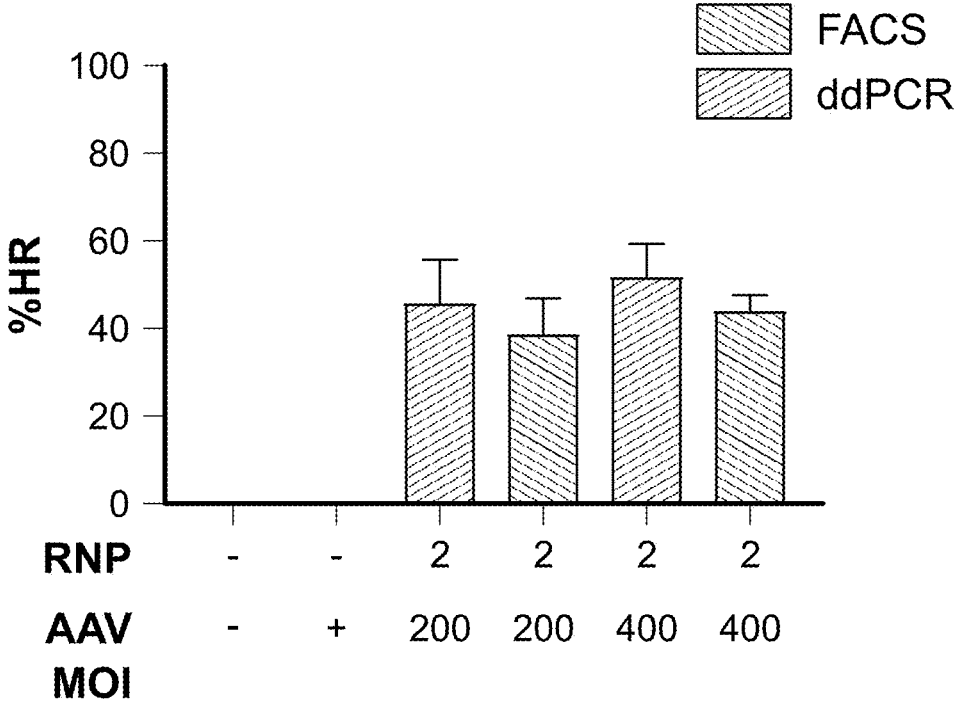

Shown in FIG. 5G are results from the digital droplet PCR assay for determining HDR. Genomic DNA was isolated from hematopoietic stem and progenitor cells (HSPCs) using a DNeasy Blood and Tissue kit (Qiagen). To assess editing rates, "in-out" droplet digital PCR was performed with the forward primer binding within the AAV insert and the reverse primer binding the WAS locus outside the region of homology. A control amplicon of similar size was generated for the ActB gene to serve as a control. All reactions were performed in duplicate. The PCR reactions were partitioned into droplets using a QX200 Droplet Generator (Bio-Rad). Amplification was performed using ddPCR Supermix for Probes without UTP (Bio-Rad), 900 nM of primers, 250 nM of Probe, 50 ng of genomic DNA, and 1% DMSO. Droplets were analyzed on the QX200 Droplet Digital PCR System (Bio-Rad) using QuantaSoft software (Bio-Rad). Data are presented as mean±SEM.

Alternative 7

Editing of the WAS Locus in CD34+ HSCs with TALEN mRNA/RNP and AAV Co-Delivery

This alternative demonstrates editing of the WAS locus in CD34+ hematopoietic stem cells using co-delivery of TALEN mRNA or RNP and an AAV donor template.

Figure 6A:
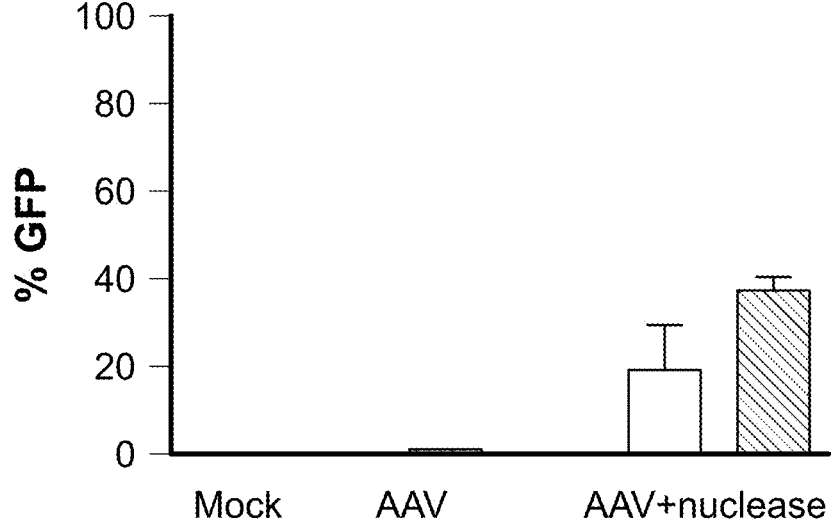
FIGS. 6A-6D show editing of the WAS locus in CD34$^+$ HSCs using co-delivery of TALEN mRNA/RNP and AAV donor template. Adult mobilized human CD34$^+$ cells that were cultured in SCGM media as described in FIG. 5, followed by electroporation using Neon electroporation system with either TALEN mRNA or RNP complex. AAV vector carrying the donor template was added immediately after electroporation. Controls included un-manipulated cells (mock) and cells transduced with AAV only without transfection of a nuclease (AAV).
Figure 6B:
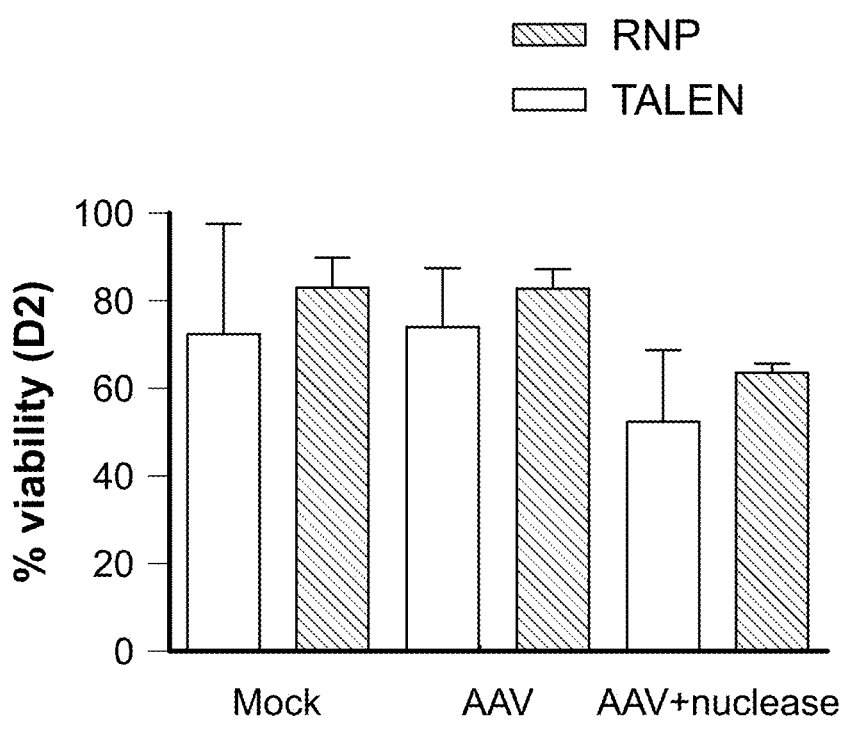
Figure 6C:
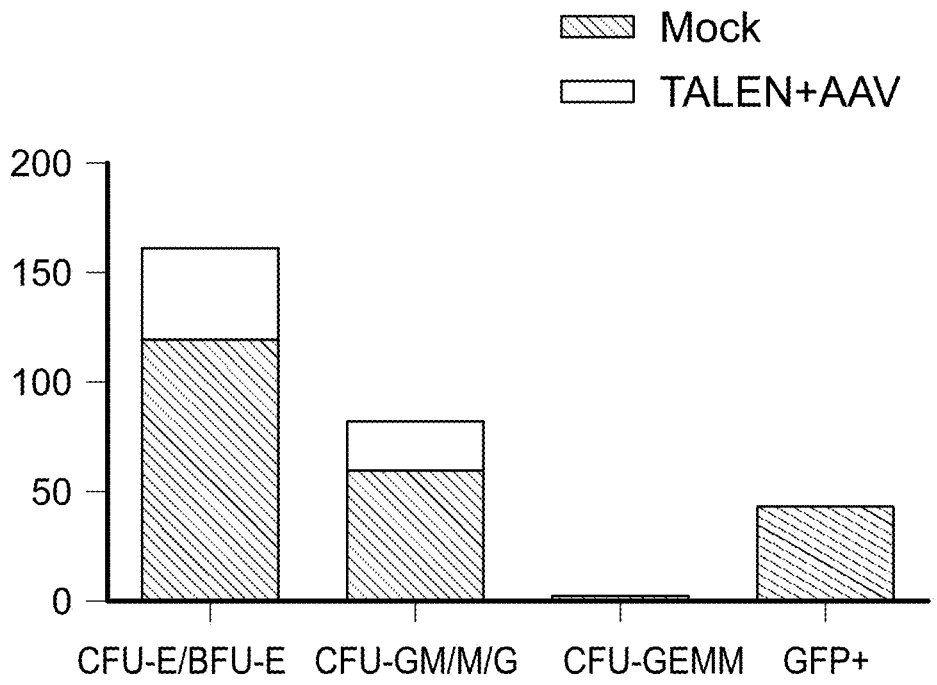
Figure 6D:
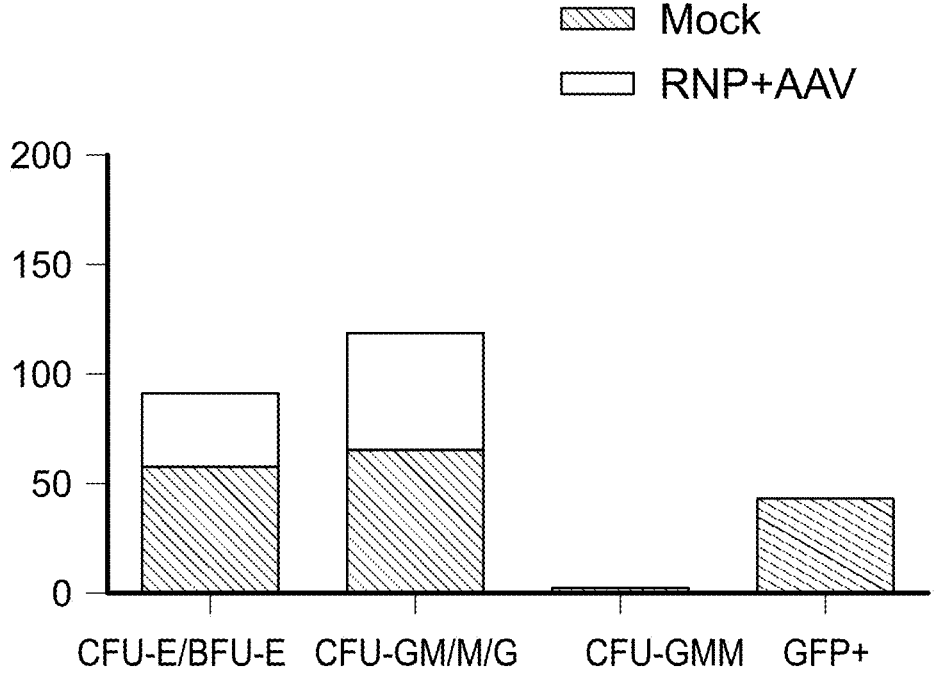

Adult mobilized human CD34+ cells were cultured in SCGM media as described in Example 6, followed by electroporation using Neon electroporation system with either TALEN mRNA or RNP complex. AAV vector carrying the donor template was added immediately after electroporation. Controls included un-manipulated cells (mock) and cells transduced with AAV only without transfection of a nuclease (AAV). FIG. 6A shows % GFP at day 5 indicative of HDR. FIG. 6B shows the viability of edited cells two days post editing. N=7 for TALEN and N=3 for RNP and represent independent donors. Edited and mock cells were plated one day post editing onto Methocult media for colony formation unit (CFU) assay. Briefly, 500 cells were plated in duplicate in Methocult H4034 media (Stemcell Technologies, incubated at 37° C. for 12-14 days and colonies enumerated based on their morphology and GFP expression. FIG. 6C shows data from TALEN and FIG. 6D shows data from RNP. CFU-E: Colony forming unit erythroid, M: Macrophage, GM: Granulocyte, macrophage, G: Granulocyte, GEMM: Granulocyte, erythroid, macrophage, megakaryocyte, BFU-E: Burst forming unit erythroid.

Alternative 8

Engraftment of Edited Human CD34+ Cells into Immune Deficient NSG Mice

This alternative demonstrates the use of the edited cells in immune deficient mice.

Figure 7A:
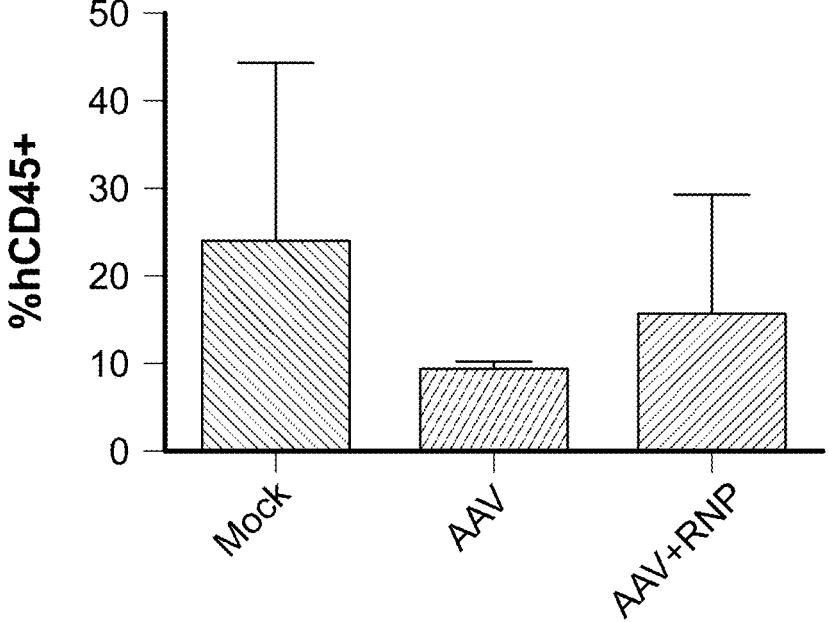
FIGS. 7A-7C show engraftment of edited human CD34$^+$ cells into immune deficient NSG mice. 2 million human CD34$^+$ cells untreated, AAV treated or treated with AAV and RNP were injected into immune deficient NSG mice preconditioned with 25 mg/kg busulfan. The mice were sacrificed 10 weeks post-transplant and BM was harvested.
Figure 7B:
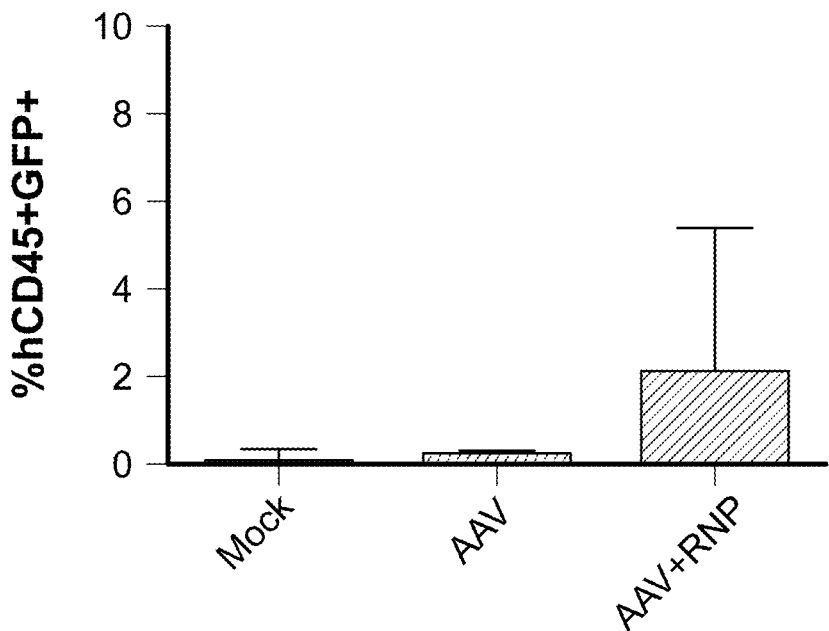
Figure 7C:
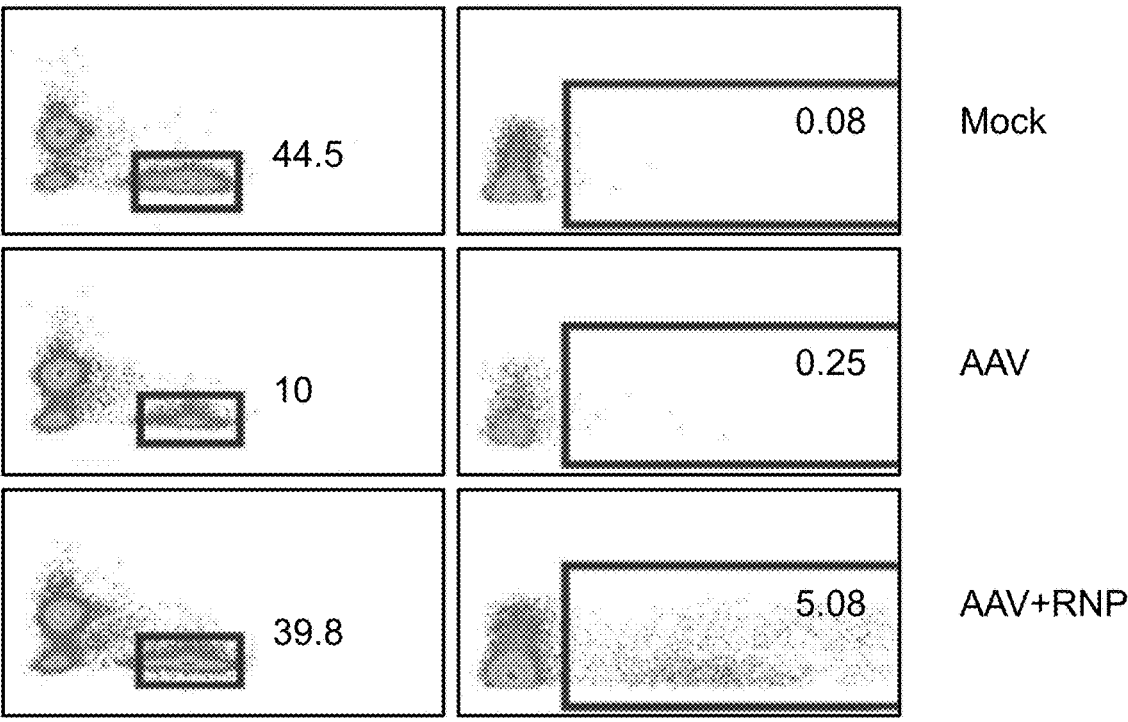
Figure 7C:
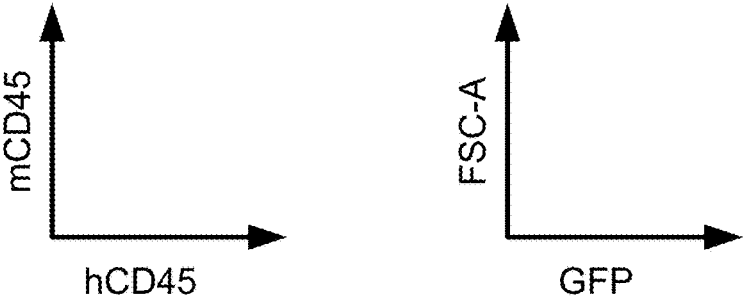
Figure 8:
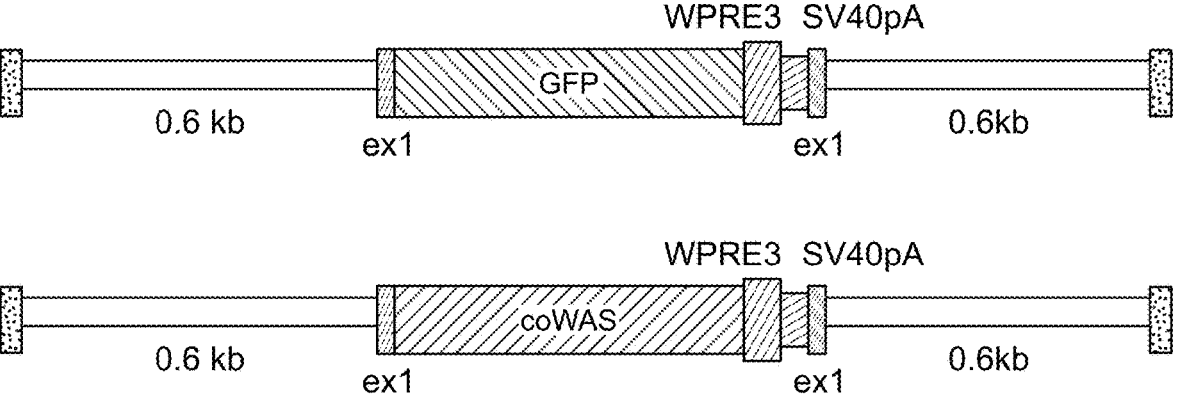
FIG. 8 shows the design of AAV vectors expressing cDNA for human codon optimized WAS gene. AAV vectors with 0.6 kb homology arms flanking either a promoter-less GFP (top) or WAS cDNA (bottom) followed by a shorter WPRE, designated WPRE3 followed by SV40 polyadenylation signal.

Two million human CD34+ cells that were either untreated, AAV treated, or treated with AAV and RNP were injected into immune deficient non-obese diabetic (NOD) severe combined immunodeficiency (scid) gamma (NSG) mice preconditioned with 25 mg/kg busulfan. The mice were sacrificed 10 weeks post-transplant and bone marrow was harvested. FIG. 7A depicts total engraftment of edited cells as defined by expression of human CD45 marker. FIG. 7B Illustrates % GFP+ cells within the engrafted cells. FIG. 7C shows FACS plots from representative mice.

Alternative 9

Percent HR in Cells for Engraftment

Figure 9A:
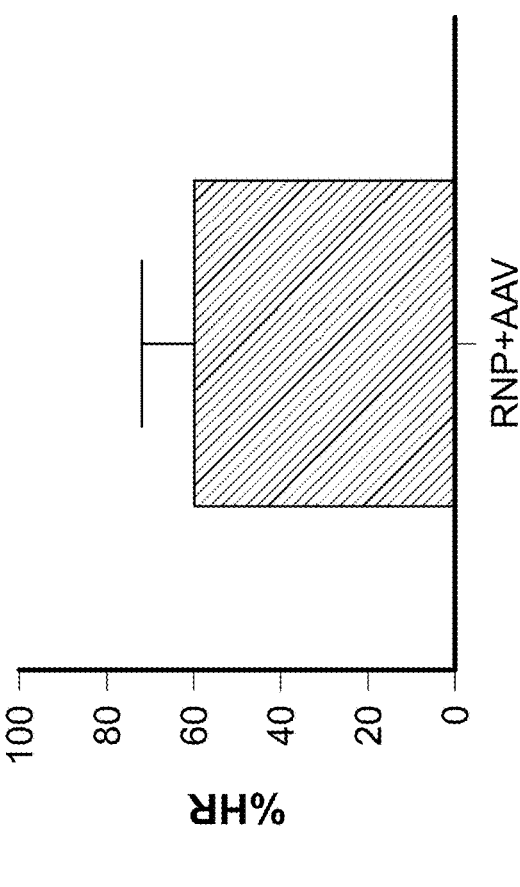
FIG. 9A shows data representative of assays for cell viability and % HR in input cells used for engraftment in NSG mice. Adult mobilized human CD34$^+$ cells were cultured in SCGM media as previously described with the exception that IL-6 (100 ng/ml) was added instead of IL-3. The cells were electroporated with 1 μg of RNP complex and AAV at an MOI of 62. Data are presented as mean±SEM. N=5 and represents independent experiments using multiple donors.
Figure 9A:
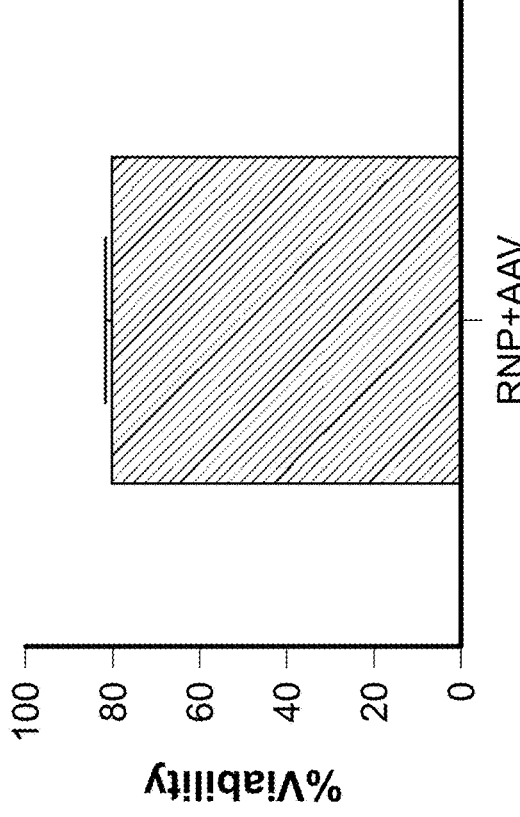
Figure 9B:
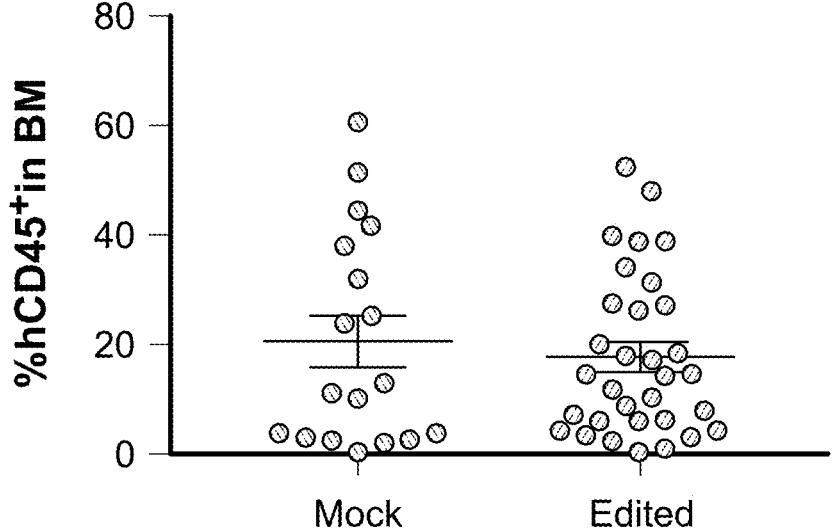
FIG. 9B shows the data representing the engraftment of edited cells in bone marrow of transplanted NSG mice. Six to 10-week old NSG mice were treated with 25 or 35 mg/kg of BUSULFEX (Henry Schein Inc.) via intraperitoneal injection, diluted 1:1 in phosphate-buffered saline. Twenty-four hours later, 2×10⁶ mock or gene edited hematopoietic stem cells (cultured as described in FIG. 5A) in phosphate-buffered saline were delivered via retro-orbital injection. Animals were euthanized 10 to 16 weeks post-transplant, bone marrow and spleens were harvested and analyzed for human cell engraftment. Dot plot depicts total engraftment of edited cells as defined by expression of human CD45 marker in BM of sacrificed mice. Dots represent individual mice. Data are presented as mean±SEM.
Figure 9C:
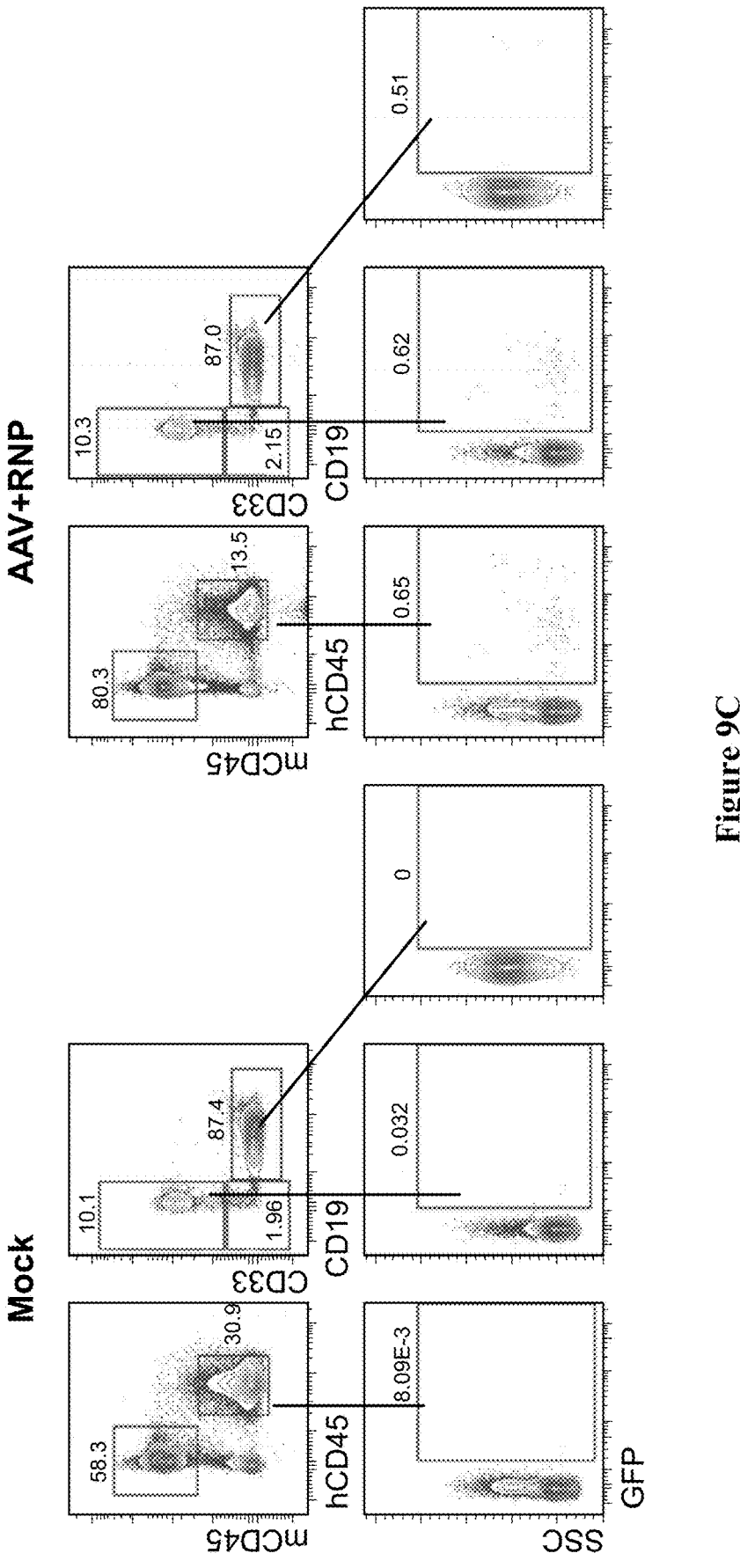
FIG. 9C shows data that represent the engraftment of edited cells in bone marrow of NSG mice 16 weeks post transplantation. Representative flow plots of cells harvested from the bone marrow of NSG mice 16 weeks following transplant. On left, bone marrow harvested from mouse transplanted with untreated cells. On right, bone marrow harvested from mouse transplanted with cells treated with AAV plus RNP. Top row, from left to right: hCD45:mCD45 chimerism, human CD45-gated CD33$^+$ and CD19$^+$ staining. Bottom row, from left to right: GFP expression among hCD45$^+$, CD33$^+$ and CD19$^+$ cells.
Figure 9D:
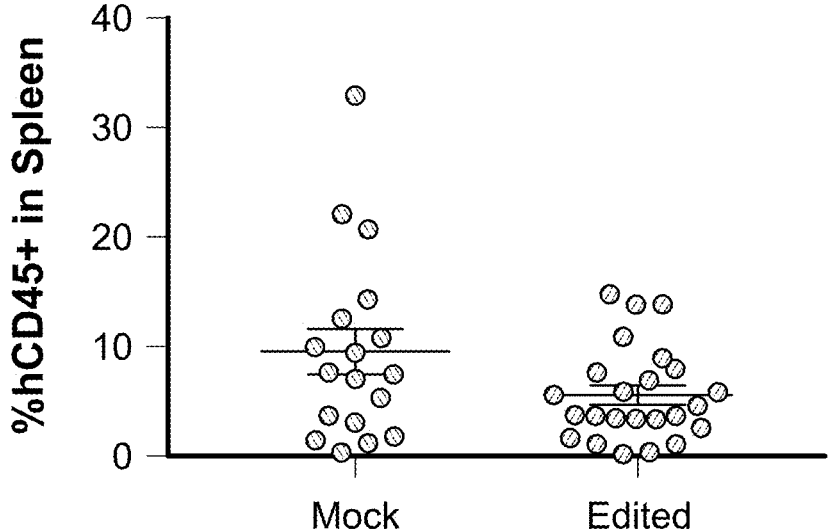
FIG. 9D shows data that represent the engraftment of edited cells in spleens of transplanted mice. Graph depicts total engraftment of edited cells at 10-16 weeks as defined by expression of human CD45 marker in spleens of sacrificed mice. Dots represent individual mice. Data are presented as mean±SEM.
Figure 9E:
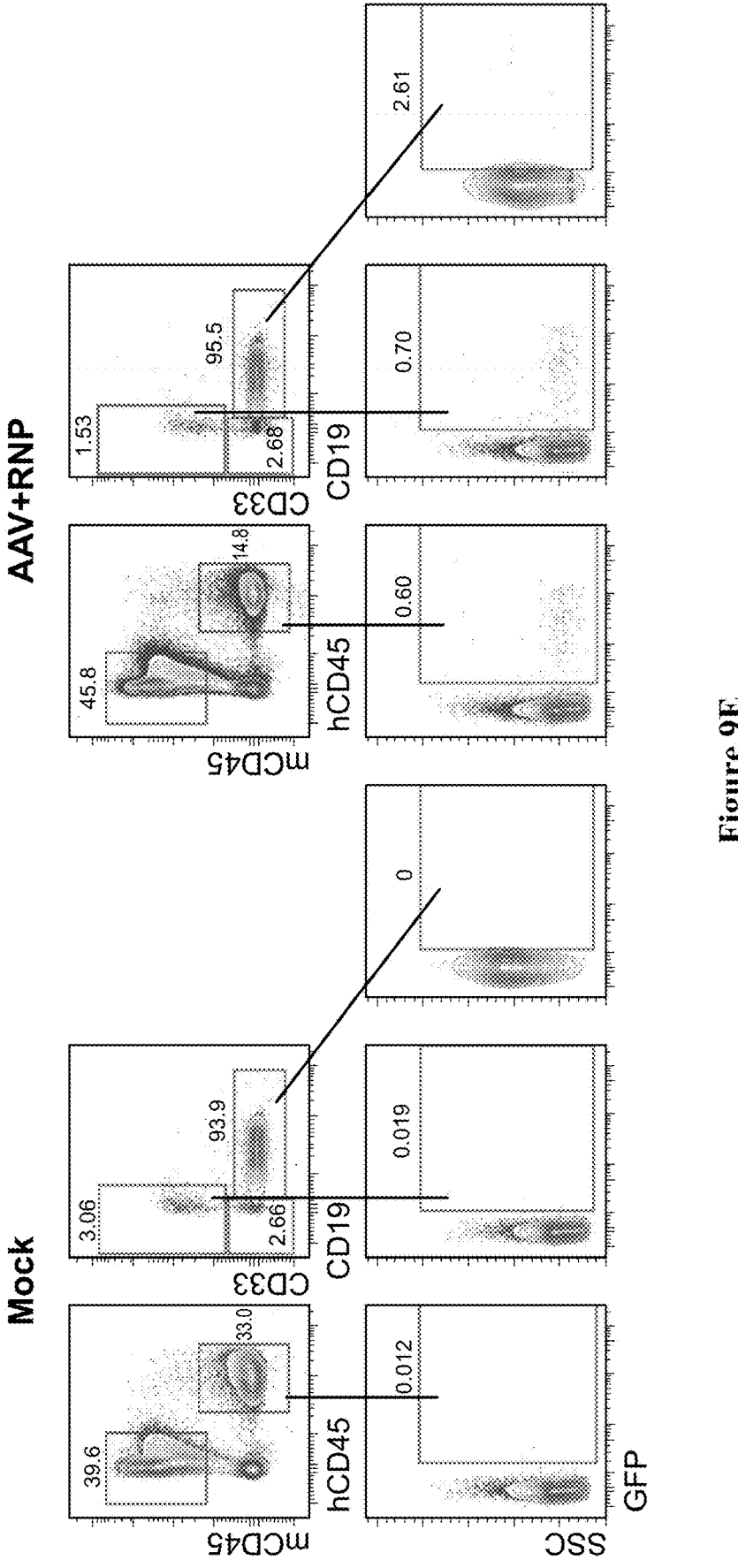
FIG. 9E shows data that represent the engraftment of edited cells in spleens of NSG Mice. Representative flow plots of cells harvested from the spleens of NSG mice 16 weeks following transplant. On left, spleen harvested from mouse transplanted with untreated cells. On right, spleen harvested from mouse transplanted with cells treated with AAV plus RNP. Top row, from left to right: hCD45:mCD45 chimerism, Human CD45-gated CD33$^+$ and CD19$^+$ staining. Bottom row, from left to right: GFP expression among hCD45$^+$, CD33$^+$ and CD19$^+$ cells.
Figure 9F:
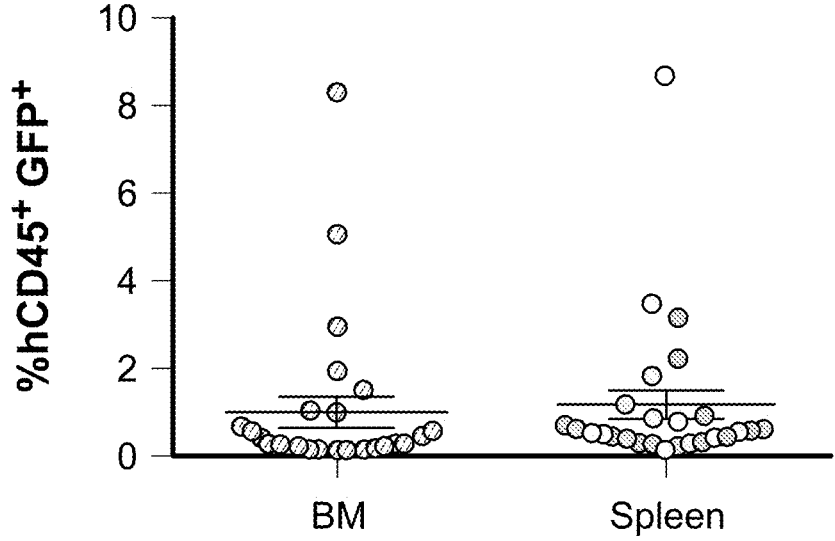
FIG. 9F shows data that represent the engraftment of GFP$^+$ cells in NSG mice. HDR-editing rate (% GFP$^+$) among hCD45$^+$ cells recovered from the bone marrow and spleens of NSG mice sacrificed at 10-16 weeks. Data are presented as mean±SEM.

Shown in FIG. 9A is the cell viability and % HR in input cells used for engraftment in NSG mice. Adult mobilized human CD34+ cells were cultured in SCGM media as previously described with the exception that IL-6 (100 ng/ml) was added instead of IL-3. The cells were electroporated with 1 μg of RNP complex and AAV at an MOI of 62. Data are presented as mean±SEM. N=5 and represents independent experiments. FIG. 9B shows the results from engraftment of edited cells in bone marrow of transplanted NSG mice. Six to 10 week old NSG mice were treated with 25 or 35 mg/kg of BUSULFEX (Henry Schein Inc.) via intraperitoneal injection, diluted 1:1 in phosphate-buffered saline. Twenty-four hours later, $2 \times 10^6$ mock or gene edited hematopoietic stem cells (cultured as described in FIG. 9A) in phosphate-buffered saline were delivered via retro-orbital injection. Animals were euthanized 10 to 16 weeks post-transplant, bone marrow and spleens were harvested and analyzed for human cell engraftment. Dot plot depicts total engraftment of edited cells as defined by expression of human CD45 marker in BM of sacrificed mice. Dots represent individual mice. Data are presented as mean±SEM. FIG. 9C shows the result of engraftment of edited Cells in bone marrow of NSG mice 16 weeks post transplantation. Representative flow plots of cells harvested from the bone marrow of NSG mice 16 weeks following cell transplantation. On left panel shows the data of bone marrow harvested from mouse transplanted with untreated cells. On right, bone marrow harvested from mouse transplanted with cells treated with AAV plus RNP. On the top row of the figure, from left to right: hCD45:mCD45 chimerism, human CD45-gated CD33+ and CD19+ staining. Bottom row, from left to right: GFP expression among hCD45+, CD33+ and CD19+ cells. FIG. 9D Engraftment of edited cells in spleens of transplanted mice. Graph depicts total engraftment of edited cells at 10-16 weeks as defined by expression of human CD45 marker in spleens of sacrificed mice. Dots represent individual mice. FIG. 9E shows results from engraftment of edited cells in spleens of NSG Mice. Representative flow plots of cells harvested from the spleens of NSG mice 16 weeks following cell transplantation are shown. On left, bone marrow harvested from mouse transplanted with untreated cells. On right, bone marrow harvested from mouse transplanted with cells treated with AAV plus RNP. Top row, from left to right: hCD45:mCD45 chimerism, Human CD45-gated CD33+ and CD19+ staining. Bottom row, from left to right: GFP expression among hCD45+, CD33+ and CD19+ cells. FIG. 9F Engraftment of GFP+ cells in NSG mice. HDR-editing rate (% GFP+) among hCD45+ cells recovered from the bone marrow and spleens of NSG mice sacrificed at 10-16 weeks. Mean±SEM shown on graph.

Alternative 10

Engraftment of Edited Cells in NSGW41 Mice

Figure 10A:
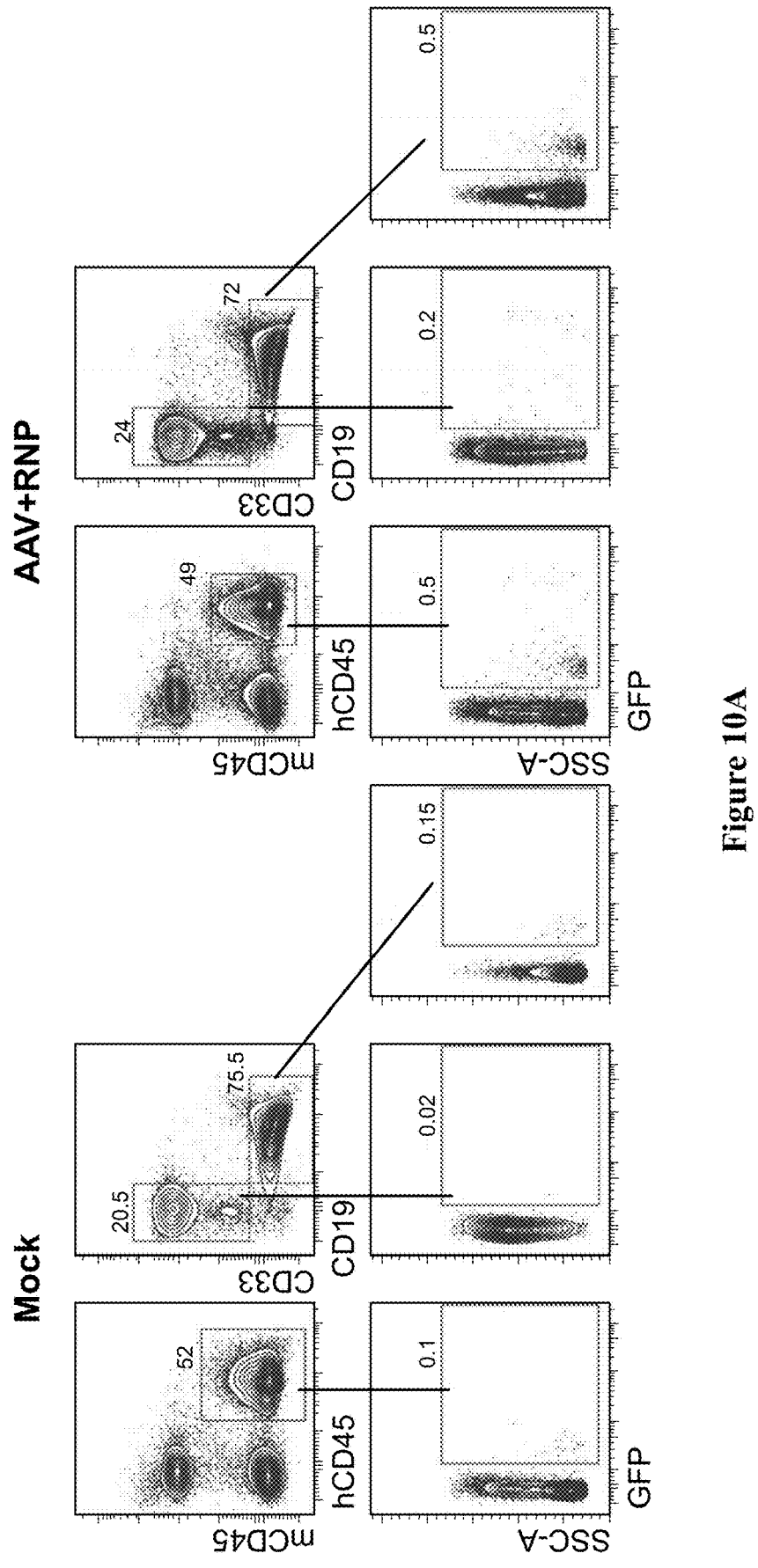
FIG. 10A shows data that represent the engraftment of edited cells in bone marrow of NSGW41 mice 16 weeks post transplantation. On right, bone marrow harvested from mouse transplanted with cells treated with AAV plus RNP. Top row, from left to right: hCD45:mCD45 chimerism, human CD45-gated CD33$^+$ and CD19$^+$ staining. Bottom row, from left to right: GFP expression among hCD45$^+$, CD33$^+$ and CD19$^+$ cells.

Shown in FIG. 10A are the results from engraftment of edited cells in bone marrows of NSGW41 mice. Representative flow plots of cells harvested from the bone marrows of NSGW41 mice 16 weeks following cell transplantation. On left, bone marrow harvested from mouse transplanted with untreated cells. On right, bone marrow harvested from mouse transplanted with cells treated with AAV plus RNP. Top row, from left to right: hCD45:mCD45 chimerism, Human CD45-gated CD33$^+$ and CD19$^+$ staining. Bottom row, from left to right: GFP expression among hCD45$^+$, CD33$^+$ and CD19$^+$ cells.

Figure 10B:
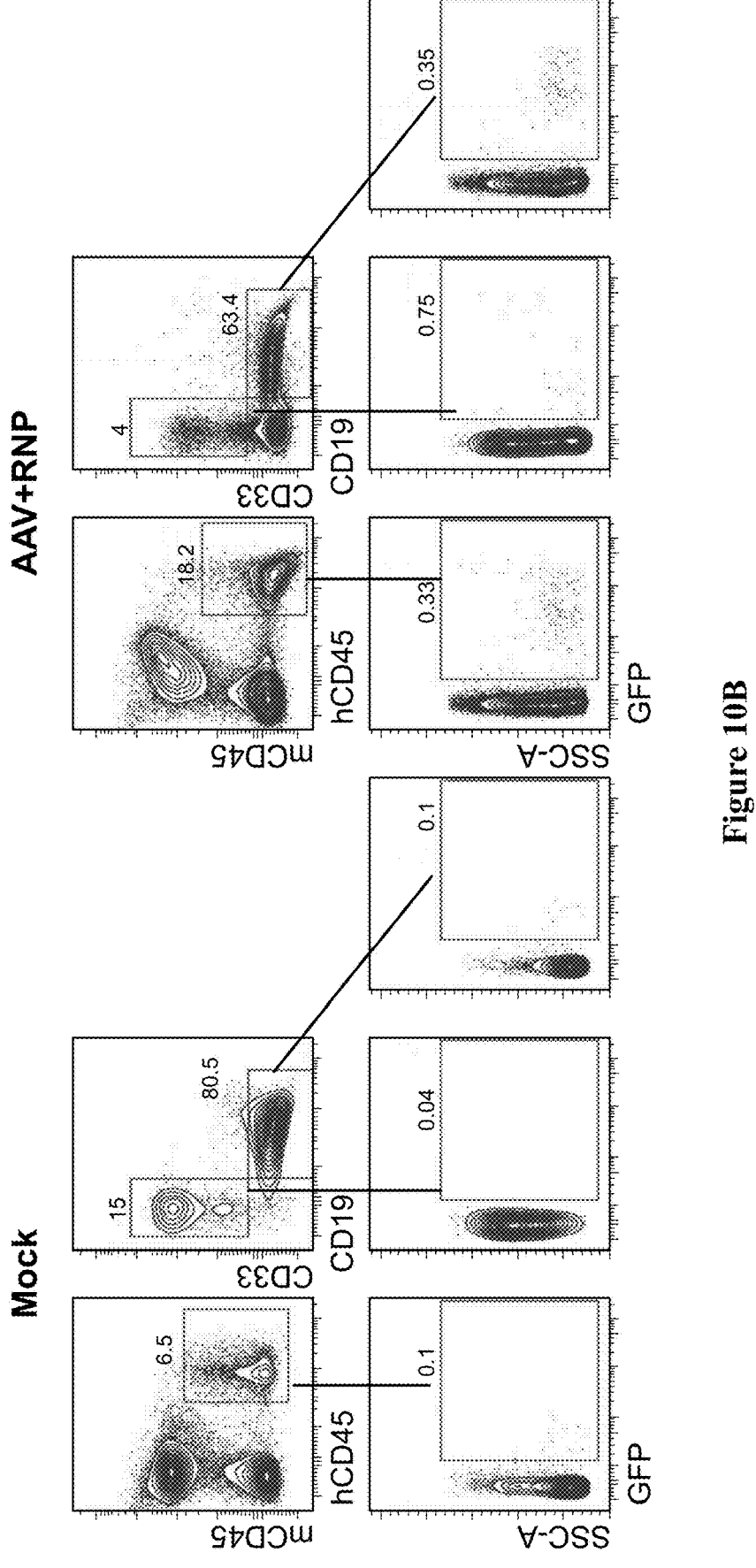
FIG. 10B shows data that represent the engraftment of edited cells in spleens of NSGW41 mice 16 weeks post transplantation. On left, spleen harvested from mouse transplanted with untreated cells. On right, spleen harvested from mouse transplanted with cells treated with AAV plus RNP. Top row, from left to right: hCD45:mCD45 chimerism, Human CD45-gated CD33$^+$ and CD19$^+$ staining. Bottom row, from left to right: GFP expression among hCD45$^+$, CD33$^+$ and CD19$^+$ cells.

Shown in FIG. 10B are the results from engraftment of edited cells in spleens of NSGW41 mice. Representative flow plots of cells harvested from the spleens of NSGW41 mice 16 weeks following cell transplantation. On left, bone marrow harvested from mouse transplanted with untreated cells. On right, bone marrow harvested from mouse transplanted with cells treated with AAV plus RNP. Top row, from left to right: hCD45:mCD45 chimerism, Human CD45-gated CD33$^+$ and CD19$^+$ staining. Bottom row, from left to right: GFP expression among hCD45$^+$, CD33$^+$ and CD19$^+$ cells.

Alternative 11

Engraftment of Edited Cells in NSGW41 Mice

Figure 11A:
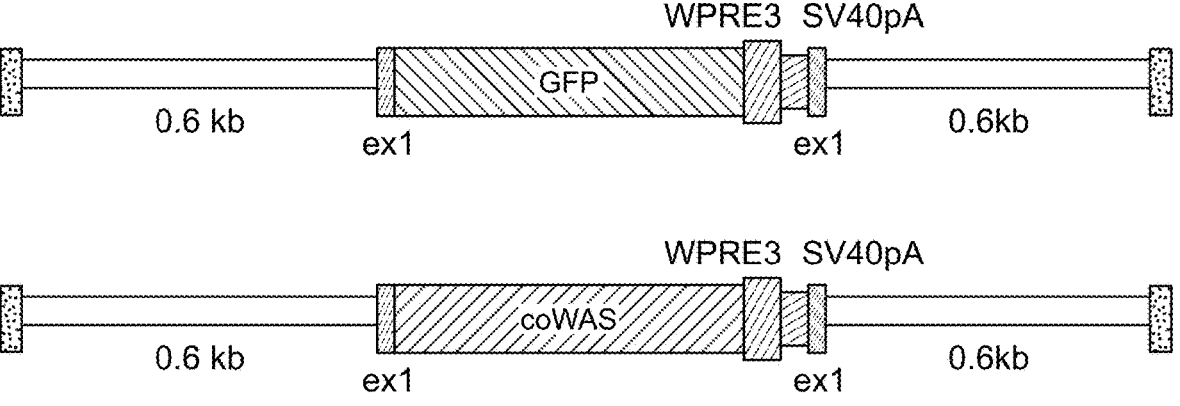
FIG. 11A shows data that represent the design of AAV vectors expressing GFP or cDNA for codon optimized WAS gene from endogenous WAS promoter. AAV vectors with 0.6 kb homology arms flanking either a promoter-less GFP (top) or WAS cDNA (bottom) followed by a shorter WPRE, designated WPRE3 followed by SV40 polyadenylation signal are shown.
Figure 11B:
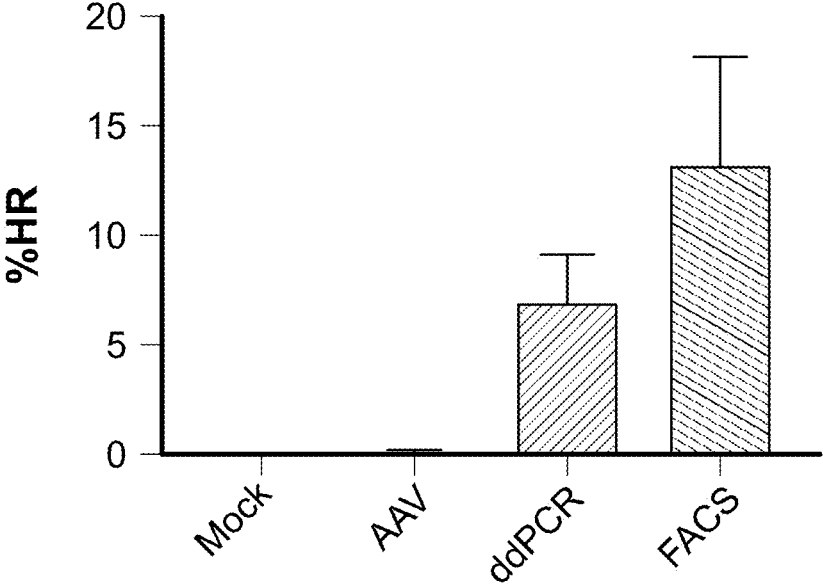
FIG. 11B shows data that represent the digital droplet PCR to determine editing rates in WAS targeted promoter-less GFP construct. In-out droplet digital PCR was performed as previously described. Droplets were analyzed on the QX200 Droplet Digital PCR System (Bio-Rad) using QuantaSoft software (Bio-Rad). All experiments were performed on female donors. The ddPCR rates were about half of HR rates by FACS suggesting that only one X chromosome was being targeted, n=3 and represents three independent experiments and donors. Data are presented as mean±SEM.
Figure 11C:
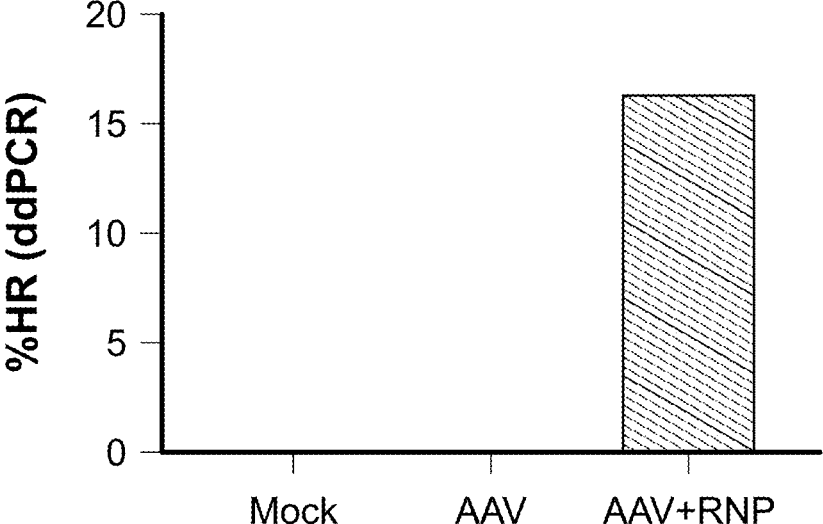
FIG. 11C shows data that represent the digital droplet PCR to determine editing rates with WAS targeted promoter-less coWAS expressing AAV vectors.

FIG. 11A shows the design of AAV vectors expressing cDNA for GFP or codon optimized WAS gene from the endogenous promoter. AAV vectors with 0.6 kb homology arms flanking either a promoterless GFP (top) or WAS cDNA (bottom) followed by a shorter WPRE, designated WPRE3 followed by SV40 polyadenylation signal. As shown in FIG. 11B is the results from the digital droplet PCR to determine editing rates in WAS targeted promoterless GFP construct. In-out droplet digital PCR was performed as previously described. Droplets were analyzed on the QX200 Droplet Digital PCR System (Bio-Rad) using QuantaSoft software (Bio-Rad). All experiments were performed on female donors. The ddPCR rates were about half of HR rates by FACS suggesting that only one X chromosome was being targeted, n=3 and represents three independent experiments and donors. Data are presented as mean±SEM. As shown in FIG. 11C is the results from the digital droplet PCR to determine editing rates with WAS targeted promoterless coWAS expressing AAV vectors.

MORE ALTERNATIVES

Further aspects of the disclosure are realized in the following numbered alternatives.

In some alternatives, a nucleic acid for homology directed repair (HDR) of Wiskott-Aldrich Syndrome (WAS) gene is provided, the nucleic acid comprising: a first sequence encoding a WAS gene; a second sequence encoding one or more guide RNA-cleavage sites; and a third sequence encoding one or more nuclease-binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the nucleic acid further comprises one or more enhancer elements. In some alternatives, the nucleic acid further comprises homology arm sequences. In some alternatives, the nucleic acid further comprises nucleic acid sequence encoding a promoter.

In some alternatives, a vector for promoting HDR of WAS protein (WASp) expression in a cell is provided, the vector comprising: a first sequence encoding a WAS gene; a second sequence encoding one or more guide RNA-cleavage sites; and a third sequence encoding one or more nuclease-binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34$^+$ HSC.

In some alternatives, a system for promoting HDR of WAS protein (WASp) expression in a cell is provided, where're the system comprises a vector of any one of the alternatives herein and a nucleic acid encoding a nuclease. In some alternatives, the vector comprises a first sequence encoding a WAS gene; a second sequence encoding one or more guide RNA-cleavage sites; and a third sequence encoding one or more nuclease-binding sites. In some alternatives, the WAS gene comprises the nucleic acid sequence set forth in SEQ ID NO: 4. In some alternatives, the second sequence comprises the nucleic acid sequence set forth in SEQ ID NO: 17. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34$^+$ HSC. In some alternatives of the system, the nuclease is a TALEN nuclease. In some alternatives of the system, the nuclease is a Cas nuclease. In some alternatives of the system, the vector and nucleic acid are configured for co-delivery to the cell. In some alternatives of the system, co-delivery to the cell modifies endogenous WAS locus. In some alternatives of the system, the cell is a primary human hematopoietic cell.

In some alternatives, a cell for expressing a WASp is provided, the cell comprising: a nucleic acid, which comprises: a first sequence encoding a WAS gene; a second sequence encoding a promoter; a third sequence encoding one or more guide RNA cleavage sites; and a fourth sequence encoding one or more nuclease binding sites. In some alternatives, the nucleic acid is in a vector. In some alternatives, the vector are an AAV. In some alternatives, the AAV are a scAAV. In some alternatives, the cell are a human cell. In some alternatives, the cell are a primary cell. In some alternatives, the cell are an autologous cell. In some alternatives, the cell are a T cell. In some alternatives, the cell are a HSC. In some alternatives, the cell are a CD34$^+$ HSC.

In some alternatives, a method of promoting HDR of a WAS gene in a subject in need thereof is provided, the method comprising: administering to a subject the cell of any one of alternatives provided herein or a vector of any one of the alternatives provided herein, and administering to the subject a nuclease. In some alternatives, the nuclease is a TALEN nuclease. In some alternatives, the nuclease is a Cas nuclease. In some alternatives, the nuclease is co-administered to the subject with the cell or with the vector. In some alternatives, the cell is from the subject and, wherein the cell is genetically modified by introducing the nucleic acid of any one of alternatives of any one of the alternatives herein or the vector of any one of the alternatives herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34$^+$ HSC. In some alternatives, the subject is male. In some alternatives, the subject is suffering from Wiskott-Aldrich syndrome (WAS). In some alternatives, the subject is suffering from X-linked thrombocytopenia (XLT).

In some alternatives, a method of treating, inhibiting, or ameliorating WAS and/or XLT or disease symptoms associated with WAS and/or XLT in a subject in need thereof is provided, the method comprising: administering to a subject the cell of any one of the alternatives herein or a vector of any one of the alternatives herein; administering to the subject a nuclease; and optionally identifying the subject as one that would benefit from receiving a therapy for WAS and/or XLT or disease symptoms associated with WAS and/or XLT and/or, optionally measuring an improvement in the progression of WAS and/or XLT or an improvement in a disease symptom associated with WAS and/or XLT in said subject. In some alternatives, the nuclease is a TALEN nuclease. In some alternatives, the nuclease is a CRISPR/Cas nuclease. In some alternatives, the nuclease is co-administered to the subject with the cell or with the vector. In some alternatives, the cell is from the subject, wherein the cell is genetically modified by introducing the nucleic acid of any one of alternatives 1-8 or the vector of any one of the alternatives herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34$^+$ HSC. In some alternatives, the subject is male. In some alternatives, the method improves thrombocytopenia. In some alternatives, the method increases platelet counts.

In some alternatives, a nucleic acid for homology directed repair (HDR) of Wiskott-Aldrich Syndrome (WAS) gene is provided, the nucleic acid comprising: a first sequence encoding a WAS gene, a second sequence encoding one or more guide RNA cleavage sites; and a third sequence encoding one or more nuclease binding sites. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the nucleic acid further comprises one or more enhancer elements. n some alternatives, the nucleic acid further comprises homology arm sequences. n some alternatives, the nucleic acid further comprises a nucleic acid sequence encoding a promoter.

In some alternatives, a vector for promoting HDR of WAS protein (WASp) expression in a cell is provided, the vector comprising a first sequence encoding a WAS gene, a second sequence encoding one or more guide RNA cleavage sites; and a third sequence encoding one or more nuclease binding sites. In some alternatives, the one or more nuclease binding sites comprises a forward and reverse transcription activator-like effector nuclease (TALEN) binding site. In some alternatives, the one or more nucleic binding sites is a clustered regularly interspaced short palindromic repeats (CRISPR) associated protein 9 (Cas9) binding site. In some alternatives, the vector further comprises one or more enhancer elements. In some alternatives, the vector is an adeno-associated viral vector (AAV). In some alternatives, the vector is a self-complementary AAV (scAAV). In some alternatives, the cell is a human cell. In some alternatives, the cell is a primary cell. In some alternatives, the cell is an autologous cell. In some alternatives, the cell is a T cell. In some alternatives, the cell is a hematopoietic stem cell (HSC). In some alternatives, the cell is a CD34+ HSC.

In some alternatives, a system for promoting HDR of WAS protein (WASp) expression in a cell is provided, the system comprising a vector of any one of the alternatives herein and a nucleic acid encoding a nuclease. In some alternatives, the nuclease is a TALEN nuclease. In some alternatives, the nuclease is a Cas nuclease. In some alternatives, the vector and nucleic acid are configured for co-delivery to the cell. In some alternatives, co-delivery to the cell modifies endogenous WAS locus. In some alternatives, the cell is a primary human hematopoietic cell.

In some alternatives, a cell for expressing a WASp is provided, the cell comprising: a nucleic acid, which comprises a first sequence encoding a WAS gene, a second sequence encoding a promoter, a third sequence encoding one or more guide RNA cleavage sites; and a fourth sequence encoding one or more nuclease binding sites. In some alternatives, the nucleic acid is in a vector. In some alternatives, the vector is an AAV. In some alternatives, the AAV is a scAAV. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC.

In some alternatives a method of promoting HDR of a WAS gene in a subject in need thereof, the method comprising: administering to a subject the cell or a vector of any one of the alternatives herein; and administering to the subject a nuclease. In some alternatives, the nuclease is a TALEN nuclease. In some alternatives, the nuclease is a Cas nuclease. In some alternatives, the nuclease is co-administered to the subject with the cell or with the vector. In some alternatives, the cell is from the subject and, wherein the cell is genetically modified by introducing the nucleic acid or the vector of any one of the alternatives herein into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC. In some alternatives, the subject is male. In some alternatives, the subject is suffering from Wiskott-Aldrich syndrome (WAS). In some alternatives, the subject is suffering from X-linked thrombocytopenia (XLT).

In some alternatives, a method of treating, inhibiting, or ameliorating WAS and/or XLT or disease symptoms associated with WAS and/or XLT in a subject in need thereof is provided, the method comprising: administering to a subject the cell or a vector of any one of the alternatives herein, administering to the subject a nuclease; and optionally identifying the subject as one that would benefit from receiving a therapy for WAS and/or XLT or disease symptoms associated with WAS and/or XLT and/or, optionally measuring an improvement in the progression of WAS and/or XLT or an improvement in a disease symptom associated with WAS and/or XLT in said subject. In some alternatives, the nuclease is a TALEN nuclease. In some alternatives, the nuclease is a CRISPR/Cas nuclease. In some alternatives, the nuclease is co-administered to the subject with the cell or with the vector. In some alternatives, the cell is from the subject, wherein the cell is genetically modified by introducing the nucleic acid or the vector of any one of the alternatives into the cell. In some alternatives, the administering is performed by adoptive cell transfer. In some alternatives, the cell is a human cell. In some alternatives, the cell is a primary cell. In some alternatives, the cell is an autologous cell. In some alternatives, the cell is a T cell. In some alternatives, the cell is a HSC. In some alternatives, the cell is a CD34+ HSC. In some alternatives, the subject is male. In some alternatives, the method improves thrombocytopenia. In some alternatives, the method increases platelet counts.

It is to be understood that the description, specific examples and data, while indicating exemplary alternatives, are given by way of illustration and are not intended to limit the various alternatives of the present disclosure. Various changes and modifications within the present disclosure will become apparent to the skilled artisan from the description and data contained herein, and thus are considered part of the various alternatives of this disclosure.

APPENDIX I

| Sequence Identification Numbers, Identifying Descriptions, and Sequences |
| --- |

```
SEQ ID NO: 1 WAS TALEN forward
ATGGCGCCGCGGCCTCCTAAGAAGAAGCGGAAAGTCGAATTCGTGGATCTGCGA
ACACTGGGCTATAGCCAGCAGCAGCAGGAGAAGATCAAACCCAAGGTGAGGTC
CACAGTCGCACAGCACCATGAAGCCCTGGTGGGCCACGGGTTCACTCACGCTCA
TATTGTCGCACTGTCTCAGCATCCAGCCGCTCTGGGAACCGTGGCAGTCACATAC
CAGCACATCATTACTGCCCTGCCCGAGGCTACCCATGAAGACATCGTGGGAGTC
GGCAAACAGTGGAGCGGCGCACGGGCCCTGGAGGCTCTGCTGACCGACGCAGG
GGAACTGAGAGGACCCCCTCTGCAGCTGGATACAGGGCAGCTGGTGAAGATTGC
TAAGAGGGGAGGGGTGACAGCAATGGAAGCCGTCCACGCAAGCAGGAACGCAC
TGACAGGGGCCCCCCTGAACCTGACCCCGGACCAAGTGGTGGCTATCGCCAGCC
ACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTG
GCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCCACGATGGCGGCA
AGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAG
CGCTCGAAACGGTGCAGCGGCTGTTGCCGGTGCTGTGCCAGGACCATGGCCTGA
CTCCGGACCAAGTGGTGGCTATCGCCAGCAACGGTGGCGGCAAGCAAGCGCTCG
AAACGGTGCAGCGGCTGTTGCCGGTGCTGTGCCAGGACCATGGCCTGACCCCGG
ACCAAGTGGTGGCTATCGCCAGCAACATTGGCGGCAAGCAAGCGCTCGAAACGG
TGCAGCGGCTGTTGCCGGTGCTGTGCCAGGACCATGGCCTGACTCCGGACCAAG
TGGTGGCTATCGCCAGCAACAATGGCGGCAAGCAAGCGCTCGAAACGGTGCAGC
GGCTGTTGCCGGTGCTGTGCCAGGACCATGGCCTGACCCCGGACCAAGTGGTGG
CTATCGCCAGCAACATTGGCGGCAAGCAAGCGCTCGAAACGGTGCAGCGGCTGT
TGCCGGTGCTGTGCCAGGACCATGGCCTGACCCCGGACCAAGTGGTGGCTATCG
CCAGCAACATTGGCGGCAAGCAAGCGCTCGAAACGGTGCAGCGGCTGTTGCCGG
TGCTGTGCCAGGACCATGGCCTGACTCCGGACCAAGTGGTGGCTATCGCCAGCA
ACGGTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTG
GCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCA
AGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAG
CGCTCGAAACGGTGCAGCGGCTGTTGCCGGTGCTGTGCCAGGACCATGGCCTGA
CCCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACCCCGG
ACCAAGTGGTGGCTATCGCCAGCCACGATGGCGGCAAGCAAGCGCTCGAAACGG
TGCAGCGGCTGTTGCCGGTGCTGTGCCAGGACCATGGCCTGACTCCGGACCAAG
TGGTGGCTATCGCCAGCAACAATGGCGGCAAGCAAGCGCTCGAAACGGTGCAGC
GGCTGTTGCCGGTGCTGTGCCAGGACCATGGCCTGACCCCGGACCAAGTGGTGG
CTATCGCCAGCAACGGTGGCGGCAAGCAAGCGCTCGAAAGCATTGTGGCCCAGC
TGAGCCGGCCTGATCCGGCGTTGGCCGCGTTGACCAACGACCACCTGGTCGCTCT
GGCTTGCCTGGGAGGACGCCCTGCTATGGACGCTGTGAAGAAAGGACTGCCCCA
CGCACCCGAACTGATTAGACGGGTGAACCGGAGAATCGGCGAGAGAACATCCC
ATAGGGTGGCAATCTCTAGAACTCAGCTGGTCAAGAGTGAACTGGAGGAAAAGA
```

APPENDIX I-continued

Sequence Identification Numbers, Identifying Descriptions, and Sequences

```
AATCAGAGCTGCGCCACAAGCTGAAATACGTGCCTCATGAGTATATCGAACTGA
TCGAGATTGCTCGCAATTCAACCCAGGACCGGATCCTGGAAATGAAAGTGATGG
AGTTCTTTATGAAAGTCTACGGATATCGGGGGAAACACCTGGGAGGGAGCAGAA
AGCCAGATGGGGCCATCTACACAGTGGGATCCCCCATCGACTATGGCGTGATTG
TCGATACTAAAGCCTACAGCGGAGGCTATAACCTGCCTATCGGCCAGGCTGACG
AGATGCAGAGATACGTGGAGGAAAACCAGACCCGCAATAAGCATATTAACCCC
AATGAATGGTGGAAAGTGTATCCTAGCTCCGTCACAGAGTTCAAGTTTCTGTTCG
TGAGCGGACACTTTAAGGGCAACTACAAAGCACAGCTGACTAGGCTGAATCATA
TCACCAACTGCAATGGAGCCGTGCTGTCTGTCGAGGAACTGCTGATCGGGGGAG
AGATGATTAAGGCTGGCACACTGACTCTGGAGGAAGTGAGGCGCAAGTTCAACA
ATGGGGAAATCAACTTCTAA

SEQ ID NO: 2 WAS TALEN reverse
ATGGCGCCGCGGCCTCCTAAGAAGAAGCGGAAAGTCGAATTCGTGGATCTGCGA
ACACTGGGCTATAGCCAGCAGCAGCAGGAGAAGATCAAACCCAAGGTGAGGTC
CACAGTCGCACAGCACCATGAAGCCCTGGTGGGCCACGGGTTCACTCACGCTCA
TATTGTCGCACTGTCTCAGCATCCAGCCGCTCTGGGAACCGTGGCAGTCACATAC
CAGCACATCATTACTGCCCTGCCCGAGGCTACCCATGAAGACATCGTGGGAGTC
GGCAAACAGTGGAGCGGCGCACGGGCCCTGGAGGCTCTGCTGACCGACGCAGG
GGAACTGAGAGGACCCCCTCTGCAGCTGGATACAGGGCAGCTGGTGAAGATTGC
TAAGAGGGGAGGGGTGACAGCAATGGAAGCCGTCCACGCAAGCAGGAACGCAC
TGACAGGGGCCCCCCTGAACCTGACCCCGGACCAAGTGGTGGCTATCGCCAGCA
ACATTGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATG
GCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACATTGGCGGCA
AGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAG
CGCTCGAAACGGTGCAGCGGCTGTTGCCGGTGCTGTGCCAGGACCATGGCCTGA
CTCCGGACCAAGTGGTGGCTATCGCCAGCAACATTGGCGGCAAGCAAGCGCTCG
AAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACG
GTGCAGCGGCTGTTGCCGGTGCTGTGCCAGGACCATGGCCTGACTCCGGACCAA
GTGGTGGCTATCGCCAGCAACGGTGGCGGCAAGCAAGCGCTCGAAACGGTGCAG
CGGCTGTTGCCGGTGCTGTGCCAGGACCATGGCCTGACCCCGGACCAAGTGGTG
GCTATCGCCAGCAACAATGGCGGCAAGCAAGCGCTCGAAACGGTGCAGCGGCTG
TTGCCGGTGCTGTGCCAGGACCATGGCCTGACCCCGGACCAAGTGGTGGCTATC
GCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGC
AACAATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACATT
GGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGC
AAGCAAGCGCTCGAAACGGTGCAGCGGCTGTTGCCGGTGCTGTGCCAGGACCAT
GGCCTGACCCCGGACCAAGTGGTGGCTATCGCCAGCCACGATGGCGGCAAGCAA
GCGCTCGAAACGGTGCAGCGGCTGTTGCCGGTGCTGTGCCAGGACCATGGCCTG
ACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACCCCG
GACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACTCCGGACCA
AGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGT
GGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTAT
CGCCAGCAACGGTGGCGGCAAGCAAGCGCTCGAAAGCATTGTGGCCCAGCTGAG
CCGGCCTGATCCGGCGTTGGCCGCGTTGACCAACGACCACCTGGTCGCTCTGGCT
TGCCTGGGAGGACGCCCTGCTATGGACGCTGTGAAGAAAGGACTGCCCCACGCA
CCCGAACTGATTAGACGGGTGAACCGGAGAATCGGCGAGAGAACATCCCATAG
GGTGGCAATCTCTAGAACTCAGCTGGTCAAGAGTGAACTGGAGGAAAAGAAATC
AGAGCTGCGCCACAAGCTGAAATACGTGCCTCATGAGTATATCGAACTGATCGA
GATTGCTCGCAATTCAACCCAGGACCGGATCCTGGAAATGAAAGTGATGGAGTT
CTTTATGAAAGTCTACGGATATCGGGGGAAACACCTGGGAGGGAGCAGAAAGCC
AGATGGGGCCATCTACACAGTGGGATCCCCCATCGACTATGGCGTGATTGTCGAT
ACTAAAGCCTACAGCGGAGGCTATAACCTGCCTATCGGCCAGGCTGACGAGATG
CAGAGATACGTGGAGGAAAACCAGACCCGCAATAAGCATATTAACCCCAATGA
ATGGTGGAAAGTGTATCCTAGCTCCGTCACAGAGTTCAAGTTTCTGTTCGTGAGC
GGACACTTTAAGGGCAACTACAAAGCACAGCTGACTAGGCTGAATCATATCACC
AACTGCAATGGAGCCGTGCTGTCTGTCGAGGAACTGCTGATCGGGGGAGAGATG
ATTAAGGCTGGCACACTGACTCTGGAGGAAGTGAGGCGCAAGTTCAACAATGGG
GAAATCAACTTCTAA SEQ ID NO: 3 CRISPR GUIDE sequence
GGTATGTTCTGCTGAACCGC SEQ ID NO: 4 WAS gene sequence
AGCAGAAGGGGTTCTGAACCTAGGTTCAGGAGAGAGGCTTTGAACCTGCACGTG
TGGGAAGCCATGGAAGTTTCCAGGAAGGACTGCAGGTCCCAACTGGAGATGTGC
CGTTCCTCCTTCAGGTACCTGGGAATGTCAGTCACACCCCAGACCTGCTCAGCTC
```

APPENDIX I-continued

Sequence Identification Numbers, Identifying Descriptions, and Sequences

```
CCCCAAACTGCTGTTCCTGTATCTGAGAGCTTCAAGTCTCCAAATGGCCTACCTC
ATACATGGGGAAACTGAGGCCTGGGGAGGCCGGGGACTGAGCTAGCATTCACTT
GTGGAAATAGTCTGGCATCATCTGGAGAAGTTAGAGACATGCAAACCCTACAGC
CCTCAGATTCCCGTCTGAGAGTCTGCATGCCTATGTGGACCAGGAGATGTGTGCG
GGAGTGAACACTGCAGTGTTGCTCCCAACAGCAAGAACCAGAAGCAGCCCAAA
GGGCTGTTACAGGAGAATATGGACACCCAGGCTGCACATGCACACCATGGAATG
CTGTATGGCAGTGGAAATAAATGAACAGCTACCACTATAGGCAAACAGGAATCA
CAGCAACAGCCAAGAGTGAAGGCGTGGAGGGACGAGACCATGCACTCACACCT
GGCCTGCCTGGCTCGCACTCCGGGCAAAGGGGTCAGAACAGTGACTGGCACACA
CGTTAAGTGCTATGTGAGTGTTAAGATAAAACTAGGATGTCCAGTGGGGAGAAA
GCAAGCCTTTGAAGATTATGTGCTTTTACAAACTTCAAGTGCAATGAAAACTAAA
CAAGATGTTGTTCAGGCATTCATATATGATATAAAGTTCCTTTCTTTAAAAAAGG
GATGGGCTGGGCACGGTGGCTCACGCCTGTAATTCTAATACTTTGGGAGGCCGA
GGCAGGTGGATCACGAGGTCGAGAAATCGAGACCATCCTGGCCAACATGGTGAA
ACCCTGTCTCTACTAAAAATACAAAAAAATTAGCTGGGCGTGGTGGCGTGTGCCT
GTAGTCCCAGCTACTTGGGAGGCTGAGGCAGGAGAGTCACTTGAACCCGGGAGG
CAAAGGTTGCAGTGAGCCGAGATCGTGCCACCGCACTCCAGCCTGGCGACAGAG
TGAGACTCCATCTCAAAAAAAAAAAGAAAAAAAAAAGTATGACAAGCAGAAAG
TAATTTGGGAGCTGCGGGGAGGCAAGGGTAAGGGATGGGGAAGTGGACCAGAG
GCATATGCGTCATTGGCAGTGTCTAAGCACTCACGATAGGCGTGGATCACAGGG
GCTCGCTCTGTAATTAAAAGGAAAAGGGTTTTTGTTGTGTTGTTGTTGTTGCTGTT
TTTGAGACAAGGGTCTTGCTCTGTCATCATCCAGGCTGGAGTGCAGTGGTGCAGT
CTCAGCTCACTGCAACCTCCGCCTCCTGGGTTCAAGCGATTCTCCTGCCTCAGCC
TCCTGAGCAGCTAGGACTACAGGTGTGTGCCACCATGCCTGGCTAATTTTTGTAT
TTTTTAGTGGAAATGGGGTTTTGCCATGTTGCCCAGGCTCGTCTTGAACTCCTGA
CCTCAAGTGATCCACTCGTCTCGGCCTCCCAAAGTGCTGGGATTACAGGTGTGAG
CTATTGTCCCCAGCCAAAAGGAAAAGTTTTACTGTAGTAACCCTTCCGGACTAGG
GACCTCGGGCCTCAGCCTCAGGCTACCTAGGTGCTTTAGAAAGGAGGCCACCCA
GGCCCATGACTACTCCTTGCCACAGGGAGCCCTGCACACAGATGTGCTAAGCTCT
CGCTGCCAGCCAGAGGGAGGAGGGTCTGAGCCAGTCAGAAGGAGATGGGCCCC
AGAGAGTAAGAAAGGGGGAGGAGGACCCAAGCTGATCCAAAAGGTGGGTCTAA
GCAGTCAAGTGGAGGAGGGTTCCAATCTGATGGCGGAGGGCCCAAGCTCAGCCT
AACGAGGAGGCCAGGCCCACCAAGGGGCCCCTGGAGGACTTGTTTCCCTTGTCC
CTTGTGGTTTTTTGCATTTCCTGTTCCCTTGCTGCTCATTGCGGAAGTTCCTCTTCT
TACCCTGCACCCAGAGCCTCGCCAGAGAAGACAAGGGCAGAAAGCACCATGAG
TGGGGGCCCAATGGGAGGAAGGCCCGGGGGCCGAGGAGCACCAGCGGTTCAGC
AGAACATACCCTCCACCCTCCTCCAGGACCACGAGAACCAGCGACTCTTTGAGA
TGCTTGGACGAAAATGCTTGGTGAGCTGGGGATCTCCTGCCCCCGCCCCGTCCC
ACCGTTTCTTCCTCTTCCTCTCCTCCTTCTCTCTCTTCCCCTCCTCCCGCTCCTCCT
TTCCCTCTCCATCATCTCCTCTCCTAGAATTTCCCGTCATAATCCACCCTTCCCAG
GAAGATCTCAATGTCTACTTGCCTTCCCTCTGGCTGCAGCTCTTCCTTTGGGCCCA
TGACTGTCATGAGGCAGGAAGGACCAGGTCTGGCTCCAAGACCTTGTGGCTACC
CC
TGACCAGACTCCACTGACCCCTGCTTTCCTCTCCCAGACGCTGGCCACTGCAGTT
GTTCAGCTGTACCTGGCGCTGCCCCCTGGAGCTGAGCACTGGACCAAGGAGCAT
TGTGGGGCTGTGTGCTTCGTGAAGGATAACCCCCAGAAGTCCTACTTCATCCGCC
TTTACGGCCTTCAGGTGACCCCCCCACCCCCGACTGGACTTGCAAGCCAGTTCTC
AACCCGCAAACCCAGATCTGTGTCCATATGTGTCCATAGCTTCAAGACCTCAGAC
CTGATCAGTGAATCCCTGAGCCCCAGAACCAAAGACTCATCCAGATGGCAAACT
CTGACTTGCCTTTCTAAGTCTGCAATGACTGGCCCCAGTCTCCGTATCAAGATCT
CTAAAGCCCCCAGTATTAGTCTGCTGCCTAAGCCTAATCTTTTCCACAAATTCCA
ATAAATGAGCACTGTATTTGTACCTGAACCTCAAATCTATTCTAAACTCAACATT
TTGCATCCCAGGAATCTCTCATCAAAACTCCTGAACCCCAGATGTTTGCCAAGCT
CCTAAGTCATAAATCTGTTCAACAAACCCCAAAGTTGAATATTCCATTGATCCTT
GAACTCCAAATCTGTCCTTCTAAATCCACAGCACAGACCCCAGAGTTCCCATATT
AAAATTCCTGAACACTCAAATACCGAGGTAGTTCTTAAGCAAAAAGTCTTTTCCA
CAATCCCCTGACCTGAACTTTCTAGGTTTAAGCCCCAAATTCATCCTTTTAAACC
CATAAAGATGGACCCAGCATAACTTCCAGATCCCAAGGCTATCAAATATCCACC
AAACTCCTAAACCATAACTCTCTCCACAAACCCCAAATTGCACTTACTTTAGCTG
GACTCCCCGCGAAACTCCCAAGTCTATGTGTCTGAACTTCAAATCTCAACTCCAA
CCCCCAAATACTAGAATCCTACCTGTCATGAATTGGGGCTGGGGTGGTGGGGGA
GGGCATGGATTGAATCTGTGAATGAGCCTCAACTTCCTAAGACTAGAGTCCTAA
ATTATGAAATTCAAGCCCCCAAGTCCCAGATCTAGGGCCCCAAACCCCAAATCC
AAACCTCTCACAAAAGTGTATGGCTCCCAGACTATACCCCACAATCCACACCCTT
AGACACCAACTCTCTGGTGCTGAGCTGAAAATCTCCAAACCAGACTATGAGGCT
CCCAAATCCAGACACCCTGCTCCCTGCCCAGCTAACAAAAGCCTGCCACCCCCG
GCG
TGCCTCAGTGCCACTGTGCCTCCCACCCTACACCTCTCCAGGCTGGTCGGCTGCT
CTGGGAACAGGAGCTGTACTCACAGCTTGTCTACTCCACCCCCACCCCCTTCTTC
CACACCTTCGCTGGAGATGTAAGTGATCAACCAGCCCTCGGGCCTCACTTGGGGT
GTGGAGAGGAGATGGGAAAGTTGCGGGGGACCTGGGAGGCGGCTGACCCCAAG
GTATGTGCAGGACTGCCAAGCGGGGCTGAACTTTGCAGACGAGGACGAGGCCCA
GGCCTTCCGGGCCCTCGTGCAGGAGAAGATACAAAAAAGGAATCAGAGGCAAA
GTGGAGGTGAGGAGGCCACAGGGGAGGAAAGGAAGTTGGGCAGAGGTGAGTGC
AAGCCTGGGGAACTAGAAAAGTCCCCTCTCATGGTCCTGGCTCCCAATCCATCTA
TCCACAGACAGACGCCAGCTACCCCCACCACCAACACCAGCCAATGAAGGTGAG
TCCTCTAGTGCAAGTAGGGGTAATAAGGGGCTAGCCCAGGAACCTGTGGCAGGG
CTGTGATAACTCTCTACACATTCCATCTTCCCAGAGAGAAGAGGAGGGCTCCCAC
```

APPENDIX I-continued

Sequence Identification Numbers, Identifying Descriptions, and Sequences

```
CCCTGCCCCTGCATCCAGGTGGAGACCAAGGAGGTGCGTGCTGATTCTTCCCTGT
GTCTCTGGATGGATGGGTAAGAGTGGATGGAGGAATGAGGAGTTGGATGGGTGC
GTAAGTGGGTGAATGGATAGGTAGATTGATAGGTATGTGGATGGACGAGCAGGT
GCATGGATGTGTGGACTGATGGATGGGTGGATGGATTGGCGGTAGATGGCTGAG
TAGAGGGATGAATTGATGGGAGGATGAAAGTCTAAGTAGATAGATGCATAGGTG
AATGGGTATGTGGATAAATGAATGAAAAGGTAGATGGATGACTGAGTAAATTAA
TCAATGAGTGAATGAATGAACAGTGAATAAATGACTAAATGACAAGTTTCAGTC
AGTGAAGAAAGCATGATTGAATGAATAAATGAGTAAATGAATATTTTAACAAAT
TCATTAGTCAATGAGCCAGTGAATGATAAAGCATGAGGGAATGAAAACATGAAT
GAATCAGTGAATGTATGAATGGTTTGTGGGATCCACCCACTTCTCCATAGACCCT
ACTTGAACCCTTCACCCACTACCTCCATGACCATCCAACACACACACAGATTTCC
CTCAAGGCTTCCGTTTCTTGCCCCTGTGCTTTGGTTGGTTGGTAAGTGGGTCAATG
AGCCAACCACCCTATTTTCCCCACAGGCCCTCCAGTGGGTCCGCTCTCCCTGGGG
CTGGCGACAGTGGACATCCAGAACCCTGACATCACGAGTTCACGATACCGTGGG
CTCCCAGCACCTGGACCTAGCCCAGCTGATAAGAAACGCTCAGGGAAGAAGAAG
ATCAGCAAAGCTGATATTGGTGCACCCAGTGGATTCAAGTGAGAGCCACTCCCC
AGTGGACCCACAGATTCCTGGGGGCAGAGGGGCACATGAACAAGTGGACAGCT
GAGTGAATGGAAGGATGGGCAGATGGGCAGATGGCTGGGTGGCTGAGTGGGTA
AATGGGTGGTTGGATAGGTAGGTGCAGGGCTGGGTCTAGGGAGAGGTAAATAAG
GCACCAAGGGTACAAAATTTAAGGAGGCACTCACTCTCAGAGGCATGCAACTGT
AATTCCTGACTCTCAGAGTGAGTGACTCACTTAAATTTTGCACCCTAGGCACCTT
ACTTGCCTCACCCTGGGCCCACTCTGGGTGGGCTGTTAGGAGAGCAGGTGGGTG
GGCAGGTGAACAAATGGATAGATAGATGAGGTAGATGATGGATGAGAAGGGCT
GGTGGGTAGGTGGGTGAGTGGATGGGTGGATGGATGGATAAATGAATGGATGA
ATGAATGGGTTGAAGAATGAATGGATAAGTGGTTGGATGGACAAGTTTATGGGT
GGATGGGTTGATGGGAGGTGCGTGGATAGATAGATGGGTGAGTGGATAGGTGTG
TGGACAGATTGATATGCAGGCTGATTGGCTCACAGACAAGGTGGATGGGGATGG
ACAGGTGGACAGATACGTGGATGAATGGACAGTTCAATGGATAAGTGAACAGA
AGTGTGTGGTTGCATGGGTAGAAAAATGAGTGGATGGATAGATGGAAAGGTGGG
CACATGGGTAGGTGGATGGGTGGATGGACAAGTGTGTGTGAGGACAGACTGGTG
GACAAATGGGTGAACAGACATATGTGGGCAGATAGTTGCAGAGACAGATGTATG
GACAGATCAGTAGTCCAACAGATGAATGTGAATGAATAGGTGGACAAATGCATG
GGATAGATGGGGAAAGAGGGATGGGTGGATGGATCAGCACCACAAACTATGGA
G
CCCTTCTAATTCCATAACTCCTGCCTATACTCATTCACTCATTCAGTCTCATTCAT
TAATTCTGGCCCCTCAGAGTCTCTTTGGGCAGGAGAGGGCAAGAGGGTTTCACTA
TGAAGGGAGGGAAGGAAGGGCAGTGAGGATTCACTGGAGTCTCTTCACCTCTCC
CAGGCATGTCAGCCACGTGGGGTGGGACCCCCAGAATGGATTTGACGTGAGTAA
CTTCAGAGTCTCTTGGACTCCACTAAACTTCCACCCACCCTTCCAAAGACCACTG
CTGAGACCCCACCCCCAGATCGTGCCCTTCCCACACCCCTCTCAGATCCCTTGCT
GGGATGGACCCAACGACAATCCATGTCGCTTGTCTCCTCGCCTTATTCCTCTACT
CCTGCCCCTGGCCTTTTTCCTCCTGGGCAGGTGAACAACCTCGACCCAGATCTGC
GGAGTCTGTTCTCCAGGGCAGGAATCAGCGAGGCCCAGCTCACCGACGCCGAGA
CCTCTAAACTTATCTACGACTTCATTGAGGACCAGGGTGGGCTGGAGGCTGTGCG
GCAGGAGATGAGGCGCCAGGGTGAGACCCTGCTTCCATACGCTCCCTTCTCTAG
CCCAAGCAGCTCATAGCTAAGATACGCACTAAGTCACTCAGTCCTTATGGGAGC
ACCTATACTGCTTCAGTCAGGAGTTGGTCAGTGGGGGTACCCATTTTACAAATGA
GCAAAACTGAGGCTCAGAAGAAATCAATGAGAGTTACAGCTATGTGTTATACCC
CCTCCACAGAGCCACTTCCGCCGCCCCCACCGCCATCTCGAGGAGGGAACCAGC
TCCCCCGGCCCCCTATTGTGGGGGGTAACAAGGGTCGTTCTGGTCCACTGCCCCC
TGTACCTTTGGGGATTGCCCCACCCCCACCAACACCCCGGGGACCCCCACCCCCA
GGCCGAGGGGGCCCTCCACCACCACCCCCTCCAGCTACTGGACGTTCTGGACCA
CTGCCCCCTCCACCCCCTGGAGCTGGTGGGCCACCCATGCCACCACCACCGCCAC
CACCGCCACCGCCGCCCAGCTCCGGGAATGGACCAGCCCCTCCCCCACTCCCTCC
TGCTCTGGTGCCTGCCGGGGGCCTGGCCCCTGGTGGGGGTCGGGGAGCGCTTTTG
GATCAAATCCGGCAGGGAATTCAGCTGAACAAGGTGAGGACAGGCAGGATGGA
GGATTGGGGGTCTAGGACTCTGGGGTGTCCCGTCTAAGTCAGGATACTGGGGGG
CTGAGGCCAGGACTGAGGAGAGTGCCAGGCCTTAGGGATTCAGTGATAGGGTTG
AAAGGTTGGTGGGAAGCCTTGAAGGGGACTGGAGTGTGTGGGAGAGAAAATATT
GATGGAGGGGCGGGGAGAAATGCTCCTTTCCCAGGCCCTAAGCCCTCTGTGCTG
ATCCCTGCCTGCTGCAGACCCCTGGGGCCCCAGAGAGCTCAGCGCTGCAGCCA
CCACCTCAGAGCTCAGAGGGACTGGTGGGGGCCCTGATGCACGTGATGCAGAAG
AGAAGCAGAGCCATCCACTCCTCCGGTGAGCTGATCCTGCCGGGGCCTCAAACC
TGGCTCCCAGGGCTAGCACTGGCCTCAAAACAATCCCAGCAGTCACCACCAATA
GTGACATCAGCCCCATCTGTTTGACAGCATTAACATGAATCTTGTGTCAGCCTCG
TTTTTGACAATGTTAACATTAAGTCATTATGTGACAATAATATAATTAACTCCAA
CTTTGACAGTAATATTAACATTAATGCCAGGGTGTGTCCACAATATTAATGTCAT
TCCCACATGTTCAGTACTACTAACATCAGCTGGCCGGGCGCGGTGGCTCATGCCT
GTAATCCAGGAACTTTGGGAGGCTAAGGCAGGAGGATCACTTGAGCCCAGGAGT
TCGAGACCAGCCTGGGCAATATAGTGAGACCTCGTTTCCATAAAAACTAAATTC
AAAAAAAGTAGTCAAGCATAGTGGTGTGTGCCTGTGGTCCCAGCTACTTGGGAG
GCTGAGGTGGGAGGATTGCTTGACCCTGGGAGGTCAAGGCAGCAGTGATCCATG
ATTGTGCCACTGCACTCCAGCCTGGGTGACAGAGATCCTATCTCAAAAAAAAAA
AAAATTAACCCATTATGTGATGACAATATTATGAAGAACACTATTGTTGACAATA
TTAATTTTAATTCCATGTATTAACAGATTTACATTAATTCATTATGACGTAACCTA
ATCTAATCTTTTAAAAAATTTTTTTGAAACAGGGTCTCGCTCTGTGTCCCAGGCTG
GAGTACAGTGGTGCAATCATGGCTCAGTGCAGCCTCAACCTCCCAGGCTCAAGC
GATCCTCCCGCCTCAGCTCCCAAAGTAGCTGGGACTACAGGCGTGTGCCACCAT
```

APPENDIX I-continued

Sequence Identification Numbers, Identifying Descriptions, and Sequences

ACCTGGCTAATTTTTGGTGTTTTTTTGGTAGTGATGAGCTCTCACTACCAAGCTCT
CACTACTCTCATGTTGCCCAGGCTGCTCTGCAACTCCAGGGCTCAAGCGATCTGC
CCCGCCTCAGCCTCCCAGAGTGCTGGGATTACAGGCATGAGCCACCAGGCCTGG
CTGTTAACCTAATCTTTTTATAATAATGTTACTATTACTCTCTTAATCTGTCAGCA
ATACTGTCACTAATCCATTATATGATGCAAATATTAGTATCAACCTACTATAGGA
ACTTCATCTTTCGACAATGATTTTTTTTTTTCTTTTGAGACGGAGTCTTGCTCTGTC
ACCCAGGCTGGAGTGCAGTGGCGCGATCTTGGCTAACTGCAGACTCTGCCTCCTG
GGTTCAAGCGATTCTCCTGCCTCAGCCTTCCGAGTAGCTGGGACTACAGGCACGC
CACTACGCCCAGCTAATTTTGATGTTATTGTCATTAACCCCATTATGTGTCAAAA
ATATTAGCGTTAACCAGACAGGAAGCAATAATATATTATCACACCTTTGCTAATA
TTATTTAAATTCACCCTATTATGTGATAAATAGGTTAACATTAACCCTTTGTTTGA
CAATATCTCGACTAACCACATTTTTGACAGCATAAACTTCAACTCCAACTAGAAC
TCAGACCCCAACTATAATCCCTTTCTTGTCCCAAATGGAAACTCTAACTTGCCCT
CCTCTAGCATGAGACCTCAGAACCCCAGGGTCCAGTCCTCACCTCCCAGGCCCTA
TGAAGCCCCCCACCAACCTCCCAGGGCATCTTATCTTTCTCTTTCCCTCCAGACG
AAGGGGAGGACCAGGCTGGCGATGAAGATGAAGATGATGAATGGGATGACTGA
GTGGCTGAGTTACTTGCTGCCCTGTGCTCCTCCCCGCAGGACATGGCTCCCCCTC
CACCTGCTCTGTGCCCACCCTCCACTCTCCTCTTCCAGGCCCCCAACCCCCCATTT
CTTCCCCACCAACCCCTCCAATGCTGTTATCCCTGCCTGGTCCTCACACTCACCCA
ACAATCCCAAGGCCCTTTTTATACAAAAATTCTCAGTTCTCTTCACTCAAGGAT
TTTTAAAGAAAATAAAAGAATTGTCTTTCTGTCTCTCTATAAA

SEQ ID NO: 5 AAV #1201
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAAGGGTTTTTGTTGTTGTTGTTGTTGCTGTTTTTGAGACAAGGG
TCTTGCTCTGTCATCATCCAGGCTGGAGTGCAGTGGTGCAGTCTCAGCTCACTGC
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGCCCAAGCTCAGCCTAACGAGGAGGCC
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTAAAGCAGC
GGTTCAGCAGAACATACCCTCCACCCTCCTCAGGACCACGAGAACCAGCGACT
CTTTGAGATGCTTGGACGAAAATGCTTGGTGAGCTGGGGATCCTCCTGCCCCCGCC
CCGTCCCCACCGTTTCTTCCTCTTCCTCTCCTCCTTCTCTCTCTTCCCCTCCTCCCG
CTCCTCCTTTCCCTCTCCATCATCTCCTCTCCTAGAATTTCCCGTCATAATCCACC
CTTCCCAGGAAGATCTCAATGTCTACTTGCCTTCCCTCTGGCTGCAGCTCTTCCTT
TGGGCCCATGACTGTCATGAGGCAGGAAGGACCAGGTCTGGCTCCAAGACCTTG
TGGCTACCCCTGACCAGACTCCACTGACCCCTGCTTTCCTCTCCCAGACGCTGGC
CACTGCAGTTGTTCAGCTGTACCTGGCGCTGCCCCCTGGAGCTGAGCACTGGACC
AAGGAGCATTGTGGGGCTGTGTGCTTCGTGAAGGATAACCCCCAGAAGTCCTAC

APPENDIX I-continued

Sequence Identification Numbers, Identifying Descriptions, and Sequences

```
TTCATCCGCCTTTACGGCCTTCAGGTGACCCCCCCACCCCCGACTGGACTTGCAA
GCCAGTTCTCAACCCGCAAACCCAGATCTGTGTCCATATGTGTCCATAGCTTCAA
GACCTCAGACCTGATCAGTGAATCCCTGAGCCCCAGAACCAAAGACTCATCCAG
ATGGCAAACTCTGACTTGCCTTTCTAAGTCTGCAATGACTGGCCCCAGTCTCCGT
ATCAAGATCTCTAAAGCCCCCAGTATTAGTCTGCTGCCTAAGCCTAATCTTTTCC
ACAAATTCCAATAAATGAGCACTGTATTTGTACCTGAACCTCAAATCTATTCTAA
ACTCAACATTTTGCATCCCAGGAATCTCTCATCAAAACTCCTGAACCCCAGATGT
TTGCCAAGCTCCTAAGTCATAAATCTGTTCAACAAACCCCAAAGTTGAATATTCC
ATTGATCCTTGAACTCCAAATCTGTCCTTCTAAATCCACAGCACAGACCCCAGAG
TTCCCATCTAGAGCATGGCTACGTAGATAAGTAGCATGGCGGGTTAATCATTAAC
TACAAGGAACCCCTAGTGATGGAGTTGGCCACTCCCTCTCTGCGCGCTCGCTCGC
TCACTGAGGCCGGGCGACCAAAGGTCGCCCGACGCCCGGGCTTTGCCCGGGCGG
CCTCAGTGAGCGAGCGAGCGCGCCAGCTGGCGTAATAGCGAAGAGGCCCGCACC
GATCGCCCTTCCCAACAGTTGCGCAGCCTGAATGGCGAATGGCGATTCCGTTGCA
ATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGT
TAATTTGCGTGATGGACAGACTCTTTTACTCGGTGGCCTCACTGATTATAAAAAC
ACTTCTCAGGATTCTGGCGTACCGTTCCTGTCTAAAATCCCTTTAATCGGCCTCCT
GTTTAGCTCCCGCTCTGATTCTAACGAGGAAAGCACGTTATACGTGCTCGTCAAA
GCAACCATAGTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGA
TTTCGGCCTATTGGTTAAAAAATGAGCTGATTTAACAAAAATTTAACGCGAATTT
TAACAAAATATTAACGTTTACAATTTAAATATTTGCTTATACAATCTTCCTGTTTT
TGGGGCTTTTCTGATTATCAACCGGGGTACATATGATTGACATGCTAGTTTTACG
ATTACCGTTCATCGATTCTCTTGTTTGCTCCAGACTCTCAGGCAATGACCTGATAG
CCTTTGTAGAGACCTCTCAAAAATAGCTACCCTCTCCGGCATGAATTTATCAGCT
AGAACGGTTGAATATCATATTGATGGTGATTTGACTGTCTCCGGCCTTTCTCACC
CGTTTGAATCTTTACCTACACATTACTCAGGCATTGCATTTAAAATATATGAGGG
TTCTAAAAATTTTTATCCTTGCGTTGAAATAAAGGCTTCTCCCGCAAAAGTATTA
CAGGGTCATAATGTTTTTGGTACAACCGATTTAGCTTTATGCTCTGAGGCTTTATT
GCTTAATTTTGCTAATTCTTTGCCTTGCCTGTATGATTTATTGGATGTTGGAATCG
CCTGATGCGGTATTTTCTCCTTACGCATCTGTGCGGTATTCACACCGCATATGGT
GCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGG
GTGCACGAGTGGGGTTACATCGAACTGGATCTCAACAGCGGTAAGATCCTTGAGA
GTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATC
CCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCG
CCCAATACGCAAACCGCCTCTCCCCGCGCGTTGCCGATTCATTAATG
```

APPENDIX I-continued

Sequence Identification Numbers, Identifying Descriptions, and Sequences

```
SEQ ID NO: 6 AAV #1244
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAAGGGTTTTTGTTGTGTTGTTGTTGTTGTTGCTGTTTTTGAGACAAGGG
TCTTGCTCTGTCATCATCCAGGCTGGAGTGCAGTGGTGCAGTCTCAGCTCACTGC
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGCCCAAGCTCAGCCTAACGAGGAGGCC
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTAAACAGC
GGTTCAGCAGAACATACCCTCCACCCTCCTCCAGGACCACGAGAACCAGCGACT
CTTTGAGATGCTTGGACGAAAATGCTTGGTGAGCTGGGGATCTCCTGCCCCCGCC
CCGTCCCCACCGTTTCTTCCTCTTCCTCTCCTCCTTCTCTCTCTTCCCCTCCTCCCG
CTCCTCCTTTCCCTCTCCATCATCTCCACTCCTAGAATTTCCCGTCATAATCCACC
CTTCCCAGGAAGATCTCAATGTCTTCTTGCCTTCCCTCTGGCTGCAGCTCTTCCTT
TGGGCCCATGACTGTCATGAGGCAGGAAGGACCAGGTCTGGCTCCAAGACCTTG
TGGCTACCCCTGACCAGACTCCACTGACCCCTGCTTTCCTCTCCCAGACGCTGGC
CACTGCAGTTGTTCAGCTGTACCTGGCGCTGCCCCCTGGAGCTGAGCACTGGACC
AAGGAGCATTGTGGGGCTGTGTGCTTCGTGAAGGATAACCCCCAGAAGTCCTAC
TTCATCCGCCTTTACGGCCTTCAGGTGACCCCCCCACCCCCGACTGGACTTGCAA
GCCAGTTCTCAACCCGCAAACCCAGATCTGTGTCCATATGTGTCCATAGCTTCAA
GACCTCAGACCTGATCAGTGAATCCCTGAGCCCCAGAACCAAAGACTCATCCAG
ATGGCAAACTCTGACTTGCCTTTCTAAGTCTGCAATGACTGGCCCCAGTCTCCGT
ATCAAGATCTCTAAAGCCCCCAGTATTAGTCTGCTGCCTAAGCCTAATCTTTTCC
ACAAATTCCAATAAATGAGCACTGTATTTGTACCTGAACCTCAAATCTATTCTAA
ACTCAACATTTTGCATCCCAGGAATCTCTCATCAAAACTCCTGAACCCCAGATGT
TTGCCAAGCTCCTAAGTCATAAATCTGTTCAACAAACCCCAAAGTTGAATATTCC
ATTGATCCTTGAACTCCAAATCTGTCCTTCTAAATCCACAGCACAGACCCCAGAG
TTCCCATCTAGAGCATGGCTACGTAGATAAGTAGCATGGCGGGTTAATCATTAAC
TACAAGGAACCCCTAGTGATGGAGTTGGCCACTCCCTCTCTGCGCGCTCGCTCGC
TCACTGAGGCCGGGCGACCAAAGGTCGCCCGACGCCCGGGCTTTGCCCGGGCGG
CCTCAGTGAGCGAGCGAGCGCGCCAGCTGGCGTAATAGCGAAGAGGCCCGCACC
GATCGCCCTTCCCAACAGTTGCGCAGCCTGAATGGCGAATGGCGATTCCGTTGCA
ATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGT
TAATTTGCGTGATGGACAGACTCTTTTACTCGGTGGCCTCACTGATTATAAAAAC
ACTTCTCAGGATTCTGGCGTACCGTTCCTGTCTAAAATCCCTTTAATCGGCCTCCT
GTTTAGCTCCCGCTCTGATTCTAACGAGGAAAGCACGTTATACGTGCTCGTCAAA
GCAACCATAGTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCT
```

APPENDIX I-continued

Sequence Identification Numbers, Identifying Descriptions, and Sequences

```
TTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGA
TTTCGGCCTATTGGTTAAAAAATGAGCTGATTTAACAAAAATTTAACGCGAATTT
TAACAAAATATTAACGTTTACAATTTAAATATTTGCTTATACAATCTTCCTGTTTT
TGGGGCTTTTCTGATTATCAACCGGGGTACATATGATTGACATGCTAGTTTTACG
ATTACCGTTCATCGATTCTCTTGTTTGCTCCAGACTCTCAGGCAATGACCTGATAG
CCTTTGTAGAGACCTCTCAAAAATAGCTACCCTCTCCGGCATGAATTTATCAGCT
AGAACGGTTGAATATCATATTGATGGTGATTTGACTGTCTCCGGCCTTTCTCACC
CGTTTGAATCTTTACCTACACATTACTCAGGCATTGCATTTAAAATATATGAGGG
TTCTAAAAATTTTTATCCTTGCGTTGAAATAAAGGCTTCTCCCGCAAAAGTATTA
CAGGGTCATAATGTTTTTGGTACAACCGATTTAGCTTTATGCTCTGAGGCTTTATT
GCTTAATTTTGCTAATTCTTTGCCTTGCCTGTATGATTTATTGGATGTTGGAATCG
CCTGATGCGGTATTTTCTCCTTACGCATCTGTGCGGTATTTCACACCGCATATGGT
GCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTT
ACTCATATATACTTTTAGATTGATTTAAAACTTCATTTTTAATTTAAAAGGATCTAG
GTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATC
CCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATG

SEQ ID NO: 7 AAV #1262
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAAGGGTTTTTGTTGTGTTGTTGTTGCTGTTTTTGAGACAAGGG
TCTTGCTCTGTCATCATCCAGGCTGGAGTGCAGTGGTGCAGTCTCAGCTCACTGC
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGGCCCAAGCTCAGCCTAACGAGGAGGCC
```

APPENDIX I-continued

Sequence Identification Numbers, Identifying Descriptions, and Sequences

```
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTAAAAATC
CACCCTTCCCAGGAAGATCTCAATGTCTACTTGCCTTCCCTCTGGCTGCAGCTCTT
CCTTTGGGCCCATGACTGTCATGAGGCAGGAAGGACCAGGTCTGGCTCCAAGAC
CTTGTGGCTACCCCTGACCAGACTCCACTGACCCCTGCTTTCCTCTCCCAGACGC
TGGCCACTGCAGTTGTTCAGCTGTACCTGGCGCTGCCCCCTGGGAGCTGAGCACTG
GACCAAGGAGCATTGTGGGGCTGTGTGCTTCGTGAAGGATAACCCCCAGAAGTC
CTACTTCATCCGCCTTTACGGCCTTCAGGTGACCCCCCCACCCCCGACTGGACTT
GCAAGCCAGTTCTCAACCCGCAAACCCAGATCTGTGTCCATATGTGTCCATAGCT
TCAAGACCTCAGACCTGATCAGTGAATCCCTGAGCCCCAGAACCAAAGACTCAT
CCAGATGGCAAACTCTGACTTGCCTTTCTAAGTCTGCAATGACTGGCCCCAGTCT
CCGTATCAAGATCTCTAAAGCCCCCAGTATTAGTCTGCTGCCTAAGCCTAATCTT
TTCCACAAATTCCAATAAATGAGCACTGTATTTGTACCTGAACCTCAAATCTATT
CTAAACTCAACATTTTGCATCCCAGGAATCTCTCATCAAAACTCCTGAACCCCAG
ATGTTTGCCAAGCTCCTAAGTCATAAATCTGTTCAACAAACCCCAAAGTTGAATA
TTCCATTGATCCTTGAACTCCAAATCTGTCCTTCTAAATCCACAGCACAGACCCC
AGAGTTCCCATCTAGAGCATGGCTACGTAGATAAGTAGCATGGCGGGTTAATCA
TTAACTACAAGGAACCCCTAGTGATGGAGTTGGCCACTCCCTCTCTGCGCGCTCG
CTCGCTCACTGAGGCCGGGCGACCAAAGGTCGCCCGACGCCCGGGCTTTGCCCG
GGCGGCCTCAGTGAGCGAGCGAGCGCGCCAGCTGGCGTAATAGCGAAGAGGCC
CGCACCGATCGCCCTTCCCAACAGTTGCGCAGCCTGAATGGCGAATGGCGATTC
CGTTGCAATGGCTGGCGGTAATATTGTTCTGGATATTACCAGCAAGGCCGATAGT
TTGAGTTCTTCTACTCAGGCAAGTGATGTTATTACTAATCAAAGAAGTATTGCGA
CAACGGTTAATTTGCGTGATGGACAGACTCTTTTACTCGGTGGCCTCACTGATTA
TAAAAACACTTCTCAGGATTCTGGCGTACCGTTCCTGTCTAAAATCCCTTTAATC
GGCCTCCTGTTTAGCTCCCGCTCTGATTCTAACGAGGAAAGCACGTTATACGTGC
TCGTCAAAGCAACCATAGTACGCGCCCTGTAGCGGCGCATTAAGCGCGGCGGGT
GTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTC
TAAATCGGGGGCTCCCTTTAGGGTTCCGATTTAGTGCTTTACGGCACCTCGACCC
CAAAAAACTTGATTAGGGTGATGGTTCACGTAGTGGGCCATCGCCCTGATAGAC
GGTTTTTCGCCCTTTGACGTTGGAGTCCACGTTCTTTAATAGTGGACTCTTGTTCC
AAACTGGAACAACACTCAACCCTATCTCGGTCTATTCTTTTGATTTATAAGGGAT
TTTGCCGATTTCGGCCTATTGGTTAAAAAATGAGCTGATTTAACAAAAATTTAAC
GCGAATTTTAACAAAATATTAACGTTTACAATTTAAATATTTGCTTATACAATCTT
CCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGA
CCTGATAGCCTTTGTAGAGACCTCTCAAAAATAGCTACCCTCTCCGGCATGAATT
TATCAGCTAGAACGGTTGAATATCATATTGATGGTGATTTGACTGTCTCCGGCCT
TTCTCACCCGTTTGAATCTTTACCTACACATTACTCAGGCATTGCATTTAAAATAT
ATGAGGGTTCTAAAAATTTTTATCCTTGCGTTGAAATAAAGGCTTCTCCCGCAAA
AGTATTACAGGGTCATAATGTTTTTGGTACAACCGATTTAGCTTTATGCTCTGAG
GCTTTATTGCTTAATTTTGCTAATTCTTTGCCTTGCCTGTATGATTTATTGGATGTT
GGAATCGCCTGATGCGGTATTTTCTCCTTACGCATCTGTGCGGTATTTCACACCG
CATATGGTGCACTCTCAGTACAATCTGCTCTGATGCCGCATAGTTAAGCCAGCCC
CGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTT
ATAGGTTAATGTCATGATAATAATGGTTTCTTAGACGTCAGGTGGCACTTTTCGG
GGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGA
AGAGTATGAGTATTCAACATTTCCGTGTCGCCCTTATTCCCTTTTTTGCGGCATTT
TGCCTTCCTGTTTTTGCTCACCCAGAAACGCTGGTGAAAGTAAAAGATGCTGAAG
```

APPENDIX I-continued

Sequence Identification Numbers, Identifying Descriptions, and Sequences

```
ATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCA
TGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTG
GGAACCGGAGCTGAATGAAGCCATACCAAACGACGAGCGTGACACCACGATGC
CTGTAGCAATGGCAACAACGTTGCGCAAACTATTAACTGGCGAACTACTTACTCT
AGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCC
TCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAA
AAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCT
ACCAGCGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGAC
TCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCG
TCGATTTTTGTGATGCTCGTCAGGGGGGCGGAGCCTATGGAAAAACGCCAGCAA
CGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGC
GGAAGAGCGCCCAATACGCAAACCGCCTCTCCCCGCGCGTTGGCCGATTCATTA
ATG

SEQ ID NO: 8 AAV #1189
AAGCTTCCCGGGGGGGATCTGGGCCACTCCCTCTCTGCGCGCTCGCTCGCTCACTG
AGGCCGGGCGACCAAAGGTCGCCCGACGCCCGGGCTTTGCCCGGGCGGCCTCAG
TGAGCGAGCGAGCGCGCAGAGAGGGAGTGGCCAACTCCATCACTAGGGGTTCCT
GGAGGGGTGGAGTCGTGACCTAGGCGATTTAAATTCATGTACAAAAAAGCAGGC
TTTAAAGGAACCAATTCAGTCGACTGGATCCGGTACCAAGGTCGGGCAGGAAGA
GGGCCTATTTCCCATGATTCCTTCATATTTGCATATACGATACAAGGCTGTTAGA
GAGATAATTAGAATTAATTTGACTGTAAACACAAAGATATTAGTACAAAATACG
TGACGTAGAAAGTAATAATTTCTTGGGTAGTTTGCAGTTTTAAAATTATGTTTTA
AAATGGACTATCATATGCTTACCGTAACTTGAAAGTATTTCGATTTCTTGGCTTTA
TATATCTTGTGGAAAGGACGAAACACCGGTATGTTCTGCTGAACCGCGTTTTAGA
GCTAGAAATAGCAAGTTAAAATAAGGCTAGTCCGTTATCAACTTGAAAAAGTGG
CACCGAGTCGGTGCTTTTTTTCTAGACCCAGCTTTCTTGTACAAAGTTGGCATTAA
CTAGTCCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGCGCGC
AGAGAGGGACAGATCCGGGCCCGCATGCGTCGACAATTCACTGGCCGTCGTTTT
ACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCC
TTCCCAACAGTTGCGCAGCCTGAATGGCGAATGGCGCCTGATGCGGTATTTTCTC
CTTACGCATCTGTGCGGTATTTCACACCGCATATGGTGCACTCTCAGTACAATCT
GCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAG
ACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTT
GTTTATTTTTCTAAATACATTCAAATATGTATCCGCTCATGAGACAACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
```

APPENDIX I-continued

Sequence Identification Numbers, Identifying Descriptions, and Sequences

```
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGT
GAGCGGATAACAATTTCACACAGGAAACAGCTATGACCATGATTACGCCAAGCT
CTCGAGATCTAGA

SEQ ID NO: 9 AAV# 1215
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTTGTACAAAAAAGCAGGCTTTAAAGGAACCAA
TTCAGTCGACTGGATCCGGTACCAAGGTCGGGCAGGAAGAGGGCCTATTTCCCA
TGATTCCTTCATATTTGCATATACGATACAAGGCTGTTAGAGAGATAATTAGAAT
TAATTTGACTGTAAACACAAAGATATTAGTACAAAATACGTGACGTAGAAAGTA
ATAATTTCTTGGGTAGTTTGCAGTTTTAAAATTATGTTTTAAAATGGACTATCATA
TGCTTACCGTAACTTGAAAGTATTTCGATTTCTTGGCTTTATATATCTTGTGGAAA
GGACGAAACACCGGTATGTTCTGCTGAACCGCGTTTTAGAGCTAGAAATAGCAA
GTTAAAATAAGGCTAGTCCGTTATCAACTTGAAAAAGTGGCACCGAGTCGGTGC
TTTTTTACGCGTGTATGACAAGCAGAAAGTAATTTGGGAGCTGCGGGGAGGCAA
GGGTAAGGGATGGGGAAGTGGACCAGAGGCATATGCGTCATTGGCAGTGTCTAA
GCACTCACGATAGGCGTGGATCACAGGGGCTCGCTCTGTAATTAAAAGGAAAAG
GGTTTTTGTTGTGTTGTTGTTGTTGCTGTTTTTGAGACAAGGGTCTTGCTCTGTCA
TCATCCAGGCTGGAGTGCAGTGGTGCAGTCTCAGCTCACTGCAACCTCCGCCTCC
TGGGTTCAAGCGATTCTCCTGCCTCAGCCTCCTGAGCAGCTAGGACTACAGGTGT
GTGCCACCATGCCTGGCTAATTTTTGTATTTTTTAGTGGAAATGGGGTTTTGCCAT
GTTGCCCAGGCTCGTCTTGAACTCCTGACCTCAAGTGATCCACTCGTCTCGGCCT
CCCAAAGTGCTGGGATTACAGGTGTGAGCTATTGTCCCCAGCCAAAAGGAAAAG
TTTTACTGTAGTAACCCTTCCGGACTAGGGACCTCGGGCCTCAGCCTCAGGCTAC
CTAGGTGCTTTAGAAAGGAGGCCACCCAGGCCCATGACTACTCCTTGCCACAGG
GAGCCCTGCACACAGATGTGCTAAGCTCTCGCTGCCAGCCAGAGGGAGGAGGGT
CTGAGCCAGTCAGAAGGAGATGGGCCCCAGAGAGTAAGAAAGGGGGAGGAGGA
CCCAAGCTGATCCAAAAGGTGGGTCTAAGCAGTCAAGTGGAGGAGGGGTTCCAAT
CTGATGGCGGAGGGCCCAAGCTCAGCCTAACGAGGAGGCCAGGCCCACCAAGG
GGCCCCTGGAGGACTTGTTTCCCTTGTCCCTTGTGGTTTTTTGCATTTCCTGTTCC
CTTGCTGCTCATTGCGGAAGTTCCTCTTCTTACCCTGCACCCAGAGCCTCGCCAG
AGAAGACAAGGGCAGAAAGCACCATGAGTGGGGGCCCAATGGGAGGAAGGCCC
GGGGGCCGAGGAGCACGAACAGAGAAACAGGAGAATATGGGCCAAACAGGATA
TCTGTGGTAAGCAGTTCCTGCCCCGGCTCAGGGCCAAGAACAGTTGGAACAGCA
GAATATGGGCCAAACAGGATATCTGTGGTAAGCAGTTCCTGCCCCGGCTCAGGG
CCAAGAACAGATGGTCCCCAGATGCGGTCCCGCCCTCAGCAGTTTCTAGAGAAC
CATCAGATGTTTCCAGGGTGCCCCAAGGACCTGAAATGACCCTGTGCCTTATTTG
AACTAACCAATCAGTTCGCTTCTCGCTTCTGTTCGCGCGCTTCTGCTCCCCGAGCT
CTATATAAGCAGAGCTCGTTTAGTGAACCGTCAGATCGCCTGGAGACGCCATCC
ACGCTGTTTTGACTTCCATAGAAGGATCTCGAGGCCACCATGGTGAGCAAGGGC
GAGGAGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAG
AACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTG
CTGGAGTTCGTGACCGCCGCCGGGATCACTCTCGGCATGGACGAGCTGTACAAG
TAAACTAGTGTCGACTGCTTTATTTGTGAAATTTGTGATGCTATTGCTTTATTTGT
AACCATTATAAGCTGCAATAAACAAGTTAACAACAACAATTGCATTCATTTTATG
TTTCAGGTTCAGGGGGAGGTGTGGGAGGTTTTTTAAACAGCCGGTTCAGCAGAAC
ATACCCTCCACCCTCCTCCAGGACCACGAGAACCAGCGACTCTTTGAGATGCTTG
```

APPENDIX I-continued

Sequence Identification Numbers, Identifying Descriptions, and Sequences

```
GACGAAAATGCTTGGTGAGCTGGGGATCTCCTGCCCCCGCCCCGTCCCCACCGTT
TCTTCCTCTTCCTCTCCTCCTTCTCTCTCTTCCCCTCCTCCCGCTCCTCCTTTCCCTC
TCCATCATCTCCTCTCCTAGAATTTCCCGTCATAATCCACCCTTCCCAGGAAGATC
TCAATGTCTACTTGCCTTCCCTCTGGCTGCAGCTCTTCCTTTGGGCCCATGACTGT
CATGAGGCAGGAAGGACCAGGTCTGGCTCCAAGACCTTGTGGCTACCCCTGACC
AGACTCCACTGACCCCTGCTTTCCTCTCCCAGACGCTGGCCACTGCAGTTGTTCA
GCTGTACCTGGCGCTGCCCCCTGGAGCTGAGCACTGGACCAAGGAGCATTGTGG
GGCTGTGTGCTTCGTGAAGGATAACCCCCAGAAGTCCTACTTCATCCGCCTTTAC
GGCCTTCAGGTGACCCCCCCACCCCCGACTGGACTTGCAAGCCAGTTCTCAACCC
GCAAACCCAGATCTGTGTCCATATGTGTCCATAGCTTCAAGACCTCAGACCTGAT
CAGTGAATCCCTGAGCCCCAGAACCAAAGACTCATCCAGATGGCAAACTCTGAC
TTGCCTTTCTAAGTCTGCAATGACTGGCCCCAGTCTCCGTATCAAGATCTCTAAA
GCCCCCAGTATTAGTCTGCTGCCTAAGCCTAATCTTTTCCACAAATTCCAATAAA
TGAGCACTGTATTTGTACCTGAACCTCAAATCTATTCTAAACTCAACATTTTGCAT
CCCAGGAATCTCTCATCAAAACTCCTGAACCCCAGATGTTTGCCAAGCTCCTAAG
TCATAAATCTGTTCAACAAACCCCAAAGTTGAATATTCCATTGATCCTTGAACTC
CAAATCTGTCCTTCTAAATCCACAGCACAGACCCCAGAGTTCCCATCTAGAGCAT
GGCTACGTAGATAAGTAGCATGGCGGGTTAATCATTAACTACAAGGAACCCCTA
GTGATGGAGTTGGCCACTCCCTCTCTGCGCGCTCGCTCGCTCACTGAGGCCGGGC
GACCAAAGGTCGCCCGACGCCCGGGCTTTGCCCGGGCGGCCTCAGTGAGCGAGC
GAGCGCGCCAGCTGGCGTAATAGCGAAGAGGCCCGCACCGATCGCCCTTCCCAA
CAGTTGCGCAGCCTGAATGGCGAATGGCGATTCCGTTGCAATGGCTGGCGGTAA
TATTGTTCTGGATATTACCAGCAAGGCCGATAGTTTGAGTTCTTCTACTCAGGCA
AGTGATGTTATTACTAATCAAAGAAGTATTGCGACAACGGTTAATTTGCGTGATG
GACAGACTCTTTTACTCGGTGGCCTCACTGATTATAAAAACACTTCTCAGGATTC
TGGCGTACCGTTCCTGTCTAAAATCCCTTTAATCGGCCTCCTGTTTAGCTCCCGCT
CTGATTCTAACGAGGAAAGCACGTTATACGTGCTCGTCAAAGCAACCATAGTAC
GCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTT
TCTCGCCACGTTCGCCGGCTTTCCCCGTCAAGCTCTAAATCGGGGGCTCCCTTTA
GGGTTCCGATTTAGTGCTTTACGGCACCTCGACCCCAAAAAACTTGATTAGGGTG
ATGGTTCACGTAGTGGGCCATCGCCCTGATAGACGGTTTTTCGCCCTTTGACGTT
GGGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTG
GTTAAAAAATGAGCTGATTTAACAAAAATTTAACGCGAATTTTAACAAAATATT
AACGTTTACAATTTAAATATTTGCTTATACAATCTTCCTGTTTTTGGGGCTTTTCT
GATTATCAACCGGGGTACATATGATTGACATGCTAGTTTTACGATTACCGTTCAT
CGATTCTCTTGTTTGCTCCAGACTCTCAGGCAATGACCTGATAGCCTTTGTAGAG
ACCTCTCAAAAATAGCTACCCTCTCCGGCATGAATTTATCAGCTAGAACGGTTGA
ATATCATATTGATGGTGATTTGACTGTCTCCGGCCTTTCTCACCCGTTTGAATCTT
TACCTACACATTACTCAGGCATTGCATTTAAAATATATGAGGGTTCTAAAAATTT
TTATCCTTGCGTTGAAATAAAGGCTTCTCCCGCAAAAGTATTACAGGGTCATAAT
GTTTTTGGTACAACCGATTTAGCTTTATGCTCTGAGGCTTTATTGCTTAATTTTGC
TAATTCTTTGCCTTGCCTGTATGATTTATTGGATGTTGGAATCGCCTGATGCGGTA
TTTTCTCCTTACGCATCTGTGCGGTATTTCACACCGCATATGGTGCACTCTCAGTA
CAATCTGCTCTGATGCCGCATAGTTAAGCCAGCCCCGACACCCGCCAACACCCG
CTGACGCGCCCTGACGGGCTTGTCTGCTCCCGGCATCCGCTTACAGACAAGCTGT
GACCGTCTCCGGGAGCTGCATGTGTCAGAGGTTTTCACCGTCATCACCGAAACGC
GCGAGACGAAAGGGCCTCGTGATACGCCTATTTTTATAGGTTAATGTCATGATAA
TAATGGTTTCTTAGACGTCAGGTGGCACTTTTCGGGGAAATGTGCGCGGAACCCC
TATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTT
CCGTGTCGCCCTTATTCCCTTTTTTGCGGCATTTTGCCTTCCTGTTTTTGCTCACCC
AGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGA
AGAACGTTTTCCAATGATGAGCACTTTTAAAGTTCTGCTATGTGGCGCGGTATTA
TCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAG
CCATACCAAACGACGAGCGTGACACCACGATGCCTGTAGCAATGGCAACAACGT
TGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGT
ATCATTGCAGCACTGGGGCCAGATGGTAAGCCCTCCCGTATCGTAGTTATCTACA
CGACGGGGAGTCAGGCAACTATGGATGAACGAAATAGACAGATCGCTGAGATA
GGTGCCTCACTGATTAAGCATTGGTAACTGTCAGACCAAGTTTACTCATATATAC
TTTAGATTGATTTAAAACTTCATTTTTAATTTAAAAGGATCTAGGTGAAGATCCTT
TTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTTCTGCGCGT
AATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAG
ATACCAAATACTGTCCTTCTAGTGTAGCCGTAGTTAGGCCACCACTTCAAGAACT
CTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGC
```

APPENDIX I-continued

Sequence Identification Numbers, Identifying Descriptions, and Sequences

```
CACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTG
GCCTTTTGCTGGCCTTTTGCTCACATGTTCTTTCCTGCGTTATCCCCTGATTCTGTG
GATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCCAATACGCAA
ACCGCCTCTCCCCGCGCGTTGGCCGATTCATTAATG

SEQ ID NO: 10 Sequence of Full chemically modified guide #1
5' 2'OMe(G(ps)G(ps)U(ps)) AUG UUC UGC UGA ACC GCG UUU UAG AGC UAG AAA
UAG CAA GUU AAA AUA AGG CUA GUC CGU UAU CAA CUU GAA AAA GUG GCA
CCG AGU CGG UGC 2'OMe(U(ps)U(ps)U(ps)) U 3'

SEQ ID NO: 11 Upstream homology arm (common in #1201, #1262 and #1244)
GTATGACAAGCAGAAAGTAATTTGGGAGCTGCGGGGAGGCAAGGGTAAGGGAT
GGGGAAGTGGACCAGAGGCATATGCGTCATTGGCAGTGTCTAAGCACTCACGAT
AGGCGTGGATCACAGGGGCTCGCTCTGTAATTAAAAGGAAAAGGGTTTTTGTTG
TGTTGTTGTTGTTGCTGTTTTTGAGACAAGGGTCTTGCTCTGTCATCATCCAGGCT
GGAGTGCAGTGGTGCAGTCTCAGCTCACTGCAACCTCCGCCTCCTGGGTTCAAGC
GATTCTCCTGCCTCAGCCTCCTGAGCAGCTAGGACTACAGGTGTGTGCCACCATG
CCTGGCTAATTTTTGTATTTTTTAGTGGAAATGGGGTTTTGCCATGTTGCCCAGGC
TCGTCTTGAACTCCTGACCTCAAGTGATCCACTCGTCTCGGACCTCCCAAAGTGCT
GGGATTACAGGTGTGAGCTATTGTCCCCAGCCAAAAGGAAAAGTTTTACTGTAG
TAACCCTTCCGGACTAGGGACCTCGGGCCTCAGCCTCAGGCTACCTAGGTGCTTT
AGAAAGGAGGCCACCCAGGCCCATGACTACTCCTTGCCACAGGGAGCCCTGCAC
ACAGATGTGCTAAGCTCTCGCTGCCAGCCAGAGGGAGGAGGGTCTGAGCCAGTC
AGAAGGAGATGGGCCCCAGAGAGTAAGAAAGGGGGAGGAGGACCCAAGCTGAT
CCAAAAGGTGGGTCTAAGCAGTCAAGTGGAGGAGGGTTCCAATCTGATGGCGGA
GGGCCCAAGCTCAGCCTAACGAGGAGGCCAGGCCCACCAAGGGGCCCCTGGAG
GACTTGTTTCCCTTGTCCCTTGTGGTTTTTTGCATTTCCTGTTCCCTTGCTGCTCAT
TGCGGAAGTTCCTCTTCTTACCCTGCACCCAGAGCCTCGCCAGAGAAGACAAGG
GCAGAAAGCACCATGAGTGGGGGCCCAATGGGAGGAAGGCCCGGGGGCCGAGG
AGCAC SEQ ID NO: 12 Downstream homology arm for #1201
CAGCGGTTCAGCAGAACATACCCTCCACCCTCCTCCAGGACCACGAGAACCAGC
GACTCTTTGAGATGCTTGGACGAAAATGCTTGGTGAGCTGGGGATCTCCTGCCCC
CGCCCCGTCCCCACCGTTTCTTCCTCTTCCTCTCCTCCTTCTCTCTCTTCCCCTCCT
CCCGCTCCTCCTTTCCCTCTCCATCATCTCCTCTCCTAGAATTTCCCGTCATAATC
CACCCTTCCCAGGAAGATCTCAATGTCTACTTGCCTTCCCTCTGGCTGCAGCTCTT
CCTTTGGGCCCATGACTGTCATGAGGCAGGAAGGACCAGGTCTGGCTCCAAGAC
CTTGTGGCTACCCCTGACCAGACTCCACTGACCCCTGCTTTCCTCTCCCAGACGC
TGGCCACTGCAGTTGTTCAGCTGTACCTGGCGCTGCCCCCTGGAGCTGAGCACTG
GACCAAGGAGCATTGTGGGGCTGTGTGCTTCGTGAAGGATAACCCCCAGAAGTC
CTACTTCATCCGCCTTTACGGCCTTCAGGTGACCCCCCCACCCCCGACTGGACTT
GCAAGCCAGTTCTCAACCCGCAAACCCAGATCTGTGTCCATATGTGTCCATAGCT
TCAAGACCTCAGACCTGATCAGTGAATCCCTGAGCCCCAGAACCAAAGACTCAT
CCAGATGGCAAACTCTGACTTGCCTTTCTAAGTCTGCAATGACTGGCCCCAGTCT
CCGTATCAAGATCTCTAAAGCCCCCAGTATTAGTCTGCTGCCTAAGCCTAATCTT
TTCCACAAATTCCAATAAATGAGCACTGTATTTGTACCTGAACCTCAAATCTATT
CTAAACTCAACATTTTGCATCCCAGGAATCTCTCATCAAAACTCCTGAACCCCAG
ATGTTTGCCAAGCTCCTAAGTCATAAATCTGTTCAACAAACCCCAAAGTTGAATA
TTCCATTGATCCTTGAACTCCAAATCTGTCCTTCTAAATCCACAGCACAGACCCC
AGAGTTCCCA SEQ ID NO: 13 Downstream homology arm #1244
CAGCGGTTCAGCAGAACATACCCTCCACCCTCCTCCAGGACCACGAGAACCAGC
GACTCTTTGAGATGCTTGGACGAAAATGCTTGGTGAGCTGGGGATCTCCTGCCCC
CGCCCCGTCCCCACCGTTTCTTCCTCTTCCTCTCCTCCTTCTCTCTCTTCCCCTCCT
CCCGCTCCTCCTTTCCCTCTCCATCATCTCCACTCCTAGAATTTCCCGTCATAATC
CACCCTTCCCAGGAAGATCTCAATGTCTTCTTGCCTTCCCTCTGGCTGCAGCTCTT
CCTTTGGGCCCATGACTGTCATGAGGCAGGAAGGACCAGGTCTGGCTCCAAGAC
CTTGTGGCTACCCCTGACCAGACTCCACTGACCCCTGCTTTCCTCTCCCAGACGC
TGGCCACTGCAGTTGTTCAGCTGTACCTGGCGCTGCCCCCTGGAGCTGAGCACTG
GACCAAGGAGCATTGTGGGGCTGTGTGCTTCGTGAAGGATAACCCCCAGAAGTC
CTACTTCATCCGCCTTTACGGCCTTCAGGTGACCCCCCCACCCCCGACTGGACTT
GCAAGCCAGTTCTCAACCCGCAAACCCAGATCTGTGTCCATATGTGTCCATAGCT
TCAAGACCTCAGACCTGATCAGTGAATCCCTGAGCCCCAGAACCAAAGACTCAT
CCAGATGGCAAACTCTGACTTGCCTTTCTAAGTCTGCAATGACTGGCCCCAGTCT
CCGTATCAAGATCTCTAAAGCCCCCAGTATTAGTCTGCTGCCTAAGCCTAATCTT
TTCCACAAATTCCAATAAATGAGCACTGTATTTGTACCTGAACCTCAAATCTATT
CTAAACTCAACATTTTGCATCCCAGGAATCTCTCATCAAAACTCCTGAACCCCAG
ATGTTTGCCAAGCTCCTAAGTCATAAATCTGTTCAACAAACCCCAAAGTTGAATA
TTCCATTGATCCTTGAACTCCAAATCTGTCCTTCTAAATCCACAGCACAGACCCC
AGAGTTCCCA
```

APPENDIX I-continued

Sequence Identification Numbers, Identifying Descriptions, and Sequences

SEQ ID NO: 14 Downstream homology arm #1262
AATCCACCCTTCCCAGGAAGATCTCAATGTCTACTTGCCTTCCCTCTGGCTGCAG
CTCTTCCTTTGGGCCCATGACTGTCATGAGGCAGGAAGGACCAGGTCTGGCTCCA
AGACCTTGTGGCTACCCCTGACCAGACTCCACTGACCCCTGCTTTCCTCTCCCAG
ACGCTGGCCACTGCAGTTGTTCAGCTGTACCTGGCGCTGCCCCCTGGAGCTGAGC
ACTGGACCAAGGAGCATTGTGGGGCTGTGTGCTTCGTGAAGGATAACCCCCAGA
AGTCCTACTTCATCCGCCTTTACGGCCTTCAGGTGACCCCCCCACCCCCGACTGG
ACTTGCAAGCCAGTTCTCAACCCGCAAACCCAGATCTGTGTCCATATGTGTCCAT
AGCTTCAAGACCTCAGACCTGATCAGTGAATCCCTGAGCCCCAGAACCAAAGAC
TCATCCAGATGGCAAACTCTGACTTGCCTTTCTAAGTCTGCAATGACTGGCCCCA
GTCTCCGTATCAAGATCTCTAAAGCCCCCAGTATTAGTCTGCTGCCTAAGCCTAA
TCTTTTCCACAAATTCCAATAAATGAGCACTGTATTTGTACCTGAACCTCAAATC
TATTCTAAACTCAACATTTTGCATCCCAGGAATCTCTCATCAAAACTCCTGAACC
CCAGATGTTTGCCAAGCTCCTAAGTCATAAATCTGTTCAACAAACCCCAAAGTTG
AATATTCCATTGATCCTTGAACTCCAAATCTGTCCTTCTAAATCCACAGCACAGA
CCCCAGAGTTCCCA SEQ ID NO: 15 WAS TALEN binding site on the genome (forward-TALEN)
CTCCTAGAATTTCCCGT SEQ ID NO: 16 WAS TALEN binding site on the genome (reverse-TALEN)
AGGAAGATCTCAATGTCT SEQ ID NO: 17 TALEN cleavage site (spacer sequence)
CATAATCCACCCTTCCC SEQ ID NO: 18 WAS exon 2
ACGCTGGCCACTGCAGTTGTTCAGCTGTACCTGGCGCTGCCCCCTGGAGCTGAGC
ACTGGACCAAGGAGCATTGTGGGGCTGTGTGCTTCGTGAAGGATAACCCCCAGA
AGTCCTACTTCATCCGCCTTTACGGCCTTCAG SEQ ID NO: 19 WAS exon 1 sequence
TCCTCTTCTTACCCTGCACCCAGAGCCTCGCCAGAGAAGACAAGGGCAGAAAGC
ACCATGAGTGGGGGCCCAATGGGAGGAAGGCCCGGGGGCCGAGGAGCACCAGC
GGTTCAGCAGAACATACCCTCCACCCTCCTCCAGGACCACGAGAACCAGCGACT
CTTTGAGATGCTTGGACGAAAATGCTTG SEQ ID NO: 20 pWNY.2xNLS.Cas9.mCherry
TCGCGCGTTTCGGTGATGACGGTGAAAACCTCTGACACATGCAGCTCCCGGAGA
CGGTCACAGCTTGTCTGTAAGCGGATGCCGGGAGCAGACAAGCCCGTCAGGGCG
CGTCAGCGGGTGTTGGCGGGTGTCGGGGCTGGCTTAACTATGCGGCATCAGAGC
AGATTGTACTGAGAGTGCACCATACACTTAGTGTAATACGACTCACTATAGGGA
GAGCGGCCGCTTTTTCAGCAAGATTAAGCCGCCACCATGGCGCCGCGGCCTCCT
AAGAAGAAGCGGAAAGTCGAATTCTACGTAATGGACAAGAAGTACTCCATTGGG
CTCGATATCGGCACAAACAGCGTCGGCTGGGCCGTCATTACGGACGAGTACAAG
GTGCCGAGCAAAAAATTCAAAGTTCTGGGCAATACCGATCGCCACAGCATAAAG
AAGAACCTCATTGGCGCCCTCCTGTTCGACTCCGGGGAGACGGCCGAAGCCACG
CGGCTCAAAAGAACAGCACGGCGCAGATATACCCGCAGAAAGAATCGGATCTG
CTACCTGCAGGAGATCTTTAGTAATGAGATGGCTAAGGTGGATGACTCTTTCTTC
CATAGGCTGGAGGAGTCCTTTTTGGTGGAGGAGGATAAAAAGCACGAGCGCCAC
CCAATCTTTGGCAATATCGTGGACGAGGTGGCGTACCATGAAAAGTACCCAACC
ATATATCATCTGAGGAAGAAGCTTGTAGACAGTACTGATAAGGCTGACTTGCGG
TTGATCTATCTCGCGCTGGCGCATATGATCAAATTTCGGGGACACTTCCTCATCG
AGGGGGACCTGAACCCAGACAACAGCGATGTCGACAAACTCTTTATCCAACTGG
TTCAGACTTACAATCAGCTTTTCGAAGAGAACCCGATCAACGCATCCGGAGTTGA
CGCCAAAGCAATCCTGAGCGCTAGGCTGTCCAAATCCCGGCGGCTCGAAAACCT
CATCGCACAGCTCCCTGGGGAGAAGAAGAACGGCCTGTTTGGTAATCTTATCGC
CCTGTCACTCGGGCTGACCCCCAACTTTAAATCTAACTTCGACCTGGCCGAAGAT
GCCAAGCTTCAACTGAGCAAAGACACCTACGATGATGATCTCGACAATCTGCTG
GCCCAGATCGGCGACCAGTACGCAGACCTTTTTTTGGCGGCAAAGAACCTGTCA
GACGCCATTCTGCTGAGTGATATTCTGCGAGTGAACACGGAGATCACCAAAGCT
CCGCTGAGCGCTAGTATGATCAAGCGCTATGATGAGCACCACCAAGACTTGACT
TTGCTGAAGGCCCTTGTCAGACAGCAACTGCCTGAGAAGTACAAGGAAATTTTCT
TCGATCAGTCTAAAAATGGCTACGCCGGATACATTGACGGCGGAGCAAGCCAGG
AGGAATTTTACAAATTTATTAAGCCCATCTTGGAAAAAATGGACGGCACCGAAG
AGCTGCTGGTAAAGCTTAACAGAGAAGATCTGTTGCGCAAACAGCGCACTTTCG
ACAATGGAAGCATCCCCCACCAGATTCACCTGGGCGAACTGCACGCTATCCTCA
GGCGGCAAGAGGATTTCTACCCCTTTTTGAAAGATAACAGGGAAAAGATTGAGA
AAATCCTCACATTTCGGATACCCTACTATGTAGGCCCCCTCGCCCGGGGAAATTC
CAGATTCGCGTGGATGACTCGCAAATCAGAAGAGACAATCACTCCCTGGAACTT
CGAGGAAGTCGTGGATAAGGGGGCCTCTGCCCAGTCCTTCATCGAAAGGATGAC
TAACTTTGATAAAAATCTGCCTAACGAAAAGGTGCTTCCTAAACACTCTCTGCTG
TACGAGTACTTCACAGTTTATAACGAGCTCACCAAGGTCAAATACGTCACAGAA
GGGATGAGAAAGCCAGCATTCCTGTCTGGAGAGCAGAAGAAAGCTATCGTGGAC
CTCCTCTTCAAGACGAACCGGAAAGTTACCGTGAAACAGCTCAAAGAAGACTAT
TTCAAAAAGATTGAATGTTTCGACTCTGTTGAAATCAGCGGAGTGGAGGATCGCT
TCAACGCATCCCTGGGAACGTATCACGATCTCCTGAAAATCATTAAAGACAAGG
ACTTCCTGGACAATGAGGAGAACGAGGACATTCTTGAGGACATTGTCCTCACCCT APPENDIX I-continued Sequence Identification Numbers, Identifying Descriptions, and Sequences

```
TACGTTGTTTGAAGATAGGGAGATGATTGAAGAACGCTTGAAAACTTACGCTCA
TCTCTTCGACGACAAAGTCATGAAACAGCTCAAGAGGCGCCGATATACAGGATG
GGGGCGGCTGTCAAGAAAACTGATCAATGGGATCCGAGACAAGCAGAGTGGAA
AGACAATCCTGGATTTTCTTAAGTCCGATGGATTTGCCAACCGGAACTTCATGCA
GTTGATCCATGATGACTCTCTCACCTTTAAGGAGGACATCCAGAAAGCACAAGTT
TCTGGCCAGGGGGACAGTCTTCACGAGCACATCGCTAATCTTGCAGGTAGCCCA
GCTATCAAAAAGGGAATACTGCAGACCGTTAAGGTCGTGGATGAACTCGTCAAA
GTAATGGGAAGGCATAAGCCCGAGAATATCGTTATCGAGATGGCCCGAGAGAAC
CAAACTACCCAGAAGGGACAGAAGAACAGTAGGGAAAGGATGAAGAGGATTGA
AGAGGGTATAAAAGAACTGGGGTCCCAAATCCTTAAGGAACACCCAGTTGAAAA
CACCCAGCTTCAGAATGAGAAGCTCTACCTGTACTACCTGCAGAACGGCAGGGA
CATGTACGTGGATCAGGAACTGGACATCAATCGGCTCTCCGACTACGACGTGGA
TCATATCGTGCCCCAGTCTTTTCTCAAAGATGATTCTATTGATAATAAAGTGTTG
ACAAGATCCGATAAAAATAGAGGGAAGAGTGATAACGTCCCCTCAGAAGAAGTT
GTCAAGAAAATGAAAAATTATTGGCGGCAGCTGCTGAACGCCAAACTGATCACA
CAACGGAAGTTCGATAATCTGACTAAGGCTGAACGAGGTGGCCTGTCTGAGTTG
GATAAAGCCGGCTTCATCAAAAGGCAGCTTGTTGAGACACGCCAGATCACCAAG
CACGTGGCCCAAATTCTCGATTCACGCATGAACACCAAGTACGATGAAAATGAC
AAACTGATTCGAGAGGTGAAAGTTATTACTCTGAAGTCTAAGCTGGTGTCCGATT
TCAGAAAGGACTTTCAGTTTTATAAGGTGAGAGAGATCAACAATTACCACCATG
CGCATGATGCCTACCTGAATGCAGTGGTAGGCACTGCACTTATCAAAAAATATCC
CAAGCTTGAATCTGAATTTGTTTACGGAGACTATAAAGTGTACGATGTTAGGAA
ATGATCGCAAAGTCTGAGCAGGAAATAGGCAAGGCCACCGCTAAGTACTTCTTT
TACAGCAATATTATGAATTTTTTCAAGACCGAGATTACACTGGCCAATGGAGAG
ATTCGGAAGCGACCACTTATCGAAACAAACGGAGAAACAGGAGAAATCGTGTG
GGACAAGGGTAGGGATTTCGCGACAGTCCGGAAGGTCCTGTCCATGCCGCAGGT
GAACATCGTTAAAAAGACCGAAGTACAGACCGGAGGCTTCTCCAAGGAAAGTAT
CCTCCCGAAAAGGAACAGCGACAAGCTGATCGCACGCAAAAAAGATTGGGACC
CCAAGAAATACGGCGGATTCGATTCTCCTACAGTCGCTTACAGTGTACTGGTTGT
GGCCAAAGTGGAGAAAGGGAAGTCTAAAAAACTCAAAAGCGTCAAGGAACTGC
TGGGCATCACAATCATGGAGCGATCAAGCTTCGAAAAAAACCCCATCGACTTTC
TCGAGGCGAAAGGATATAAAGAGGTCAAAAAAGACCTCATCATTAAGCTTCCCA
AGTACTCTCTCTTTGAGCTTGAAAACGGCCGGAAACGAATGCTCGCTAGTGCGG
GCGAGCTGCAGAAAGGTAACGAGCTGGCACTGCCCTCTAAATACGTTAATTTCTT
GTATCTGGCCAGCCACTATGAAAAGCTCAAAGGCTCTCCCGAAGATAATGAGCA
GAAGCAGCTGTTCGTGGAACAACACAAACACTACCTTGATGAGATCATCGAGCA
AATAAGCGAATTCTCCAAAAGAGTGATCCTCGCCGACGCTAACCTCGATAAGGT
GCTTTCTGCTTACAATAAGCACAGGGATAAGCCCATCAGGGAGCAGGCAGAAAA
CATTATCCACTTGTTTACTCTGACCAACTTGGGCGCGCCTGCAGCCTTCAAGTAC
TTCGACACCACCATAGACAGAAAGCGGTACACCTCTACAAAGGAGGTCCTGGAC
GCCACACTGATTCATCAGTCAATTACGGGGCTCTATGAAACAAGAATCGACCTCT
CTCAGCTCGGTGGAGACAGCAGGGCTGACCCCAAGAAGAAGAGGAAGGTGGCT
AGCGGAAGCGGAGGTGAGGGCAGAGGAAGTCTTCTAACATGCGGTGACGTGGA
GGAGAATCCGGGCCCTGTGAGCAAGGGCGAGGAGGATAACATGGCCATCATCA
AGGAGTTCATGCGCTTCAAGGTGCACATGGAGGGCTCCGTGAACGGCCACGAGT
TCGAGATCGAGGGCGAGGGCGAGGGCCGCCCCTACGAGGGCACCCAGACCGCC
AAGCTGAAGGTGACCAAGGGTGGCCCCCTGCCCTTCGCCTGGGACATCCTGTCC
CCTCAGTTCATGTACGGCTCCAAGGCCTACGTGAAGCACCCCGCCGACATCCCCG
ACTACTTGAAGCTGTCCTTCCCCGAGGGCTTCAAGTGGGAGCGCGTGATGAACTT
CGAGGACGGCGGCGTGGTGACCGTGACCCAGGACTCCTCTCTGCAGGACGGCGA
GTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAG
GACGGCGCCCTGAAGGGCGAGATCAAGCAGAGGCTGAAGCTGAAGGACGGCGG
CCACTACGACGCTGAGGTCAAGACCACCTACAAGGCCAAGAAGCCCGTGCAGCT
GCCCGGCGCCTACAACGTCAACATCAAGTTGGACATCACCTCCCACAACGAGGA
CTACACCATCGTGGAACAGTACGAACGCGCCGAGGGCCGCCACTCCACCGGCGG
CATGGACGAGCTGTACAAGTGAGGTACCCGTACGAGCTTGGCGTAATCATGGTC
ATAGCTGTTTCCTGTGTGAAATTGTTATCCGCTCACAATTCCACACAACATACGA
GCCGGAAGCATAAAGTGTAAAGCCTGGGGTGCCTAATGAGTGAGCTAACTCACA
TTAATTGCGTTGCGCTCACTGCCCGCTTTCCAGTCGGGAAACCTGTCGTGCCAGC
TGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGC
GGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAA
AAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAAC
AGGATTAGCAGAGCGAGGTATGTAGGCGGTGCTACAGAGTTCTTGAAGTGGTGG
CCTAACTACGGCTACACTAGAAGAACAGTATTTGGTATCTGCGCTCTGCTGAAGC
CAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAG
ATCCTTTTAAATTAAAAATGAAGTTTTAAATCAATCTAAAGTATATATGAGTAAA
```

APPENDIX I-continued

Sequence Identification Numbers, Identifying Descriptions, and Sequences

```
CTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATAC
GGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTT
CCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACT
CATGGTTATGGCAGCACTGCATAATTCTCTTACTGTCATGCCATCCGTAAGATGC
TTTTCTGTGACTGGTGAGTACTCAACCAAGTCATTCTGAGAATAGTGTATGCGGC
GACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGG
CAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACAT
TTCCCCGAAAAGTGCCACCTGACGTCTAAGAAACCATTATTATCATGACATTAAC
CTATAAAAATAGGCGTATCACGAGGCCCTTTCGTC

SEQ ID NO: 21 1190 scAAV.U6.guideRNA2
AAGCTTCCCGGGGGGATCTGGGCCACTCCCTCTCTGCGCGCTCGCTCGCTCACTG
AGGCCGGGCGACCAAAGGTCGCCCGACGCCCGGGCTTTGCCCGGGCGGCCTCAG
TGAGCGAGCGAGCGCGCAGAGAGGGGAGTGGCCAACTCCATCACTAGGGGTTCCT
GGAGGGGTGGAGTCGTGACCTAGGCGATTTAAATTCATGTACAAAAAAGCAGGC
TTTAAAGGAACCAATTCAGTCGACTGGATCCGGTACCAAGGTCGGGCAGGAAGA
GGGCCTATTTCCCATGATTCCTTCATATTTGCATATACGATACAAGGCTGTTAGA
GAGATAATTAGAATTAATTTGACTGTAAACACAAAGATATTAGTACAAAATACG
TGACGTAGAAAGTAATAATTTCTTGGGTAGTTTGCAGTTTTAAAATTATGTTTTA
AAATGGACTATCATATGCTTACCGTAACTTGAAAGTATTTCGATTTCTTGGCTTTA
TATATCTTGTGGAAAGGACGAAACACCGCAAAGAGTCGCTGGTTCTCGGTTTTAG
AGCTAGAAATAGCAAGTTAAAATAAGGCTAGTCCGTTATCAACTTGAAAAAGTG
GCACCGAGTCGGTGCTTTTTTTCTAGACCCAGCTTTCTTGTACAAAGTTGGCATTA
ACTAGTCCACTCCCTCTCTGCGCGCTCGCTCGCTCACTGAGGCCGGGCGACCAAA
GGTCGCCCGACGCCCGGGCTTTGCCCGGGCGGCCTCAGTGAGCGAGCGAGCGCG
CAGAGAGGGACAGATCCGGGCCCGCATGCGTCGACAATTCACTGGCCGTCGTTT
TACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCC
TTCCCAACAGTTGCGCAGCCTGAATGGCGAATGGCGCCTGATGCGGTATTTTCTC
CTTACGCATCTGTGCGGTATTTCACACCGCATATGGTGCACTCTCAGTACAATCT
GCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAG
ACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
```

APPENDIX I-continued

Sequence Identification Numbers, Identifying Descriptions, and Sequences

```
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGT
GAGCGGATAACAATTTCACACAGGAAACAGCTATGACCATGATTACGCCAAGCT
CTCGAGATCTAGA
```

SEQ ID NO: 22 #1191 scAAV.U6.guideRNA3
```
AAGCTTCCCGGGGGGATCTGGGCCACTCCCTCTCTGCGCGCTCGCTCGCTCACTG
AGGCCGGGCGACCAAAGGTCGCCCGACGCCCGGGCTTTGCCCGGGCGGCCTCAG
TGAGCGAGCGAGCGCGCAGAGAGGGAGTGGCCAACTCCATCACTAGGGGTTCCT
GGAGGGGTGGAGTCGTGACCTAGGCGATTTAAATTCATGTACAAAAAAGCAGGC
TTTAAAGGAACCAATTCAGTCGACTGGATCCGGTACCAAGGTCGGGCAGGAAGA
GGGCCTATTTCCCATGATTCCTTCATATTTGCATATACGATACAAGGCTGTTAGA
GAGATAATTAGAATTAATTTGACTGTAAACACAAAGATATTAGTACAAAATACG
TGACGTAGAAAGTAATAATTTCTTGGGTAGTTTGCAGTTTTAAAATTATGTTTTA
AAATGGACTATCATATGCTTACCGTAACTTGAAAGTATTTCGATTTCTTGGCTTTA
TATATCTTGTGGAAAGGACGAAACACCGCAAGCATCTCAAAGAGTCGCGTTTTA
GAGCTAGAAATAGCAAGTTAAAATAAGGCTAGTCCGTTATCAACTTGAAAAAGT
GGCACCGAGTCGGTGCTTTTTTTCTAGACCCAGCTTTCTTGTACAAAGTTGGCATT
AACTAGTCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGC
GCAGAGAGGGACAGATCCGGGCCCGCATGCGTCGACAATTCACTGGCCGTCGTT
TTACAACGTCGTGACTGGGAAAACCCTGGCGTTACCCAACTTAATCGCCTTGCAG
CACATCCCCCTTTCGCCAGCTGGCGTAATAGCGAAGAGGCCCGCACCGATCGCC
CTTCCCAACAGTTGCGCAGCCTGAATGGCGAATGGCGCCTGATGCGGTATTTTCT
CCTTACGCATCTGTGCGGTATTTCACACCGCATATGGTGCACTCTCAGTACAATC
TGCTCTGATGCCGCATAGTTAAGCCAGCCCCGACACCCGCCAACACCCGCTGAC
GCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGA
GACGAAAGGGCCTCGTGATACGCCTATTTTTATAGGTTAATGTCATGATAATAAT
GGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGT
GAGCGGATAACAATTTCACACAGGAAACAGCTATGACCATGATTACGCCAAGCT
CTCGAGATCTAGA
```

SEQ ID NO: 23 #1192 scAAV.U6.guideRNA4
```
AAGCTTCCCGGGGGGATCTGGGCCACTCCCTCTCTGCGCGCTCGCTCGCTCACTG
AGGCCGGGCGACCAAAGGTCGCCCGACGCCCGGGCTTTGCCCGGGCGGCCTCAG
```

APPENDIX I-continued

Sequence Identification Numbers, Identifying Descriptions, and Sequences

```
TGAGCGAGCGAGCGCGCAGAGAGGGAGTGGCCAACTCCATCACTAGGGGTTCCT
GGAGGGGTGGAGTCGTGACCTAGGCGATTTAAATTCATGTACAAAAAAGCAGGC
TTTAAAGGAACCAATTCAGTCGACTGGATCCGGTACCAAGGTCGGGCAGGAAGA
GGGCCTATTTCCCATGATTCCTTCATATTTGCATATACGATACAAGGCTGTTAGA
GAGATAATTAGAATTAATTTGACTGTAAACACAAAGATATTAGTACAAAATACG
TGACGTAGAAAGTAATAATTTCTTGGGTAGTTTGCAGTTTTAAAATTATGTTTTA
AAATGGACTATCATATGCTTACCGTAACTTGAAAGTATTTCGATTTCTTGGCTTTA
TATATCTTGTGGAAAGGACGAAACACCGACCATGAGTGGGGGCCCAATGTTTTA
GAGCTAGAAATAGCAAGTTAAAATAAGGCTAGTCCGTTATCAACTTGAAAAAGT
GGCACCGAGTCGGTGCTTTTTTTCTAGACCCAGCTTTCTTGTACAAAGTTGGCATT
AACTAGTCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGC
GCAGAGAGGGACAGATCCGGGCCCGCATGCGTCGACAATTCACTGGCCGTCGTT
TTACAACGTCGTGACTGGGAAAACCCTGGCGTTACCCAACTTAATCGCCTTGCAG
CACATCCCCCTTTCGCCAGCTGGCGTAATAGCGAAGAGGCCCGCACCGATCGCC
CTTCCCAACAGTTGCGCAGCCTGAATGGCGAATGGCGCCTGATGCGGTATTTTCT
CCTTACGCATCTGTGCGGTATTTCACACCGCATATGGTGCACTCTCAGTACAATC
TGCTCTGATGCCGCATAGTTAAGCCAGCCCCGACACCCGCCAACACCCGCTGAC
GCGCCCTGACGGGCTTGTCTGCTCCCGGCATCCGCTTACAGACAAGCTGTGACCG
TCTCCGGGAGCTGCATGTGTCAGAGGTTTTCACCGTCATCACCGAAACGCGCGA
GACGAAAGGGCCTCGTGATACGCCTATTTTTATAGGTTAATGTCATGATAATAAT
GGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGT
GAGCGGATAACAATTTCACACAGGAAACAGCTATGACCATGATTACGCCAAGCT
CTCGAGATCTAGA

SEQ ID NO: 24 WAS TALEN #2 forward
ATGGCGCCGCGGCCTCCTAAGAAGAAGCGGAAAGTCGAATTCGTGGATCTGCGA
ACACTGGGCTATAGCCAGCAGCAGCAGGAGAAGATCAAACCCAAGGTGAGGTC
CACAGTCGCACAGCACCATGAAGCCCTGGTGGGCCACGGGTTCACTCACGCTCA
TATTGTCGCACTGTCTCAGCATCCAGCCGCTCTGGGAACCGTGGCAGTCACATAC
CAGCACATCATTACTGCCCTGCCCGAGGCTACCCATGAAGACATCGTGGGAGTC
GGCAAACAGTGGAGCGGCGCACGGGCCCTGGAGGCTCTGCTGACCGACGCAGG
GGAACTGAGAGGACCCCCTCTGCAGCTGGATACAGGGCAGCTGGTGAAGATTGC
TAAGAGGGGAGGGGTGACAGCAATGGAAGCCGTCCACGCAAGCAGGAACGCAC
TGACAGGGGCCCCCTGAACCTGACCCCGGACCAAGTGGTGGCTATCGCCAGCC
ACGATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACGGTG
GCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACAATGGCGGCA
AGCAAGCGCTCGAAACGGTGCAGCGGCTGTTGCCGGTGCTGTGCCAGGACCATG
```

Sequence Identification Numbers, Identifying Descriptions, and Sequences

GCCTGACCCCGGACCAAGTGGTGGCTATCGCCAGCAACAATGGCGGCAAGCAAG
CGCTCGAAACGGTGCAGCGGCTGTTGCCGGTGCTGTGCCAGGACCATGGCCTGA
CTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACG
GTGCAGCGGCTGTTGCCGGTGCTGTGCCAGGACCATGGCCTGACTCCGGACCAA
GTGGTGGCTATCGCCAGCAACAATGGCGGCAAGCAAGCGCTCGAAACGGTGCAG
CGGCTGTTGCCGGTGCTGTGCCAGGACCATGGCCTGACCCCGGACCAAGTGGTG
GCTATCGCCAGCCACGATGGCGGCAAGCAAGCGCTCGAAACGGTGCAGCGGCTG
TTGCCGGTGCTGTGCCAGGACCATGGCCTGACCCCGGACCAAGTGGTGGCTATC
GCCAGCAACATTGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGC
AACAATGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCCACGAT
GGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCAACGGTGGCGGC
AAGCAAGCGCTCGAAACGGTGCAGCGGCTGTTGCCGGTGCTGTGCCAGGACCAT
GGCCTGACCCCGGACCAAGTGGTGGCTATCGCCAGCCACGATGGCGGCAAGCAA
GCGCTCGAAACGGTGCAGCGGCTGTTGCCGGTGCTGTGCCAGGACCATGGCCTG
ACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACCCCG
GACCAAGTGGTGGCTATCGCCAGCAACGGTGGCGGCAAGCAAGCGCTCGAAAC
GGTGCAGCGGCTGTTGCCGGTGCTGTGCCAGGACCATGGCCTGACTCCGGACCA
AGTGGTGGCTATCGCCAGCCACGATGGCGGCAAGCAAGCGCTCGAAACGGTGCA
GCGGCTGTTGCCGGTGCTGTGCCAGGACCATGGCCTGACCCCGGACCAAGTGGT
GGCTATCGCCAGCCACGATGGCGGCAAGCAAGCGCTCGAAACGGTGCAGCGGCT
GTTGCCGGTGCTGTGCCAGGACCATGGCCTGACCCCGGACCAAGTGGTGGCTAT
CGCCAGCAACGGTGGCGGCAAGCAAGCGCTCGAAAGCATTGTGGCCCAGCTGAG
CCGGCCTGATCCGGCGTTGGCCGCGTTGACCAACGACCACCTGGTCGCTCTGGCT
TGCCTGGGAGGACGCCCTGCTATGGACGCTGTGAAGAAAGGACTGCCCCACGCA
CCCGAACTGATTAGACGGGTGAACCGGAGAATCGGCGAGAGAACATCCCATAG
GGTGGCAATCTCTAGAACTCAGCTGGTCAAGAGTGAACTGGAGGAAAAGAAATC
AGAGCTGCGCCACAAGCTGAAATACGTGCCTCATGAGTATATCGAACTGATCGA
GATTGCTCGCAATTCAACCCAGGACCGGATCCTGGAAATGAAAGTGATGGAGTT
CTTTATGAAAGTCTACGGATATCGGGGGAAACACCTGGGAGGGAGCAGAAAGCC
AGATGGGGCCATCTACACAGTGGGATCCCCCATCGACTATGGCGTGATTGTCGAT
ACTAAAGCCTACAGCGGAGGCTATAACCTGCCTATCGGCCAGGCTGACGAGATG
CAGAGATACGTGGAGGAAAACCAGACCCGCAATAAGCATATTAACCCCAATGA
ATGGTGGAAAGTGTATCCTAGCTCCGTCACAGAGTTCAAGTTTCTGTTCGTGAGC
GGACACTTTAAGGGCAACTACAAAGCACAGCTGACTAGGCTGAATCATATCACC
AACTGCAATGGAGCCGTGCTGTCTGTCGAGGAACTGCTGATCGGGGGAGAGATG
ATTAAGGCTGGCACACTGACTCTGGAGGAAGTGAGGCGCAAGTTCAACAATGGG
GAAATCAACTTCTAA

SEQ ID NO: 25 WAS TALEN #2 Reverse
ATGGCGCCGCGGCCTCCTAAGAAGAAGCGGAAAGTCGAATTCGTGGATCTGCGA
ACACTGGGCTATAGCCAGCAGCAGCAGGAGAAGATCAAACCCAAGGTGAGGTC
CACAGTCGCACAGCACCATGAAGCCCTGGTGGGCCACGGGTTCACTCACGCTCA
TATTGTCGCACTGTCTCAGCATCCAGCCGCTCTGGGAACCGTGGCAGTCACATAC
CAGCACATCATTACTGCCCTGCCCGAGGCTACCCATGAAGACATCGTGGGAGTC
GGCAAACAGTGGAGCGGCGCACGGGCCCTGGAGGCTCTGCTGACCGACGCAGG
GGAACTGAGAGGACCCCCTCTGCAGCTGGATACAGGGCAGCTGGTGAAGATTGC
TAAGAGGGGAGGGGTGACAGCAATGGAAGCCGTCCACGCAAGCAGGAACGCAC
TGACAGGGGCCCCCCTGAACCTGACCCCGGACCAAGTGGTGGCTATCGCCAGCA
ACAATGGCGGCAAGCAAGCGCTCGAAACGGTGCAGCGGCTGTTGCCGGTGCTGT
GCCAGGACCATGGCCTGACCCCGGACCAAGTGGTGGCTATCGCCAGCAACAATG
GCGGCAAGCAAGCGCTCGAAACGGTGCAGCGGCTGTTGCCGGTGCTGTGCCAGG
ACCATGGCCTGACCCCGGACCAAGTGGTGGCTATCGCCAGCAACGGTGGCGGCA
AGCAAGCGCTCGAAACGGTGCAGCGGCTGTTGCCGGTGCTGTGCCAGGACCATG
GCCTGACCCCGGACCAAGTGGTGGCTATCGCCAGCCACGATGGCGGCAAGCAAG
CGCTCGAAACGGTGCAGCGGCTGTTGCCGGTGCTGTGCCAGGACCATGGCCTGA
CTCCGGACCAAGTGGTGGCTATCGCCAGCCACGATGGCGGCAAGCAAGCGCTCG
AAACGGTGCAGCGGCTGTTGCCGGTGCTGTGCCAGGACCATGGCCTGACCCCGG
ACCAAGTGGTGGCTATCGCCAGCAACGGTGGCGGCAAGCAAGCGCTCGAAACG
GTGCAGCGGCTGTTGCCGGTGCTGTGCCAGGACCATGGCCTGACTCCGGACCAA
GTGGTGGCTATCGCCAGCAACGGTGGCGGCAAGCAAGCGCTCGAAACGGTGCAG
CGGCTGTTGCCGGTGCTGTGCCAGGACCATGGCCTGACCCCGGACCAAGTGGTG
GCTATCGCCAGCCACGATGGCGGCAAGCAAGCGCTCGAAACGGTGCAGCGGCTG
TTGCCGGTGCTGTGCCAGGACCATGGCCTGACCCCGGACCAAGTGGTGGCTATC
GCCAGCCACGATGGCGGCAAGCAAGCGCTCGAAACGGTGCAGCGGCTGTTGCCG
GTGCTGTGCCAGGACCATGGCCTGACTCCGGACCAAGTGGTGGCTATCGCCAGC
AACGGTGGCGGCAAGCAAGCGCTCGAAACGGTGCAGCGGCTGTTGCCGGTGCTG
TGCCAGGACCATGGCCTGACCCCGGACCAAGTGGTGGCTATCGCCAGCAACAAT
GGCGGCAAGCAAGCGCTCGAAACGGTGCAGCGGCTGTTGCCGGTGCTGTGCCAG
GACCATGGCCTGACCCCGGACCAAGTGGTGGCTATCGCCAGCCACGATGGCGGC
AAGCAAGCGCTCGAAACGGTGCAGCGGCTGTTGCCGGTGCTGTGCCAGGACCAT
GGCCTGACCCCGGACCAAGTGGTGGCTATCGCCAGCCACGATGGCGGCAAGCAA
GCGCTCGAAACGGTGCAGCGGCTGTTGCCGGTGCTGTGCCAGGACCATGGCCTG Sequence Identification Numbers, Identifying Descriptions, and Sequences

```
ACCCCGGACCAAGTGGTGGCTATCGCCAGCAACGGTGGCGGCAAGCAAGCGCTC
GAAACGGTGCAGCGGCTGTTGCCGGTGCTGTGCCAGGACCATGGCCTGACCCCG
GACCAAGTGGTGGCTATCGCCAGCCACGATGGCGGCAAGCAAGCGCTCGAAACG
GTGCAGCGGCTGTTGCCGGTGCTGTGCCAGGACCATGGCCTGACTCCGGACCAA
GTGGTGGCTATCGCCAGCAACATTGGCGGCAAGCAAGCGCTCGAAACGGTGCAG
CGGCTGTTGCCGGTGCTGTGCCAGGACCATGGCCTGACCCCGGACCAAGTGGTG
GCTATCGCCAGCAACGGTGGCGGCAAGCAAGCGCTCGAAAGCATTGTGGCCCAG
CTGAGCCGGCCTGATCCGGCGTTGGCCGCGTTGACCAACGACCACCTGGTCGCTC
TGGCTTGCCTGGGAGGACGCCCTGCTATGGACGCTGTGAAGAAAGGACTGCCCC
ACGCACCCGAACTGATTAGACGGGTGAACCGGAGAATCGGCGAGAGAACATCC
CATAGGGTGGCAATCTCTAGAACTCAGCTGGTCAAGAGTGAACTGGAGGAAAAG
AAATCAGAGCTGCGCCACAAGCTGAAATACGTGCCTCATGAGTATATCGAACTG
ATCGAGATTGCTCGCAATTCAACCCAGGACCGGATCCTGGAAATGAAAGTGATG
GAGTTCTTTATGAAAGTCTACGGATATCGGGGGAAACACCTGGGAGGGAGCAGA
AAGCCAGATGGGGCCATCTACACAGTGGGATCCCCCATCGACTATGGCGTGATT
GTCGATACTAAAGCCTACAGCGGAGGCTATAACCTGCCTATCGGCCAGGCTGAC
GAGATGCAGAGATACGTGGAGGAAAACCAGACCCGCAATAAGCATATTAACCC
CAATGAATGGTGGAAAGTGTATCCTAGCTCCGTCACAGAGTTCAAGTTTCTGTTC
GTGAGCGGACACTTTAAGGGCAACTACAAAGCACAGCTGACTAGGCTGAATCAT
ATCACCAACTGCAATGGAGCCGTGCTGTCTGTCGAGGAACTGCTGATCGGGGGA
GAGATGATTAAGGCTGGCACACTGACTCTGGAGGAAGTGAGGCGCAAGTTCAAC
AATGGGGAAATCAACTTCTAA

SEQ ID NO: 26 #1380 AAV.WASATGcoWAS.WPRE3.pA
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTAGGCTCGTCTTGAACTCCTGACCTCAAGTGAT
CCACTCGTCTCGGCCTCCCAAAGTGCTGGGATTACAGGTGTGAGCTATTGTCCCC
AGCCAAAAGGAAAAGTTTTACTGTAGTAACCCTTCCGGACTAGGGACCTCGGGC
CTCAGCCTCAGGCTACCTAGGTGCTTTAGAAAGGAGGCCACCCAGGCCCATGAC
TACTCCTTGCCACAGGGAGCCCTGCACACAGATGTGCTAAGCTCTCGCTGCCAGC
CAGAGGGAGGAGGGTCTGAGCCAGTCAGAAGGAGATGGGCCCCAGAGAGTAAG
AAAGGGGGAGGAGGACCCAAGCTGATCCAAAAGGTGGGTCTAAGCAGTCAAGT
GGAGGAGGGTTCCAATCTGATGGCGGAGGGCCCAAGCTCAGCCTAACGAGGAG
GCCAGGCCCACCAAGGGGCCCCTGGAGGACTTGTTTCCCTTGTCCCTTGTGGTTT
TTTGCATTTCCTGTTCCCTTGCTGCTCATTGCGGAAGTTCCTCTTCTTACCCTGCA
CCCAGAGCCTCGCCAGAGAAGACAAGGGCAGAAAGCACCATGGGAGGAAGACC
CGGCGGCCGAGGAGCGCCAGCAGTGCAACAAAACATTCCGTCAACCCTGCTGCA
GGACCACGAAAACCAGAGGCTGTTTGAAATGTTGGGACGGAAGTGTCTCACTCT
CGCCACAGCCGTCGTCCAGCTTTATCTTGCGCTTCCTCCCGGTGCTGAGCATTGG
ACTAAAGAGCATTGCGGCGCGGTCTGTTTTGTCAAGGATAATCCCCAAAAATCAT
ATTTCATTAGGTTGTACGGACTCCAAGCTGGACGCCTTCTGTGGGAACAAGAACT
CTATAGCCAGCTCGTATATAGCACACCGACCCCTTTCTTCCATACTTTCGCGGGA
GACGACTGTCAGGCGGGCTTGAACTTTGCGGACGAGGATGAAGCTCAGGCTTTC
CGAGCATTGGTTCAAGAAAAAATCCAGAAAAGAAATCAGCGACAGTCCGGAGA
TCGCCGGCAGCTGCCGCCGCCACCTACACCGGCCAATGAGGAACGGAGGGGAG
GCCTTCCGCCACTTCCATTGCATCCAGGCGGCGATCAGGGTGGGCCACCAGTAG
GGCCCTTGAGTTTGGGTCTCGCTACTGTGGATATACAGAACCCGGACATAACATC
TAGCCGCTACCGCGGACTGCCGGCTCCAGGTCCGTCCCCGCTGATAAAAAGCG
CTCCGGCAAAAAGAAGATATCTAAAGCAGATATCGGTGCGCCCTCCGGTTTCAA
GCATGTCTCCCATGTAGGATGGGACCCGCAAAATGGATTCGACGTTAATAACCTC
GATCCGGACCTGAGGAGTCTCTTCTCTCGCGCGGGTATCAGCGAGGCACAGCTT
ACTGATGCCGAAACAAGTAAGTTGATATACGACTTTATCGAGGATCAAGGAGGG
CTGGAAGCGGTCAGGCAAGAAATGCGGCGACAAGAACCTTTGCCCCCGCCCCCG
CCCCCGTCCAGAGGCGGGAACCAGCTTCCACGCCCACCTATCGTTGGAGGGAAT
AAAGGCAGGTCTGGGCCACTCCCTCCGGTACCGTTGGGGATCGCTCCACCGCCTC
CTACGCCTAGGGGACCCCCGCCTCCTGGTCGGGGGGGACCGCCCCCTCCGCCGC
CTCCAGCCACTGGTCGAAGTGGACCCCTCCCGCCTCCTCCACCCGGCGCCGGGG
GCCCACCGATGCCACCTCCTCCTCCGCCCCCACCGCCTCCCCCTTCTTCCGGCAA
CGGTCCCGCACCTCCGCCCCTCCCTCCGGCATTGGTCCCCGCGGGGGGCCTCGCG
CCTGGTGGTGGCCGGGGTGCACTTCTGGATCAAATCCGACAGGGCATACAGTTG
AATAAGACGCCCGGCGCCCCTGAAAGCTCAGCTCTGCAACCGCCGCCTCAGTCC
TCTGAAGGGTTGGTAGGCGCGCTCATGCATGTAATGCAGAAGCGCAGTCGCGCT
ATCCACTCATCAGATGAAGGTGAAGACCAGGCCGGTGACGAGGACGAAGACGA
TGAATGGGACGATTGACTGAACTGAACTAGTGTCGACGATAATCAACCTCTGGA
TTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCT
TTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAAT
TCCGTGGGTCGACTGCTTTATTTGTGAAATTTGTGATGCTATTGCTTTATTTGTAA
CCATTATAAGCTGCAATAAACAAGTTAACAACAACAATTGCATTCATTTTATGTTT
TCAGGTTCAGGGGGAGGTGTGGGAGGTTTTTTAAACAGCGGTTCAGCAGAACAT
ACCCTCCACCCTCCTCCAGGACCACGAGAACCAGCGACTCTTTGAGATGCTTGGA
CGAAAATGCTTGGTGAGCTGGGGATCTCCTGCCCCCGCCCCGTCCCCACCGTTTC
TTCCTCTTCCTCTCCTCCTTCTCTCTCTTCCCCTCCTCCCGCTCCTCCTTTCCCTCTC
CATCATCTCCTCTCCTAGAATTTCCCGTCATAATCCACCCTTCCCAGGAAGATCTC
```

APPENDIX I-continued

Sequence Identification Numbers, Identifying Descriptions, and Sequences

```
AATGTCTACTTGCCTTCCCTCTGGCTGCAGCTCTTCCTTTGGGCCCATGACTGTCA
TGAGGCAGGAAGGACCAGGTCTGGCTCCAAGACCTTGTGGCTACCCCTGACCAG
ACTCCACTGACCCCTGCTTTCCTCTCCCAGACGCTGGCCACTGCAGTTGTTCAGC
TGTACCTGGCGCTGCCCCCTGGAGCTGAGCACTGGACCAAGGAGCATTGTGGGG
CTGTGTGCTTCGTGAAGGATAACCCCCAGAAGTCCTACTTCATCCGCCTTTACGG
CCTTCAGGTGACCCCCCCACCCCCGACTGGACTTGCAAGCCAGTTCTCAACCCGC
AAACCCAGATCTGTGTCCATATGTGTCCATAGCTTCAAGTCTAGAGCATGGCTAC
GTAGATAAGTAGCATGGCGGGTTAATCATTAACTACAAGGAACCCCTAGTGATG
GAGTTGGCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGC
GCCAGCTGGCGTAATAGCGAAGAGGCCCGCACCGATCGCCCTTCCCAACAGTTG
CGCAGCCTGAATGGCGAATGGCGATTCCGTTGCAATGGCTGGCGGTAATATTGTT
CTGGATATTACCAGCAAGGCCGATAGTTTGAGTTCTTCTACTCAGGCAAGTGATG
TTATTACTAATCAAAGAAGTATTGCGACAACGGTTAATTTGCGTGATGGACAGAC
TCTTTTACTCGGTGGCCTCACTGATTATAAAAACACTTCTCAGGATTCTGGCGTA
CCGTTCCTGTCTAAAATCCCTTTAATCGGCCTCCTGTTTAGCTCCCGCTCTGATTC
TAACGAGGAAAGCACGTTATACGTGCTCGTCAAAGCAACCATAGTACGCGCCCT
GTAGCGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCC
GATTTAGTGCTTTACGGCACCTCGACCCCAAAAAACTTGATTAGGGTGATGGTTC
ACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCT
CGGTCTATTCTTTTGATTTATAAGGGATTTTGCCGATTTCGGCCTATTGGTTAAAA
AATGAGCTGATTTAACAAAAATTTAACGCGAATTTTAACAAAATATTAACGTTTA
CAATTTAAATATTTGCTTATACAATCTTCCTGTTTTTGGGGCTTTTCTGATTATCA
ACCGGGGTACATATGATTGACATGCTAGTTTTACGATTACCGTTCATCGATTCTC
TTGTTTGCTCCAGACTCTCAGGCAATGACCTGATAGCCTTTGTAGAGACCTCTCA
AAAATAGCTACCCTCTCCGGCATGAATTTATCAGCTAGAACGGTTGAATATCATA
TTGATGGTGATTTGACTGTCTCCGGCCTTTCTCACCCGTTTGAATCTTTACCTACA
CATTACTCAGGCATTGCATTTAAAATATATGAGGGTTCTAAAAATTTTTATCCTT
GCGTTGAAATAAAGGCTTCTCCCGCAAAAGTATTACAGGGTCATAATGTTTTTGG
TACAACCGATTTAGCTTTATGCTCTGAGGCTTTATTGCTTAATTTTGCTAATTCTT
TGCCTTGCCTGTATGATTTATTGGATGTTGGAATCGCCTGATGCGGTATTTTCTCC
TTACGCATCTGTGCGGTATTTCACACCGCATATGGTGCACTCTCAGTACAATCTG
CTCTGATGCCGCATAGTTAAGCCAGCCCCGACACCCGCCAACACCCGCTGACGC
GCCCTGACGGGCTTGTCTGCTCCCGGCATCCGCTTACAGACAAGCTGTGACCGTC
TCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTG
TTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGT
CGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACA
TCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGT
ATTGACGCCGGGCAAGAGCAACTCGGTCGCCGCATACACTATTCTCAGAATGAC
TTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTA
CTTCTGACAACGATCGGAGGACCGAAGGAGCTAACCGCTTTTTTTGCACAACATG
GGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGC
AAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATG
```

APPENDIX I-continued

Sequence Identification Numbers, Identifying Descriptions, and Sequences

SEQ ID NO: 27 WAS TALEN#1forward RVD sequence
```
HD NG HD HD NG NI NN NI NI NG NG NG HD HD HD NN NG
 |  |  |  |  |  | |  |  |  |  |  |  |  |  |  |  |
 C  T  C  C  T  A G  A  A TT T  C  C  G T
```

SEQ ID NO: 28 WAS TALEN#1 reverse RVD sequence
```
NI NN NI HD NI NG NG NN NI NN NI NG HD NG NG HD HD NG
 |  |  |  |  |  | |  |  |  |  |  |  |  |  |  |  | I
 A  G  A  C  A TT G  A  G  A  T  C T  T  C  C  T
```

SEQ ID NO: 29 WAS TALEN#2 forward RVD sequence
```
HD NG NN NN HD NG NN HD NI NN HD NG HD NG NG HD HD NG
 |  |  |  |  | |  |  |  | |  |  | | |  |  |  |  I
 C  T  G  G  C T G  C  A G  C TC T  T  C    CT
```

SEQ ID NO: 30 WAS TALEN#2 reverse RVD sequence
```
NN NN NG HD HD NG NG HD HD NG NN HD HD NG HD NI NG
 |  |  |  | |  | |  |  |  |  |  | |  |  |  |  ||
 G  G  T  CC    TT C  C  T  G  C  C  T  CA T
```

SEQ ID NO: 31 WAS GUIDE#1 sequence
GGTATGTTCTGCTGAACCGC

SEQ ID NO: 32 WAS GUIDE#2 sequence
CAAAGAGTCGCTGGTTCTCG

SEQ ID NO: 33 WAS GUIDE#3 sequence
CAAGCATCTCAAAGAGTCGC

SEQ ID NO: 34 WAS GUIDE#4 sequence
ACCATGAGTGGGGGCCCAAT

SEQ ID NO: 35 pAAV.DT(#1201)
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAAGGGTTTTTGTTGTGTTGTTGTTGTTGCTGTTTTTGAGACAAGGG
TCTTGCTCTGTCATCATCCAGGCTGGAGTGCAGTGGTGCAGTCTCAGCTCACTGC
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGCCCAAGCTCAGCCTAACGAGGAGGCC
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT

APPENDIX I-continued

Sequence Identification Numbers, Identifying Descriptions, and Sequences

```
GCATTCATTTTATGTTTCAGGTTCAGGGGGAGGTGTGGGAGGTTTTTTAAACAGC
GGTTCAGCAGAACATACCCTCCACCCTCCTCCAGGACCACGAGAACCAGCGACT
CTTTGAGATGCTTGGACGAAAATGCTTGGTGAGCTGGGGATCTCCTGCCCCCGCC
CCGTCCCCACCGTTTCTTCCTCTTCCTCTCCTCCTTCTCTCTCTTCCCCTCCTCCCG
CTCCTCCTTTCCCTCTCCATCATCTCCTCTCCTAGAATTTCCCGTCATAATCCACC
CTTCCCAGGAAGATCTCAATGTCTACTTGCCTTCCCTCTGGCTGCAGCTCTTCCTT
TGGGCCCATGACTGTCATGAGGCAGGAAGGACCAGGTCTGGCTCCAAGACCTTG
TGGCTACCCCTGACCAGACTCCACTGACCCCTGCTTTCCTCTCCCAGACGCTGGC
CACTGCAGTTGTTCAGCTGTACCTGGCGCTGCCCCCTGGAGCTGAGCACTGGACC
AAGGAGCATTGTGGGGCTGTGTGCTTCGTGAAGGATAACCCCCAGAAGTCCTAC
TTCATCCGCCTTTACGGCCTTCAGGTGACCCCCCCACCCCCGACTGGACTTGCAA
GCCAGTTCTCAACCCGCAAACCCAGATCTGTGTCCATATGTGTCCATAGCTTCAA
GACCTCAGACCTGATCAGTGAATCCCTGAGCCCCAGAACCAAAGACTCATCCAG
ATGGCAAACTCTGACTTGCCTTTCTAAGTCTGCAATGACTGGCCCCAGTCTCCGT
ATCAAGATCTCTAAAGCCCCCAGTATTAGTCTGCTGCCTAAGCCTAATCTTTTCC
ACAAATTCCAATAAATGAGCACTGTATTTGTACCTGAACCTCAAATCTATTCTAA
ACTCAACATTTTGCATCCCAGGAATCTCTCATCAAAACTCCTGAACCCCAGATGT
TTGCCAAGCTCCTAAGTCATAAATCTGTTCAACAAACCCCAAAGTTGAATATTCC
ATTGATCCTTGAACTCCAAATCTGTCCTTCTAAATCCACAGCACAGACCCCCAGAG
TTCCCATCTAGAGCATGGCTACGTAGATAAGTAGCATGGCGGGTTAATCATTAAC
TACAAGGAACCCCTAGTGATGGAGTTGGCCACTCCCTCTCTGCGCGCTCGCTCGC
TCACTGAGGCCGGGCGACCAAAGGTCGCCCGACGCCCGGGCTTTGCCCGGGCGG
CCTCAGTGAGCGAGCGAGCGCGCCAGCTGGCGTAATAGCGAAGAGGCCCGCACC
GATCGCCCTTCCCAACAGTTGCGCAGCCTGAATGGCGAATGGCGATTCCGTTGCA
ATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGT
TAATTTGCGTGATGGACAGACTCTTTTACTCGGTGGCCTCACTGATTATAAAAAC
ACTTCTCAGGATTCTGGCGTACCGTTCCTGTCTAAAATCCCTTTAATCGGCCTCCT
GTTTAGCTCCCGCTCTGATTCTAACGAGGAAAGCACGTTATACGTGCTCGTCAAA
GCAACCATAGTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGA
TTTCGGCCTATTGGTTAAAAAATGAGCTGATTTAACAAAAATTTAACGCGAATTT
TAACAAAATATTAACGTTTACAATTTAAATATTTGCTTATACAATCTTCCTGTTTT
TGGGGCTTTTCTGATTATCAACCGGGGTACATATGATTGACATGCTAGTTTTACG
ATTACCGTTCATCGATTCTCTTGTTTGCTCCAGACTCTCAGGCAATGACCTGATAG
CCTTTGTAGAGACCTCTCAAAAATAGCTACCCTCTCCGGCATGAATTTATCAGCT
AGAACGGTTGAATATCATATTGATGGTGATTTGACTGTCTCCGGCCTTTCTCACC
CGTTTGAATCTTTACCTACACATTACTCAGGCATTGCATTTAAAATATATGAGGG
TTCTAAAAATTTTTATCCTTGCGTTGAAATAAAGGCTTCTCCCGCAAAAGTATTA
CAGGGTCATAATGTTTTTGGTACAACCGATTTAGCTTTATGCTCTGAGGCTTTATT
GCTTAATTTTGCTAATTCTTTGCCTTGCCTGTATGATTTATTGGATGTTGGAATCG
CCTGATGCGGTATTTTCTCCTTACGCATCTGTGCGGTATTTCACACCGCATATGGT
GCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTG
GTTTGTTTGCCGGATCAAGAGCTACCAACTCTTTTTTCCGAAGGTAACTGGCTTCA
GCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACG
```

APPENDIX I-continued

Sequence Identification Numbers, Identifying Descriptions, and Sequences

```
ATAGTTACCGGATAAGGCGCAGCGGTCGGGCTGAACGGGGGGTTCGTGCACACA
GCCCAGCTTGGGAGCGAACGACCTACACCGAACTGAGATACCTACAGCGTGAGCT
ATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATC
CCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATG
```

SEQ ID NO: 36 pAAV.DT-M (#1244)
```
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAGGGGTTTTTGTTGTGTTGTTGTTGTTGCTGTTTTTGAGACAAGGG
TCTTGCTCTGTCATCATCCAGGCTGGAGTGCAGTGGTGCAGTCTCAGCTCACTGC
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGCCCAAGCTCAGCCTAACGAGGAGGCC
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTAAACAGC
GGTTCAGCAGAACATACCTCCACCCTCCTCCAGGACCACGAGAACCAGCGACT
CTTTGAGATGCTTGGACGAAAATGCTTGGTGAGCTGGGGATCTCCTGCCCCCGCC
CCGTCCCCACCGTTTCTTCCTCTTCCTCTCCTCCTTCTCTCTCTTCCCCTCCTCCCG
CTCCTCCTTTCCCTCTCCATCATCTCCACTCCTAGAATTTCCCGTCATAATCCACC
CTTCCCAGGAAGATCTCAATGTCTTCTTGCCTTCCCTCTGGCTGCAGCTCTTCCTT
TGGGCCCATGACTGTCATGAGGCAGGAAGGACCAGGTCTGGCTCCAAGACCTTG
TGGCTACCCCTGACCAGACTCCACTGACCCCTGCTTTCCTCTCCCAGACGCTGGC
CACTGCAGTTGTTCAGCTGTACCTGGCGCTGCCCCCTGGAGCTGAGCACTGGACC
AAGGAGCATTGTGGGGCTGTGTGCTTCGTGAAGGATAACCCCCAGAAGTCCTAC
TTCATCCGCCTTTACGGCCTTCAGGTGACCCCCCCACCCCCGACTGGACTTGCAA
GCCAGTTCTCAACCCGCAAACCCAGATCTGTGTCCATATGTGTCCATAGCTTCAA
GACCTCAGACCTGATCAGTGAATCCCTGAGCCCCAGAACCAAAGACTCATCCAG
ATGGCAAACTCTGACTTGCCTTTCTAAGTCTGCAATGACTGGCCCCAGTCTCCGT
ATCAAGATCTCTAAAGCCCCCAGTATTAGTCTGCTGCCTAAGCCTAATCTTTTCC
ACAAATTCCAATAAATGAGCACTGTATTTGTACCTGAACCTCAAATCTATTCTAA
ACTCAACATTTTGCATCCCAGGAATCTCTCATCAAAACTCCTGAACCCCAGATGT
TTGCCAAGCTCCTAAGTCATAAATCTGTTCAACAAACCCCAAAGTTGAATATTCC
ATTGATCCTTGAACTCCAAATCTGTCCTTCTAAATCCACAGCACAGACCCCCAGAG
TTCCCATCTAGAGCATGGCTACGTAGATAAGTAGCATGGCGGGTTAATCATTAAC
TACAAGGAACCCCTAGTGATGGAGTTGGCCACTCCCTCTCTGCGCGCTCGCTCGC
```

APPENDIX I-continued

Sequence Identification Numbers, Identifying Descriptions, and Sequences

```
TCACTGAGGCCGGGCGACCAAAGGTCGCCCGACGCCCGGGCTTTGCCCGGGCGG
CCTCAGTGAGCGAGCGAGCGCGCCAGCTGGCGTAATAGCGAAGAGGCCCGCACC
GATCGCCCTTCCCAACAGTTGCGCAGCCTGAATGGCGAATGGCGATTCCGTTGCA
ATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGT
TAATTTGCGTGATGGACAGACTCTTTTACTCGGTGGCCTCACTGATTATAAAAAC
ACTTCTCAGGATTCTGGCGTACCGTTCCTGTCTAAAATCCCTTTAATCGGCCTCCT
GTTTAGCTCCCGCTCTGATTCTAACGAGGAAAGCACGTTATACGTGCTCGTCAAA
GCAACCATAGTACGCGCCCTGTAGCGGCGCATTAAGCGCGGCGGGTGTGGTGGT
TACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCCGA
TTTCGGCCTATTGGTTAAAAAATGAGCTGATTTAACAAAAATTTAACGCGAATTT
TAACAAAATATTAACGTTTACAATTTAAATATTTGCTTATACAATCTTCCTGTTTT
TGGGGCTTTTCTGATTATCAACCGGGGTACATATGATTGACATGCTAGTTTTACG
ATTACCGTTCATCGATTCTCTTGTTTGCTCCAGACTCTCAGGCAATGACCTGATAG
CCTTTGTAGAGACCTCTCAAAAATAGCTACCCTCTCCGGCATGAATTTATCAGCT
AGAACGGTTGAATATCATATTGATGGTGATTTGACTGTCTCCGGCCTTTCTCACC
CGTTTGAATCTTTACCTACACATTACTCAGGCATTGCATTTAAAATATATGAGGG
TTCTAAAAATTTTTATCCTTGCGTTGAAATAAAGGCTTCTCCCGCAAAAGTATTA
CAGGGTCATAATGTTTTTGGTACAACCGATTTAGCTTTATGCTCTGAGGCTTTATT
GCTTAATTTTGCTAATTCTTTGCCTTGCCTGTATGATTTATTGGATGTTGGAATCG
CCTGATGCGGTATTTTCTCCTTACGCATCTGTGCGGTATTTCACACCGCATATGGT
GCACTCTCAGTACAATCTGCTCTGATGCCGCATAGTTAAGCCAGCCCCGACACCC
GCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCAT
CACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCA
TGAGACAATAACCCTGATAAATGCTTCAATAATATTGAAAAAGGAAGAGTATGA
GTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATG
TGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATC
CCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATG

SEQ ID NO: 37 pAAV.DT-D (#1262)
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTGTATGACAAGCAGAAAGTAATTTGGGAGCTG
CGGGGAGGCAAGGGTAAGGGATGGGGAAGTGGACCAGAGGCATATGCGTCATT
GGCAGTGTCTAAGCACTCACGATAGGCGTGGATCACAGGGGCTCGCTCTGTAAT
TAAAAGGAAAAGGGTTTTTGTTGTGTTGTTGTTGTTGCTGTTTTTGAGACAAGGG
TCTTGCTCTGTCATCATCCAGGCTGGAGTGCAGTGGTGCAGTCTCAGCTCACTGC
```

APPENDIX I-continued

Sequence Identification Numbers, Identifying Descriptions, and Sequences

```
AACCTCCGCCTCCTGGGTTCAAGCGATTCTCCTGCCTCAGCCTCCTGAGCAGCTA
GGACTACAGGTGTGTGCCACCATGCCTGGCTAATTTTTGTATTTTTTAGTGGAAA
TGGGGTTTTGCCATGTTGCCCAGGCTCGTCTTGAACTCCTGACCTCAAGTGATCC
ACTCGTCTCGGCCTCCCAAAGTGCTGGGATTACAGGTGTGAGCTATTGTCCCCAG
CCAAAAGGAAAAGTTTTACTGTAGTAACCCTTCCGGACTAGGGACCTCGGGCCT
CAGCCTCAGGCTACCTAGGTGCTTTAGAAAGGAGGCCACCCAGGCCCATGACTA
CTCCTTGCCACAGGGAGCCCTGCACACAGATGTGCTAAGCTCTCGCTGCCAGCCA
GAGGGAGGAGGGTCTGAGCCAGTCAGAAGGAGATGGGCCCCAGAGAGTAAGAA
AGGGGGAGGAGGACCCAAGCTGATCCAAAAGGTGGGTCTAAGCAGTCAAGTGG
AGGAGGGTTCCAATCTGATGGCGGAGGGCCCAAGCTCAGCCTAACGAGGAGGCC
AGGCCCACCAAGGGGCCCCTGGAGGACTTGTTTCCCTTGTCCCTTGTGGTTTTTT
GCATTTCCTGTTCCCTTGCTGCTCATTGCGGAAGTTCCTCTTCTTACCCTGCACCC
AGAGCCTCGCCAGAGAAGACAAGGGCAGAAAGCACCATGAGTGGGGGCCCAAT
GGGAGGAAGGCCCGGGGGCCGAGGAGCACGAACAGAGAAACAGGAGAATATG
GGCCAAACAGGATATCTGTGGTAAGCAGTTCCTGCCCCGGCTCAGGGCCAAGAA
CAGTTGGAACAGCAGAATATGGGCCAAACAGGATATCTGTGGTAAGCAGTTCCT
GCCCCGGCTCAGGGCCAAGAACAGATGGTCCCCAGATGCGGTCCCGCCCTCAGC
AGTTTCTAGAGAACCATCAGATGTTTCCAGGGTGCCCCAAGGACCTGAAATGAC
CCTGTGCCTTATTTGAACTAACCAATCAGTTCGCTTCTCGCTTCTGTTCGCGCGCT
TCTGCTCCCCGAGCTCTATATAAGCAGAGCTCGTTTAGTGAACCGTCAGATCGCC
TGGAGACGCCATCCACGCTGTTTTGACTTCCATAGAAGGATCTCGAGGCCACCAT
GGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCG
ATGCCACCTACGGCAAGCTGACCCTGAAGTTCATCTGCACCACCGGCAAGCTGC
CCGTGCCCTGGCCCACCCTCGTGACCACCCTGACCTACGGCGTGCAGTGCTTCAG
CCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGAC
CCGCGCCGAGGTGAAGTTCGAGGGCGACACCCTGGTGAACCGCATCGAGCTGAA
GGGCATCGACTTCAAGGAGGACGGCAACATCCTGGGGCACAAGCTGGAGTACA
ACTACAACAGCCACAACGTCTATATCATGGCCGACAAGCAGAAGAACGGCATCA
AGGTGAACTTCAAGATCCGCCACAACATCGAGGACGGCAGCGTGCAGCTCGCCG
ACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGA
CGAGCTGTACAAGTAAACTAGTGTCGACTGCTTTATTTGTGAAATTTGTGATGCT
ATTGCTTTATTTGTAACCATTATAAGCTGCAATAAACAAGTTAACAACAACAATT
GCATTCATTTTATGTTTCAGGTTCAGGGGGAGGTGTGGGAGGTTTTTTAAAAATC
CACCCTTCCCAGGAAGATCTCAATGTCTACTTGCCTTCCCTCTGGCTGCAGCTCTT
CCTTTGGGCCCATGACTGTCATGAGGCAGGAAGGACCAGGTCTGGCTCCAAGAC
CTTGTGGCTACCCCTGACCAGACTCCACTGACCCCTGCTTTCCTCTCCCAGACGC
TGGCCACTGCAGTTGTTCAGCTGTACCTGGCGCTGCCCCCTGGAGCTGAGCACTG
GACCAAGGAGCATTGTGGGGCTGTGTGCTTCGTGAAGGATAACCCCCAGAAGTC
CTACTTCATCCGCCTTTACGGCCTTCAGGTGACCCCCCCACCCCCGACTGGACTT
GCAAGCCAGTTCTCAACCCGCAAACCCAGATCTGTGTCCATATGTGTCCATAGCT
TCAAGACCTCAGACCTGATCAGTGAATCCCTGAGCCCCAGAACCAAAGACTCAT
CCAGATGGCAAACTCTGACTTGCCTTTCTAAGTCTGCAATGACTGGCCCCAGTCT
CCGTATCAAGATCTCTAAAGCCCCCAGTATTAGTCTGCTGCCTAAGCCTAATCTT
TTCCACAAATTCCAATAAATGAGCACTGTATTTGTACCTGAACCTCAAATCTATT
CTAAACTCAACATTTTGCATCCCAGGAATCTCTCATCAAAACTCCTGAACCCCAG
ATGTTTGCCAAGCTCCTAAGTCATAAATCTGTTCAACAAACCCCAAAGTTGAATA
TTCCATTGATCCTTGAACTCCAAATCTGTCCTTCTAAATCCACAGCACAGACCCC
AGAGTTCCCATCTAGAGCATGGCTACGTAGATAAGTAGCATGGCGGGTTAATCA
TTAACTACAAGGAACCCCTAGTGATGGAGTTGGCCACTCCCTCTCTGCGCGCTCG
CTCGCTCACTGAGGCCGGGCGACCAAAGGTCGCCCGACGCCCGGGCTTTGCCCG
GGCGGCCTCAGTGAGCGAGCGAGCGCGCCAGCTGGCGTAATAGCGAAGAGGCC
CGCACCGATCGCCCTTCCCAACAGTTGCGCAGCCTGAATGGCGAATGGCGATTC
CGTTGCAATGGCTGGCGGTAATATTGTTCTGGATATTACCAGCAAGGCCGATAGT
TTGAGTTCTTCTACTCAGGCAAGTGATGTTATTACTAATCAAAGAAGTATTGCGA
CAACGGTTAATTTGCGTGATGGACAGACTCTTTTACTCGGTGGCCTCACTGATTA
TAAAAACACTTCTCAGGATTCTGGCGTACCGTTCCTGTCTAAAATCCCTTTAATC
GGCCTCCTGTTTAGCTCCCGCTCTGATTCTAACGAGGAAAGCACGTTATACGTGC
TCGTCAAAGCAACCATAGTACGCGCCCTGTAGCGGCGCATTAAGCGCGGCGGGT
GTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTC
TAAATCGGGGGCTCCCTTTAGGGTTCCGATTTAGTGCTTTACGGCACCTCGACCC
CAAAAAACTTGATTAGGGTGATGGTTCACGTAGTGGGCCATCGCCCTGATAGAC
GGTTTTTCGCCCTTTGACGTTGGAGTCCACGTTCTTTAATAGTGGACTCTTGTTCC
AAACTGGAACAACACTCAACCCTATCTCGGTCTATTCTTTTGATTTATAAGGGAT
TTTGCCGATTTCGGCCTATTGGTTAAAAAATGAGCTGATTTAACAAAAATTTAAC
GCGAATTTTAACAAAATATTAACGTTTACAATTTAAATATTTGCTTATACAATCTT
CCTGTTTTTGGGGCTTTTCTGATTATCAACCGGGGTACATATGATTGACATGCTA
GTTTTACGATTACCGTTCATCGATTCTCTTGTTTGCTCCAGACTCTCAGGCAATGA
CCTGATAGCCTTTGTAGAGACCTCTCAAAAATAGCTACCCTCTCCGGCATGAATT
TATCAGCTAGAACGGTTGAATATCATATTGATGGTGATTTGACTGTCTCCGGCCT
TTCTCACCCGTTTGAATCTTTACCTACACATTACTCAGGCATTGCATTTAAAATAT
ATGAGGGTTCTAAAAATTTTTATCCTTGCGTTGAAATAAAGGCTTCTCCCGCAAA
AGTATTACAGGGTCATAATGTTTTTGGTACAACCGATTTAGCTTTATGCTCTGAG
GCTTTATTGCTTAATTTTGCTAATTCTTTGCCTTGCCTGTATGATTTATTGGATGTT
```

APPENDIX I-continued

Sequence Identification Numbers, Identifying Descriptions, and Sequences

```
GGAATCGCCTGATGCGGTATTTTCTCCTTACGCATCTGTGCGGTATTTCACACCG
CATATGGTGCACTCTCAGTACAATCTGCTCTGATGCCGCATAGTTAAGCCAGCCC
CGACACCCGCCAACACCCGCTGACGCGCCCTGACGGGCTTGTCTGCTCCCGGCAT
CCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTT
ATAGGTTAATGTCATGATAATAATGGTTTCTTAGACGTCAGGTGGCACTTTTCGG
GGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGA
AGAGTATGAGTATTCAACATTTCCGTGTCGCCCTTATTCCCTTTTTTGCGGCATTT
TGCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCA
TGAGTGATAACACTGCGGCCAACTTACTTCTGACAACGATCGGAGGACCGAAGG
AGCTAACCGCTTTTTTGCACAACATGGGGGATCATGTAACTCGCCTTGATCGTTG
GGAACCGGAGCTGAATGAAGCCATACCAAACGACGAGCGTGACACCACGATGC
CTGTAGCAATGGCAACAACGTTGCGCAAACTATTAACTGGCGAACTACTTACTCT
AGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCC
TCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAA
AAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCT
ACCAGCGGTGGTTTGTTTGCCGGATCAAGAGCTACCAACTCTTTTTCCGAAGGTA
ACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGAC
TCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTA
TCCGGTAAGCGGCAGGGTCGGAACAGGAGAGCGCACGAGGGAGCTTCCAGGGG
GAAACGCCTGGTATCTTTATAGTCCTGTCGGGTTTCGCCACCTCTGACTTGAGCG
TCGATTTTTGTGATGCTCGTCAGGGGGGCGGAGCCTATGGAAAAACGCCAGCAA
CGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGC
GGAAGAGCGCCCAATACGCAAACCGCCTCTCCCCGCGCGTTGGCCGATTCATTA
ATG

SEQ ID NO: 38 pscAAV.G(#1189)
AAGCTTCCCGGGGGGATCTGGGCCACTCCCTCTCTGCGCGCTCGCTCGCTCACTG
AGGCCGGGCGACCAAAGGTCGCCCGACGCCCGGGCTTTGCCCGGGCGGCCTCAG
TGAGCGAGCGAGCGCGCAGAGAGGGAGTGGCCAACTCCATCACTAGGGGTTCCT
GGAGGGGTGGAGTCGTGACCTAGGCGATTTAAATTCATGTACAAAAAAGCAGGC
TTTAAAGGAACCAATTCAGTCGACTGGATCCGGTACCAAGGTCGGGCAGGAAGA
GGGCCTATTTCCCATGATTCCTTCATATTTGCATATACGATACAAGGCTGTTAGA
GAGATAATTAGAATTAATTTGACTGTAAACACAAAGATATTAGTACAAAATACG
TGACGTAGAAAGTAATAATTTCTTGGGTAGTTTGCAGTTTTAAAATTATGTTTTA
AAATGGACTATCATATGCTTACCGTAACTTGAAAGTATTTCGATTTCTTGGCTTTA
TATATCTTGTGGAAAGGACGAAACACCGGTATGTTCTGCTGAACCGCGTTTTAGA
GCTAGAAATAGCAAGTTAAAATAAGGCTAGTCCGTTATCAACTTGAAAAAGTGG
CACCGAGTCGGTGCTTTTTTTCTAGACCCAGCTTTCTTGTACAAAGTTGGCATTAA
CTAGTCCACTCCCTCTCTGCGCGCTCGCTCGCTCACTGAGGCCGGGCGACCAAAG
GTCGCCCGACGCCCGGGCTTTGCCCGGGCGGCCTCAGTGAGCGAGCGAGCGCGC
AGAGAGGGACAGATCCGGGCCCGCATGCGTCGACAATTCACTGGCCGTCGTTTT
ACAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGCCC
TTCCCAACAGTTGCGCAGCCTGAATGGCGAATGGCGCCTGATGCGGTATTTTCTC
CTTACGCATCTGTGCGGTATTTCACACCGCATATGGTGCACTCTCAGTACAATCT
GCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAG
ACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTG
ATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTAC
ATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACT
```

Sequence Identification Numbers, Identifying Descriptions, and Sequences

```
TACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCG
CAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCC
GACTGGAAAGCGGGCAGTGAGCGCAACGCAATTAATGTGAGTTAGCTCACTCAT
TAGGCACCCCAGGCTTTACACTTTATGCTTCCGGCTCGTATGTTGTGTGGAATTGT
GAGCGGATAACAATTTCACACAGGAAACAGCTATGACCATGATTACGCCAAGCT
CTCGAGATCTAGA
```

SEQ ID NO: 39 pAAV.DTG(#1215)

```
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTTGTACAAAAAAGCAGGCTTTAAAGGAACCAA
TTCAGTCGACTGGATCCGGTACCAAGGTCGGGCAGGAAGAGGGCCTATTTCCCA
TGATTCCTTCATATTTGCATATACGATACAAGGCTGTTAGAGAGATAATTAGAAT
TAATTTGACTGTAAACACAAAGATATTAGTACAAAATACGTGACGTAGAAAGTA
ATAATTTCTTGGGTAGTTTGCAGTTTTAAAATTATGTTTTAAAATGGACTATCATA
TGCTTACCGTAACTTGAAAGTATTTCGATTTCTTGGCTTTATATATCTTGTGGAAA
GGACGAAACACCGGTATGTTCTGCTGAACCGCGTTTTAGAGCTAGAAATAGCAA
GTTAAAATAAGGCTAGTCCGTTATCAACTTGAAAAAGTGGCACCGAGTCGGTGC
TTTTTTACGCGTGTATGACAAGCAGAAAGTAATTTGGGAGCTGCGGGGAGGCAA
GGGTAAGGGATGGGGAAGTGGACCAGAGGCATATGCGTCATTGGCAGTGTCTAA
GCACTCACGATAGGCGTGGATCACAGGGGCTCGCTCTGTAATTAAAAGGAAAAG
GGTTTTTGTTGTGTTGTTGTTGTTGCTGTTTTTGAGACAAGGGTCTTGCTCTGTCA
TCATCCAGGCTGGAGTGCAGTGGTGCAGTCTCAGCTCACTGCAACCTCCGCCTCC
TGGGTTCAAGCGATTCTCCTGCCTCAGCCTCCTGAGCAGCTAGGACTACAGGTGT
GTGCCACCATGCCTGGCTAATTTTTGTATTTTTTAGTGGAAATGGGGTTTTGCCAT
GTTGCCCAGGCTCGTCTTGAACTCCTGACCTCAAGTGATCCACTCGTCTCGGCCT
CCCAAAGTGCTGGGATTACAGGTGTGAGCTATTGTCCCCAGCCAAAAGGAAAAG
TTTTACTGTAGTAACCCTTCCGGACTAGGGACCTCGGGCCTCAGCCTCAGGCTAC
CTAGGTGCTTTAGAAAGGAGGCCACCCAGGCCCATGACTACTCCTTGCCACAGG
GAGCCCTGCACACAGATGTGCTAAGCTCTCGCTGCCAGCCAGAGGGAGGAGGGT
CTGAGCCAGTCAGAAGGAGATGGGCCCCAGAGAGTAAGAAAGGGGGAGGAGGA
CCCAAGCTGATCCAAAAGGTGGGTCTAAGCAGTCAAGTGGAGGAGGGTTCCAAT
CTGATGGCGGAGGGCCCAAGCTCAGCCTAACGAGGAGGCCAGGCCCACCAAGG
GGCCCCTGGAGGACTTGTTTCCCTTGCCCTTGTGGTTTTTTGCATTTCCTGTTCC
CTTGCTGCTCATTGCGGAAGTTCCTCTTCTTACCCTGCACCCAGAGCCTCGCCAG
AGAAGACAAGGGCAGAAAGCACCATGAGTGGGGGCCCAATGGGAGGAAGGCCC
GGGGGCCGAGGAGCACGAACAGAGAAACAGGAGAATATGGGCCAAACAGGATA
TCTGTGGTAAGCAGTTCCTGCCCCGGCTCAGGGCCAAGAACAGTTGGAACAGCA
GAATATGGGCCAAACAGGATATCTGTGGTAAGCAGTTCCTGCCCCGGCTCAGGG
CCAAGAACAGATGGTCCCCAGATGCGGTCCCGCCCTCAGCAGTTTCTAGAGAAC
CATCAGATGTTTCCAGGGTGCCCCAAGGACCTGAAATGACCCTGTGCCTTATTTG
AACTAACCAATCAGTTCGCTTCTCGCTTCTGTTCGCGCGCTTCTGCTCCCCGAGCT
CTATATAAGCAGAGCTCGTTTAGTGAACCGTCAGATCGCCTGGAGACGCCATCC
ACGCTGTTTTGACTTCCATAGAAGGATCTCGAGGCCACCATGGTGAGCAAGGGC
GAGGAGCTGTTCACCGGGGTGGTGCCCATCCTGGTCGAGCTGGACGGCGACGTA
AACGGCCACAAGTTCAGCGTGTCCGGCGAGGGCGAGGGCGATGCCACCTACGGC
AAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCA
```

APPENDIX I-continued

Sequence Identification Numbers, Identifying Descriptions, and Sequences

```
AGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAG
AACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTG
CTGGAGTTCGTGACCGCCGCCGGGATCACTCTCGGCATGGACGAGCTGTACAAG
TAAACTAGTGTCGACTGCTTTATTTGTGAAATTTGTGATGCTATTGCTTTATTTGT
AACCATTATAAGCTGCAATAAACAAGTTAACAACAACAATTGCATTCATTTTATG
TTTCAGGTTCAGGGGGAGGTGTGGGAGGTTTTTTAAACAGCGGTTCAGCAGAAC
ATACCCTCCACCCTCCTCCAGGACCACGAGAACCAGCGACTCTTTGAGATGCTTG
GACGAAAATGCTTGGTGAGCTGGGGATCTCCTGCCCCCGCCCCGTCCCCACCGTT
TCTTCCTCTTCCTCTCCTCCTTCTCTCTCTTCCCCTCCTCCCGCTCCTCCTTTCCCTC
TCCATCATCTCCTCTCCTAGAATTTCCCGTCATAATCCACCCTTCCCAGGAAGATC
TCAATGTCTACTTGCCTTCCCTCTGGCTGCAGCTCTTCCTTTGGGCCCATGACTGT
CATGAGGCAGGAAGGACCAGGTCTGGCTCCAAGACCTTGTGGCTACCCCTGACC
AGACTCCACTGACCCCTGCTTTCCTCTCCCAGACGCTGGCCACTGCAGTTGTTCA
GCTGTACCTGGCGCTGCCCCCTGGAGCTGAGCACTGGACCAAGGAGCATTGTGG
GGCTGTGTGCTTCGTGAAGGATAACCCCCAGAAGTCCTACTTCATCCGCCTTTAC
GGCCTTCAGGTGACCCCCCCACCCCCGACTGGACTTGCAAGCCAGTTCTCAACCC
GCAAACCCAGATCTGTGTCCATATGTGTCCATAGCTTCAAGACCTCAGACCTGAT
CAGTGAATCCCTGAGCCCCAGAACCAAAGACTCATCCAGATGGCAAACTCTGAC
TTGCCTTTCTAAGTCTGCAATGACTGGCCCCAGTCTCCGTATCAAGATCTCTAAA
GCCCCCAGTATTAGTCTGCTGCCTAAGCCTAATCTTTTCCACAAATTCCAATAAA
TGAGCACTGTATTTGTACCTGAACCTCAAATCTATTCTAAACTCAACATTTTGCAT
CCCAGGAATCTCTCATCAAAACTCCTGAACCCCAGATGTTGCCAAGCTCCTAAG
TCATAAATCTGTTCAACAAACCCCAAAGTTGAATATTCCATTGATCCTTGAACTC
CAAATCTGTCCTTCTAAATCCACAGCACAGACCCCAGAGTTCCCATCTAGAGCAT
GGCTACGTAGATAAGTAGCATGGCGGGTTAATCATTAACTACAAGGAACCCCTA
GTGATGGAGTTGGCCACTCCCTCTCTGCGCGCTCGCTCGCTCACTGAGGCCGGGC
GACCAAAGGTCGCCCGACGCCCGGGCTTTGCCCGGGCGGCCTCAGTGAGCGAGC
GAGCGCGCCAGCTGGCGTAATAGCGAAGAGGCCCGCACCGATCGCCCTTCCCAA
CAGTTGCGCAGCCTGAATGGCGAATGGCGATTCCGTTGCAATGGCTGGCGGTAA
TATTGTTCTGGATATTACCAGCAAGGCCGATAGTTTGAGTTCTTCTACTCAGGCA
AGTGATGTTATTACTAATCAAAGAAGTATTGCGACAACGGTTAATTTGCGTGATG
GACAGACTCTTTTACTCGGTGGCCTCACTGATTATAAAAACACTTCTCAGGATTC
TGGCGTACCGTTCCTGTCTAAAATCCCTTTAATCGGCCTCCTGTTTAGCTCCCGCT
CTGATTCTAACGAGGAAAGCACGTTATACGTGCTCGTCAAAGCAACCATAGTAC
GCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTT
TCTCGCCACGTTCGCCGGCTTTCCCCGTCAAGCTCTAAATCGGGGGCTCCCTTTA
GGGTTCCGATTTAGTGCTTTACGGCACCTCGACCCCAAAAAACTTGATTAGGGTG
ATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAAC
CCTATCTCGGTCTATTCTTTTGATTTATAAGGGATTTTGCCGATTTCGGCCTATTG
GTTAAAAAATGAGCTGATTTAACAAAAATTTAACGCGAATTTTAACAAAATATT
AACGTTTACAATTTAAATATTTGCTTATACAATCTTCCTGTTTTTGGGGCTTTTCT
GATTATCAACCGGGGTACATATGATTGACATGCTAGTTTTACGATTACCGTTCAT
CGATTCTCTTGTTTGCTCCAGACTCTCAGGCAATGACCTGATAGCCTTTGTAGAG
ACCTCTCAAAAATAGCTACCCTCTCCGGCATGAATTTATCAGCTAGAACGGTTGA
ATATCATATTGATGGTGATTTGACTGTCTCCGGCCTTTCTCACCCGTTTGAATCTT
TACCTACACATTACTCAGGCATTGCATTTAAAATATATGAGGGTTCTAAAAATTT
TTATCCTTGCGTTGAAATAAAGGCTTCTCCCGCAAAAGTATTACAGGGTCATAAT
GTTTTTGGTACAACCGATTTAGCTTTATGCTCTGAGGCTTTATTGCTTAATTTTGC
TAATTCTTTGCCTTGCCTGTATGATTTATTGGATGTTGGAATCGCCTGATGCGGTA
TTTTCTCCTTACGCATCTGTGCGGTATTTCACACCGCATATGGTGCACTCTCAGTA
CAATCTGCTCTGATGCCGCATAGTTAAGCCAGCCCCGACACCCGCCAACACCCG
CTGACGCGCCCTGACGGGCTTGTCTGCTCCCGGCATCCGCTTACAGACAAGCTGT
GACCGTCTCCGGGAGCTGCATGTGTCAGAGGTTTTCACCGTCATCACCGAAACGC
GCGAGACGAAAGGGCCTCGTGATACGCCTATTTTTATAGGTTAATGTCATGATAA
TAATGGTTTCTTAGACGTCAGGTGGCACTTTTCGGGGAAATGTGCGCGGAACCCC
TATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTT
CCGTGTCGCCCTTATTCCCTTTTTTGCGGCATTTTGCCTTCCTGTTTTTGCTCACCC
AGAAACGCTGGTGAAAGTAAAAGATGCTGAAGATCAGTTGGGTGCACGAGTGG
GTTACATCGAACTGGATCTCAACAGCGGTAAGATCCTTGAGAGTTTTCGCCCCGA
AGAACGTTTTCCAATGATGAGCACTTTTAAAGTTCTGCTATGTGGCGCGGTATTA
TCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCC
AACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAG
CCATACCAAACGACGAGCGTGACACCACGATGCCTGTAGCAATGGCAACAACGT
TGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGT
ATCATTGCAGCACTGGGGCCAGATGGTAAGCCCTCCCGTATCGTAGTTATCTACA
CGACGGGGAGTCAGGCAACTATGGATGAACGAAATAGACAGATCGCTGAGATA
GGTGCCTCACTGATTAAGCATTGGTAACTGTCAGACCAAGTTTACTCATATATAC
```

APPENDIX I-continued

Sequence Identification Numbers, Identifying Descriptions, and Sequences

```
TTTAGATTGATTTAAAACTTCATTTTTAATTTAAAAGGATCTAGGTGAAGATCCTT
TTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAG
ATACCAAATACTGTCCTTCTAGTGTAGCCGTAGTTAGGCCACCACTTCAAGAACT
CTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGA
GCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTG
GCCTTTTGCTGGCCTTTTGCTCACATGTTCTTTCCTGCGTTATCCCCTGATTCTGTG
GATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCCAATACGCAA
ACCGCCTCTCCCCGCGCGTTGGCCGATTCATTAATG

SEQ ID NO: 40 pAAV.ATG.GFP (#1374)
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTAGGCTCGTCTTGAACTCCTGACCTCAAGTGAT
CCACTCGTCTCGGCCTCCCAAAGTGCTGGGATTACAGGTGTGAGCTATTGTCCCC
AGCCAAAAGGAAAAGTTTTACTGTAGTAACCCTTCCGGACTAGGGACCTCGGGC
CTCAGCCTCAGGCTACCTAGGTGCTTTAGAAAGGAGGCCACCCAGGCCCATGAC
TACTCCTTGCCACAGGGAGCCCTGCACACAGATGTGCTAAGCTCTCGCTGCCAGC
CAGAGGGAGGAGGGTCTGAGCCAGTCAGAAGGAGATGGGCCCCAGAGAGTAAG
AAAGGGGGAGGAGGACCCAAGCTGATCCAAAAGGTGGGTCTAAGCAGTCAAGT
GGAGGAGGGTTCCAATCTGATGGCGGAGGGCCCAAGCTCAGCCTAACGAGGAG
GCCAGGCCCACCAAGGGGCCCCTGGAGGACTTGTTTCCCTTGTCCCTTGTGGTTT
TTTGCATTTCCTGTTCCCTTGCTGCTCATTGCGGAAGTTCCTCTTCTTACCCTGCA
CCCAGAGCCTCGCCAGAGAAGACAAGGGCAGAAAGCACCATGGTGAGCAAGGG
CGAGGAGCTGTTCACCGGGGTGGTGCCCATCCTGGTCGAGCTGGACGGCGACGT
AAACGGCCACAAGTTCAGCGTGTCCGGCGAGGGCGAGGGCGATGCCACCTACGG
CAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGA
AGTTCGAGGGCGACACCCTGGTGAACCGCATCGAGCTGAAGGGCATCGACTTCA
AGGAGGACGGCAACATCCTGGGGCACAAGCTGGAGTACAACTACAACAGCCAC
AACGTCTATATCATGGCCGACAAGCAGAAGAACGGCATCAAGGTGAACTTCAAG
ATCCGCCACAACATCGAGGACGGCAGCGTGCAGCTCGCCGACCACTACCAGCAG
AACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTG
CTGGAGTTCGTGACCGCCGCGGGATCACTCTCGGCATGGACGAGCTGTACAAG
TAAGATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTAGTT
CTTGCCACGGCGGAACTCATCGCCGCCTGCCTTGCCCGCTGCTGGACAGGGGCTC
GGCTGTTGGGCACTGACAATTCCGTGGGTCGACTGCTTTATTTGTGAAATTTGTG
ATGCTATTGCTTTATTTGTAACCATTATAAGCTGCAATAAACAAGTTAACAACAA
CAATTGCATTCATTTTATGTTTCAGGTTCAGGGGGAGGTGTGGGAGGTTTTTTAA
ACAGCGGTTCAGCAGAACATACCCTCCACCCTCCTCCAGGACCACGAGAACCAG
CGACTCTTTGAGATGCTTGGACGAAAATGCTTGGTGAGCTGGGGATCTCCTGCCC
CCGCCCCGTCCCCACCGTTTCTTCCTCTTCCTCTCCTCCTTCTCTCTCTTCCCCTCC
TCCCGCTCCTCCTTTCCCTCTCCATCATCTCCTCTCCTAGAATTTCCCGTCATAAT
CCACCCTTCCCAGGAAGATCTCAATGTCTACTTGCCTTCCCTCTGGCTGCAGCTCT
TCCTTTGGGCCCATGACTGTCATGAGGCAGGAAGGACCAGGTCTGGCTCCAAGA
CCTTGTGGCTACCCCTGACCAGACTCCACTGACCCCTGCTTTCCTCTCCCAGACG
CTGGCCACTGCAGTTGTTCAGCTGTACCTGGCGCTGCCCCCTGGAGCTGAGCACT
GGACCAAGGAGCATTGTGGGGCTGTGTGCTTCGTGAAGGATAACCCCCAGAAGT
CCTACTTCATCCGCCTTTACGGCCTTCAGGTGACCCCCCCCACCCCCGACTGGACT
TGCAAGCCAGTTCTCAACCCGCAAACCCAGATCTGTGTCCATATGTGTCCATAGC
TTCAAGTCTAGAGCATGGCTACGTAGATAAGTAGCATGGCGGGTTAATCATTAA
CTACAAGGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCG
GCCTCAGTGAGCGAGCGAGCGCGCAGCTGGCGTAATAGCGAAGAGGCCCGCA
CCGATCGCCCTTCCCAACAGTTGCGCAGCCTGAATGGCGAATGGCGATTCCGTTG
CAATGGCTGGCGGTAATATTGTTCTGGATATTACCAGCAAGGCCGATAGTTTGAG
TTCTTCTACTCAGGCAAGTGATGTTATTACTAATCAAAGAAGTATTGCGACAACG
GTTAATTTGCGTGATGGACAGACTCTTTTACTCGGTGGCCTCACTGATTATAAAA
ACACTTCTCAGGATTCTGGCGTACCGTTCCTGTCTAAAATCCCTTTAATCGGCCTC
CTGTTTAGCTCCCGCTCTGATTCTAACGAGGAAAGCACGTTATACGTGCTCGTCA
AAGCAACCATAGTACGCGCCCTGTAGCGGCGCATTAAGCGCGGCGGGTGTGGTG
GTTACGCGCAGCGTGACCGCTACACTTGCCAGCGCCCTAGCGCCCGCTCCTTTCG
```

APPENDIX I-continued

Sequence Identification Numbers, Identifying Descriptions, and Sequences

```
CTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAA
AACTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTG
GAACAACACTCAACCCTATCTCGGTCTATTCTTTTGATTTATAAGGGATTTTGCCG
ATTTCGGCCTATTGGTTAAAAAATGAGCTGATTTAACAAAAATTTAACGCGAATT
TTAACAAAATATTAACGTTTACAATTTAAATATTTGCTTATACAATCTTCCTGTTT
TTGGGGCTTTTCTGATTATCAACCGGGGTACATATGATTGACATGCTAGTTTTAC
GATTACCGTTCATCGATTCTCTTGTTTGCTCCAGACTCTCAGGCAATGACCTGATA
GCCTTTGTAGAGACCTCTCAAAAATAGCTACCCTCTCCGGCATGAATTTATCAGC
TAGAACGGTTGAATATCATATTGATGGTGATTTGACTGTCTCCGGCCTTTCTCAC
CCGTTTGAATCTTTACCTACACATTACTCAGGCATTGCATTTAAAATATATGAGG
GTTCTAAAAATTTTTATCCTTGCGTTGAAATAAAGGCTTCTCCCGCAAAAGTATT
ACAGGGTCATAATGTTTTTGGTACAACCGATTTAGCTTTATGCTCTGAGGCTTTAT
TGCTTAATTTTGCTAATTCTTTGCCTTGCCTGTATGATTTATTGGATGTTGGAATC
GCCTGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACACC
CGCCAACACCCGCTGACGCGCCCTGACGGGCTTGTCTGCTCCCGGCATCCGCTTA
CAGACAAGCTGTGACCGTCTCCGGGAGCTGCATGTGTCAGAGGTTTTCACCGTCA
TCACCGAAACGCGCGAGACGAAAGGGCCTCGTGATACGCCTATTTTTATAGGTT
AATGTCATGATAATAATGGTTTCTTAGACGTCAGGTGGCACTTTTCGGGGAAATG
TGCGCGGAACCCCTATTTGTTTATTTTTCTAAATACATTCAAATATGTATCCGCTC
ATGAGACAATAACCCTGATAAATGCTTCAATAATATTGAAAAAGGAAGAGTATG
AGTATTCAACATTTCCGTGTCGCCCTTATTCCCTTTTTTGCGGCATTTTGCCTTCCT
GTTTTTGCTCACCCAGAAACGCTGGTGAAAGTAAAAGATGCTGAAGATCAGTTG
GGTGCACGAGTGGGTTACATCGAACTGGATCTCAACAGCGGTAAGATCCTTGAG
AGTTTTCGCCCCGAAGAACGTTTTCCAATGATGAGCACTTTTAAAGTTCTGCTAT
GTGGCGCGGTATTATCCCGTATTGACGCCGGGCAAGAGCAACTCGGTCGCCGCA
TACACTATTCTCAGAATGACTTGGTTGAGTACTCACCAGTCACAGAAAAGCATCT
TACGGATGGCATGACAGTAAGAGAATTATGCAGTGCTGCCATAACCATGAGTGA
TAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCC
GGCAACAATTAATAGACTGGATGGAGGCGGATAAAGTTGCAGGACCACTTCTGC
GCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATC
GTAGTTATCTACACGACGGGGAGTCAGGCAACTATGGATGAACGAAATAGACAG
ATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAG
GTGAAGATCCTTTTTGATAATCTCATGACCAAAATCCCTTAACGTGAGTTTTCGTT
CCACTGAGCGTCAGACCCCGTAGAAAAGATCAAAGGATCTTCTTGAGATCCTTTT
TTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACC
ACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATC
CCCTGATTCTGTGGATAACCGTATTACCGCCTTTGAGTGAGCTGATACCGCTCGC
CGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATG
```

SEQ ID NO: 41 pAAV.ATG.coWAS (#1380)
```
CAGCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTG
GCCAACTCCATCACTAGGGGTTCCTTGTAGTTAATGATTAACCCGCCATGCTACT
TATCTACGTAGCCATGCTCTAGCGGCCTCGGCCTCTGCATAAATAAAAAAAATTA
GTCAGCCATGAGCTTGGACGCGTAGGCTCGTCTTGAACTCCTGACCTCAAGTGAT
CCACTCGTCTCGGCCTCCCAAAGTGCTGGGATTACAGGTGTGAGCTATTGTCCCC
AGCCAAAAGGAAAAGTTTTACTGTAGTAACCCTTCCGGACTAGGGACCTCGGGC
CTCAGCCTCAGGCTACCTAGGTGCTTTAGAAAGGAGGCCACCCAGGCCCATGAC
TACTCCTTGCCACAGGGAGCCCTGCACACAGATGTGCTAAGCTCTCGCTGCCAGC
CAGAGGGAGGAGGGTCTGAGCCAGTCAGAAGGAGATGGGCCCCAGAGAGTAAG
AAAGGGGGAGGAGGACCCAAGCTGATCCAAAAGGTGGGTCTAAGCAGTCAAGT
GGAGGAGGGTTCCAATCTGATGGCGGAGGGCCCAAGCTCAGCCTAACGAGGAG
GCCAGGCCCACCAAGGGGCCCCTGGAGGACTTGTTTCCCTTGTCCCTTGTGGTTT
TTTGCATTTCCTGTTCCCTTGCTGCTCATTGCGGAAGTTCCTCTTCTTACCCTGCA
CCCAGAGCCTCGCCAGAGAAGACAAGGGCAGAAAGCACCATGGGAGGAAGACC
CGGCGGCCGAGGAGCGCCAGCAGTGCAACAAAACATTCCGTCAACCCTGCTGCA
GGACCACGAAAACCAGAGGCTGTTTGAAATGTTGGGACGGAAGTGTCTCACTCT
CGCCACAGCCGTCGTCCAGCTTTATCTTGCGCTTCCTCCCGGTGCTGAGCATTGG
ACTAAAGAGCATTGCGGCGCGGTCTGTTTTGTCAAGGATAATCCCCAAAAATCAT
```

APPENDIX I-continued

Sequence Identification Numbers, Identifying Descriptions, and Sequences

```
ATTTCATTAGGTTGTACGGACTCCAAGCTGGACGCCTTCTGTGGGAACAAGAACT
CTATAGCCAGCTCGTATATAGCACACCGACCCCTTTCTTCCATACTTTCGCGGGA
GACGACTGTCAGGCGGGCTTGAACTTTGCGGACGAGGATGAAGCTCAGGCTTTC
CGAGCATTGGTTCAAGAAAAAATCCAGAAAAGAAATCAGCGACAGTCCGGAGA
TCGCCGGCAGCTGCCGCCGCCACCTACACCGGCCAATGAGGAACGGAGGGGAG
GCCTTCCGCCACTTCCATTGCATCCAGGCGGCGATCAGGGTGGGCCACCAGTAG
GGCCCTTGAGTTTGGGTCTCGCTACTGTGGATATACAGAACCCGGACATAACATC
TAGCCGCTACCGCGGACTGCCGGCTCCAGGTCCGTCCCCCGCTGATAAAAAGCG
CTCCGGCAAAAAGAAGATATCTAAAGCAGATATCGGTGCGCCCTCCGGTTTCAA
GCATGTCTCCCATGTAGGATGGGACCCGCAAAATGGATTCGACGTTAATAACCTC
GATCCGGACCTGAGGAGTCTCTTCTCTCGCGCGGGTATCAGCGAGGCACAGCTT
ACTGATGCCGAAACAAGTAAGTTGATATACGACTTTATCGAGGATCAAGGAGGG
CTGGAAGCGGTCAGGCAAGAAATGCGGCGACAAGAACCTTTGCCCCCGCCCCCG
CCCCCGTCCAGAGGCGGGAACCAGCTTCCACGCCCACCTATCGTTGGAGGGAAT
AAAGGCAGGTCTGGGCCACTCCCTCCGGTACCGTTGGGGATCGCTCCACCGCCTC
CTACGCCTAGGGGACCCCCGCCTCCTGGTCGGGGGGGACCGCCCCCCTCCGCCGC
CTCCAGCCACTGGTCGAAGTGGACCCCTCCCGCCTCCTCCACCCGGCGCCGGGG
GCCCACCGATGCCACCTCCTCCTCCGCCCCCACCGCCTCCCCCTTCTTCCGGCAA
CGGTCCCGCACCTCCGCCCCTCCCTCCGGCATTGGTCCCCGCGGGGGGCCTCGCG
CCTGGTGGTGGCCGGGGTGCACTTCTGGATCAAATCCGACAGGGCATACAGTTG
AATAAGACGCCCGGCGCCCCTGAAAGCTCAGCTCTGCAACCGCCGCCTCAGTCC
TCTGAAGGGTTGGTAGGCGCGCTCATGCATGTAATGCAGAAGCGCAGTCGCGCT
ATCCACTCATCAGATGAAGGTGAAGACCAGGCCGGTGACGAGGACGAAGACGA
TGAATGGGACGATTGACTGAACTGAACTAGTGTCGACGATAATCAACCTCTGGA
TTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCT
TTCATTTTCTCCTCCTTGTATAAATCCTGGTTAGTTCTTGCCACGGCGGAACTCAT
CGCCGCCTGCCTTGCCCGCTGCTGGACAGGGGCTCGGCTGTTGGGCACTGACAAT
TCCGTGGGTCGACTGCTTTATTTGTGAAATTTGTGATGCTATTGCTTTATTTGTAA
CCATTATAAGCTGCAATAAACAAGTTAACAACAACAATTGCATTCATTTTATGTT
TCAGGTTCAGGGGGAGGTGTGGGAGGTTTTTTAAACAGCGGTTCAGCAGAACAT
ACCCTCCACCCTCCTCCAGGACCACGAGAACCAGCGACTCTTTGAGATGCTTGGA
CGAAAATGCTTGGTGAGCTGGGGATCTCCTGCCCCCGCCCCGTCCCCACCGTTTC
TTCCTCTTCCTCTCCTCCTTCTCTCTCTTCCCCTCCTCCCGCTCCTCCTTTCCCTCTC
CATCATCTCCTCTCCTAGAATTTCCCGTCATAATCCACCCTTCCCAGGAAGATCTC
AATGTCTACTTGCCTTCCCTCTGGCTGCAGCTCTTCCTTTGGGCCCATGACTGTCA
TGAGGCAGGAAGGACCAGGTCTGGCTCCAAGACCTTGTGGCTACCCCTGACCAG
ACTCCACTGACCCCTGCTTTCCTCTCCCAGACGCTGGCCACTGCAGTTGTTCAGC
TGTACCTGGCGCTGCCCCCTGGAGCTGAGCACTGGACCAAGGAGCATTGTGGGG
CTGTGTGCTTCGTGAAGGATAACCCCCAGAAGTCCTACTTCATCCGCCTTTACGG
CCTTCAGGTGACCCCCCCACCCCCGACTGGACTTGCAAGCCAGTTCTCAACCCGC
AAACCCAGATCTGTGTCCATATGTGTCCATAGCTTCAAGTCTAGAGCATGGCTAC
GTAGATAAGTAGCATGGCGGGTTAATCATTAACTACAAGGAACCCCTAGTGATG
GAGTTGGCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGC
GCCAGCTGGCGTAATAGCGAAGAGGCCCGCACCGATCGCCCTTCCCAACAGTTG
CGCAGCCTGAATGGCGAATGGCGATTCCGTTGCAATGGCTGGCGGTAATATTGTT
CTGGATATTACCAGCAAGGCCGATAGTTTGAGTTCTTCTACTCAGGCAAGTGATG
TTATTACTAATCAAAGAAGTATTGCGACAACGGTTAATTTGCGTGATGGACAGAC
TCTTTTACTCGGTGGCCTCACTGATTATAAAAACACTTCTCAGGATTCTGGCGTA
CCGTTCCTGTCTAAAATCCCTTTAATCGGCCTCCTGTTTAGCTCCCGCTCTGATTC
TAACGAGGAAAGCACGTTATACGTGCTCGTCAAAGCAACCATAGTACGCGCCCT
GTAGCGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTTCTCGCC
ACGTTCGCCGGCTTTCCCCGTCAAGCTCTAAATCGGGGGCTCCCTTTAGGGTTCC
GATTTAGTGCTTTACGGCACCTCGACCCCAAAAAACTTGATTAGGGTGATGGTTC
ACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCT
CGGTCTATTCTTTTGATTTATAAGGGATTTTGCCGATTTCGGCCTATTGGTTAAAA
AATGAGCTGATTTAACAAAAATTTAACGCGAATTTTAACAAAATATTAACGTTTA
CAATTTAAATATTTGCTTATACAATCTTCCTGTTTTTGGGGCTTTTCTGATTATCA
ACCGGGGTACATATGATTGACATGCTAGTTTTACGATTACCGTTCATCGATTCTC
TTGTTTGCTCCAGACTCTCAGGCAATGACCTGATAGCCTTTGTAGAGACCTCTCA
AAAATAGCTACCCTCTCCGGCATGAATTTATCAGCTAGAACGGTTGAATATCATA
TTGATGGTGATTTGACTGTCTCCGGCCTTTCTCACCCGTTTGAATCTTTACCTACA
CATTACTCAGGCATTGCATTTAAAATATATGAGGGTTCTAAAAATTTTTATCCTT
GCGTTGAAATAAAGGCTTCTCCCGCAAAAGTATTACAGGGTCATAATGTTTTTGG
TACAACCGATTTAGCTTTATGCTCTGAGGCTTTATTGCTTAATTTTGCTAATTCTT
TGCCTTGCCTGTATGATTTATTGGATGTTGGAATCGCCTGATGCGGTATTTTCTCC
TTACGCATCTGTGCGGTATTTCACACCGCATATGGTGCACTCTCAGTACAATCTG
CTCTGATGCCGCATAGTTAAGCCAGCCCCGACACCCGCCAACACCCGCTGACGC
GCCCTGACGGGCTTGTCTGCTCCCGGCATCCGCTTACAGACAAGCTGTGACCGTC
TCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTG
TTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGT
CGCCCTTATTCCCTTTTTTGCGGCATTTTGCCTTCCTGTTTTTGCTCACCCAGAAA
```

APPENDIX I-continued

Sequence Identification Numbers, Identifying Descriptions, and Sequences

```
CGCTGGTGAAAGTAAAAGATGCTGAAGATCAGTTGGGTGCACGAGTGGGTTACA
TCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGT
ATTGACGCCGGGCAAGAGCAACTCGGTCGCCGCATACACTATTCTCAGAATGAC
TTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTA
CTTCTGACAACGATCGGAGGACCGAAGGAGCTAACCGCTTTTTTGCACAACATG
GGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGC
AAACTATTAACTGGCGAACTACTTACTCTAGCTTCCCGGCAACAATTAATAGACT
GGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTG
CCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTG
ATAATCTCATGACCAAATCCCTTAACGTGAGTTTTCGTTCCACTGAGCGTCAGA
CCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACG
CTTCCCGAAGGGAGAAAGGCGGACAGGTATCCGGTAAGCGGCAGGGTCGGAAC
AGGAGAGCGCACGAGGGGAGCTTCCAGGGGGAAACGCCTGGTATCTTTATAGTCC
TGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCC
TTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACC
GCCTCTCCCCGCGCGTTGGCCGATTCATTAATG
```

What is claimed is:

1. A method of modifying a cell, comprising introducing into a cell:
   (a) a Cas nuclease or a nucleic acid encoding the Cas nuclease, wherein the Cas nuclease is capable of cleaving a Wiskott-Aldrich Syndrome (WAS) locus in a cell genome;
   (b) a guide RNA (gRNA), wherein the gRNA is encoded by a nucleotide sequence set forth in any one of SEQ ID NOs: 31-34; and
   (c) a vector comprising a WAS gene or portion thereof.

2. The method of claim 1, wherein the nuclease comprises a Cas9 nuclease.

3. The method of claim 1, wherein the vector is an adeno-associated viral (AAV) vector.

4. The method of claim 1, wherein the vector comprises a WAS cDNA.

5. The method of claim 4, wherein the vector lacks a promoter operably linked to the WAS cDNA.

6. The method of claim 4, wherein the WAS cDNA is inserted into a first exon of a WAS gene.

7. The method of claim 1, wherein the vector comprises an enhancer.

8. The method of claim 1, wherein the vector comprises a nucleic acid homologous to the WAS locus.

9. The method of claim 1, wherein the cell is selected from a T cell or a hematopoietic stem cell (HSC).

10. The method of claim 9, wherein the cell is a CD34+ HSC.

11. The method of claim 1, wherein the cell is obtained from a human male subject.

12. A cell prepared by the method of claim 1.

13. A method of treating, inhibiting or ameliorating Wiskott-Aldrich syndrome (WAS) or X-linked thrombocytopenia (XLT) in a subject, comprising: administering the cell of claim 12 to the subject.

14. The method of claim 13, wherein the cell is autologous to the subject.

15. The method of claim 1, wherein the gRNA is encoded by the nucleotide sequence of SEQ ID NO: 31.

16. The method of claim 1, wherein the gRNA is encoded by the nucleotide sequence of SEQ ID NO: 32.

17. The method of claim 1, wherein the gRNA is encoded by the nucleotide sequence of SEQ ID NO: 33.

18. The method of claim 1, wherein the gRNA is encoded by the nucleotide sequence of SEQ ID NO: 34.

19. The method of claim 13, wherein the subject is male.

* * * * *